United States Patent
Funahashi et al.

(10) Patent No.: US 10,517,861 B2
(45) Date of Patent: Dec. 31, 2019

(54) BIOMARKERS FOR PREDICTING AND ASSESSING RESPONSIVENESS OF ENDOMETRIAL CANCER SUBJECTS TO LENVATINIB COMPOUNDS

(71) Applicant: Eisai R&D Management Co., Ltd., Tokyo (JP)

(72) Inventors: Yasuhiro Funahashi, Tsukuba (JP); Tadashi Kadowaki, Tsukuba (JP); Pallavi Sachdev, Woodcliff Lake, NJ (US)

(73) Assignee: Eisai R&D Management Co., Ltd., Tokyo (JP)

( * ) Notice: Subject to any disclaimer, the term of this patent is extended or adjusted under 35 U.S.C. 154(b) by 215 days.

(21) Appl. No.: 14/890,207

(22) PCT Filed: May 12, 2014

(86) PCT No.: PCT/JP2014/063134
§ 371 (c)(1),
(2) Date: Nov. 10, 2015

(87) PCT Pub. No.: WO2014/185540
PCT Pub. Date: Nov. 20, 2014

(65) Prior Publication Data
US 2016/0089366 A1    Mar. 31, 2016

Related U.S. Application Data

(60) Provisional application No. 61/823,034, filed on May 14, 2013.

(51) Int. Cl.
*A61K 31/47* (2006.01)
*G01N 33/574* (2006.01)

(52) U.S. Cl.
CPC ....... *A61K 31/47* (2013.01); *G01N 33/57442* (2013.01); *G01N 2333/475* (2013.01); *G01N 2333/515* (2013.01); *G01N 2800/52* (2013.01)

(58) Field of Classification Search
None
See application file for complete search history.

(56) References Cited

U.S. PATENT DOCUMENTS

| | | |
|---|---|---|
| 4,526,988 A | 7/1985 | Hertel |
| 4,563,417 A | 1/1986 | Albarella et al. |
| 4,582,789 A | 4/1986 | Sheldon, III et al. |
| 4,742,003 A | 5/1988 | Derynck et al. |
| 4,764,454 A | 8/1988 | Ichijima et al. |
| 5,120,548 A | 6/1992 | McClelland et al. |
| 5,180,818 A | 1/1993 | Cech et al. |
| 5,211,951 A | 5/1993 | Sparer et al. |
| 5,445,934 A | 8/1995 | Fodor et al. |
| 5,464,826 A | 11/1995 | Grindey et al. |
| 5,487,889 A | 1/1996 | Eckert et al. |
| 5,553,037 A | 9/1996 | Tachibana |
| 5,624,937 A | 4/1997 | Reel et al. |
| 5,650,376 A | 7/1997 | Badaye et al. |
| 5,656,454 A | 8/1997 | Lee et al. |
| 5,658,374 A | 8/1997 | Glover |
| 5,733,913 A | 3/1998 | Blankley et al. |
| 5,747,651 A | 5/1998 | Lemischka |
| 5,750,376 A | 5/1998 | Weiss et al. |
| 5,770,599 A | 6/1998 | Gibson |
| 5,792,783 A | 8/1998 | Tang et al. |
| 5,891,996 A | 4/1999 | Mateo de Acosta del Rio et al. |
| 5,948,438 A | 9/1999 | Staniforth et al. |
| 6,027,880 A | 2/2000 | Cronin et al. |
| 6,057,100 A | 5/2000 | Heyneker |
| 6,143,764 A | 11/2000 | Kubo et al. |
| 6,156,501 A | 12/2000 | McGall et al. |
| 6,156,522 A | 12/2000 | Keay et al. |
| 6,217,866 B1 | 4/2001 | Schlessinger et al. |
| 6,242,002 B1 | 6/2001 | Tritthart et al. |
| 6,261,776 B1 | 7/2001 | Pirrung et al. |
| 6,346,398 B1 | 2/2002 | Pavco et al. |
| 6,351,255 B1 | 2/2002 | Ishizuka et al. |
| 6,475,525 B1 | 11/2002 | Komuro et al. |
| 6,476,040 B1 | 11/2002 | Norris et al. |
| 6,524,583 B1 | 2/2003 | Thorpe et al. |
| 6,534,535 B1 | 3/2003 | Zhu et al. |
| 6,544,552 B2 | 4/2003 | Sparks et al. |
| 6,576,424 B2 | 6/2003 | Fodor et al. |

(Continued)

FOREIGN PATENT DOCUMENTS

| | | |
|---|---|---|
| CA | 2 361 057 | 7/2000 |
| CA | 2606719 | 12/2006 |

(Continued)

OTHER PUBLICATIONS

Boss, D.S., et al., British Journal of Cancer, 106: 1598-1604, 2012.*
Emoto, M. et al., Gynecologic Oncology, 95: 474-482, 2004.*
Saito, M., et al., Pathology International, 57: 140-147, 2007.*
"Carboxymethyl Cellulose Sodium." Chemical Land 21. Retrieved Apr. 24, 2012. <http://www.chemicalland21.comlindustrialchem/perfonnancepolymer/CARBOXYMETHYL%20CELLULOSE%20SODIUM%20SAL T.htm>, 2 pages.
"Carboxymethylcellulose Sodium." Merck Index: An Encyclopedia of Chemicals, Drugs, & Biologicals: 13th Ed. New Jersey: Merck & Co (2001), p. 308.
"Current Protocols in Molecular Biology", John Wiley & Sons Section 11.4-11.13 (1987), 62 pages.

(Continued)

*Primary Examiner* — Mark Halvorson
(74) *Attorney, Agent, or Firm* — Fish & Richardson P.C.

(57) ABSTRACT

Biomarkers are provided that predict whether a subject having endometrial cancer will or will not respond to a therapy comprising lenvatinib or a pharmaceutically acceptable salt thereof (e.g., lenvatinib mesylate). The biomarkers, compositions, and methods described herein are useful in selecting appropriate treatment modalities for and treating a subject having, suspected of having, or at risk of developing an endometrial cancer.

15 Claims, 6 Drawing Sheets

(56) References Cited

U.S. PATENT DOCUMENTS

| | | |
|---|---|---|
| 6,596,311 B1 | 7/2003 | Dobetti et al. |
| 6,676,941 B2 | 1/2004 | Thorpe et al. |
| 6,762,180 B1 | 7/2004 | Roth et al. |
| 6,797,823 B1 | 9/2004 | Kubo et al. |
| 6,811,779 B2 | 11/2004 | Rockwell et al. |
| 6,812,341 B1 | 11/2004 | Conrad |
| 6,821,987 B2 | 11/2004 | Kubo et al. |
| 7,005,430 B2 | 2/2006 | Ueno et al. |
| 7,074,880 B2 | 7/2006 | Rhine et al. |
| 7,101,663 B2 | 9/2006 | Godfrey et al. |
| 7,135,466 B2 | 11/2006 | Sakai et al. |
| 7,169,789 B2 | 1/2007 | Kubo et al. |
| 7,211,587 B2 | 5/2007 | Kubo et al. |
| 7,253,286 B2 | 8/2007 | Funahashi et al. |
| 7,435,590 B2 | 10/2008 | Komurasaki |
| 7,485,658 B2 | 2/2009 | Bolger et al. |
| 7,495,104 B2 | 2/2009 | Miwa et al. |
| 7,547,703 B2 | 6/2009 | Roth et al. |
| 7,550,483 B2 | 6/2009 | Sakaguchi et al. |
| 7,612,092 B2 | 11/2009 | Funahashi et al. |
| 7,612,208 B2 | 11/2009 | Matsushima et al. |
| 7,683,172 B2 | 3/2010 | Naito et al. |
| 7,725,303 B2 | 5/2010 | Tramontana |
| 7,759,518 B2 | 7/2010 | Maderna et al. |
| 7,790,885 B2 | 9/2010 | Nagai et al. |
| 7,820,664 B2 | 10/2010 | Vernier et al. |
| 7,846,941 B2 | 12/2010 | Zhang et al. |
| 7,855,290 B2 | 12/2010 | Matsushima et al. |
| 7,863,288 B2 | 1/2011 | Ibrahim et al. |
| 7,973,160 B2 | 7/2011 | Funahashi et al. |
| 7,994,159 B2 | 8/2011 | Yamamoto et al. |
| 7,998,948 B2 | 8/2011 | Hiroshi et al. |
| 8,044,240 B2 | 10/2011 | Dimock |
| 8,063,049 B2 | 11/2011 | Koh et al. |
| 8,101,799 B2 | 1/2012 | Maderna et al. |
| 8,143,271 B2 | 3/2012 | Ibrahim et al. |
| 8,252,842 B2 | 8/2012 | Dimock |
| 8,288,538 B2 | 10/2012 | Matsushima et al. |
| 8,372,981 B2 | 2/2013 | Funahashi et al. |
| 8,377,938 B2 | 2/2013 | Matsushima et al. |
| 8,415,469 B2 | 4/2013 | Ibrahim et al. |
| 8,466,316 B2 | 6/2013 | Dimock |
| 8,470,818 B2 | 6/2013 | Ibrahim et al. |
| 8,492,560 B2 | 7/2013 | Stokes et al. |
| 8,580,254 B2 | 11/2013 | Adam et al. |
| 8,648,116 B2 | 2/2014 | Vernier et al. |
| 8,759,577 B2 | 6/2014 | Dimock |
| 8,808,742 B2 | 8/2014 | Quart et al. |
| 8,815,241 B2 | 8/2014 | Yamamoto |
| 8,871,450 B2 * | 10/2014 | Hacker ............ G01N 33/57419 435/7.1 |
| 8,969,379 B2 | 3/2015 | Furitsu et al. |
| 2002/0010203 A1 | 1/2002 | Lipson et al. |
| 2002/0040127 A1 | 4/2002 | Jiang et al. |
| 2003/0013208 A1 | 1/2003 | Jendoubi |
| 2003/0087907 A1 | 5/2003 | Kubo et al. |
| 2003/0113713 A1 | 6/2003 | Glezer et al. |
| 2003/0124129 A1 | 7/2003 | Oliner |
| 2003/0215523 A1 | 11/2003 | Ozawa et al. |
| 2004/0002505 A1 | 1/2004 | Ozawa et al. |
| 2004/0009965 A1 | 1/2004 | Collins et al. |
| 2004/0034026 A1 | 2/2004 | Wood et al. |
| 2004/0053908 A1 | 3/2004 | Funahashi et al. |
| 2004/0086915 A1 | 5/2004 | Lin et al. |
| 2004/0132727 A1 | 7/2004 | Sakai et al. |
| 2004/0132772 A1 | 7/2004 | Awad et al. |
| 2004/0152759 A1 | 8/2004 | Abrams et al. |
| 2004/0162333 A1 | 8/2004 | Mezaache et al. |
| 2004/0167134 A1 | 8/2004 | Bruns et al. |
| 2004/0171068 A1 | 9/2004 | Wehland et al. |
| 2004/0191254 A1 | 9/2004 | Fagin |
| 2004/0224972 A1 | 11/2004 | Ozawa et al. |
| 2004/0229876 A1 | 11/2004 | Kubo et al. |
| 2004/0242506 A1 | 12/2004 | Barges Causeret et al. |
| 2004/0253205 A1 | 12/2004 | Yamamoto et al. |
| 2004/0259834 A1 | 12/2004 | Kasprzyk et al. |
| 2005/0014727 A1 | 1/2005 | Muller et al. |
| 2005/0049264 A1 | 3/2005 | Miwa et al. |
| 2005/0119303 A1 | 6/2005 | Wakabayashi et al. |
| 2005/0176802 A1 | 8/2005 | Tang et al. |
| 2005/0187236 A1 | 8/2005 | Tsuruoka et al. |
| 2005/0209452 A1 | 9/2005 | Bornsen et al. |
| 2005/0272688 A1 | 12/2005 | Higgins et al. |
| 2005/0277652 A1 | 12/2005 | Matsushima et al. |
| 2005/0288521 A1 | 12/2005 | Naidu et al. |
| 2006/0004017 A1 | 1/2006 | Stokes et al. |
| 2006/0004029 A1 | 1/2006 | Tsuruoka et al. |
| 2006/0018909 A1 | 1/2006 | Oliner et al. |
| 2006/0057195 A1 | 3/2006 | Nonomura et al. |
| 2006/0079494 A1 | 4/2006 | Santi et al. |
| 2006/0135486 A1 | 6/2006 | Owa et al. |
| 2006/0160832 A1 | 7/2006 | Funahashi et al. |
| 2006/0178399 A1 | 8/2006 | Nishizawa et al. |
| 2006/0189629 A1 | 8/2006 | Bolger et al. |
| 2006/0252777 A1 | 11/2006 | Kim et al. |
| 2006/0292192 A1 | 12/2006 | Hasenzahl et al. |
| 2007/0004773 A1 | 1/2007 | Sakaguchi et al. |
| 2007/0014856 A1 | 1/2007 | Takagi et al. |
| 2007/0027318 A1 | 2/2007 | Kubo et al. |
| 2007/0032521 A1 | 2/2007 | Moussy et al. |
| 2007/0037849 A1 | 2/2007 | Naito et al. |
| 2007/0078159 A1 | 4/2007 | Matsushima |
| 2007/0117842 A1 | 5/2007 | Arimoto et al. |
| 2007/0214604 A1 | 9/2007 | Yi |
| 2007/0298111 A1 | 12/2007 | Ueki |
| 2008/0207617 A1 | 8/2008 | Miwa et al. |
| 2008/0214557 A1 | 9/2008 | Ueki et al. |
| 2008/0214604 A1 | 9/2008 | Furitsu et al. |
| 2008/0241835 A1 | 10/2008 | Mehraban et al. |
| 2008/0286282 A1 | 11/2008 | Semba et al. |
| 2009/0042213 A1 | 2/2009 | Hoofnagle et al. |
| 2009/0047278 A1 | 2/2009 | Owa et al. |
| 2009/0047365 A1 | 2/2009 | Owa et al. |
| 2009/0053236 A1 | 2/2009 | Yamamoto |
| 2009/0191212 A1 | 7/2009 | Oliner et al. |
| 2009/0202541 A1 | 8/2009 | Bruns et al. |
| 2009/0209580 A1 | 8/2009 | Matsui |
| 2009/0247576 A1 | 10/2009 | Kamata |
| 2009/0264464 A1 | 10/2009 | Yamamoto et al. |
| 2009/0304694 A1 | 12/2009 | Oliner et al. |
| 2009/0311175 A1 | 12/2009 | Brose |
| 2010/0048503 A1 | 2/2010 | Yamamoto |
| 2010/0048620 A1 | 2/2010 | Yamamoto |
| 2010/0092490 A1 | 4/2010 | Uenaka et al. |
| 2010/0105031 A1 | 4/2010 | Matsui et al. |
| 2010/0239688 A1 | 9/2010 | Yamamoto |
| 2010/0324087 A1 | 12/2010 | Yamamoto |
| 2011/0020410 A1 | 1/2011 | Nonomura et al. |
| 2011/0060049 A1 | 1/2011 | Vernier et al. |
| 2011/0028498 A1 | 2/2011 | Ryan et al. |
| 2011/0104161 A1 | 5/2011 | Burgess et al. |
| 2011/0118470 A1 | 5/2011 | Funahashi et al. |
| 2011/0158983 A1 | 6/2011 | Bascomb et al. |
| 2011/0166174 A1 | 7/2011 | Zhang et al. |
| 2011/0207756 A1 | 8/2011 | Matsui |
| 2011/0293615 A1 | 12/2011 | Yamamoto |
| 2011/0311546 A1 | 12/2011 | Oliner et al. |
| 2012/0022076 A1 | 1/2012 | Maderna et al. |
| 2012/0053177 A1 | 3/2012 | Ibrahim et al. |
| 2012/0077837 A1 | 3/2012 | Okamoto et al. |
| 2012/0077842 A1 | 3/2012 | Bando |
| 2012/0207753 A1 | 8/2012 | Yu et al. |
| 2012/0219522 A1 | 8/2012 | Xi |
| 2012/0244209 A1 | 9/2012 | Roth et al. |
| 2012/0263677 A1 | 10/2012 | Eagle et al. |
| 2012/0283206 A1 | 11/2012 | Bruns et al. |
| 2013/0085152 A1 | 4/2013 | Matsui et al. |
| 2013/0123274 A1 | 5/2013 | Nakagawa et al. |
| 2013/0142799 A1 | 6/2013 | Oliner et al. |
| 2013/0237565 A1 | 9/2013 | Furitsu et al. |
| 2013/0296365 A1 | 11/2013 | Bando |
| 2014/0148483 A1 | 5/2014 | Semba et al. |

(56) References Cited

U.S. PATENT DOCUMENTS

| | | | |
|---|---|---|---|
| 2014/0243316 A1 | 8/2014 | Takaishi et al. | |
| 2015/0366866 A1 | 12/2015 | Ali et al. | |
| 2017/0191137 A1 | 7/2017 | Semba et al. | |

FOREIGN PATENT DOCUMENTS

| | | |
|---|---|---|
| CH | 656535 | 7/1986 |
| CN | 1293041 | 5/2001 |
| CN | 1473041 | 2/2004 |
| CN | 1478078 | 2/2004 |
| CN | 1634043 | 7/2005 |
| CN | 1772052 | 5/2006 |
| CN | 1890220 | 1/2007 |
| CN | 101001629 | 7/2007 |
| CN | 101029022 | 9/2007 |
| CN | 101198590 | 6/2008 |
| CN | 101316590 | 12/2008 |
| CN | 101454286 | 6/2009 |
| CN | 101454311 | 6/2009 |
| CN | 101616671 | 12/2009 |
| CN | 102470133 | 5/2012 |
| EP | 0 203 126 | 12/1986 |
| EP | 0 297 580 | 1/1989 |
| EP | 0 405 425 | 1/1991 |
| EP | 0 408 496 | 1/1991 |
| EP | 0 427 519 | 5/1991 |
| EP | 0 602 851 | 6/1994 |
| EP | 0 684 637 | 11/1995 |
| EP | 0 684 820 | 12/1995 |
| EP | 0 712 863 | 5/1996 |
| EP | 0 795 556 | 9/1997 |
| EP | 0 837 063 | 4/1998 |
| EP | 0 860 433 | 8/1998 |
| EP | 0 870 842 | 10/1998 |
| EP | 0 930 305 | 7/1999 |
| EP | 0 930 310 | 7/1999 |
| EP | 1 029 853 | 8/2000 |
| EP | 1 044 969 | 10/2000 |
| EP | 0 543 942 | 1/2001 |
| EP | 1 153 920 | 11/2001 |
| EP | 1 382 604 | 1/2004 |
| EP | 1 411 046 | 4/2004 |
| EP | 1 415 987 | 5/2004 |
| EP | 1 447 045 | 8/2004 |
| EP | 1 447 405 | 8/2004 |
| EP | 1 473 043 | 11/2004 |
| EP | 1 506 962 | 2/2005 |
| EP | 1 522 540 | 4/2005 |
| EP | 1 535 910 | 6/2005 |
| EP | 1 552 833 | 7/2005 |
| EP | 1 566 379 | 8/2005 |
| EP | 1 604 665 | 12/2005 |
| EP | 1 331 005 | 4/2006 |
| EP | 1 683 785 | 7/2006 |
| EP | 1 698 623 | 9/2006 |
| EP | 1 719 763 | 11/2006 |
| EP | 1 777 218 | 4/2007 |
| EP | 1 797 877 | 6/2007 |
| EP | 1 797 881 | 6/2007 |
| EP | 1 859 793 | 11/2007 |
| EP | 1 859 797 | 11/2007 |
| EP | 1 889 836 | 2/2008 |
| EP | 1 894 918 | 3/2008 |
| EP | 1 925 676 | 5/2008 |
| EP | 1 925 941 | 5/2008 |
| EP | 1 949 902 | 7/2008 |
| EP | 1 964 837 | 9/2008 |
| EP | 2 058 302 | 5/2009 |
| EP | 2062886 | 5/2009 |
| EP | 2 116 246 | 11/2009 |
| EP | 2 119 707 | 11/2009 |
| EP | 2 133 094 | 12/2009 |
| EP | 2 133 095 | 12/2009 |
| EP | 2 218 712 | 8/2010 |
| EP | 2293071 | 3/2011 |
| EP | 2 711 433 | 3/2014 |
| EP | 2711433 | 3/2014 |
| GB | 2253848 | 9/1992 |
| GB | 2456907 | 8/2009 |
| IL | 148756 | 10/2007 |
| IN | 236500 | 11/2009 |
| JP | 61148115 | 7/1986 |
| JP | 63-028427 | 6/1988 |
| JP | 1022874 | 1/1989 |
| JP | 2291295 | 12/1990 |
| JP | 4341454 | 11/1992 |
| JP | H05194259 | 8/1993 |
| JP | 6153952 | 6/1994 |
| JP | 6287148 | 10/1994 |
| JP | 7176103 | 7/1995 |
| JP | 8045927 | 2/1996 |
| JP | 8048078 | 2/1996 |
| JP | 9023885 | 1/1997 |
| JP | 9234074 | 9/1997 |
| JP | 10-114655 | 5/1998 |
| JP | 10-147524 | 6/1998 |
| JP | 3088018 | 6/1998 |
| JP | 10-316576 | 12/1998 |
| JP | 11-501343 | 2/1999 |
| JP | 11-143429 | 5/1999 |
| JP | 11-158149 | 6/1999 |
| JP | 11-322596 | 11/1999 |
| JP | 3040486 | 5/2000 |
| JP | 3420549 | 10/2000 |
| JP | 2000-325080 | 11/2000 |
| JP | 2000-328080 | 11/2000 |
| JP | 2001-047890 | 2/2001 |
| JP | 2001-131071 | 5/2001 |
| JP | 2002-003365 | 1/2002 |
| JP | 2002-505269 | 2/2002 |
| JP | 2002-114710 | 4/2002 |
| JP | 2002-509872 | 4/2002 |
| JP | 2002-536056 | 10/2002 |
| JP | 2002-536414 | 10/2002 |
| JP | 2003-012668 | 1/2003 |
| JP | 2003-026576 | 1/2003 |
| JP | 2003-033472 | 2/2003 |
| JP | 2003-252737 | 9/2003 |
| JP | 2003-525595 | 9/2003 |
| JP | 2004-513964 | 5/2004 |
| JP | 2004-155773 | 6/2004 |
| JP | 2004-517859 | 6/2004 |
| JP | 2004-531549 | 10/2004 |
| JP | 2005-272474 | 10/2004 |
| JP | 2005-501074 | 1/2005 |
| JP | 2005-504111 | 2/2005 |
| JP | 2005-124034 | 5/2005 |
| JP | 2005-520834 | 7/2005 |
| JP | 3712393 | 11/2005 |
| JP | 2006-508981 | 3/2006 |
| JP | 2006-515884 | 6/2006 |
| JP | 2006-230816 | 9/2006 |
| JP | 2007-153894 | 6/2007 |
| JP | 2008-546797 | 12/2008 |
| JP | 2009-132660 | 6/2009 |
| JP | 2010-502209 | 1/2010 |
| JP | 2010-535233 | 11/2010 |
| JP | 2014-521308 | 8/2014 |
| KR | 10-2003-40552 | 5/2003 |
| KR | 10-0589032 | 11/2005 |
| RU | 2328489 | 7/2008 |
| RU | 2404992 | 10/2008 |
| RU | 2362771 | 7/2009 |
| WO | 1986/003222 | 6/1986 |
| WO | 1992/020642 | 11/1992 |
| WO | 1993/011748 | 6/1993 |
| WO | 1994/009010 | 4/1994 |
| WO | 1995/015758 | 6/1995 |
| WO | 1995/017181 | 6/1995 |
| WO | 1995/019774 | 7/1995 |
| WO | 1996/009294 | 3/1996 |
| WO | 1996/026997 | 9/1996 |
| WO | 1996/030347 | 10/1996 |
| WO | 1996/033980 | 10/1996 |

(56) References Cited

FOREIGN PATENT DOCUMENTS

| | | |
|---|---|---|
| WO | 1996/039145 | 12/1996 |
| WO | 1996/040080 | 12/1996 |
| WO | 1996/040142 | 12/1996 |
| WO | 1997/003069 | 1/1997 |
| WO | 1997/013760 | 4/1997 |
| WO | 1997/013771 | 4/1997 |
| WO | 1997/017329 | 5/1997 |
| WO | 1997/021437 | 6/1997 |
| WO | 1997/038984 | 10/1997 |
| WO | 1997/048693 | 12/1997 |
| WO | 1998/000134 | 1/1998 |
| WO | 1998/002434 | 1/1998 |
| WO | 1998/002437 | 1/1998 |
| WO | 1998/002438 | 1/1998 |
| WO | 1998/013350 | 4/1998 |
| WO | 1998/014437 | 4/1998 |
| WO | 1998/023613 | 6/1998 |
| WO | 1998/029137 | 7/1998 |
| WO | 1998/032436 | 7/1998 |
| WO | 1998/035958 | 8/1998 |
| WO | 1998/037079 | 8/1998 |
| WO | 1998/050346 | 11/1998 |
| WO | 1998/052558 | 11/1998 |
| WO | 1999/000357 | 1/1999 |
| WO | 1999/032106 | 7/1999 |
| WO | 1999/032110 | 7/1999 |
| WO | 1999/032111 | 7/1999 |
| WO | 1999/032436 | 7/1999 |
| WO | 1999/035132 | 7/1999 |
| WO | 1999/035146 | 7/1999 |
| WO | 1999/043654 | 9/1999 |
| WO | 1999/062890 | 12/1999 |
| WO | 2000/019985 | 4/2000 |
| WO | 2000/031048 | 6/2000 |
| WO | 2000/042012 | 7/2000 |
| WO | 2000/043366 | 7/2000 |
| WO | 2000/043384 | 7/2000 |
| WO | 2000/044728 | 8/2000 |
| WO | 2000/047212 | 8/2000 |
| WO | 2000/050405 | 8/2000 |
| WO | 2000/071097 | 11/2000 |
| WO | 2001/002369 | 1/2001 |
| WO | 2001/023375 | 4/2001 |
| WO | 2001/027081 | 4/2001 |
| WO | 2001/032926 | 5/2001 |
| WO | 2001/036403 | 5/2001 |
| WO | 2001/040217 | 6/2001 |
| WO | 2001/045689 | 6/2001 |
| WO | 2001/047890 | 7/2001 |
| WO | 2001/047931 | 7/2001 |
| WO | 2001/060814 | 8/2001 |
| WO | 2002/016348 | 2/2002 |
| WO | 2002/032872 | 4/2002 |
| WO | 2002/036117 | 5/2002 |
| WO | 2002/041882 | 5/2002 |
| WO | 2002/044156 | 6/2002 |
| WO | 2002/072578 | 9/2002 |
| WO | 2002/080975 | 10/2002 |
| WO | 2002/088110 | 11/2002 |
| WO | 2002/092091 | 11/2002 |
| WO | 2002/096361 | 12/2002 |
| WO | 2003/000660 | 1/2003 |
| WO | 2003/006462 | 1/2003 |
| WO | 2003/013529 | 2/2003 |
| WO | 2003/024386 | 3/2003 |
| WO | 2003/027102 | 3/2003 |
| WO | 2003/028711 | 4/2003 |
| WO | 2003/033472 | 4/2003 |
| WO | 2003/050090 | 6/2003 |
| WO | 2003/074045 | 9/2003 |
| WO | 2003/075840 | 9/2003 |
| WO | 2003/079020 | 9/2003 |
| WO | 2003/087026 | 10/2003 |
| WO | 2003/099771 | 12/2003 |
| WO | 2004/006862 | 1/2004 |
| WO | 2004/020434 | 3/2004 |
| WO | 2004/032872 | 4/2004 |
| WO | 2004/032937 | 4/2004 |
| WO | 2004/035052 | 4/2004 |
| WO | 2004/039782 | 5/2004 |
| WO | 2004/041308 | 5/2004 |
| WO | 2004/043472 | 5/2004 |
| WO | 2004/045523 | 6/2004 |
| WO | 2004/064730 | 8/2004 |
| WO | 2004/076412 | 9/2004 |
| WO | 2004/078144 | 9/2004 |
| WO | 2004/080462 | 9/2004 |
| WO | 2004/080966 | 9/2004 |
| WO | 2004/089286 | 10/2004 |
| WO | 2004/101526 | 11/2004 |
| WO | 2005/004870 | 1/2005 |
| WO | 2005/021537 | 3/2005 |
| WO | 2005/027972 | 3/2005 |
| WO | 2005/030140 | 4/2005 |
| WO | 2005/044788 | 5/2005 |
| WO | 2005/051366 | 6/2005 |
| WO | 2005/056764 | 6/2005 |
| WO | 2005/063713 | 7/2005 |
| WO | WO 2005/070891 | 8/2005 |
| WO | 2005/082854 | 9/2005 |
| WO | 2005/082855 | 9/2005 |
| WO | 2005/092896 | 10/2005 |
| WO | 2005/117867 | 12/2005 |
| WO | 2005/117887 | 12/2005 |
| WO | 2006/004636 | 1/2006 |
| WO | 2006/014325 | 2/2006 |
| WO | 2006/030826 | 3/2006 |
| WO | 2006/030941 | 3/2006 |
| WO | 2006/030947 | 3/2006 |
| WO | 2006/036941 | 4/2006 |
| WO | 2006/038552 | 4/2006 |
| WO | 2006/062984 | 6/2006 |
| WO | 2006/090930 | 8/2006 |
| WO | 2006/090931 | 8/2006 |
| WO | 2006/137474 | 12/2006 |
| WO | 2007/000347 | 1/2007 |
| WO | 2007/002325 | 1/2007 |
| WO | 2007/014335 | 2/2007 |
| WO | 2007/015569 | 2/2007 |
| WO | 2007/015578 | 2/2007 |
| WO | 2007/023768 | 3/2007 |
| WO | 2007/040565 | 4/2007 |
| WO | 2007/052849 | 5/2007 |
| WO | 2007/052850 | 5/2007 |
| WO | 2007/061127 | 5/2007 |
| WO | 2007/061130 | 5/2007 |
| WO | 2007/136103 | 11/2007 |
| WO | 2008/023698 | 2/2008 |
| WO | 2008/026577 | 3/2008 |
| WO | 2008/026748 | 3/2008 |
| WO | WO 2008/053602 | 5/2008 |
| WO | 2008/088088 | 7/2008 |
| WO | 2008/093855 | 8/2008 |
| WO | 2008/102870 | 8/2008 |
| WO | 2008/155387 | 12/2008 |
| WO | 2009018238 | 2/2009 |
| WO | 2009/060945 | 5/2009 |
| WO | 2009/077874 | 6/2009 |
| WO | 2009/096377 | 8/2009 |
| WO | 2009/140549 | 11/2009 |
| WO | 2009/150256 | 12/2009 |
| WO | 2010/006225 | 1/2010 |
| WO | WO 2010/048304 | 4/2010 |
| WO | 2011/017583 | 2/2011 |
| WO | 2011/022335 | 2/2011 |
| WO | WO 2011/021597 | 2/2011 |
| WO | 2011/162343 | 12/2011 |
| WO | 2012/154935 | 11/2012 |
| WO | 2012157672 | 11/2012 |
| WO | WO 2012/154935 | 11/2012 |
| WO | 2012/166899 | 12/2012 |
| WO | WO 2014/113729 | 7/2014 |

(56) References Cited

FOREIGN PATENT DOCUMENTS

| WO | 2014/133022 | 9/2014 |
|---|---|---|
| WO | WO 2014/185540 | 11/2014 |

OTHER PUBLICATIONS

"Molecular Targets and Cancer Therapeutics," Poster Session A. A92, Nov. 6, 2015, p. 64 (134 total pages).
"Pharmacokinetics (PK) and tolerability of GW786034, a VEGFR tyrosine kinase inhibitor, after daily oral administration to patients with solid tumors." Proc. Am. Soc. Clin. Oncology, (Abstract 3054), 2004, 2 pages.
"Recent Results and Ongoing Trials with Panitumumab (ABX-EGF), a Fully Human Anti-Epidermal Growth Factor Receptor Antibody, in Metastatic Colorectal Cancer", Clinical Colorectal Cancer. 2005; 5(1):21-23.
"Arzneimittelwirkungen Lehrbuch der Pharmakologie und Toxikologie," Ernst Mutschler Ed Mutschler E et al., Arzneimittelwirkungen Lehrbuch der Pharmakologie und Toxikologie, Wissenschaftliche Verlagsgesellschaft, Stuttgart, Jan. 1, 1999, p.1-5, XP007919509 (English translation).
"Chapter 2.2 Loslichkeit, Losungsgeschwindigkeit, Loslichkeitsverbesserung," Rudolf Voigt Ed—Voigt R et al., Pharmazeutische Technologie fur Studium und Beruf, DT. Apotheker-Verl, Stuttgart; DE, Jan. 1, 2000, p. 40-52, XP008143620 (English translation).
"Clinical Trial: AMG 706 20040273 Thyroid Cancer Study: Stage 4 Cancer Treatments, Chat w/a Cancer Info Expert About Stage 4 Cancer Treatment Options," accessed from www.CancerCenter.com, 4 pages (2005).
AACR American Association Cancer Research, 92nd Annual Meeting, 42:583, Mar. 24-28, 2001, New Orleans, LA, USA, 3126, 2 pages.
Abrams et al., SU11248 Inhibits KIT and Platelet-derived Growth Factor Receptor Beta in Preclinical Models of Human Small Cell Lung CancerMolecular Cancer Therapeutics., 2: 471-478, 2003.
Abuzar et al., "Synthesis of some new 7-chloro-4-substituted quinolines as potential antiparasitic agents," Eur. J. Med. Chem., 21(1):5-8 (1986).
Additional Response in IL App. Ser. No. 188670, dated Oct. 25, 2011, 4 pages (with English translation).
Advisory Action for U.S. Appl. No. 12/092,539 dated Jun. 28, 2011, 3 pages.
Advisory Action in U.S. Appl. No. 12/315,291, dated Mar. 24, 2011, 10 pages.
Agarwal et al.; "Binding of discoidin domain receptor 2 to collagen I: an atomic force microscopy investigation," Biochemistry, 41(37):11091-11098 (2002).
Agnieszka et al., "Emergence of potential biomarkers of response to anti-angiogenic anti-tumor agents," International Journal of Cancer, Sep. 2010, 127(6):1251-1258.
Almarsson et al., "High-Throughput Surveys of Crystal Form Diversity of Highly Polymorphic Pharmaceutical Compounds," Crystal Growth & Design, Sep. 10, 2003, 3(6):927-933.
Altschul et al., "Basic Local Alignment Search Tool", J. Mol. Biol. 215:403-410 (1990).
Amended Claims filed in EP App. Ser. No. 11798224.9, filed Aug. 2, 2013, 35 pages.
Amended Claims filed in KR App. Ser. No. 10-2010-7011023, filed Jul. 17, 2013, 15 pages (with English translation).
Amended Claims filed in RU App. Ser. No. 2013140169, dated Aug. 29, 2013, 17 pages (with English translation).
Amended Claims in BR App. Ser. No. BR112012003592-4, dated Oct. 23, 2014, 12 pages (with English translation).
Amended claims in EP App. Ser. No. 04807580.8, dated Jun. 16, 2014, 7 pages.
Amended Claims in MY App. Ser. No. PI2011700172, dated in Jul. 3, 2014, 15 pages.
Amended description filed after receipt of search report for EP Patent App. No. 10809938.3, filed Dec. 8, 2011, 2 pages.
Amended description filed after receipt of search report for EP Patent App. No. 10809938.3, filed Sep. 14, 2010, 2 pages.
Amended Drawing in IL Ser. Appl. No. 217197, dated Oct. 22, 2014, 4 pages (with English translation).
Amended Drawing in PH App. Ser. No. 1-2011-502441, dated Oct. 17, 2014, 2 pages.
Amended drawings in EP App. Ser. No. 10809938.3, dated Nov. 11, 2014, 14 pages.
Amended set of Claims in EP App. Ser. No. 11798224.9, dated Sep. 19, 2014, 53 pages.
Amended Specification filed in AU App. Ser. No. 2012246490, filed Aug. 2, 2013, 15 pages.
Amendment after Allowance filed on Jan. 4, 2011 for CA App. Ser. No. 2426461, 12 pages.
Amendment and Argument filed on Apr. 27, 2012 in response to the JP Office Action for JP2007-542863, 13 pages and English translation.
Amendment and RCE submission documents filed in U.S. Appl. No. 12/039,381, dated Oct. 23, 2013, 13 pages.
Amendment and Request for Continued Examiner (RCE) in U.S. Appl. No. 13/083,338, dated Oct. 10, 2014, 5 pages.
Amendment and Response filed in U.S. Appl. No. 11/997,543, dated Dec. 19, 2013, 38 pages.
Amendment and Response for Application No. IL Patent Application No. 195282 dated Jul. 11, 2013, 13 pages (with English translation).
Amendment and Response to Final Office Action under 37 C.F.R. §1.116 for U.S. Appl. No. 12/092,539, filed Jun. 15, 2011, 9 pages.
Amendment and Response to Final Office Action under 37 C.F.R. §1.116 for U.S. Appl. No. 12/864,817, filed Dec. 5, 2011, 10 pages.
Amendment and Response to Non-Final Office Action for U.S. Appl. No. 11/997,543, filed Aug. 19, 2011, 34 pages.
Amendment and Response to Office Action under 37 C.F.R § 1.111 for U.S. Appl. No. 12/439,339, dated Aug. 22, 2013, 14 pages.
Amendment and Response to Office Action under 37 C.F.R. § 1.111 dated Apr. 2, 2013 for U.S. Appl. No. 13/083,338, 9 pages.
Amendment and Response to Office Action under 37 C.F.R. §1.111 for U.S. Appl. No. 11/997,719, filed Dec. 23, 2010, 21 pages.
Amendment and Response to Office Action under 37 C.F.R. §1.111 for U.S. Appl. No. 12/092,539, filed Mar. 11, 2011, 9 pages.
Amendment and Response to Office Action under 37 C.F.R. §1.111 for U.S. Appl. No. 12/439,339, filed Feb. 7, 2012, 11 pages.
Amendment and Response to Office Action under 37 C.F.R. §1.111 for U.S. Appl. No. 12/524,754, filed Feb. 17, 2012, 13 pages.
Amendment and Response to Office Action under 37 C.F.R. §1.111 for U.S. Appl. No. 12/741,682, filed Jul. 30, 2012, 49 pages.
Amendment and Response to Office Action under 37 C.F.R. §1.111 for U.S. Appl. No. 12/864,817, filed Aug. 9, 2011, 12 pages.
Amendment and Response to Office Action under 37 C.F.R. §1.111 for U.S. Appl. No. 13/205,328, filed Apr. 11, 2012, 12 pages.
Amendment and Response to Office Action under 37 C.F.R. §1.116 for U.S. Appl. No. 11/997,543, filed Jan. 9, 2012, 27 pages.
Amendment and Response to Office Action under 37 C.F.R. §1.116 for U.S. Appl. No. 12/439,339, filed Jul. 30, 2012, 9 pages.
Amendment filed in BR App. Ser. No. BR112012032462-4, dated Nov. 4, 2013, 21 pages (with English translation).
Amendment filed in EP App. Ser. No. 12774278.1, filed Aug. 13, 2013, 12 pages.
Amendment filed in EP App. Ser. No. 12793322.4, dated Nov. 28, 2013, 6 pages.
Amendment filed in JP App. Ser. No. 2008-532141, filed Jul. 5, 2013, 2 pages (with English translation).
Amendment filed in KR App. Ser. No. 10-2008-7027527, dated Jan. 27, 2014, 12 pages (with English translation).
Amendment filed in KR App. Ser. No. 10-2008-7029472, dated May 1, 2014, 14 pages (with English translation).
Amendment filed in KR App. Ser. No. 10-2008-7029472, dated Nov. 20, 2013, 81 pages (with English translation).
Amendment filed in KR App. Ser. No. 10-2009-7005657, dated May 7, 2014, 15 pages (with English translation).
Amendment filed in KR App. Ser. No. 10-2009-7017694, dated Feb. 28, 2014, 7 pages.

(56) References Cited

OTHER PUBLICATIONS

Amendment filed in KR App. Ser. No. 10-2013-7020616, dated Nov. 22, 2013, 22 pages (with English translation).
Amendment filed in U.S. Appl. No. 13/805,826, dated Sep. 9, 2013, 14 pages.
Amendment filed on Apr. 11, 2006 for CN App. Ser. No. 01819710.8, 35 pages (with English translation).
Amendment filed on Apr. 17, 2002 for TW App. Ser. No. 90125928, 26 pages (with English translation).
Amendment filed on Apr. 19, 2005 for JP App. Ser. No. 2002-536056, 26 pages (with English translation).
Amendment filed on Aug. 13, 2013 in JP App. Ser. No. P2009-540099, 8 pages (with English translation).
Amendment filed on Aug. 17, 2004 for ZA App. Ser. No. 2003/3567, 39 pages.
Amendment filed on Aug. 29, 2013 in CN App. Ser. No. 201280010898.X, 24 pages (with English translation).
Amendment filed on Aug. 4, 2004 for ZA App. Ser. No. 2003/3567, 95 pages.
Amendment filed on Aug. 6, 2013, for JP App. Ser. No. 2009-551518, 6 pages (with English translation).
Amendment filed on Dec. 12, 2011 for JO Patent App. No. 55/2011, 6 pages (with English translation).
Amendment filed on Dec. 15, 2011 for VN App. Ser. No. 1-2011-03484, 5 pages (with English translation).
Amendment filed on Dec. 22, 2011 for ZA App. Ser. No. 2011/08697, 2 pages.
Amendment filed on Feb. 9, 2011 for TW App. Ser. No. 100104281, 2 pages.
Amendment filed on Jan. 11, 2010 for CN App. Ser. No. 200580026468.7, 4 pages (with English translation).
Amendment filed on Jan. 26, 2010 for CN App. Ser. No. 200710007097.9, 9 pages (with English translation).
Amendment filed on Jul. 2, 2009 for CN App. Ser. No. 200710007097.9, 9 pages (with English translation).
Amendment filed on Jun. 22, 2010 for CN App. Ser. No. 200710007097.9, 9 pages (with English translation).
Amendment filed on Mar. 20, 2012 for KR Patent App. No. 10-2012-7003846, 7 pages (with English translation).
Amendment filed on Mar. 23, 2009 for JP Patent Application No. 2005-124034, 29 pages (with English translation).
Amendment filed on Mar. 6, 2006 for KR App. Ser. No. 10-2003-7005506, 34 pages (with English translation).
Amendment filed on Mar. 7, 2005 for JP App. Ser. No. 2002-536056, 23 pages (with English translation).
Amendment filed on Mar. 8, 2006 for KR App. Ser. No. 10-2005-7020292, 33 pages (with English translation).
Amendment filed on May 10, 2012 for JP Patent Application No. 2011-527665, 5 pages (with English translation).
Amendment filed on May 21, 2009 for JP App. Ser. No. 2005-124034, 14 pages (with English translation).
Amendment filed on May 28, 2003 for CN App. Ser. No. 01819710.8, 8 pages (with English translation).
Amendment filed on Nov. 19, 2009 for CN App. Ser. No. 200710007097.9, 9 pages (with English translation).
Amendment filed on Nov. 24, 2011 for KR App. Ser. No. 10-2007-7001347, 7 pages (with English translation).
Amendment filed on Oct. 1, 2013 in IN App. Ser. No. 10502/CHENP/2012, 10 pages.
Amendment filed on Oct. 25, 2005 for KR App. Ser. No. 10-2003-7005506, 53 pages (with English translation).
Amendment filed on Oct. 28, 2011 for LB Patent App. No. 9292, 2 pages.
Amendment filed on Oct. 9, 2006 for CN App. Ser. No. 01819710.8, 28 pages (with English translation).
Amendment filed on Sep. 13, 2005 for CN App. Ser. No. 01819710.8, 51 pages (with English translation).
Amendment filed on Sep. 23, 2009 for CN App. Ser. No. 200580026468.7, 11 pages (with English translation).
Amendment filed on Sep. 23, 2013 in AU App. Ser. No. 2011270165, 35 pages.
Amendment for Chinese Patent Application No. 201080030508.6 dated Feb. 7, 2013, 17 pages with English translation.
Amendment for IN App. Ser. No. 7026/CHENP/2013, dated Sep. 5, 2013, 8 pages.
Amendment in AU App. Ser. No. 2005217325, dated Aug. 9, 2006, 11 pages.
Amendment in AU App. Ser. No. 2005217328, dated Aug. 9, 2006, 10 pages.
Amendment in AU App. Ser. No. 2006282456, dated Apr. 26, 2012, 6 pages.
Amendment in AU App. Ser. No. 2006282456, dated Jan. 25, 2008, 26 pages.
Amendment in AU App. Ser. No. 2007289787, dated Apr. 7, 2009, 16 pages.
Amendment in BD App. Ser. No. 184/2006, dated May 6, 2008, 3 pages.
Amendment in BD App. Ser. No. 184/2006, dated Sep. 26, 2007, 4 pages.
Amendment in BR App. Ser. No. PI0616799/3, dated May 29, 2012, 6 pages.
Amendment in Canadian App. Ser. No. 2828946, dated Aug. 30, 2013, 14 pages.
Amendment in CN App. Ser. No. 200580001760.3, dated May 15, 2007, 31 pages (with English translation).
Amendment in CN App. Ser. No. 200680021939.X, dated Dec. 18, 2007, 23 pages (with English translation).
Amendment in CN App. Ser. No. 200780019520.5, dated Nov. 27, 2008, 10 pages (with English translation).
Amendment in CN App. Ser. No. 2008800045113, dated Aug. 7, 2009, 36 pages (with English translation).
Amendment in EP App. Ser. No. 05719973.9, dated Oct. 30, 2006, 2 pages.
Amendment in EP App. Ser. No. 06796594.7, dated Apr. 19, 2012, 3 pages.
Amendment in EP App. Ser. No. 06796594.7, dated Jan. 11, 2008, 3 pages.
Amendment in EP App. Ser. No. 06796594.7, dated Nov. 16, 2007, 3 pages.
Amendment in EP App. Ser. No. 07793075.8, dated Jan. 26, 2011, 12 pages.
Amendment in EP App. Ser. No. 07793075.8, dated Mar. 3, 2009, 5 pages.
Amendment in EP App. Ser. No. 08711837.8, dated Sep. 8, 2009, 23 pages.
Amendment in EP App. Ser. No. 09713617.0, dated Sep. 1, 2010, 3 pages.
Amendment in IL App. Ser. No. 188670, dated May 2, 2012, 7 pages (with English translation).
Amendment in IL App. Ser. No. 197002, dated Feb. 11, 2009, 4 pages.
Amendment in IL App. Ser. No. 200466, dated Aug. 18, 2009, 28 pages.
Amendment in IN App. Ser. No. 1424/CHENP/2008, dated Apr. 27, 2012, 4 pages.
Amendment in IN App. Ser. No. 2371/CHENP/2012, dated Oct. 30, 2014, 2 pages.
Amendment in Israeli App. Ser. No. 200090, dated Oct. 2, 2013, 10 pages (with English translation).
Amendment in JO App. Ser. No. 280/2006, dated Oct. 19, 2007, 3 pages (with English translation).
Amendment in JP App. Ser. No. 2007-532099, dated Dec. 25, 2007, 6 pages (with English translation).
Amendment in JP App. Ser. No. 2007-532099, dated Sep. 25, 2007, 28 pages (with English translation).
Amendment in JP App. Ser. No. 2008-530917, dated Dec. 13, 2012, 6 pages (with English translation).
Amendment in JP App. Ser. No. 2009-554285, dated Aug. 19, 2010, 7 pages (with English translation).
Amendment in JP App. Ser. No. P2009-510543, dated Nov. 9, 2009, 25 pages (with English translation).

(56) References Cited

OTHER PUBLICATIONS

Amendment in Korean App. Ser. No. 10-2012-7033886, dated Sep. 27, 2013, 34 pages (with English translation).
Amendment in KR App. Ser. No. 10-2006-7013907, dated Sep. 28, 2007, 10 pages (with English translation).
Amendment in KR App. Ser. No. 10-2006-7013940, dated Oct. 1, 2007, 43 pages (with English translation).
Amendment in KR App. Ser. No. 10-2007-7026886, dated Dec. 27, 2007, 4 pages (with English translation).
Amendment in KR App. Ser. No. 10-2007-7026886, dated Nov. 21, 2007, 9 pages (with English translation).
Amendment in KR App. Ser. No. 10-2007-7026886, dated Oct. 27, 2009, 4 pages (with English translation).
Amendment in KR App. Ser. No. 10-2008-7029577, dated Apr. 1, 2009, 6 pages (with English translation).
Amendment in KR App. Ser. No. 10-2009-7013723, dated Aug. 10, 2009, 17 pages (with English translation).
Amendment in KR App. Ser. No. 10-2010-7011023, dated Oct. 21, 2014, 31 pages.
Amendment in KR App. Ser. No. 10-2010-7018835, dated Dec. 1, 2014, 18 pages (with English translation).
Amendment in KR App. Ser. No. 10-2012-7003846, dated Nov. 26, 2014, 20 pages (with English translation).
Amendment in Mexican App. Ser. No. MX/a/2012/014776, dated Oct. 21, 2013, 10 pages (with English translation).
Amendment in MY App. Ser. No. PI20071922, dated Jul. 17, 2008, 243 pages.
Amendment in NO App. Ser. No. 20080460, dated May 14, 2012, 4 pages (with English translation).
Amendment in PH App. Ser. No. Jan. 2007-502319, dated May 14, 2012, 3 pages.
Amendment in Russian App. Ser. No. 2012158142, dated Oct. 17, 2013, 48 pages (with English translation).
Amendment in SA App. Ser. No. 06270287, dated Oct. 22, 2007, 12 pages.
Amendment in SG App. Ser. No. 200718614/1, dated Aug. 24, 2010, 13 pages.
Amendment in TH App. Ser. No. 0601004017, dated Sep. 25, 2007, 6 pages (with English translation).
Amendment in TW App. Ser. No. 100104281, dated Oct. 22, 2014, 8 pages.
Amendment in U.S. Appl. No. 11/662,425, dated Sep. 2, 2014, 6 pages.
Amendment in U.S. Appl. No. 11/892,785, dated Dec. 17, 2008, 17 pages.
Amendment in U.S. Appl. No. 11/065,631, dated May 28, 2008, 16 pages.
Amendment Response to Office Action under 37 C.F.R. § 1.111 and Information Disclosure Statement for U.S. Appl. No. 13/624,278, filed Jun. 28, 2013, 23 pages.
Amendments received before examination for EP App. Ser. No. 01976786.2, dated Sep. 10, 2004, 126 pages.
Amendments to the specification filed on Mar. 26, 2012 for AU Patent Appl. No. 2010285740, 15 pages.
American Association for Cancer Research, "Redefining the Frontiers of Science," 94th Annual Meeting, vol. 44, 2nd Edition, Washington Convention Center, Washington, DC (Jul. 11-14, 2003), 3 pages.
Amino et al., "YM-231146, a Novel Orally Sioavailable Inhibitor of Vascular Endothelial Growth Factor Receptor-2, Is Effective against Paclitaxel Resistant Tumors", Biological and Pharmaceutical Bulletin. 28:2096-2101, 2005.
Anderson and Flora, "Preparation of Water-Soluble Compounds Through Salt Formation," Practice of Medicinal Chem., 1996, pp. 739-754.
Anderson et al, "Clinical, Safety, and Economic Evidence in Radioactive Iodine-Refractory Differentiated Thyroid Cancer: A Systematic Literature Review", Thyroid, 23(4):392-407, 2013.

Anderson et al., "Preparation of Water-soluble Compounds through Salt Formation. The Practice of Medicinal Chemistry," Technomics, 347-349 and 355-356 (Sep. 25, 1999).
Anonymous, "Scientific Discussion," EMEA, URL: htttp://www.ema.europa.eu/docs/en_GB/document_library/EPARScientific_Discussion/human/000406/WC500022203.pdf, 1-61 (2004) (XP007918143).
Antibodies: A Laboratory Manual, E. Harlow and D. Lane, ed. Cold Spring Harbor Laboratory (Cold Spring Harbour, NY, 1988), 190 pages.
Appeal for Reversal in CO App. Ser. No. 12-022608, dated Jan. 28, 2014, 17 pages (with English translation).
Appeal in SA App. Serial. No. 06270287, dated Jun. 23, 2010, 4 pages (with English translation).
Applicant Interview Summary Under 37 C.F.R § 1.133(b) for U.S. Appl. No. 12/439,339, dated May 31, 2013, 7 pages.
Applicant Observation for CN App. Ser. No. 200780017371.9, filed May 29, 2013, 6 pages (with English translation).
Application for Patent Term Adjustment in U.S. Appl. No. 12/439,339, dated Dec. 18, 2014, 8 pages.
Approval of request for amendments for EP App. Ser. No. 04025700.8, dated Mar. 13, 2008, 1 page.
Argument and Amendment for JP App. Ser. No. 2008-556208, filed Mar. 21, 2013, 15 pages (with English translation).
Argument and Amendment for CN 200880002425.9 filed on Jul. 18, 2011, 8 pages with English translation.
Argument and Amendment for JP App. Ser. No. 2008-532141, filed Nov. 29, 2012, 12 pages (with English translation).
Argument and Amendment for JP. App. Ser. No. 2008-516724, filed Nov. 28, 2012, 22 pages (with English translation).
Argument and Amendment for JP. App. Ser. No. 2009-123432, dated Jun. 12, 2012, 12 pages (with English translation).
Argument and Amendment for JP. App. Ser. No. 2009-529019, dated Jul. 3, 2012, 14 pages (with English translation).
Argument Brief filed in KR App. Ser. No. 10-2008-7029577, dated Feb. 27, 2014, 30 pages (with English translation).
Argument Brief filed on Mar. 6, 2006 for KR App. Ser. No. 10-2003-7005506, 45 pages (with English translation).
Argument Brief filed on Mar. 8, 2006 for KR App. Ser. No. 10-2005-7020292, 42 pages (with English translation).
Argument Brief filed on Nov. 24, 2011 for KR App. Ser. No. 10-2007-7001347, 52 pages (with English translation).
Argument Brief filed on Oct. 25, 2005 for KR App. Ser. No. 10-2003-7005506, 20 pages (with English translation).
Argument Brief in KR App. Ser. No. 10-2007-7026886, dated Oct. 27, 2009, 7 pages (with English translation).
Argument filed in KR App. Ser. No. 10-2009-7017694, dated Feb. 28, 2014, 48 pages.
Argument filed on Apr. 19, 2005 for JP App. Ser. No. 2002-536056, 6 pages (with English translation).
Argument filed on Aug. 13, 2013 in JP App. Ser. No. 2009-540099, 10 pages (with English translation).
Argument filed on Aug. 6, 2013 for JP Patent Application No. 2009-551518, 18 pages (with English translation).
Argument filed on Mar. 23, 2009 for JP App. Ser. No. 2005-124034, 12 pages (with English translation).
Argument filed on May 21, 2009 for JP App. Ser. No. 2005-124034, 5 pages (with English translation).
Asai et al., "Mechanism of Ret Activation by a Mutation of Aspartic Acid 631 Identified in Sporadic Pheochromocytoma", Biochemical and Biophysical Research Communications, 255, 587-590 (1999).
Asano et al., "Inhibition of Tumor Growth and Metastasis by an Immunoneutralizing Monoclonal Antibody to Human Vascular Endothelial Growth Factor/Vascular Permeability Factor121", Cancer Research., 55, 5296-5301, 1995.
Asano et al., "Broad-spectrum preclinical combination activity of eribulin combined with various anticancer agents in human breast cancer, lung cancer, ovarian cancer, and melanoma xenograft models," European J Cancer, 50(Suppl 6):20, Nov. 19, 2014.
Asuno Shinyaku ("The New Drugs of Tomorrow"), editing/printing by Technomics, Inc., 81-83 (Dec. 2006) (English translation), 14 pages.

(56) References Cited

OTHER PUBLICATIONS

Australian ("""AU""") Office Action dated Oct. 29, 2009 for corresponding AU Application No. 2006285673, 3 pages.
Australian ("AU") Notice of Allowance dated Nov. 22, 2010 for corresponding AU Application No. 2006285673, 3 pages.
Australian ("AU") Office Action dated May 19, 2010 for corresponding AU Application No. 2006285673, 2 pages.
Australian ("AU") Office Action dated May 7, 2009 for corresponding AU Application No. 2006285673, 2 pages.
Australian Office Action directed at Appl. No. 2007252506 dated Jan. 13, 2012, 2 pages.
Australian Office Action directed at Appl. No. 2007252506 dated Nov. 7, 2011, 5 pages.
Australian Office Action for App. Ser. No. 2008205847, dated Apr. 11, 2012, 2 pages.
Australian Office Action for App. Ser. No. 2008211952, dated Apr. 3, 2012, 2 pages.
Australian Office Action for Application No. 2006309551 dated Feb. 2, 2012, 2 pages.
Australian Office Action for Application No. AU2006309551 dated Apr. 28, 2011, 3 pages.
Australian Response to Office Action directed at Appl. No. 2007252506 filed on Jan. 4, 2012, 74 pages.
Australian Response to Office Action directed at Appl. No. 2007252506 filed on Mar. 2, 2012, 4 pages.
Australian Response to Office Action for Application No. 2006309551 filed on Jan. 27, 2012, 81 pages.
Bainbridge et al., "A peptide encoded by exon 6 of VEGF (EG3306) inhibits VEGF-induced angiogenesis in vitro and ischaemic retinal neovascularisation in vivo", Biochem Biophys Res Commun., 302, 793-799, 2003.
Bajwa et al., "Animalarials. 1. Heterocyclic Analogs of N-Substituted Naphthalenebisoxazines"; Journal of Medicinal Chemistry; 1972; 16(2): 134-138.
Baker et al., "Blockade of vascular endothelial growth factor receptor and epidermal growth factor receptor signaling for therapy of metastatic human pancreatic cancer," Cancer Res., 62:1996-2003 (2002).
Bankston et al., "A Scaleable synthesis of BAY 43-9006: A Potent Raf Kinase Inhibitor for the Treatment of Cancer", Organic Process Res Dev., 6:777-81 (2002).
Bartsch et al., "A RET double mutation in the germline of a kindred with FMTC", Exp. Clin Endocrinol Diabetes, 108, 128-132, 2000.
Bastin et al., "Salt Selection and Optimisation Procedures for Pharmaceutical New Chemical Entities," Organic Process Research & Development, 4(5):427-435 (2000) (XP002228592).
Beebe et al., "Pharmacological Characterization of CP-547,632, a Novel Vascular Endothelial Growth Factor Receptor-2 Tyrosine Kinase Inhibitor for Cancer Therapy 1", Cancer Research. 63:7301-9, 2003.
Behr et al., Improved Treatment of Medullary Thyroid Cancer in a Nude Mouse Model by Combined Radioimmunochemotherapy: Doxorubicin Potentiates the Therapeutic Efficacy of Radiolabeled Antibodies in a Radioresistant Tumor Type, 57 Cancer Res. 5309-5319 (Dec. 1, 1997).
Bellone et al., "Growth Stimulation of Colorectal Carcinoma Cells via the c-kit Receptor is Inhibited by TGF-β-1," Journal of Cellular Physiology, 172:1-11 (1997).
Benjamin et al., "Selective ablation of immature blood vessels in established human tumors follows vascular endothelial growth factor withdrawal," J. Clin. Invest., 103(2):159-165 (1999).
Berdel et al., "Recombinant Human Stem Cell Factor Stimulates Growth of a Human Glioblastoma Cell Line Expressing c-kit Protooncogene," Cancer Res., 52:3498-3502 (1992).
Berge et al., "Pharmaceutical Salts," Journal of Pharmaceutical Sciences, 66(1):1-19 (Jan. 1977) (XP002550655).
Bergers et al., "Benefits of targeting both pericytes and endothelial cells in the tumor vasculature with kinase inhibitors," J. Clin. Invest., 111(9):1287-1295 (2003).

Berndt et al., "A New Hot Spot for Mutations in the ret Protooncogene Causing Familial Medually Thyroid Carcinoma and Multiple Endocrine Neoplasia Type 2A", Journal of Clinical Endocrinology and Metabolism, 83, 770-774 (1998).
Bernex et al., "Spatial and temporal patterns of c-kit-expressing cells in WlacZ/+ and WlacZ/WlacZ mouse embryos", Development 122:3023-3033 (1996).
Besson et al., "PTEN/MMAC1/TEP1 in signal transduction and tumorigenesis," EP J Biochem., 1999, 263:605-611.
Blume-Jensen et al., "Activation of the Human c-kit Product by Ligand-Induced Dimerization Mediates Circular Actin Reorganization and Chemotaxis," The EMBO Journal, 10(13):4121-4128 (1991).
Boissan et al., "c-Kit and c-kit mutations in mastocytosis and other hematological diseases," J. Leukocyte Biol., 67:135-148 (2000).
Bold et al., "New anilinophthalazines as potent and orally well absorbed inhibitors of the VEGF receptor tyrosine kinases useful as antagonists of tumor-driven angiogenesis", Journal of Medicinal Chemistry., 43:2310-2323 (2000).
Bonferoni et al, "Influence of medium on dissolution-erosion behavior of Na carboxymethylcellulose and on viscoelastic properties of gels," International journal of pharmaceutics, 1995, vol. 117, No. 1, pp. 41-48.
Bramhall, S., "The Matrix Metalloproteinases and Their Inhibitors in Pancreatic Cancer", International J. Pancreatol., 21, 1-12, 1997.
Brief communication to applicant for EP App. Ser. No. 01976786.2, dated Sep. 9, 2005, 1 page.
Brose et al, "Sorafenib in radioactive iodine-refractory, locally advanced or metastatic differentiated thyroid cancer: a randomised, double-blind, phase 3 trial", The Lancet, 384:319-328, Jul. 26, 2014.
Brueggen et al., "Preclinical profile of ABP309, a potent $2^{nd}$ generation VEGF receptor tyrosine kinase inhibitor belonging to the class of aminonicotinamides," EORTC-NCI-AACR Symp Mol Targets Cancer Ther., 2, (Abstract 172), 2004, 2 pages.
Bruns et al., "Effect of the vascular endothelial growth factor receptor-2 antibody DC101 plus gemcitabine on growth, metastasis and angiogenesis of human pancreatic cancer growing orthotopically in nude mice," J. Cancer, 102:101-108 (2002).
Burwell, Jr, "The Cleavage of Ethers," Chem Rev., 54(4):615-685, Feb. 26, 1954.
Bussolino et al., "Role of Soluble Mediators in Angiogenesis," Eur. J. Cancer, 32A(14):2401-2412 (1996).
CA Notice of Allowance for Appl. No. 2,620,594 dated May 3, 2012, 1 page.
Cairns et al., "New antiallergic pyrano[3,2g]quinoline-2,8-dicarboxylic acids with potential for the topical treatment of asthma," J. Med. Chem., 28(12):1832-1842 (1985).
Canadian ("CA") Office Action dated Jan. 14, 2010 for corresponding CA Application No. 2,620,594, 3 pages.
Canadian ("CA") Office Action dated Jan. 6, 2011 for corresponding CA Application No. 2,620,594, 3 pages.
Canadian Office Action for App. Ser. No. 2426461, dated Dec. 6, 2007, 5 pages.
Canadian Office Action for App. Ser. No. 2426461, dated Feb. 10, 2010, 2 pages.
Canadian Office Action for App. Ser. No. 2426461, dated May 8, 2009, 2 pages.
Canadian Office Action for App. Ser. No. 2426461, dated Nov. 20, 2008, 3 pages.
CancerCare, "Types of Lung Cancer," Cancer Care, Inc. [online] [retrieved on Nov. 12, 2009]. Retrieved from the Internet: www.lungcancer.org/reading/types.php?printable=true (2009), 1 page.
Cappellen et al., "Frequent activating mutations of FGFR3 in human bladder and cervix carcinomas," Nat. Genet., 23:18-20 (1999).
Carey, "Organic Chemistry 4e: Chapter 24: Phenols," McGraw Hill, http://www.mhhe.com/physsci/chemistry/carey/student/olc/ch24reactionsarylethers.html. Accessed Oct. 3, 2014, 2000, 4 pages.
Carlomagno et al., "Point Mutation of the RET Proto-Oncogene in the TT Human Medullary Thyroid Carcinoma cell Line", Biochemical and Biophysical Research Communications, 207, 1022-1028 (1995).

(56) References Cited

OTHER PUBLICATIONS

Carlomagno et al., "BAY 43/9006 inhibition of oncogenic RET mutants," J. Natl. Cancer Inst., 98(5):326-34 (2006).
Carlomagno et al., "ZD6474, an orally available inhibitor of KDR tyrosine kinase activity, efficiently blocks oncogenic RET kinases," Cancer Res., 62:7284-7290 (2002).
Carniti et al., "The RetC620R Mutation Affects Renal and Enteric Development in a mouse Model of Hirschprung's Disease", American Journal of Pathology, 168, 1262-1275, (2006).
Carter et al., "Inhibition of drug-resistant mutants of ABL, KIT and EGF receptor kinases", Proceedings of the National Academy of Sciences of the United States of America., 102, 11011-11016, 2005.
Cell Technology, Supplementary Volume, "Bio-Experiment Illustrated Volume 5, No Fear of Proteins", Visual Laboratory Notebook Series, Section 6, Immunostaining, pp. 127-163, Shujunsha, Co., Ltd., 1997 (Japanese).
Certificate of Correction in U.S. Appl. No. 12/741,682, dated Aug. 4, 2015, 2 pages.
Chaki et al., "mGlu2/3 and mGlu5 receptors: Potential targets for novel antidepressants," Neuropharmacology, 2013, 66:40-52.
Chen et al., "FGFR3 as a therapeutic target of the small molecule inhibitor PKC412 in hematopoietic malignancies," Oncogene, 24:8259-8267 (2005).
Chesi et al., "Activated fibroblast growth factor receptor 3 is an oncogene that contributes to tumor progression in multiple myeloma," Blood, 97:729-736 (2001).
Chesi et al., "Frequent translocation t(4;14)(p16.3;q32.3) in multiple myeloma is associated with increased expression and activating mutations of fibroblast growth factor receptor 3," Nat. Genet., 16:260-264 (1997).
Cheung et al., "Discovery of indazolylpyrimidines as potent inhibitors of VEGFR2 tyrosine kinase," Proceedings of the American Association for Cancer Research, 44, 9, (Abstract 40), 2003, 2 pages.
Chikahisa et al, "TSU-68 KDR/flk-1 inhibitor, can modulate the anti-tumor activity of paclitaxel by the induction of endothelial cell and tumor cell apoptosis," 61st Annual Meeting of the Japanese Cancer Association, 2002, 61(1374):443, 5 total pages (with English translation).
Childhood Papillary Thyroid Carcinoma, Cancer Research, 60: 2786-2789 (2000).
Chinese ("CN") Office Action dated Dec. 4, 2009 for corresponding CN Application No. 200680036592.6, 8 pages with English translation.
Chinese Office Action directed at Appl. No. 200780017371.9 dated Oct. 20, 2010, 13 pages with English translation.
Chinese Office Action for App. Ser. No. 200580026468.7, dated Jun. 26, 2009, 25 pages (with English translation).
Chinese Office Action for App. Ser. No. 200710007097.9, dated Mar. 6, 2009, 5 pages.
Chinese Office Action for App. Ser. No. 200780017371.9, dated Mar. 7, 2012, 8 pages with English translation.
Chinese Office Action for App. Ser. No. 200880002425.9, dated Mar. 7, 2012, 7 pages (with English translation).
Chinese Office Action for App. Ser. No. 200880003336.6, dated May 24, 2011, 24 pages (with English translation).
Chinese Office Action for App. Ser. No. 200880115011.7, dated Feb. 20, 2012, 10 pages (with English translation).
Chinese Office Action for App. Ser. No. 201080030508.6, dated Nov. 30, 2012, 13 pages, (with English translation).
Chinese Office Action for Application No. 200680041355.9 dated Aug. 24, 2010, 10 pages (with English translation).
Chinese Office Action for Application No. 200680041355.9 dated Mar. 5, 2010, 21 pages (with English translation).
Chinese Office Action for CN 200680020317.5 dated Aug. 3, 2012 with English translation, 11 pages.
Chinese Office Action with the English translation dated, dated Feb. 29, 2012, for Application No. 200680036592.6, 7 pages.
Chinese Response to Office Action directed at Appl. No. 200780017371.9 filed on Feb. 24, 2011, 10 pages with English translation.
Chinese Response to Office Action for Application No. 200680041355.9 filed on Jul. 19, 2010, 4 pages with English translation.
Chinese Response to Office Action for Application No. 200680041355.9 filed on Nov. 8, 2010, 6 pages with English translation.
Chinese Response to the Chinese Decision of Rejection, filed on Feb. 7, 2013, for corresponding Chinese Application No. 200680036592.6, 27 pages.
Ciardiello et al., "ZD1839 (IRESSA), an EGFR-selective tyrosine kinase inhibitor, enhances taxane activity in bcl-2 overexpressing, multidrug-resistant MCF-7 ADR human breast cancer cells," Int. J. Cancer, 98:463-469 (2002).
Clark et al., "Safety and Pharmacokinetics of the Dual Action Raf Kinase and Vascular Endothelial Growth Factor Receptor Inhibitor, BAY43-9006, in Patients with Advanced Refractory Solid Tumors," Clin. Cancer Res., 11:5472-5480 (2005).
ClinicalTrials.gov, "A Study of E7080 Alone, and in Combination With Everolimus in Subjects With Unresectable Advanced or Metastatic Renal Cell Carcinoma Following One Prior Vascular Endothelial Growth Factor (VEGF)-Targeted Treatment," National Institutes of Health, Food and Drug Administration, National Library of Medicine, [online] [retrieved on Sep. 27, 2010]. Retrieved from the Internet: http://clinicaltrials.gov/ct2/show/NCT01136733, (May 26, 2010), 3 pages.
CN200780032071.8 Office Action dated Oct. 13, 2010, 29 pages with English translation.
CN200780032071.8 Response to Office Action filed on Feb. 16, 2011, 62 pages with English translation.
CN200880003336.6 Response to Office Action filed on Oct. 8, 2011, 10 pages.
Cohen et al., "Expression of Stem Cell Factor and c-kit in Human Neuroblastoma," Blood, 84(10):3465-3472 (1994).
Colombian Office Action for App. Ser. No. 12-022608, dated Oct. 7, 2013, 10 pages (with English translation).
Comments re Board of Appeal in EP App. Ser. No. 04807580.8, dated Jul. 7, 2014, 3 pages.
Communication about intention to grant a European patent for EP App. Ser. No. 01976786.2, dated Sep. 4, 2006, 173 pages.
Communication about intention to grant a European patent for EP App. Ser. No. 04025700.8, dated Oct. 15, 2007, 392 pages.
Communication about intention to grant a European patent for EP App. Ser. No. 05783232.1, dated Nov. 20, 2008, 70 pages.
Communication about intention to grant a European patent for EP App. Ser. No. 06023078.6, dated Jul. 18, 2008, 169 pages.
Communication from the Examining Division for EP App. Ser. No. 01976786.2, dated Aug. 17, 2005, 4 pages.
Communication from the Examining Division for EP App. Ser. No. 01976786.2, dated Mar. 21, 2006, 3 pages.
Communication from the Examining Division for EP App. Ser. No. 01976786.2, dated Sep. 19, 2005, 4 pages.
Communication from the Examining Division for EP App. Ser. No. 04025700.8, dated Apr. 10, 2006, 3 pages.
Communication from the Examining Division for EP App. Ser. No. 04025700.8, dated Oct. 23, 2006, 2 pages.
Communication from the Examining Division for EP App. Ser. No. 05783232.1, dated Feb. 7, 2008, 1 pages.
Communication from the Examining Division for EP App. Ser. No. 06023078.6, dated Aug. 2, 2007, 1 page.
Communication from the Examining Division for EP App. Ser. No. 06023078.6, dated Sep. 26, 2007, 2 pages.
Communication re Intention to Grant Patent in EP App. Ser. No. 07793075.8, dated Nov. 9, 2012, 97 pages.
Communication re Intention to Grant Patent in EP App. Ser. No. 07805959.9, dated Jun. 21, 2011, 70 pages.
Communication regarding the expiry of opposition period for EP App. Ser. No. 01976786.2, dated Jan. 4, 2008, 1 page.
Communication regarding the expiry of opposition period for EP App. Ser. No. 04025700.8, dated May 7, 2009, 1 page.
Communication regarding the expiry of opposition period for EP App. Ser. No. 05783232.1, dated Feb. 19, 2010, 1 page.
Communication regarding the expiry of opposition period for EP App. Ser. No. 06023078.6, dated Nov. 4, 2009, 1 page.

(56) References Cited

OTHER PUBLICATIONS

Continuation Patent Application, Preliminary Amendment and Information Disclosure Statement for U.S. Appl. No. 13/923,858, filed Jun. 21, 2013, 97 pages.
Corbin et al., "Sensitivity of oncogenic KIT mutants to the kinase inhibitors MLN518 and PD180970", Blood., 104, 3754-3757, 2004.
Correction Request in CO App. Ser. No. 12-022608, dated Dec. 24, 2014, 3 pages (with English translation).
Corvi et al., "RET IPCM-1: a novel fusion gene in papillary thyroid carcinoma", Oncogene, 19:4236-4242 (2000).
Coupling Reagents, "Advanced Automated Peptide Protein Technologies," Published Aug. 3, 2007, 4 pages.
Croom et al., "Imatinib mesylate," Drugs, 63(5):513-522 (2003).
Da Silva et al., "A novel germ-line point mutation in RET exon 8 (Gly(533)Cys) in a large kindred with familial medullary thyroid carcinoma," J. Clin. Endocrinol. Metab., 88:5438-5443 (2003).
Dankort et al., "Braf V660E cooperaties with Pten loss to induce metastic melanoma," Nature Genetics, 2009, 41(5):544-552.
David et al., "A Phase I Trial of the Epidermal Growth Factor Receptor (EGFR)-Directed Bispecific Antibody (BsAB) MDX-447 in Patients with Solid Tumors. (Meeting abstract).", ASCO 18: 433, Abstract 1999.
Davies et al., "Mutations of the BRAF gene in human cancer," Nature, Jun. 27, 2002, 417:949-954.
De Lange et al., "Phase II trial of cisplatin and gemcitabine in patients with advanced gastric cancer," Annals of Oncology, 15:484-488 (2004).
Decision of Final Rejection issued in CN App. Ser. No. 200780017371.9, dated Jul. 3, 2013, 16 pages (with English translation).
Decision of Grant in RU App. Ser. No. 2008110932, dated Feb. 6, 2009, 29 pages (with English translation).
Decision of Rejection dated Oct. 30, 2012 issued for corresponding Chinese Application No. 200680036592.6, 8 pages with full English language translation.
Decision to grant a European patent for EP App. Ser. No. 01976786.2, dated Feb. 1, 2007, 2 pages.
Decision to grant a European patent for EP App. Ser. No. 04025700.8, dated Jun. 5, 2008, 2 pages.
Decision to grant a European patent for EP App. Ser. No. 05783232.1, dated Mar. 19, 2009, 2 pages.
Decision to grant a European patent for EP App. Ser. No. 06023078.6, dated Dec. 4, 2008, 2 pages.
Decision to Grant European Patent in EP App. Ser. No. 10809938.3, dated Jan. 8, 2016, 2 pages.
Decision to Grant Patent in EP App. Ser. No. 05719973.9, dated Jun. 1, 2012, 1 page.
Decision to Grant Patent in EP App. Ser. No. 07805959.9, dated Nov. 4, 2011, 2 pages.
Decision to Grant Patent in JP App. Ser. No. 2007-532099, dated Jan. 8, 2008, 5 pages (with English translation).
Decision to Grant Patent in JP App. Ser. 2008-530917, dated Jan. 15, 2013, 6 pages (with English translation).
Decision to Grant Patent in JP App. Ser. No. 2008-532065, dated Nov. 13, 2012, 6 pages (with English translation).
Decision to Grant Patent in JP App. Ser. No. P2009-510543, dated Feb. 2, 2010, 6 pages (with English translation).
Deficiencies in sequence listing for EP App. Ser. No. 06023078.6, dated Dec. 5, 2006, 3 pages.
Demand for Appeal Trial filed in JP App. Ser. No. 2008-532141, filed Jul. 5, 2013, 10 pages (with English translation).
Deplanque et al., "Anti-Angiogenic Agents: Clinical Trial Design and Therapies in Development," European Journal of Cancer, 36:1713-1724 (2000).
Dermer, "Another Anniversary for the War on Cancer," Bio/Technology, 12:320 (1994).
Dezso et al., Systems biology analysis to identify biomarkers for lenvatinib in the preclinical cancer cell line panels. Abstract of the presentation #6 (abstract 1371), AACR Annual Meeting, 2015, 2 pages.
Dezso et al., Systems biology analysis to identify biomarkers for lenvatinib in the preclinical cancer cell line panels. Poster of a presentation, 3667, AACR Annual Meeting, 2015,1 page.
Di Lorenzo et al., "Targeted Therapy in the Treatment of Metastatic Renal Cell Cancer", Oncology, 77(Suppl.1):122-131 (2010).
Di Raimondo et al., "Antiogenic Factors in multiple myeloma: higher levels in bone than in peripheral blood," Haematologica, 85:800-805 (2000).
Dias et al., "IL-12 Regulates VEGF and MMPs in a Murine Breast Cancer Model", International J. Cancer., 78, 361-5, 1998.
Dietrich, "BRAF Inhibition in Refractory Hairy-Cell Leukemia," N Eng J Med., 366(21):2038-2040 (May 24, 2012).
Dourisboure et al, "Penetrance and Clinical Manifestations of Non-Hotspot Germ line RET Mutation, C630R, in a Family with Medullary Thyroid Carcinoma", Thyroid, 15, 668-671, 2005.
Dupont et al., "Phase 1 study of VEGF Trap in patients with solid tumors and lymphoma," Proc. Am. Soc. Clin. Oncology, (Abstract 776), 2003, 2 pages.
Dvorakova et al., "Exon 5 of the RET proto-oncogene: A newly detected risk exon for familial medullary thyroid carcinoma, a novel germ-line mutation Gly321Arg", Journal of Endocrinological Investigation, 28, 905-909, 2005.
El-Abseri et al., "Chemoprevention of UV Light-Induced Skin Tumorigenesis by Inhibition of the Epidermal Growth Factor Receptor", Cancer Research., 64, 3958-3965, 2004.
Elisei et al., "Identification of a novel point mutation in the RET gene (Ala883Thr), which is associated with medullary thyroid carcinoma phenotype only in homozygous condition," J. Clin. Endocrinol. Metab., 89:5823-5827 (2004).
Elisei et al., "Subgroup Analyses of a Phase 3 Multicenter, Double-Blind, Placebo-Controlled Trial of Lenvatinib (E7080) in Patients with 131I-Refractory Differentiated Thyroid Cancer," Poster, No. 1033P, presented at European Society for Medical Oncology 2014 Congress, Sep. 26-30, 2014, 1 page.
Emanuel et al., "A Vascular Endothelial Growth Factor Receptor-2 Kinase Inhibitor Potentiates the Activity of the Conventional Chemotherapeutic Agents Paclitaxel and Doxorubicin in Tumor Xenograft Models", Molecular Pharmacology., 66, 635-647, 2004.
EP Communication under Rule 71(3) EPC for Application No. 06832529.9 dated Nov. 25, 2011, 35 pages.
EP07806561.2 Office Action dated Dec. 9, 2011, 5 pages.
EP07806561.2 Office Action dated Feb. 7, 2011, 1 page.
EP07806561.2 Response to Office Action filed on Aug. 9, 2011, 134 pages.
Erber et al., "Combined inhibition of VEGF and PDGF signaling enforces tumor vessel regression by interfering with pericyte-mediated endothelial cell survival mechanisms," FASEB J., 18(2):338-340 (2004).
Erdem et al, "Correlation of E-cadherin, VEGF, COX-2 expression to prognostic parameters in papillary thyroid carcinoma", Experimental Mole Pathol., 90:312-317, Feb. 16, 2011.
European Office Action for App. Ser. No. 04719054.1, dated Oct. 30, 2009, 5 pages.
European Office Action for App. Ser. No. 04807580.8, dated Apr. 18, 2011, 11 pages.
European Office Action for App. Ser. No. 04807580.8, dated Dec. 3, 2010, 7 pages.
European Office Action for App. Ser. No. 04807580.8, dated Oct. 25, 2011, 17 pages.
European Office Action for App. Ser. No. 04818213.3, dated Feb. 2, 2012, 5 pages.
European Office Action for App. Ser. No. 07743994.1, dated Oct. 10, 2012, 8 pages.
European Office Action for Application No. 06832529.9 dated Oct. 15, 2009, 1 page.
European Office Action for Application No. 06832529.9 dated Sep. 12, 2011, 3 pages.
European Response to EESR directed at Appl. No. 07743994.1-2123 filed on Nov. 23, 2010, 22 pages.
European Response to Office Action for Application No. 06832529.9 filed on Apr. 22, 2010, 82 pages.
European Response to Office Action for Application No. 06832529.9 filed on Oct. 4, 2011, 27 pages.

(56) References Cited

OTHER PUBLICATIONS

European Search Report dated Jul. 23, 2010 for European application No. 06782407, 8 pages.
European Search Report dated May 4, 2010 for European Application No. 07743994, 9 pages.
European Search Report directed at application No. 06768437.3, dated Oct. 11, 2010, 10 pages.
European Search Report directed at application No. 06832529.9, dated Jul. 29, 2009, 6 pages.
European Search Report directed at application No. 06833681.7, dated Nov. 24, 2010, 15 pages.
European Search Report directed at application No. 07806561.2, dated Jan. 19, 2011, 16 pages.
European Search Report directed at application No. 10015141.4, dated Sep. 9, 2011, 6 pages.
European Search Report for App. Ser. No. 03791389.4, dated Jul. 7, 2011, 5 pages.
European Search Report for App. Ser. No. 04025700.8, dated Jan. 13, 2005, 3 pages.
European Search Report for App. Ser. No. 04719054.1, dated Apr. 17, 2009, 4 pages.
European Search Report for App. Ser. No. 04818213.3, dated Jul. 30, 2007, 3 pages.
European Search Report for App. Ser. No. 05783232.1, dated Sep. 7, 2007, 5 pages.
European Search Report for App. Ser. No. 06023078.6, dated Mar. 16, 2007, 5 pages.
European Search Report for App. Ser. No. 06767145.3, dated May 23, 2011, 7 pages.
European Search Report for App. Ser. No. 10809938.3, dated Jan. 2, 2013, 5 pages.
European Search Report for EP 08704376.6 dated Jun. 14, 2012, 12 pages.
Examination Report dated Feb. 18, 2005 for NZ App. Ser. No. 525324, 1 page.
Examination Report dated Feb. 21, 2008 for AU App. Ser. No. 2006203099, 2 pages.
Examination Report dated Jan. 30, 2013 for AU App. Ser. No. 2009210098, 10 pages.
Examination Report dated Mar. 26, 2008 for AU App. Ser. No. 2006236039, 2 pages.
Examination Report dated May 4, 2006 for AU App. Ser. No. 2001295986, 2 pages.
Examination Report dated Nov. 24, 2012 for AU App. Ser. No. 2008325608, 3 pages.
Examination Report dated Oct. 13, 2003 for NZ App. Ser. No. 525324, 2 pages.
Examination Report dated Sep. 2, 2004 for NZ App. Ser. No. 525324, 1 page.
Examination Report dated Sep. 20, 2005 for AU App. Ser. No. 2001295986, 3 page.
Examination report from EP 040257008 dated Apr. 10, 2006, 3 pages.
Examination Report in AU App. Ser. No. 2005217325, dated Aug. 1, 2007, 2 pages.
Examination Report in AU App. Ser. No. 2005217328, dated Aug. 1, 2007, 2 pages.
Examination Report in AU App. Ser. No. 2007288793, dated Dec. 22, 2011, 2 pages.
Examination Report in AU App. Ser. No. 2007289787, dated Nov. 25, 2011, 2 pages.
Examination Report in AU App. Ser. No. 2008217931, dated Jun. 28, 2012, 3 pages.
Examination Report in PK App. Ser. No. 155/2005, dated Mar. 11, 2009, 2 pages.
Experimental Medicine, Supplementary Volume, "A New Handbook of Genetic Engineering", Section 4, Yodosha, 2003(Japanese).
Explanation of Circumstances Concerning Accelerated Examination filed May 10, 2012 for JP Patent Application No. 2011-527665, 21 pages (with English Translation).

Extended European Search Report dated Feb. 21, 2013 for EP App. Ser. No. 12195436.6, 8 pages.
Extended European Search Report for App. Ser. No. 08846814.5, dated Jun. 18, 2012, 11 pages.
Extended European Search Report in EP App. Ser. No. 06796594.7, dated Sep. 7, 2011, 5 pages.
Extended European Search Report in EP App. Ser. No. 07793075.8, dated Sep. 8, 2010, 6 pages.
Extended European Search Report in EP Ser. Appl. No. 07805959.9, dated Nov. 16, 2010, 6 pages.
Extended European Search Report in EP App. Ser. No. 08711837.8, dated Mar. 28, 2011, 5 pages.
Extended European Search Report in EP App. Ser. No. 09713617.0, dated Apr. 28, 2011, 5 pages.
Extended European Search Report dated Dec. 7, 2012 issued in connection with Corresponding European Application No. 06797249.7, 6 pages.
Extended Search Report in EP App. Ser. No. 12786619.2, dated Nov. 25, 2014, 6 pages.
Ezzat et al., "Dual Inhibition of RET and FGFR4 Retains Medullary Thyroid Cancer Cell Growth," Clinical Cancer Research, Feb. 2005, 11:1336-1341.
Fargnoli et al., "Preclinical studies of BMS-582664, an alanine prodrug of BMS-540215, a potent, dual inhibitor of VEGFR-2 and FGFR-1 kinases," AACR American Association Cancer Research, 96th Annual Meeting, 46 (Abstract 3033), Anaheim, Orange County CA USA Apr. 16-20, 2005, 2 pages.
Final Office Action for U.S. Appl. No. 12/092,539 dated May 9, 2011, 10 pages.
Finn et al., "A multicenter, open-label, phase 3 trial to compare the efficacy and safety of lenvatinib (E7080) versus sorafenib in first-line treatment of subjects with unresectable hepatocellular carinoma," Am Soc Clin Oncol Annual Meeting Abstract, May 31, 2014, 5 pages.
First Office Action dated Mar. 6, 2012 for the corresponding JP application, JP2007-542863, 17 pages and English translation.
FMC BioPolymer; http://www.Fmcbiopolymer.com/portals/pharm/contect/docs/fmc_alubra_brochurefinal.pdf; accessed Mar. 16, 2015, 6 pages.
Folkman et al., "Angiogenesis," The Journal of Biological Chemistry, 267(16):10931-10934 (1992).
Folkman et al., "Seminars in Medicine of the Beth Israel Hospital, Boston: Clinical Applications of Research on Angiogenesis," The New England Journal of Medicine, 333(26):1757-1763 (1995).
Folkman et al., "What is the Evidence That Tumors are Angiogenesis Dependent?," Journal of the National Cancer Institute, 82(1):4-6 (1990).
Folkman, "New Perspective in Clinical Oncology From Angiogenesis Research," J. Eur. J. Cancer, 32A(4):2534-2539 (1996).
Fong et al., "SU5416 Is a Potent and Selective Inhibitor of the Vascular Endothelial Growth Factor.Receptor (Flk-1/KDR) That Inhibits Tyrosine Kinase Catalysis, Tumor Vascularization, and Growth of Multiple Tumor Types", Cancer Research., 59, 99-106, 1999.
Forbes et al., "Dissolution kinetics and solubilities of p-aminosalicylic acid and its salts," International Journal of Pharmaceutics, 126:199-208 (1995).
Formality Requirement dated Jun. 18, 2003 for PH App. Ser. No. 1-2003-500266, 3 pages.
Freshney, R. Ian, "Culture of Animal Cells, A Manual of Basic Technique," Alan R. Liss, New York, 29-32 (1983).
Frings, "New Molecular Targeted Therapeutic Drugs Clinical Results of Bevacizumab in Non-Small Cell Lung Cancer (NSCLC)", Jap. J. Lung Cancer, Jun. 2006, 46(3):277-281 (with English Translation).
Fugazzola et al., "Molecular and biochemical analysis of RET/PTC4, a novel oncogenic rearrangement between RET and ELE1 genes, in a post-Chernobyl papillary thyroid cancer", Oncogene, 13, 1093-1097, 1996.
Fujii et al., "Angiogenesis Inhibitor/Kekkan Shinsei Sogaiyaku," Clin Gastroenterol., May 25, 2004, 19:220-227.
Fujii et al., "MP-412, a dual EGFR/HER2 tyrosine kinase inhibitor: 2. In vivo antitumor effects," Am. Assoc. Cancer Research, A3394, 2005, 2 pages.

(56) References Cited

OTHER PUBLICATIONS

Funahashi et al., "Analysis of plasma biomarker and tumor genetic alterations form a phase II trial of lenvatinib in patietns with advanced endometrial cancer," Poster for a presentation on May 31, 2013 at ASCO Annual Meeting (Chicago, IL, May 31-Jun. 4, 2013), May 31, 2013, 1 page.

Funahashi et al., "Analysis of plasma biomarker and tumor genetic alterations form a phase II trial of lenvatinib in patietns with advanced endometrial cancer," Abstract of the presentation #2 (abstract 5591), Retrieved from website http://meetinglibrary.asco.org/print/1163381, 2013, 1 page.

Funahashi et al., "P-2123, Lenvatinib treatment of differentiated thyroid cancer (DTC): Analysis to identify biomarkers associated with response," The 71$^{st}$ Annual Meeting of the Japanese Cancer Association, Sep. 19-21, 2012, p. 339.

Furitsu et al., "Identification of Mutations in the Coding Sequence of the Proto-Oncogene c-kit in a Human Mast Cell Leukemia Cell Line Causing Ligand-Independent Activation of c-kit Product," J. Clin. Invest., 92:1736-1744 (1993).

Furitsu et al., "Stable medicinal compositions of quinolinecarboxamide derivative," Database Caplus Chemical Abstracts Service, Columbus, OH, US (2006) (XP002520305), 11 pages.

Furuta et al., "Synthesis and Biological Evaluation of Selective Inhibitors of PDGF Receptor Auto Phosphorylation," #64, American Chemical Society, 226$^{th}$ ACS National Meeting, New York, NY (Sep. 7-11, 2003), 72 pages.

Gall-Istok et al., "Notes on the Synthesis of 4-Amino-6,7-Di-Sec-Butoxyquinoline, -6,7-Methylene-Dioxyquinoline and its N-Alkylaminoacetyl Derivatives," Acta Chimica Hungarica, 112(2):241-247 (1983).

Gardner et al., "In Vitro Activity Sorghum-Selective Fluorophenyl Urea Herbicides," Pesticide Biochemistry and Physiology, 24(3):285-297 (1985).

Gatzemeier et al., "Phase III comparative study of high-dose cisplatin versus a combination of paclitaxel and cisplatin in patients with advanced non-small-cell lung cancer," J. Clin. Oncol., 18(19):3390-3399 (2000).

Genitourinary Cancers, Prostate Cancer Genitourinary, http://www.merkmanuals.com/professional/print/sec17/ch241/ch241e.html Mar. 16, 2011, 7 pages.

Gild et al, "Multikinase inhibitors: a new option for the treatment of thyroid cancer", Nature Reviews Endocrinol., 7:617-624, Oct. 2011.

Giles, "The vascular endothelial growth factor (VEGF) signaling pathway: a therapeutic target in patients with hematologic malignancies," Oncologist 6(suppl 5):32-39 (2001).

Gingrich et al., "A New Class of Potent Vascular Endothelial Growth Factor Receptor Tyrosine . . . Clinical Candidate CEP-7055", Journal of Medicinal Chemistry., 46: 5375-88, 2003.

Glen, "Pre-clinical investigation and clinical development of E7080, a multi-targeted tyrosine inhibitor: implications for melanoma," Ph.D. thesis submitted to the Faculty of Medicine, Division of Cancer Sciences and Molecular Pathology, University of Glasgow, Aug. 2010, 2 pages.

Goede, "Identification of serum angiopoietin-2 as a biomarker—for clinical outcome of colorectal cancer patients treated with bevacizumab-containing therapy," British Journal of Cancer, Oct. 2010, 103(9):1407-1414.

Golkar et al., "Mastocytosis," Lancet, 349:1379-1385 (1997).

Gould, "Salt Selection for Basic Drugs," *International Journal of Pharmaceutics*, 33:201-217, (1986) (XP025813036).

Grieco et al., "PTC is a Novel Rearranged Form of the ret Proto-Oncogene and Is Frequently Detected in Vivo in Human Thyroid Papillary Carcinomas", Cell, 60: 557-563 (1990).

Guo et al., "Expression of gastric cancer-associated MG7 antigen in gastric cancer, precancerous lesions and H. pylori-associated gastric diseases", Word J. Gastroenterol, 8(6):1009-1013 (2002).

Guo et al., "In Vitro Pharmacological Characterization of TKI-28, a Broad-Spectrum Tyrosine Kinase Inhibitor with Anti-Tumor and Anti-Angiogenic Effects", Cancer Biol Ther., 4, p. 1125-1132, 2005.

Gura, "Cancer Models Systems for Identifying new drugs are often faulty," Science, 278:1041-1042 (1997).

Gutheil et al., Targeted Antiangiogenic Therapy for Cancer Using Vitaxin: a Humanized Monoclonal Antibody to the Integrin alphavbeta3 1 Clinical Cancer Research., 6, 3056-61, 2000.

Haleblian,"Characterization of habits and crystalline modification of solids and their pharmaceutical applications," J. Pharm. Sci., 64(8):1269-1288 (1975).

Haller, "Chemotherapy for advanced pancreatic cancer," Int. J. Radiation Oncol. Biol. Phys., 56:16-23 (2003).

Hamby et al., "Structure-Activity Relationships for a Novel Series of Pyrido[2,3-d]pyrimidine Tyrosine Kinase Inhibitors", Journal of Medicinal Chemistry., 40, 2296-2303, 1997.

Hamel et al., "The Road Less Travelled: c-kit and Stem Cell Factor," Journal of Neuro-Oncology, 35:327-333 (1997).

Hara et al., "Amplification of c-myc, K-sam, and c-met in Gastric Cancers: Detection by Fluorescence In Situ Hybridization", Laboratory Investigation, 78, 1143-1153, 1998.

Hattori et al., "Immunohistochemical detection of K-sam protein in stomach cancer," Clin. Cancer Res., 2(8):1373-1381 (1996).

Havel et al., "E7080 (lenvatinib) in addition to best supportive care (BSC) versus (BSC) alone in third-line or greater nonsquamous, non-small cell lung cancer (NSCLC)," Am Soc Clin Oncol Annual Meeting Abstract, May 31, 2014, abstract 8043, 4 pages.

Hayamo et al., "Pericytes in experimental MDA-MB231 tumor angiogenesis," *Histochemistry and Cell Biology*, 117(6):527-534, Abstract (Jun. 2002).

Hayek et al., "An In Vivo Model for Study of the Angiogenic Effects of Basic Fibroblast Growth Factor," Biochemical and Biophysical Research Communications, 147(2):876-880 (1987).

Haymo et al., "Pericytes in experimental MDA-MB231 tumor angiogenesis," Histochemistry and Cell Biology, 117(6):527-534 (2002) (abstract).

Hearing Notice dated May 4, 2012, in India Patent Application No. 383/CHENP/2008.

Heinemann, V., et al., "Comparison of the Cellular Pharmacokinetics and Toxicity of . . . 1-beta-d-Arabinofuranosylcytosine", Cancer Research, 48, 4024-4031, 1988.

Heinrich et al., "Kinase Mutations and Imatinib Response in Patients with Metastatic Gastrointestinal Stromal Tumor", Journal of Clinical Oncology, vol. 21, No. 23:4342-4349 (2003).

Heinrich et al., "Inhibition of c-kit receptor tyrosine kinase activity by STI 571, a selective tyrosine kinase inhibitor," Blood, 96(3):925-932 (2000) (XP001097629).

Heinrich et al., "Inhibition of KIT tyrosine kinase activity: a novel molecular approach to the treatment of KIT-positive malignancies," J. Clin. Oncol., 20(6):1692-1703 (2002).

Helfrich et al., "Angiopoietin-2 Levels Are Associated with Disease—Progression in Metastatic Malignant Melanoma," Clinical Cancer Research, Feb. 2009, 15(4):1384-1392.

Hennequin et al., "Design and Structure-Activity Relationship of a New Class of Potent VEGF Receptor Tyrosine Kinase Inhibitors", Journal of Medicinal Chemistry., 42: 5369-5389, 1999.

Hennequin et al., "Novel 4-Anilinoquinazolines with C-7 Basic Side Chains: Design and Structure Activity Relationship of a Series of Potent, Orally Active, VEGF Receptor Tyrosine Kinase Inhibitors," J. Med. Chem., 45:1300-1312 (2002).

Herbst et al., "AMG 706 first in human, open-label, dose-finding study evaluating the safety and pharmacokinetics (PK) in subjects with advanced sold tumors," EORTC-NCI-AACR Symp Mol Targets Cancer Ther., 2, (Abstract 151), 2004, 1 page.

Hertel LW., et al., "Evaluation of the Antitumor Activity of Gemcitabine (2',2' -Difluoro-2'-deoxycytidine)", Cancer Research, 50, 4417-4422, 1990.

Hibi et al., "Coexpression of the Stem Cell Factor and the c-kit Genes in Small-Cell Lung Cancer," Oncogene, 6:2291-2296 (1991).

Higgins et al., "Pharmacological manipulation of mGlu2 receptors influences cognitive performance in the rodent," Neuropharmacology, 2004, 46:907-917.

Highlights of Prescribing Information: GLEEVEC® (imatinib mesylate) Tablets for Oral Use (Initial U.S. Approval 2001; Label Revised Jan. 2012), 38 pages.

(56) References Cited

OTHER PUBLICATIONS

Hines et al., "Coexpression of the c-kit and Stem Cell Factor Genes in Breast Carcinomas," Cell Growth & Differentiation, 6:769-779 (1995).
Hogaboam et al., "Novel Role of Transmembrane SCF for Mast Cell Activation and Eotaxin Production in Mast Cell-Fibroblast Interactions," J. Immunol., 160:6166-6171 (1998).
Hori et al., "Suppression of Solid Tumor Growth by Immunoneutralizing Monoclonal Antibody against Human Basic Fibroblast Growth Factor", Cancer Research., 51, 6180-4, 1991.
Hu-Lowe et al., "SU014813 is a novel multireceptor tyrosine kinase inhibitor with potent antiangiogenic and antitumor activity," AACR American Association Cancer Research., 96th Annual Meeting, 46, (Abstract 2031), Anaheim, Orange County, CA, USA Apr., 2005, 2 pages.
Hurwitz et al., "Bevacizumab plus irinotecan, fluorouracil, and leucovorin for metastatic colorectal cancer," N. Engl. J. Med., 350(23):2335-2342 (2004).
Huston et al., "Protein engineering of antibody binding sites: Recovery of specific activity in an anti-digoxin single-chain Fv analogue produced in *Escherichia coli*", Proc. Natl. Acad. Sci. USA 85:5879-83, 1988.
Ikeda et al., "Changes in Phenotype and Proliferative Potential of Human Acute Myeloblastic Leukemia Cells in Culture with Stem Cell Factor," Experimental Hematology, 21:1686-1694 (1993).
Ikeda et al., "Expression and Functional Role of the Proto-Oncogene c-kit in Acute Myeloblastic Leukemia Cells," Blood, 78(11):2962-2968 (1991).
Ikuta et al., "E7080, a Multi-Tyrosine Kinase Inhibitor, Suppresses the Progression of Malignant Pleural Mesothelioma with Different Proangiogenic Cytokine Production Profiles," Clin Cancer Res., Nov. 24, 2009, 15(23):7229-7237.
Inai et al., "Inhibition of vascular endothelial growth factor (VEGF) signaling in cancer causes loss of endothelial fenestrations, regression of tumor vessels, and appearance of basement membrane ghosts," American Journal of Pathology, 165:35-52 (2004).
Indian Office Action for App. Ser. No. 1571/CHENP/2007, dated Oct. 30, 2012, 2 pages.
Indian Office Action in App. Ser. No. 6415/CHENP/2008, dated Oct. 3, 2013, 2 pages.
Indian Patent Application No. 2572/CHENP/2006 filed Jul. 13, 2006, 1 page.
Information about decision on request for EP App. Ser. No. 06023078.6, dated Mar. 21, 2007, 1 page.
Inoue et al., "Molecular Target Therapy Targeting Angiogenesis Pathways," The Nishinihon Journal of Urology, 66:425-432 (2004).
International Preliminary Report in International App. Ser. No. PCT/IB2008/003880, dated Aug. 11, 2009, 4 pages.
International Preliminary Report in International App. Ser. No. PCT/JP2007/066185, dated Mar. 5, 2009, 6 pages.
International Preliminary Report in International App. Ser. No. PCT/JP2007/066635, dated Mar. 12, 2009, 9 page.
International Preliminary Report in International App. Ser. No. PCT/JP2008/053066, dated Sep. 11, 2009, 12 pages.
International Preliminary Report in International App. Ser. No. PCT/JP2008/071881, dated Jul. 14, 2011, 7 pages pages.
International Preliminary Report in International App. Ser. No. PCT/JP2009/0524001, dated Oct. 14, 2010, 5 pages.
International Preliminary Report in Patentability in International App. Ser. No. PCT/JP2006/316331, dated Feb. 26, 2008, 5 pages.
International Preliminary Report on Patentability for App. Ser. No. PCT/JP2012/057949, dated Oct. 10, 2013, 7 pages.
International Preliminary Report on Patentability for International Application No. PCT/JP2001/09221, dated Jan. 8, 2003, 9 pages.
International Preliminary Report on Patentability for International Application No. PCT/JP2003/010964 dated Aug. 10, 2004, 7 pages.
International Preliminary Report on Patentability for International Application No. PCT/JP2004/003087, dated Feb. 13, 2006, 5 pages.
International Preliminary Report on Patentability for International Application No. PCT/JP2005/016941, dated Mar. 20, 2007, 10 pages.
International Preliminary Report on Patentability for International Application No. PCT/JP2006/312487, dated Dec. 24, 2007, 7 pages.
International Preliminary Report on Patentability for International Application No. PCT/JP2007/060560 dated Nov. 18, 2008, 6 pages with English translation.
International Preliminary Report on Patentability for International Application No. PCT/JP2007/060560, dated Dec. 10, 2008, 7 pages.
International Preliminary Report on Patentability for International Application No. PCT/JP2007/067088 dated Mar. 3, 2009, 16 pages with English translation.
International Preliminary Report on Patentability for International Application No. PCT/JP2008/051024 dated Jul. 21, 2009, 15 pages with English translation.
International Preliminary Report on Patentability for International Application No. PCT/JP2008/051697, dated Aug. 4, 2009, 18 pages.
International Preliminary Report on Patentability for International Application No. PCT/JP2008/070321, dated May 11, 2010, 15 pages with English translation.
International Preliminary Report on Patentability for International Application No. PCT/JP2009/051244 dated Aug. 31, 2010, 12 pages (with English translation).
International Preliminary Report on Patentability for International Application No. PCT/JP2010/063804 dated Mar. 13, 2012, 6 pages.
International Preliminary Report on Patentability for International Application No. PCT/JP2011/064430, dated Jan. 24, 2013, 6 pages.
International Preliminary Report on Patentability in International App. No. PCT/JP2013/084052, dated Jul. 2, 2015, 7 pages.
International Preliminary Report on Patentability in International App. Ser. No. PCT/JP2005/003701, dated Sep. 16, 2006, 7 pages.
International Preliminary Report on Patentability in International App. Ser. No. PCT/JP2005/003704, dated Sep. 19, 2006, 7 pages.
International Preliminary Report on Patentability in International App. Ser. No. PCT/JP2012/060279, dated Oct. 23, 2013, 11 pages.
International Preliminary Report on Patentability in International App. Ser. No. PCT/JP2012/062509, dated Nov. 28, 2013, 11 pages.
International Preliminary Report on Patentability in International Application No. PCT/JP2006/315563 dated Feb. 5, 2008, 10 pages with English translation.
International Preliminary Report on Patentability in International Application No. PCT/JP2006/315698 dated Feb. 5, 2008, 17 pages English translation.
International Preliminary Report on Patentability in International Application No. PCT/JP2006/322514 dated May 7, 2008, 8 pages.
International Preliminary Report on Patentability in International Application No. PCT/JP2006/322516 dated May 7, 2008, 8 pages.
International Preliminary Report on Patentability in International Application No. PCT/JP2014/063134, dated Sep. 9, 2014, 8 pages.
International Preliminary Report on Patentability in PCT App. Ser. No. PCT/US2012/040183, dated Apr. 3, 2014, 9 pages.
International Search Report and Written Opinion dated Sep. 14, 2010 for International Application No. PCT/JP2010/063804, 11 pages.
International Search Report and Written Opinion for PCT Application No. PCT/JP2011/064430, dated Sep. 13, 2011, 8 pages.
International Search Report and Written Opinion in International App. Ser. No. PCT/JP2008/071881, dated Jan. 27, 2009, 12 pages.
International Search Report and Written Opinion in International App. Ser. No. PCT/JP2009/052401, dated Mar. 10, 2009, 9 pages.
International Search Report and Written Opinion in International Application No. PCT/JP2014/063134, dated Sep. 9, 2014, 8 pages.
International Search Report dated Apr. 1, 2008 for International Application No. PCT/JP2008/051024, 6 pages.
International Search Report dated Jan. 20, 2009 for International Application No. PCT/JP2008/070321, 8 pages.
International Search Report dated Jan. 23, 2007 for International Application No. PCT/JP2006/322514, 10 pages.
International Search Report dated Jan. 23, 2007 for International Application No. PCT/JP2006/323881, 6 pages.
International Search Report dated Mar. 24, 2009 for International Application No. PCT/JP2009/051244, 6 pages.

(56) References Cited

OTHER PUBLICATIONS

International Search Report dated Mar. 4, 2008 for International Application No. PCT/JP2008/051697, 7 pages.
International Search Report dated Nov. 20, 2007 for International Application No. PCT/JP2007/067088, 6 pages.
International Search Report dated Oct. 17, 2006 for International Application No. PCT/JP2006/315698, 5 pages.
International Search Report dated Sep. 11, 2007 for International Application No. PCT/JP2007/060560, 6 pages.
International Search Report dated Sep. 4, 2007 for International Application No. PCT/JP2007/063525, 7 pages.
International Search Report dated Sep. 5, 2006 for International Application No. PCT/JP2006/315563, 2 pages.
International Search Report for App. Ser. No. PCT/JP2005/016941, dated Nov. 15, 2005, 4 pages.
International Search Report for International Application No. PCT/JP2001/09221, dated Jan. 15, 2002, 9 pages.
International Search Report for International Application No. PCT/JP2004/003087, dated Jul. 13, 2004, 3 pages.
International Search Report for International Application No. PCT/JP2006/317307, dated Dec. 12, 2006, 3 pages.
International Search Report for PCT/JP2012/060279, dated May 29, 2012, 5 pages.
International Search Report in International App. Ser. No. PCT/IB2008/003880, dated Aug. 11, 2009, 7 pages.
International Search Report in International App. Ser. No. PCT/JP2005/003701, dated May 31, 2005, 6 pages (with English translation).
International Search Report in International App. Ser. No. PCT/JP2005/003704, dated May 31, 2005, 6 pages (with English translation).
International Search Report in International App. Ser. No. PCT/JP2006/316331, dated Oct. 17, 2006, 5 pages (with English translation).
International Search Report in International App. Ser. No. PCT/JP2007/066185, dated Sep. 25, 2007, 4 pages.
International Search Report in International App. Ser. No. PCT/JP2007/066635, dated Oct. 16, 2007, 5 pages.
International Search Report in International App. Ser. No. PCT/JP2008/053066, dated May 20, 2008, 8 pages.
International Search Report in International Application No. PCT/JP2006/322516 dated Jan. 23, 2007, 5 pages.
International Search Report in International Application No. PCT/JP2013/084052, dated Mar. 4, 2014, 2 pages.
Interview Summary in U.S. Appl. No. 12/558,982, dated Oct. 20, 2011, 3 pages.
Invitation to declare maintenance of the application for EP App. Ser. No. 01976786.2, dated Jul. 12, 2004, 1 page.
Invitation to declare maintenance of the application for EP App. Ser. No. 05783232.1, dated Sep. 25, 2007, 1 page.
Invitation to declare maintenance of the application for EP App. Ser. No. 06023078.6, dated May 2, 2007, 1 page.
Israel 200090 Office Actions dated Jun. 22, 2010, 3 pages (with English translation).
Israel 200090 Response to Office Action filed on Oct. 12, 2010, 3 pages.
Israel Appl. No. 195282 IDS List filed on Jul. 1, 2010, 3 pages.
Israel Office Action directed at Appl. No. 195282 dated Jan. 26, 2010, 4 pages with English translation.
Israel Office Action directed at Appl. No. 205512 dated Nov. 13, 2011, 4 pages with English translation.
Israel Response (IDS List) to Office Action directed at Appl. No. 195282 filed on May 3, 2010, 6 pages with English translation.
Israeli Office Action dated Mar. 27, 2012 for Israeli Application No. 189589, 3 pages with English translation.
Israeli Office Action for App. Ser. No. 155447, dated Oct. 16, 2007, 3 pages (with English translation).
Israeli Office Action for App. Ser. No. 189677, dated Feb. 18, 2009, 2 pages (with English translation).
Israeli Office Action for App. Ser. No. 195282, dated Feb. 5, 2012, 3 pages (with English translation).
Israeli Office Action for App. Ser. No. 199907, dated Apr. 22, 2012, 3 pages (with English translation).
Israeli Office Action dated May 16, 2010 for corresponding Israeli Application No. 189589, 3 pages with English translation.
Issue Notification in U.S. Appl. No. 11/508,322, dated Dec. 1, 2010, 1 page.
Issue Notification in U.S. Appl. No. 12/031,568, dated Jan. 30, 2013, 4 pages (with English translation).
Issue Notification in U.S. Appl. No. 12/315,291, dated Jul. 27, 2011, 5 pages.
Issue Notification in U.S. Appl. No. 12/558,982, dated Sep. 26, 2012, 1 page.
Issued Notification in U.S. Appl. No. 11/892,785, dated Aug. 18, 2010, 1 page.
Itoh et al., "Preferential alternative splicing in cancer generates a K-sam messenger RNA with higher transforming activity," Cancer Res., 54:3237-3241 (1994).
Jakeman et al., "Developmental Expression of Binding Sites and Messenger Ribonucleic Acid for Vascular Endothelial Growth Factor Suggests a Role for This Protein in Vasculogenesis and Angiogenesis," Endocrinology, 133(2):848-859 (1993).
Jang et al., "Mutations in Fibroblast Growth Factor Receptor 2 and Fibroblast Growth Factor Receptor 3 Genes Associated with Human Gastric and Colorectal Cancers", Cancer Research,61:3541-3543 (2001).
Japanese Allowance for App. Ser. No. P2005-515330, dated Apr. 21, 2009, 2 pages.
Japanese Allowance for App. Ser. No. P2005-516605, dated Dec. 7, 2010, 5 pages (with English translation).
Japanese Classification of Gastric Carcinoma "Igan-Toriatsukai Kiyaku" (Jun. 1999, 13th ed.) and an English translation, 10 pages.
Japanese Decision to Grant a Patent dated Jan. 30, 2013 for Japanese Application No. 2007-533350, 3 pages with English translation.
Japanese Notice of Reasons for Rejection dated May 15, 2012 for Japanese Application No. 2007-533350, 6 pages with English translation.
Japanese Office Action dated Apr. 11, 2005 for App. Ser. No. 2002-536056, 6 pages (with English translation).
Japanese Office Action for App. Ser. No. 2005-516605, dated Jun. 1, 2010, 3 pages.
Japanese Office Action for App. Ser. No. 2005-516605, dated Nov. 4, 2009, 7 pages (with English translation).
Japanese Office Action for App. Ser. No. 2007-522356, dated Feb. 8, 2011, 5 pages (with English translation).
Japanese Office Action for App. Ser. No. P2008-516724, dated Oct. 9, 2012, 6 pages (with English translation).
Jhiang, "The RET proto-oncogene inn human cancers," Oncogene, 19:5590-5597 (2000).
Jiang, "ZD6474: an Agent That Selectively Targets Both VEGFR Tyrosine Kinase and EGFR Tyrosine Kinase", Jap. J. Lung Cancer, Jun. 2006, 46(3):283-288 (with English translation).
Jimenez et al., "Pheochromocytoma and medullary thyroid carcinoma: a new genotype-phenotype correlation of the RET protooncogene 891 germline mutation," J. Clin. Endocrinol. Metab., 89:4142-4145 (2004).
Joao et al., "Somatic trinucleotide change encompassing codons 882 and 883 of the RET proto-oncogene in a patient with sporadic medullary thyroid carcinoma", European Journal of Endocrinology, 142,573-575, (2000).
Johnson et al., "Influence of ionic strength on matrix integrity and drug release from hydroxypropyl cellulose compacts," International journal of pharmaceutics, 1993, vol. 90, No. 2, pp. 151-159.
Johnson et al., "Paclitaxel plus carboplatin in advanced non-small-cell lung cancer: a phase II trial," J. Clin. Oncol., 14(7):2054-2060 (1996).
Joly et al., "In vitro and in vivo characterization of exel-7647, a novel spectrum selective receptor tyrosine kinase inhibitor that modulates angiogenesis and tumor cell proliferation," EORTC-NCI-AACR Symp Mol Targets Cancer Ther., (Abstract 134), 2004, 1 page.

(56) References Cited

OTHER PUBLICATIONS

Jung et al., "Effects of combination anti-vascular endothelial growth factor receptor and anti-epidermal growth factor receptor therapies on the growth of gastric cancer in a nude mouse model," Eur. J. Cancer, 38:1133-1140 (2002).
Juurikivi et al., "Inhibition of c-kit tyrosine kinase by imatinib mesylate induces apoptosis in mast cells in rheumatoid synovia: a potential approach to the treatment of arthritis," Ann Rheum. Dis., 64:1126-1131 (2005).
Kanai et al., "Development Status and Future Prospects of Novel Molecular Target Drugs for Hepatocellular Carcinoma", Journal of the Japanese Society of Gastroenterology, 106:1727-1735 (2009).
Kanai et al., "Current status and future perspective of molecular targeted therapy for hepatocellular carcinoma," Journal of the Japanese Society of Gastroenterology, 106:1727-1735 (2009) (English translation).
Kanakura et al., "Expression, Function and Activation of the Proto-Oncogene c-kit Product in Human Leukemia Cells," Leukemia and Lymphorma, 10:35-41 (1993).
Kashuk et al., "Phenotype-genotype correlation in Hirschsprung disease is illuminated by comparative analysis of the RET protein sequence," PNAS, 102(25):8949-8954 (2005).
Kato et al., "Effects of lenvatinib on tumor-associated macrophages enhance antitumor activity of PD-1 signal Inhibitors," Eisai Co., Ltd, poster, Nov. 6, 2015, 1 page.
Kawano et al., "Presentation Abstract, Abstract Number; 1619, Combination of VEGFR inhibitor lenvatinib (E7080) and Met/EphB4inhibitor golvatinib (E7050) overcomes VEGFR inhibitor—resistant tumor vascular", Annual Meeting 2013, Walter E. Washington Convention Center, Washington, D.C., Apr. 6-10, 2013, 1 page.
Kay et al., "Eosinophils and Eosinophil-Associated Cytokines in Allergic Inflammation," Int. Arch. Allergy Immunol., 113:196-199 (1997).
Kelly et al., "Randomized phase III trial of paclitaxel plus carboplatin versus vinorelbine plus cisplatin in the treatment of patients with advanced non—small-cell lung cancer: a Southwest Oncology Group trial," J. Clin. Oncol., 19(13):3210-3218 (2001).
Kew, "Positive and negative allosteric modulation of metabotropic glutamate receptors: emerging therapeutic potential," Pharmacology & Therapeutics, 2004, 104:233-244.
Kharkyevitch, "Farmakologiya," Third ed (revised and supplemented), Moscow, "Meditsina," 1987, 5 pages (with English Translation).
Kibbe, Handbook of Pharmaceutical Excipients. Third Edition, 2000, pp. 6-1 through 6-6.
Kim et al., "RET Oligonucleotide Microarray for the Detection of RET Mutations in Multiple Endocrine Neoplasia Type 2 Syndromes", Clinical Cancer Research, 8,457-463, (2002).
Kim et al., "A phase II study of irinotecan plus cisplatin for patients with advanced stage IIIB or IV NSCLC previously treated with nonplatinum-based chemotherapy," Cancer, 107(4):799-805 (2006).
Kim et al., "An orally administered multitarget tyrosine kinase inhibitor, SU11248, is a novel potent inhibitor of thyroid oncogenic RET/papillary thyroid cancer kinases," J. Clin. Endocrinol. Metlab., 91(10):4070-4076 (2006).
Kim, "Technology evaluation: Matuzumab, Merck KGaA", Curr Opin Mol Ther. 2004; 6(1 ):96-103.
Kinlaw et al., "Multiple endocrine neoplasia 2A due to a unique C6095 RET mutation presents with pheochromocytoma and reduced penetrance of medullary thyroid carcinoma", Clin Endocrinol, 69, 676-682, 2005.
Kitamura et al., "Regulation of Development, Survival and Neoplastic Growth of Mast Cells through the c-kit Receptor," Int. Arch Allergy Immunol., 107:54-56 (1995).
Kitteringham et al., "A Simple Method for the Synthesis of Unsymmetrical Ureas," Synthetic Communications, 30(11):1937-1943 (2000).
Kleespies et al., "Tyrosine kinase inhibitors and gemcitabine: New treatment options in pancreatic cancer,?" Drug Resistance Updates, 9:1-18 (2006).

Klugbauer and Rabes, "The transcription coactivator HT1 F1 and a related protein are fused to the RET receptor tyrosine kinase in childhood papillary thyroid carcinomas", Oncogene, 18: 4388-4393 (1999).
Klugbauer et al., "A Novel Type of RET Rearrangement (PTC8) in Childhood Papillary Thyroid Carcinomas and Characterization of the Involved Gene (RFG8)", Cancer Research, 60: 7028-7032 (2000).
Klugbauer et al., "Detection of a Novel Type of RET Rearrangement (PTC5) in Thyroid Carcinomas after Chernobyl and Analysis of the Involved RET-fused Gene RFGS", Cancer Research, 58:198-203 (1998).
Ko, "Stomach Cancer," Cancer Supportive Care.com [published online Feb. 2003], [retrieved on Dec. 28, 2011]. Retrieved from the Internet: http://web.archive.org/web/20030224212825/http://www.cancersupportivecare.com/stomach.html.
Kolibaba et al., "Protein Tyrosine Kinases and Cancer," Biochimica et Biophysica Acta, 1333:F217-F248 (1997).
Korean ("KR") Notice of Allowance dated Aug. 25, 2010 corresponding KR Application No. 10-2008-7005195, 3 pages with English translation.
Korean ("KR") Office Action dated Dec. 24, 2009 for corresponding KR Application No. 10-2008-7005195, 7 pages with English translation.
Korean ("KR") Office Action dated May 29, 2010 for corresponding KR Application No. 10-2008-7005195, 6 pages with English translation.
Korean Office Action for App. Ser. No. 10-2003-7005506, dated Jan. 5, 2006, 5 pages (with English translation).
Korean Office Action for App. Ser. No. 10-2005-7020292, dated Dec. 8, 2005, 5 pages (with English translation).
Korean Office Action for App. Ser. No. 10-2006-7013993, dated Jul. 31, 2007, 9 pages (with English translation).
Korean Office Action for App. Ser. No. 10-2007-7001347, dated Apr. 27, 2012, 6 pages (with English translation).
Korean Office Action for App. Ser. No. 10-2007-7001347, dated Sep. 28, 2011 (with English translation).
Korean Office Action for App. Ser. No. 10-2009-7005657, dated Sep. 30, 2013, 27 pages (with English translation).
Korean Office Action in KR App. Ser. No. 10-2008-7029472, dated Sep. 30, 2013, 27 pages (with English translation).
Kotva et al., "Substances with Antineoplastic Activity, LIII. N-(δ-(4-Pyrrolo[2,3-d]Pyrimidinylthio)Valeryl]} Amino Acids and Analogous Derivatives of Di-and Triglycine," Collection Czechoslov. Chem. Commun., 38:1438-1444 (1973).
Koyama et al, "Anti-tumor effect of E7080, a novel angiogenesis inhibitor," *Folia Pharmacol. Japan.*, 2008, 132: 100-104 (with English translation).
Kremer, "Lenvatinib Advisory Board", The presentation document, American Society of Clinical Oncology, Annual meeting 2014, May 31, 2014, 138 pages.
Kruckeberg et al., "Pyrosequencing Technology as a Method for the Diagnosis of Multiple Endocrine Neoplasia Type 2", Clinical Chemistry, 50, 522-529, 2004.
Krystal et al., "Indolinone Tyrosine Kinase Inhibitors Block Kit Activation and Growth of Small Cell Lung Cancer Cells", Cancer Research., 61, 3660-3668, 2001.
Kubo et al., "A novel series of 4-phenoxyquinolines: potent and highly selective inhibitors of pdgf receptor autophosphorylation", Bioorganic and Medicinal Chemistry Letters., 7, 2935-2940, 1997.
Kubo et al., "Novel Potent Orally Active Selective VEGFR-2 Tyrosine Kinase Inhibitors: . . . ureas", Journal of Medicinal Chemistry., 48, 1359-1366, 2005.
Kumar et al., "Survival and Failure Outcomes in Primary Thyroid Lymphomas: A Single Centre Experience of Combined Modality Approach," Journal of Thyroid Research, vol. 2013, Jun. 18, 2013, 6 pages.
Kumar et al., "Discovery and biological evaluation of GW654652: A pan inhibitor of VEGF receptors," Proceedings of the American Association for Cancer Research, 44, 9, (Abstract 39), 2003, 2 pages.

(56) References Cited

OTHER PUBLICATIONS

Laird et al., "SU6668 Is a Potent Antiangiogenic and Antitumor Agent That Induces Regression of Established Tumors1", Cancer Research., 60, 4152-4160, 2000.

Lam et al., "High prevalence of RET proto-oncogene activation (RET/PTe) in papillary thyroid carcinomas", Eur J Endocrinology, 147: 741-745 (2002).

Lasota et al., "Mutations in Exons 9 and 13 of KIT Gene Are Rare Events in Gastrointestinal Stromal Tumors," American Journal of Pathology, 157(4):1091-1095 (2000).

LeDoussal et al. "Bispecific-antibody-mediated targeting of radiolabeled bivalent haptens: theoretical, experimental and clinical results", Int. J. Cancer Suppl. 7: 58-62, 1992.

Lee et al., "In vivoTargetModulation and Biological Activity of CHIR-258, aMultitargeted Growth Factor Receptor Kinase Inhibitor, in Colon CancerModels", Clinical Cancer Research., 11, 3633-3641, 2005.

Lennartsson et al., The Stem Cell Factor Receptor/c-Kit as a Drug Target in Cancer, Current Cancer Drug Targets, 6:561-571 (2006).

Lenvatinib in Wikipedia: The Free Encyclopedia, http://en/wikipeida/org/wiki/Lenvatinib (accessed Dec. 18, 2013), 2 pages.

Lesueur et al., "Polymorphisms in RET and its coreceptors and ligands as genetic modifiers of multiple endocrine neoplasia type 2A," Cancer Res., 66:1177-1180 (2006).

*Leukemias, Hematology, and Oncology*, http://www.merkmanuals.com/professional/print/sec11/ch142a.html Mar. 16, 2011, 5 pages.

Lev et al., "A Specific Combination of Substrates is Involved in Signal Transduction by the Kit-Encoded Receptor," The EMBO Journal, 10(3):647-654 (1991).

Li et al., "Abrogation of c-kit/Steel factor-dependent tumorigenesis by kinase defective mutants of the c-kit receptor: c-kit kinase defective mutants as candidate tools for cancer gene therapy," Cancer Res., 56:4343-4346 (1996) (XP002522473).

Li et al., "ABT-869 a novel multi-targeted receptor tyrosine kinase inhibitor: characterization of FLT3 phosphorylation in a model of acute myelogenous leukemia," AACR American Association Cancer Research, 96th Annual Meeting, 46:1407, (Abstract 5981), Anaheim, Orange County CA USA Apr. 16-20, 2005, 2 pages.

Lin et al., "The vascular endothelial growth factor receptor tyrosine kinase inhibitor PTK787/ZK222584 inhibits growth and migration of multiple myeloma cells in the bone marrow microenvironment," Cancer Res., 62(17):5019-5026 (2002).

Liu et al., "Structure of Human Methionine Aminopeptidase-2 Complexed with Fumagillin", Science., 282, 1324-1327, 1998.

Llovet et al., "Plasma biomarkers as predictors of outcome in patients with advanced hepatocellular carcinoma," Clinical Cancer Res, 2012, 18(8):2290-2300.

Logie et al., "Activating mutations of the tyrosine kinase receptor FGFR3 are associated with benign skin tumors in mice and humans," Human Mol. Genet., 14:1153-1160 (2005).

Longley et al., "Altered Metabolism of Mast-Cell Growth Factor (c-kit Ligand) in Cutaneous Mastocytosis," The New England Journal of Medicine, 328(18):1302-1307 (1993).

Longley et al., "Classes of c-KIT activating mutations: proposed mechanisms of action and implications for disease classification and therapy," Leuk. Res., 25:571-576 (2001).

Longley et al., "Somatic c-KIT Activating Mutation in Urticaria Pigmentosa and Aggressive Mastocytosis: Establishment of Clonality in a Human Mast Cell Neoplasm," Nature Genetics, 12:312-314 (1996).

Lu et al., "Tailoring in Vitro Selection for a Picomolar Affinity Human Antibody Directed Against Vascular Endothelial Growth Factor Receptor 2 for Enhanced Neutralizing Activity," J Biol Chem., 2003, 278(44):43496-43507.

Lukacs et al., "Stem Cell Factor (c-kit Ligand) Influences Eosinophil Recruitment and Histamine Levels in Allergic Airway Inflammation," J. Immunol., 156:3945-3951 (1996).

Machens et al., "Genotype-Phenotype Correlations in Hereditary Medullary Thyroid Carcinoma: Oncological Features and Biochemical Properties", Journal of Clinical Endocrinology and Metabolism, 86(3):1104-1109 (2001).

Maintenance and Response to EP Search Report in EP App. Ser. No. 06796594.7, dated Dec. 21, 2011, 43 pages.

Maintenance of the application for EP App. Ser. No. 01976786.2, dated Sep. 6, 2004, 1 page.

Maintenance of the application for EP App. Ser. No. 05783232.1, dated Nov. 9, 2007, 1 pages.

Maintenance of the application for EP App. Ser. No. 06023078.6, dated Jun. 19, 2007, 1 page.

Marchetti et al., "Clinical Features and Outcome of Patients with Non-Small-Cell Lung Cancer Harboring BRAF Mutations," J Clin Oncol., 29(26):3574-3579 (Aug. 8, 2011).

Masferrer et al., "COX-2 Inhibitors a New Class of Antiangiogenic Agents", Annals of N.Y. Acad. Science., 889:84-6, 1999.

Matsui et al., "Multi-Kinase Inhibitor E7080 Suppresses Lymph Node and Lung Metastases of Human Mammary Breast Tumor MDA-MB-231 via Inhibition of Vascular Endothelial Growth Factor-Receptor (VEGF-R) 2 and VEGF-R3 Kinase," Clin Cancer Res., 2008, 14:5459-5465.

Matsui et al., "E7080 (ER-203492-00), a Novel VEGF Receptor Tyrosine Kinase Inhibitor-I. Characterization as an Angiogenesis Inhibitor," Abstract # 51, AACR, Toronto, Canada (Apr. 5-9, 2003), 1 page (abstract only).

Matsui et al., "E7080, a novel inhibitor that targets multiple kinases, has potent antitumor activities against stem cell factor producing human small cell lung cancer H146, based on angionenesis inhibition," Int. J. Cancer, 122:664-671 (2008).

Matsui et al., "E7080, a novel multi-receptor Tyrosine Kinase Inhibitor, inhibited in vitro / in vivo VEGF- and SCF-driven angiogenesis SCLC cell line," Abstract #146, EORTC-NCI-AACR, Geneva, Switzerland (Sep. 28-Oct. 1, 2004) (abstract only).

Matsui et al., "E7080, a novel multi-targeted tyrosine kinase inhibitor, exhibits anti-angiogenic activity via inhibition of KIT signaling in a small cell lung cancer xenograft model," Eur. J. Cancer, 2004, 2(8):47 (abstract only).

Matsui et al., "Mechanism of antitumor activity of E7080, a selective VEGFR and FGFR tyrosine kinase inhibitor (TKI), in combination with selective mutant BRAF inhibition," J Clin Oncol., May 20, 2011, 29(15), Suppl., Asco Meeting Abstracts, Part 1, Abstract No. 8567, 2 pages.

Matsui et al., "Quantitative analysis of the profile of tumor vessels may be useful as predictive biomarkers for E7080," Abstract #4631, 98th AACR annual meeting, Los Angeles, CA, (Apr. 14-18, 2007), 1 page.

Matsui et al., "VEGFRs inhibitor E7080 inhibits lymph node metastasis of human breast carcinoma, by preventing murine lymphatic endothelial cells from lymphangiogenesis," Abstract #PD12-8, *18th EORTC-NCI-AACR Symposium on "Molecular Targets and Cancer Therapeutics*," Prague, Czech Republic (Nov. 7-10, 2006), 1 page.

Matsui, "Extracellular matrix of linitis plastica as a possible new therapeutic target," Surgical Treatment, Sep. 2003, 89(3):301-306 (with English translation).

Matsushima et al., "Preparation of pyridine and pyrimidine derivatives as inhibitors of hepatocyte growth factor receptor (HGFR)," Hcaplus, 2005, 977021.

McCarty et al., "ZD6474, a vascular endothelial growth factor receptor tyrosine kinase inhibitor with additional activity against epidermal growth factor receptor tyrosine kinase, inhibits orthotopic growth and angiogenesis of gastric cancer," Mol. Cancer Ther., 3(9):1041-1048 (2004).

McCulloch et al., "Astragalus-based Chinese herbs and platinum-based chemotherapy for advanced non-small-cell lung cancer: meta-analysis of randomized trials," J. Clin. Oncol., 24(3):419-430 (2006).

Meltzer, "The Pharmacological Basis for the Treatment of Perennial Allergic Rhinitis and Non-Allergic Rhinitis with Topical Corticosteroids," Allergy, 52:33-40 (1997).

Memorandum in Response to Office Action in IL App. Ser. No. I97141, dated Apr. 8, 2013, 18 pages (with English translation).

(56) References Cited

OTHER PUBLICATIONS

Mendel et al., "In vivo antitumor activity of SU11248, a novel tyrosine kinase inhibitor targeting vascular endothelial growth factor and platelet-derived growth factor receptors: determination of a pharmacokinetic/pharmacodynamic relationship," Clin. Cancer Res., 9:327-337 (2003).
Metcalfe et al., "Lineage Commitment in the Progeny of Murine Hematopoietic Preprogenitor Cells: Influence of Thrombopoietin and Interleukin 5," Proc. Nat'l Acad. Sci. USA, 95:6408-6412 (1998).
Metcalfe et al., "Mast cells," Physiol. Rev., 77(4):1033-1079 (1997).
Metcalfe, "Classification and Diagnosis of Mastocytosis: Current Status," J. Invest. Dermatol., 96:2S-4S (1991).
Mexican Office Action in App. Ser. No. MX/a/2010/008187, dated Aug. 21, 2013, 6 pages (with English translation).
Micke et al., "Characterization of c-kit expression in small cell lung cancer: prognostic and therapeutic implications," Clin. Cancer Res., 9:188-194 (2003).
Miknis et al., "AARY-334543, A potent, orally active small molecule inhibitor of EGFR and ErbB-2," Am. Assoc. Cancer Res. Abstract 3399, 2005, 2 pages.
Miller et al., "Genomic amplification of MET with boundaries within fragile site FRA7G and upregulation of MET pathways in esophageal adenocarcinoma," Oncogene, 2005, 25(3):409-418.
Miller et al., "Paclitaxel plus bevacizumab versus paclitaxel alone for metastatic breast cancer," N. Engl. J. Med., 357(26):2666-2676 (2007).
Milstein and Cuello, "Hybrid hybridomas and their use in immunohistochemistry", Nature 305: 537-9, 1983.
Mitchell et al, "The influence of additives on the cloud point, disintegration and dissolution of hydroxypropylmethylcellulose gels and matrix tablets," International iournal of pharmaceutics, 1990, vol. 66, No. 1/3, pp. 233-242.
Miyauchi et al., "Two Germline Missense Mutations of Co dons 804 and 806 of the RET proto-oncogene in the Same 15 Allele in a Patient with Multiple Endocrine Neoplasia Type 2B without Codon 915 Mutation", Japanese Journal of D Cancer Research, 90, 1-5, (1999).
Miyazaki et al., "Synthesis, Structure and Biological Activity Relationship of E7080 and its Derivatives as Novel and Potent Antiangiogenic Protein Tyrosine Kinase Inhibitors Including the VEGF Receptors, FGFR1 Receptor and PDGF Receptor," AIMECS03, Kyoto, Japan (Oct. 14-17, 2003), 1 page.
Mohammadi et al., "Crystal structure of an angiogenesis inhibitor bound to the FGF receptor tyrosine kinase domain", EMBO J., 17, 5896-5904, 1998.
Mologni et al., "Inhibition of RET tyrosine kinase by SU5416," J. Mol. Endocrinol., 37(2):199-212 (2006).
Montalbetti and Falque, "Tetrahedron report No. 740: Amide bond formation and peptide coupling," Tetrahedron, 2005, 61:10827-10852.
Morgan et al., "Dynamic contrast-enhanced magnetic resonance imaging as a biomarker for the pharmacological response of PTK787/ZK 222584, an inhibitor of the vascular endothelial growth factor receptor tyrosine kinases, in patients with advanced colorectal cancer and liver metastases: results from two phase I studies," J. Clin. Oncol., 21(21):3955-3964 (2003).
Morikawa et al., "Angiogenesis and Pericytes," The Cell, 37(4):164-168 (2005) (English translation).
Morris et al., "An Integrated Approach to the Selection of optimal Salt Form for a New Drug Candidate," International Journal of Pharmaceutics, 105:209-217 (1994) (XP023724810).
Mototsugu, "mTOR inhibitors," Nippohn Rinsho, Jun. 2010, 68(6):1067-1072 (with English abstract).
Myers et al., "The Preparation and SAR of 4-(Anilino), 4-(Phenoxy), and 4-(Thiophenoxy)-Quinazolines: Inhibitors of p56lck and EGF-R Tyrosine Kinase Activity," Bioorgan. & Med. Chem. Letters, 7:417-420 (1997).
Naclerio et al., "Rhinitis and Inhalant Allergens," JAMA, 278(22):1842-1848 (1997).

Nagata et al., "Elevated Expression of the Proto-Oncogene c-kit in Patients with Mastocytosis," Leukemia, 12:175-181 (1998).
Nakagawa et al., "E7050: A dual c-Met and VEGFR-2 tyrosine kinase inhibitor promotes tumor regression and prolongs survival in mouse xengraft models," Cancer Sci., Jan. 2010, 101(1):210-215.
Nakamura et al., "KRN633: A Selective inhibitor of vascular endothelial growth factor receptor-2 tyrosine kinase that suppresses tumor angiogenesis and growth", Molecular Cancer Therapeutics., 2004, 3:1639-49.
Nakamura et al., "E7080 (ER-203492-00), a Novel VEGF Receptor Tyrosine Kinase Inhibitor-II. Effects on Growth of Human Tumor Xenografts and Life Span of Mice in Colon 38 Orthotopic Transplantation Model," Abstract #52, *AACR, Toronto, Canada* (Apr. 5-9, 2003).
Nakamura et al., "In vitro selectivity and potency of KRN95 1, a novel inhibitor of VEGF receptor tyrosine kinases," Proceedings of the American Association for Cancer Research, 45, 594, (Abstract 2571), 2004, 1 page.
Nakanishi, "Molecular diversity of glutamate receptors and implications for brain function," Science, 1992, pp. 597-603.
Nakata et al., "Fusion of a Novel Gene, ELKS, to RET Due to Translocation t(1 0; 12) (q11; p13) in a Papillary Thyroid Carcinoma", Genes Chromosomes Cancer, 25: 97-103 (1999).
Nakazawa et al., "Maximizing the efficacy of anti-angiogenesis cancer therapy: A multi-targeting strategy by tyrosine kinase inhibitors," AACR Annual Meeting 2014, Presentation Abstract and Poster, Apr. 5-9, 2014, 2 pages (abstract only).
Nakazawa, "Combination strategy of lenvatinib: Maximizing its anti-angiogenesis efficacy," Tsukuba Res Laboratory, Eisai Co., Ltd., Ibaraki, Japan, Jun. 27, 2014, 10 pages.
Naran et al., "Inhibition of HGF/MET as therapy for malignancy," Expert Opin. Ther. Targets, 2009, p. 569-581.
Naruse et al., "Antitumor activity of the selective epidermal growth factor receptor-tyrosine kinase inhibitor (EGFR-TKI) Iressa (ZD1839) in an EGFR-expressing multidrug-resistant cell line in vitro and in vivo," Int. J. Cancer, 98:310-315 (2002).
Naski et al., "Graded activation of fibroblast growth factor receptor 3 by mutations causing achondroplasia and thanatophoric dysplasia," Nat. Genet., 13:233-237 (1996).
Natali et al., "Breast Cancer is Associated with Loss of the c-kit Oncogene Product" Int. J. Cancer, 52:713-717 (1992).
NCBI GenBank Accession No. NM_000222, Coffey et al. (Feb. 11, 2008), 7 pages.
Neidle, "Cancer Drug Design and Discovery" Elsevier/Academic Press, 2008, pp. 427-431.
Nicolaus, "Symbiotic Approach to Drug Design," Decision Making Drug Res., Jan. 1983, 173-186.
Nishikawa et al., "Cys611Ser mutation in RET proto-oncogene in a kindred with medullary thryroid carcinoma and Hirschsprung's disease", European Journal of Human Genetics, 11,364-368 (2003).
Nishio et al, "Phase 1 study of lenvatinib combined with carboplatin and paclitaxel in patients with non-small-cell lung cancer", British Journal of Cancer, 2013, 109:538-544.
Nocka et al., "Expression of c-kit gene products in known cellular targets of W mutations in normal and W mutant mice—evidence for an impaired c-kit kinase in mutant mice," *Cold Spring Harbor Laboratory Press*, 3:816-826 (1989) (XP002522472).
Non-Final Office Action in U.S. Appl. No. 10/577,531, dated Sep. 23, 2008, 17 pages.
Non-Final Office Action in U.S. Appl. No. 10/797,903, dated Aug. 20, 2009, 10 pages.
Non-Final Office Action in U.S. Appl. No. 10/797,903, dated Dec. 11, 2007, 12 pages.
Noriyuki et al., "Anti-tumor effect of E7080, a novel angiogenesis inhibitor," Database BIOSIS [Online] Biosciences Information Service, Philadelphia, PA, US: Database accession No. PREV200800475929, Aug. 2008, XP002677323, 1 page.
Notice of Acceptance dated Aug. 10, 2004 for ZA Patent App. No. 2003/3567, 1 page.
Notice of Acceptance dated Aug. 3, 2006 for AU App. Ser. No. 2001295986, 4 pages.
Notice of Acceptance dated May 13, 2008 for AU App. Ser. No. 2006236039, 4 pages.

(56) References Cited

OTHER PUBLICATIONS

Notice of Acceptance for AU App. Ser. No. 2009210098, dated Jun. 4, 2013, 3 pages.
Notice of Acceptance in AU App. Ser. No. 2005217325, dated Nov. 20, 2007, 3 pages.
Notice of Acceptance in AU App. Ser. No. 2005217328, dated Sep. 24, 2007, 3 pages.
Notice of Acceptance in AU App. Ser. No. 2006282456, dated Aug. 17, 2009, 1 page.
Notice of Acceptance in AU App. Ser. No. 2007288793, dated Apr. 10, 2012, 3 pages.
Notice of Acceptance in AU App. Ser. No. 2007289787, dated Mar. 16, 2012, 3 pages.
Notice of Acceptance in DB App. Ser. No. 60/2005, dated Nov. 16, 2006, 1 page.
Notice of Acceptance in NZ App. Ser. No. 547517, dated Mar. 6, 2009, 1 page.
Notice of Acceptance in NZ App. Ser. No. 566793, dated Feb. 12, 2010, 2 pages.
Notice of Acceptance of Complete Specification dated Mar. 4, 2005 for NZ App. Ser. No. 525324, 1 page.
Notice of Allowability dated Nov. 28, 2007 for PH App. Ser. No. 1-2003-500266, 1 page.
Notice of Allowability in PH App. Ser. No. 1-2007-502319, dated Feb. 29, 2012, 1 page.
Notice of Allowance dated Apr. 19, 2005 for RU App. Ser. No. 2003114740, 79 pages (with English translation).
Notice of Allowance dated Apr. 19, 2011 for JP App. Ser. No. 2007-522356, 5 pages.
Notice of Allowance dated Apr. 24, 2012 for U.S. Appl. No. 12/524,754, 10 pages.
Notice of Allowance dated Apr. 29, 2010 for AU App. Ser. No. 2005283422, 3 pages.
Notice of Allowance dated Aug. 2, 2005 for JP App. Ser. No. 2002-536056, 2 pages (with English translation).
Notice of Allowance dated Aug. 7, 2012 for Japanese App. Ser. No. P2007-529565, 6 pages (with English translation).
Notice of Allowance dated Dec. 15, 2006 for CN App. Ser. No. 01819710.8, 4 pages.
Notice of Allowance dated Dec. 26, 2007 for IL App. Ser. No. 155447, 2 pages (with English translation).
Notice of Allowance dated Feb. 15, 2013 for NZ App. Ser. No. 598291, 1 page.
Notice of Allowance dated Feb. 27, 2009 for U.S. Appl. No. 11/293,785, 4 pages.
Notice of Allowance dated Feb. 5, 2010 for CN App. Ser. No. 200580026468.7, 5 pages (with English translation).
Notice of Allowance dated Jul. 17, 2012 for JP App. Ser. No. P2011-527665, 4 pages (with English translation).
Notice of Allowance dated Jul. 21, 2009 for JP App. Ser. No. 2005-124034, 6 pages (with English translation).
Notice of Allowance dated Jun. 13, 2006 for U.S. Appl. No. 10/420,466, 2 pages.
Notice of Allowance dated Jun. 20, 2012 for EP App. Ser. No. 06782407.8, 35 pages.
Notice of Allowance dated Jun. 25, 2012 for EP App. Ser. No. 07806561.2, 7 pages.
Notice of Allowance dated Jun. 3, 2008 for U.S. Appl. No. 11/293,785, 6 pages.
Notice of Allowance dated Mar. 14, 2010 for IL App. Ser. No. 189677, 3 pages (with English translation).
Notice of Allowance dated Mar. 16, 2007 for U.S. Appl. No. 10/420,466, 3 pages.
Notice of Allowance dated Mar. 21, 2013 for EP App. Ser. No. 07793075.8, 2 pages.
Notice of Allowance dated Mar. 22, 2012 for U.S. Appl. No. 12/986,638, 12 pages.
Notice of Allowance dated Mar. 8, 2013 for CA App. Ser. No. 2627598, 1 page.
Notice of Allowance dated May 16, 2013 for EP App. Ser. No. 06796594.7, 2 pages.
Notice of Allowance dated May 18, 2009 for U.S. Appl. No. 11/293,785, 4 pages.
Notice of Allowance dated May 6, 2013 for EP App. Ser. No. 04818213.3, 22 pages.
Notice of Allowance dated Nov. 14, 2011 for IL App. Ser. No. 181697, 4 pages (with English translation).
Notice of Allowance dated Nov. 19, 2008 for U.S. Appl. No. 11/293,785, 4 pages.
Notice of Allowance dated Nov. 2, 2012 for EP App. Ser. No. 06782407.8, 2 pages.
Notice of Allowance dated Nov. 2, 2012 for EP App. Ser. No. 07806561.2, 2 pages.
Notice of Allowance dated Oct. 14, 2010 for CA App. Ser. No. 2426461, 1 page.
Notice of Allowance dated Oct. 17, 2011 for CA App. Ser. No. 2579810, 1 page.
Notice of Allowance dated Oct. 18, 2006 for MX App. Ser. No. PA/a/2003/003362, 4 pages (with English translation).
Notice of Allowance dated Oct. 20, 2008 for TW App. Ser. No. 90125928, 4 pages (with English translation).
Notice of Allowance dated Oct. 31, 2008 for NO App. Ser. No. 20031731, 4 pages (with English translation).
Notice of Allowance dated Oct. 9, 2010 for CN App. Ser. No. 200710007097.9, 4 pages (with English translation).
Notice of Allowance dated Sep. 12, 2005 for U.S. Appl. No. 10/420,466, 2 pages.
Notice of Allowance dated Sep. 20, 2011 for JP App. Ser. No. 2006-535174, 4 pages.
Notice of Allowance dated Sep. 25, 2012 for U.S. Appl. No. 12/986,638, 56 page.
Notice of Allowance dated Sep. 4, 2012 in JP App. Ser. No. P2009-123432, 5 pages (with English translation).
Notice of Allowance for CN App. Ser. No. 200980103218.7, dated May 27, 2013, 4 pages (with English translation).
Notice of Allowance for JP App. Ser. No. 2008-516724, dated Jan. 22, 2013, 4 pages, with English translation.
Notice of Allowance for JP App. Ser. No. P2008-532141, dated Sep. 10, 2013, 5 pages (with English translation).
Notice of Allowance for U.S. Appl. No. 12/524,754, dated Jan. 18, 2013, 9 pages.
Notice of Allowance for U.S. Appl. No. 12/741,682, dated Feb. 19, 2013, 65 pages.
Notice of Allowance for U.S. Appl. No. 12/741,682, dated Jun. 19, 2013, 10 pages.
Notice of Allowance for U.S. Appl. No. 12/524,754 dated Oct. 9, 2012, 36 pages.
Notice of Allowance for U.S. Appl. No. 11/997,719, dated Sep. 13, 2013, 20 pages.
Notice of Allowance for U.S. Appl. No. 13/083,338, dated Jun. 4, 2013, 57 pages.
Notice of Allowance for U.S. Appl. No. 13/083,338, dated Sep. 26, 2013, 28 pages.
Notice of Allowance for U.S. Appl. No. 13/205,328, dated Jun. 10, 2013, 58 pages.
Notice of Allowance for U.S. Appl. No. 13/205,328, dated Oct. 3, 2013, 11 pages.
Notice of Allowance in AU App. Ser. No. 2010285740, dated Nov. 19, 2014, 1 page.
Notice of Allowance in AU App. Ser. No. 2011270165, dated Dec. 14, 2015, 3 pages.
Notice of Allowance in CA App. Ser. No. 2605854, dated Apr. 7, 2010, 1 page.
Notice of Allowance in CA App. Ser. No. 2652442, dated Apr. 16, 2014, 1 page.
Notice of Allowance in CA App. Ser. No. 2661333, dated Dec. 19, 2013, 1 page.
Notice of Allowance in CA App. Ser. No. 2661702, dated Sep. 26, 2013, 1 page.
Notice of Allowance in CA App. Ser. No. 2676796, dated Oct. 8, 2015, 1 page.

(56) References Cited

OTHER PUBLICATIONS

Notice of Allowance in CA App. Ser. No. 2771403, dated Oct. 22, 2014, 1 page.
Notice of Allowance in CN App. Ser. No. 200680021939.X, dated Jan. 11, 2012, 4 pages (with English translation).
Notice of Allowance in CN App. Ser. No. 200780019200.X, dated Jan. 15, 2013, 4 pages (with English translation).
Notice of Allowance in CN App. Ser. No. 200780019520.5, dated Apr. 27, 2011, 4 pages (with English translation).
Notice of Allowance in CN App. Ser. No. 201180030568.2, dated Sep. 9, 2014, 4 pages (with English translation).
Notice of Allowance in CN App. Ser. No. 201280010898.X, dated Sep. 2, 2015, 4 pages (with English translation).
Notice of Allowance in EP App. Ser. No. 04807580.8, dated Dec. 15, 2014, 103 pages.
Notice of Allowance in EP App. Ser. No. 04818213.3, dated Sep. 19, 2013, 2 pages.
Notice of Allowance in EP App. Ser. No. 07743994.1, dated May 8, 2015, 51 pages.
Notice of Allowance in EP App. Ser. No. 08704376.6, dated Aug. 19, 2014, 62 pages.
Notice of Allowance in EP App. Ser. No. 08846814.5, dated Jan. 8, 2015, 36 pages.
Notice of Allowance in EP App. Ser. No. 10809938.3, dated Sep. 3, 2015, 30 pages.
Notice of Allowance in EP App. Ser. No. 11798224.9, dated Sep. 29, 2015, 37 pages.
Notice of Allowance in EP App. Ser. No. 12774278.1, dated Jun. 29, 2015, 34 pages.
Notice of Allowance in HU App. Ser. No. P0302603, dated Aug. 19, 2015, 5 pages (with English translation).
Notice of Allowance in ID App. Ser No. W-00 2008 00601, dated Oct. 17, 2012, 12 pages (with English translation).
Notice of Allowance in IL App. Ser. No. 195282, dated Aug. 11, 2014, 5 pages (with English translation).
Notice of Allowance in IL App. Ser. No. 197141, dated Oct. 27, 2013, 2 pages (with English translation).
Notice of Allowance in IL App. Ser. No. 200090, dated Nov. 18, 2013, 5 pages (with English translation).
Notice of Allowance in IL App. Ser. No. 205512, dated Feb. 15, 2015, 5 pages (with English translation).
Notice of Allowance in IL App. Ser. No. 207089, dated Nov. 10, 2014, 5 pages (with English translation).
Notice of Allowance in JP App. Ser. No. 2011-206481, dated Aug. 4, 2015, 7 pages (with English translation).
Notice of Allowance in JP App. Ser. No. P2009-540099, dated Oct. 21, 2014, 6 pages (with English translation).
Notice of Allowance in JP App. Ser. No. P2009-551518, dated Oct. 22, 2013, 5 pages (with English translation).
Notice of Allowance in KR App. Ser. No. 10-2006-7013907, dated Jan. 14, 2008, 3 pages (with English translation).
Notice of Allowance in KR App. Ser. No. 10-2006-7013940, dated Jan. 14, 2008, 3 pages (with English translation).
Notice of Allowance in KR App. Ser. No. 10-2008-7013685, dated Nov. 29, 2013, 3 pages (with English translation).
Notice of Allowance in KR App. Ser. No. 10-2008-7027527, dated Mar. 3, 2014, 4 pages (with English translation).
Notice of Allowance in KR App. Ser. No. 10-2008-7029472, dated Sep. 16, 2014, 3 pages (with English translation).
Notice of Allowance in KR App. Ser. No. 10-2009-7005657, dated Sep. 19, 2014, 3 pages (with English translation).
Notice of Allowance in KR App. Ser. No. 10-2009-7017694, dated Jul. 28, 2014, 3 pages (with English translation).
Notice of Allowance in KR App. Ser. No. 10-2010-7011023, dated Mar. 24, 2015, 3 pages (with English translation).
Notice of Allowance in KR App. Ser. No. 10-2010-7018835, dated Jan. 20, 2015, 3 pages (with English translation).
Notice of Allowance in KR App. Ser. No. 10-2012-7003846, dated Feb. 3, 2015, 3 pages.
Notice of Allowance in MK App. Ser. No. P/2015/231, dated Oct. 13, 2015, 2 pages (with English translation).
Notice of Allowance in MX App. Ser. No. MX/a/2008/002156, dated Oct. 15, 2010, 3 pages (with English translation).
Notice of Allowance in MX App. Ser. No. MX/a/2010/008187, dated Jul. 17, 2014, 3 pages (with English translation).
Notice of Allowance in MX App. Ser. No. MX/a/2012/014776, dated Mar. 18, 2015, 3 pages (with English tranlsation).
Notice of Allowance in MX App. Ser. No. MX/a/2013/009931, dated Jun. 29, 2015, 3 pages.
Notice of Allowance in MY App. Ser. No. PI20071922, dated Jan. 15, 2010, 3 pages.
Notice of Allowance in PK App. Ser. No. 1024/2006, dated Nov. 2, 2010, 1 page.
Notice of Allowance in PK App. Ser. No. 375/2008, dated Nov. 2, 2010, 1 page.
Notice of Allowance in RU App. Ser. No. 2006134254, dated Jan. 14, 2008, 30 pages (with English translation).
Notice of Allowance in RU App. Ser. No. 2012103471, dated Dec. 19, 2014, 12 pages (with English translation).
Notice of Allowance in RU App. Ser. No. 2012158142, dated May 5, 2015, 15 pages (with English translation).
Notice of Allowance in TW App. Ser. No. 095130665, dated Sep. 7, 2012, 4 pages (with English translation).
Notice of Allowance in TW App. Ser. No. 100104281, dated Jun. 9, 2015, 4 pages (with English translation).
Notice of Allowance in UA App. Ser. No. a201203132, dated Mar. 21, 2014, 6 pages.
Notice of Allowance in U.S. Appl. No. 11/892,785, dated Apr. 5, 2010, 23 pages.
Notice of Allowance in U.S. Appl. No. 10/797,903, dated Mar. 10, 2011, 22 pages.
Notice of Allowance in U.S. Appl. No. 11/508,322, dated Sep. 15, 2009, 6 pages.
Notice of Allowance in U.S. Appl. No. 11/662,425, dated Oct. 21, 2014, 49 pages.
Notice of Allowance in U.S. Appl. No. 11/997,719, dated Dec. 2, 2014, 21 pages.
Notice of Allowance in U.S. Appl. No. 11/997,719, dated Jun. 5, 2014, 14 pages.
Notice of Allowance in U.S. Appl. No. 12/031,568, dated Jun. 1, 2012, 23 pages.
Notice of Allowance in U.S. Appl. No. 12/031,568, dated Oct. 19, 2011, 11 pages.
Notice of Allowance in U.S. Appl. No. 12/031,568, dated Sep. 18, 2012, 6 pages.
Notice of Allowance in U.S. Appl. No. 12/315,291, dated Apr. 26, 2011, 6 pages.
Notice of Allowance in U.S. Appl. No. 12/439,339, dated Apr. 1, 2014, 17 pages.
Notice of Allowance in U.S. Appl. No. 12/439,339, dated Nov. 7, 2013, 64 pages.
Notice of Allowance in U.S. Appl. No. 12/524,754, dated Feb. 13, 2014, 18 pages.
Notice of Allowance in U.S. Appl. No. 12/524,754, dated Nov. 22, 2013, 12 pages.
Notice of Allowance in U.S. Appl. No. 12/524,754, dated Sep. 18, 2014, 35 pages.
Notice of Allowance in U.S. Appl. No. 12/558,982, dated Apr. 3, 2012, 11 pages.
Notice of Allowance in U.S. Appl. No. 12/558,982, dated May 25, 2012, 20 pages.
Notice of Allowance in U.S. Appl. No. 12/741,682, dated Feb. 7, 2014, 11 pages.
Notice of Allowance in U.S. Appl. No. 12/741,682, dated May 15, 2014, 13 pages.
Notice of Allowance in U.S. Appl. No. 12/741,682, dated Oct. 21, 2013, 12 pages.
Notice of Allowance in U.S. Appl. No. 12/741,682, dated Oct. 6, 2014, 11 pages.
Notice of Allowance in U.S. Appl. No. 13/083,338, dated Dec. 5, 2014, 19 pages.

(56) References Cited

OTHER PUBLICATIONS

Notice of Allowance in U.S. Appl. No. 13/083,338, dated Feb. 6, 2014, 15 pages.
Notice of Allowance in U.S. Appl. No. 13/083,338, dated Jul. 10, 2014, 20 pages.
Notice of Allowance in U.S. Appl. No. 13/205,328, dated Jan. 30, 2014, 11 pages.
Notice of Allowance in U.S. Appl. No. 13/205,328, dated May 8, 2014, 10 pages.
Notice of Allowance in U.S. Appl. No. 13/624,278, dated Jun. 25, 2014, 57 pages.
Notice of Allowance in U.S. Appl. No. 13/624,278, dated Oct. 31, 2014, 14 pages.
Notice of Allowance in U.S. Appl. No. 13/624,278, dated Sep. 16, 2013, 20 pages.
Notice of Allowance in U.S. Appl. No. 13/805,826, dated Dec. 17, 2014, 15 pages.
Notice of Allowance in U.S. Appl. No. 13/983,891, dated Mar. 20, 2014, 9 pages.
Notice of Allowance in U.S. Appl. No. 14/002,018, dated Oct. 24, 2014, 70 pages.
Notice of Allowance in U.S. Appl. No. 14/438,366, dated Dec. 18, 2015, 5 pages.
Notice of Allowance in U.S. Appl. No. 11/065,631, dated Jan. 2, 2009, 6 pages.
Notice of Allowance in U.S. Appl. No. 11/065,631, dated Sep. 9, 2008, 10 pages.
Notice of Allowance in VN App. Ser. No. 1-2008-00723, dated Aug. 19, 2010, 2 pages (with English translation).
Notice of Allowance in VN App. Ser. No. 1-2011-03484, dated Apr. 28, 2014, 2 pages.
Notice of Allowance in ZA App. Ser. No. 2007/09572, dated Mar. 12, 2009, 1 pages.
Notice of Allowance issued in CN App. Ser. No. 200880115011.7, dated Aug. 5, 2013, 4 pages (with English translation).
Notice of Allowance issued in CN App. Ser. No. 201080030508.6, dated Jul. 4, 2013, 4 pages (with English translation).
Notice of Allowance issued in EP App. Ser. No. 10015141.4, dated Jul. 1, 2013, 41 pages.
Notice of Allowance issued in IL App. Ser. No. 175363, dated Aug. 13, 2013, 2 pages (with English translation).
Notice of Allowance issued in JP App. Ser. No. P2008-556208, dated Jul. 9, 2013, 4 pages (with English translation).
Notice of Allowance issued in U.S. Appl. No. 12/524,754, dated Jul. 19, 2013, 11 pages.
Notice of Appeal in U.S. Appl. No. 11/662,425, dated Sep. 5, 2014, 11 pages.
Notice of Appeal in U.S. Appl. No. 12/039,381, dated Aug. 29, 2014, 9 pages.
Notice of Appeal, Pre-appeal Brief Request for Review and Petition for Extension of Time in U.S. Appl. No. 13/923,858, dated Nov. 25, 2015, 8 pages.
Notice of decision for patent dated Apr. 17, 2006 for KR App. Ser. No. 10-2005-7020292, 4 pages (with English translation).
Notice of decision for patent dated Jun. 12, 2006 for KR App. Ser. No. 10-2003-7005506, 4 pages (with English translation).
Notice of Final Rejection in KR App. Ser. No. 10-2009-7013723, dated Jul. 29, 2011, 4 pages (with English translation).
Notice of Grant in KR App. Ser. No. 10-2007-7026886, dated Dec. 31, 2009, 5 pages (with English translation).
Notice of Non-Substantive Deficiencies Prior to Allowance in IL App. Ser. No. 197141, dated Feb. 3, 2013, 16 pages (with English translation).
Notice of Panel Decision from Pre-Appeal Brief Review in U.S. Appl. No. 13/923,858, dated Jan. 7, 2016, 2 pages.
Notice of Reasons for Rejection issued in JP App. Ser. No. P2009-540099, dated Jul. 2, 2013, 7 pages (with English translation).
Notice of Reasons for Rejection dated Nov. 13, 2012 issued for corresponding Japanese Application No. 2007-533350 with full English language translation.
Notice Prior to Allowance in IL App. Ser. No. 188670, dated Sep. 12, 2011, 2 pages (with English translation).
Notice Prior to Allowance in IL App. Ser. No. 197002, dated Oct. 28, 2012, 2 pages (with English translation).
Notice Prior to Examination dated Jun. 29, 2008 for IL App. Ser. No. 189677, 3 pages (with English translation).
Notice Prior to Examination dated Mar. 9, 2009 for IL App. Ser. No. 181697, 3 pages (with English translation).
Notice Prior to Examination in IL App. Ser. No. 188670, dated Aug. 13, 2009, 3 pages (with English translation).
Notice Prior to Examination in IL App. Ser. No. 197002, dated Mar. 23, 2010, 3 pages (with English translation).
Notice Prior to Examination in IL App. Ser. No. 197141, dated Mar. 23, 2010, 3 pages (with English translation).
Notice Prior to Examination in IL App. Ser. No. 200466, dated Jun. 22, 2010, 3 pages (with English translation).
Notice Requesting Submission of Opinion in KR Application No. 10-2006-7013993 dated Jul. 31, 2007, 9 pages (with English translation).
Notification dated Apr. 25, 2008 for PH App. Ser. No. 1-2003-500266, 1 page.
Notification of Defects for IL App. Ser. No. 195282, dated Apr. 10, 2013, 4 pages (with English Translation).
Notification of Non-Compliant Amendment filed on Jan. 13, 2005 for U.S. Appl. No. 10/420,466.
Noy et al., "Tumor-Associated Macrophages From Mechanisms to Therapy," Immunity, Jul. 2014, 41:49-61.
Nugiel et al., "Synthesis and evaluation of indenopyrazoles as cyclin-dependent kinase inhibitors. 2. Probing the indeno ring substituent pattern," J. Med. Chem., 45(24):5224-5232 (2002).
Nyati et al., "Radiosensitization by Pan ErbB Inhibitor CI-1033 in Vitro and in Vivo", Clinical Cancer Research., 10:691-700, 2004.
Observation for CN App. Ser. No. 200880115011.7, dated Apr. 11, 2013, 10 pages (with English translation).
Observations for CN App. Ser. No. 201080030508.6, dated May 27, 2013, 7 pages (with English translation).
Ocqueteau et al., Expression of the CD117 antigen (C-Kit) on normal and myelomatous plasma cells, Br. J. Haematol., 95:489-493 (1996).
Office Action dated Apr. 11, 2013 for IL App. Ser. No. 217197, 4 pages (with English translation).
Office Action dated Apr. 16, 2013 for CA App. Ser. No. 2652442, 2 pages.
Office Action dated Apr. 27, 2010 for CN App. Ser. No. 200710007097.9, 7 pages (with English translation).
Office Action dated Apr. 28, 2009 for JP App. Ser. No. 2005-124034, 3 pages (with English translation).
Office Action dated Apr. 8, 2013 for U.S. Appl. No. 11/997,719, 55 pages.
Office Action dated Apr. 9, 2013 for CN App. Ser. No. 201080030508.6, 6 pages (with English translation).
Office Action dated Aug. 11, 2006 for CN App. Ser. No. 01819710.8, 6 pages (with English translation).
Office Action dated Aug. 3, 2012 for CN App. Ser. No. 200680020317.5 (with English translation).
Office Action dated Aug. 8, 2003 for PH App. Ser. No. 1-2003-500266, 1 page.
Office Action dated Dec. 20, 2010 for IL App. Ser. No. 181697, 3 pages (with English translation).
Office Action dated Dec. 25, 2009 for CN App. Ser. No. 200710007097.9, 6 pages (with English translation).
Office Action dated Feb. 10, 2006 for CN App. Ser. No. 01819710.8, 8 pages (with English translation).
Office Action dated Jan. 27, 2009 for JP App. Ser. No. 2005-124034, 8 pages (with English translation).
Office Action dated Jul. 15, 2011 for CA App. Ser. No. 2579810, 2 pages.
Office Action dated Jul. 21, 2006 for PH App. Ser. No. 1-2003-500266, 1 pages.
Office Action dated Jul. 24, 2009 for CN App. Ser. No. 200710007096.4, 8 pages (with English translation).
Office Action dated Jul. 27, 2005 for KR App. Ser. No. 10-2003-7005506, 4 pages (with English translation).

(56) References Cited

OTHER PUBLICATIONS

Office Action dated Jun. 26, 2009 for CN App. Ser. No. 200580026468.7, 25 pages (with English translation).
Office Action dated Jun. 27, 2007 for PH App. Ser. No. 1-2003-500266, 1 page.
Office Action dated Jun. 5, 2012 for JP App. Ser. No. 2009-123432, 4 pages (with English translation).
Office Action dated Jun. 7, 2006 for MX App. Ser. No. PA/a/2003/003362, 6 pages (with English translation).
Office Action dated Mar. 14, 2013 for CN App. Ser. No. 200780017371.9, 9 pages (with English translation).
Office Action dated Mar. 21, 2007 for PH App. Ser. No. 1-2003-500266, 1 page.
Office Action dated Mar. 29, 2013 for U.S. Appl. No. 13/624,278, 73 pages.
Office Action dated Mar. 6, 2009 for CN App. Ser. No. 200710007097.9 (with English translation).
Office Action dated Mar. 7, 2007 for NO App. Ser. No. 20031731, 3 pages (with English translation).
Office Action dated May 13, 2005 for CN App. Ser. No. 01819710.8, 8 pages (with English translation).
Office Action dated May 16, 2008 for NO App. Ser. No. 20031731, 2 pages (with English translation).
Office Action dated May 3, 2013 for CA App. Ser. No. 2661702, 2 pages.
Office Action dated Nov. 13, 2012 for JP App. Ser. No. P2008-532141, 8 pages (with English translation).
Office Action dated Nov. 20, 2009 for CN App. Ser. No. 200580026468.7, 9 pages (with English translation).
Office Action dated Nov. 26, 2007 for MX App. Ser. No. PA/a/2005/013764, 6 pages (with English translation).
Office Action dated Oct. 11, 2007 for TW App. Ser. No. 90125928, 5 pages (with English translation).
Office Action dated Oct. 15, 2012 for IL App. Ser. No. 200090, 5 pages (with English translation).
Office Action dated Oct. 15, 2012 for NZ App. Ser. No. 598291, 2 pages.
Office Action dated Oct. 4, 2005 for MX App. Ser. No. PA/a/2003/003362, 8 pages (with English translation).
Office Action dated Oct. 4, 2007 for NO App. Ser. No. 20031731, 2 pages (with English translation).
Office Action dated Sep. 11, 2009 for CN App. Ser. No. 200710007097.9, 8 pages (with English translation).
Office Action dated Sep. 19, 2012 for CA App. Ser. No. 2627598, 3 pages.
Office Action dated Sep. 28, 2011 for KR App. Ser. No. 10-2007-7001347, 12 pages (with English translation).
Office Action dated Sep. 28, 2012 for CN App. Ser. No. 200780017371.9, 9 pages (with English translation).
Office Action dated Sep. 29, 2012 for CN App. Ser. No. 200980103218.7, 13 pages (with English translation).
Office Action dated Sep. 5, 2008 for NO App. Ser. No. 20031731, 2 pages (with English translation).
Office Action dated Sep. 5, 2012 for CN App. Ser. No. 200880003336.6, 12 pages (with English translation).
Office Action dated Sep. 5, 2012 for CN App. Ser. No. 200880115011.7, 6 pages (with English translation).
Office Action dated Sep. 7, 2007 for PH App. Ser. No. 1-2003-500266, 1 page.
Office Action directed at Israel Application No. 207089 dated Nov. 13, 2011, 4 pages (with English translation).
Office Action for Canadian Application No. 2,620,594, dated Aug. 15, 2011, 2 pages.
Office Action for EP App. Ser. No. 08846814.5, dated Apr. 16, 2013, 5 pages.
Office Action for IL 199907 dated Jun. 17, 2010, 3 pages with English translation.
Office Action for IL App. Ser. No. 175363, dated Jan. 2, 2013, 2 pages, with English translation.
Office Action for IL App. Ser. No. 200090, dated Jul. 24, 2013, 5 pages (with English translation).
Office Action for IL App. Ser. No. 205512, dated Dec. 20, 2012, 8 pages, with English translation.
Office Action for IL App. Ser. No. 207089, dated Jan. 6, 2013, 5 pages (with English translation).
Office Action for Indian Application No. 1908/DELNP/2008, dated Feb. 2, 2012, 2 pages.
Office Action for JP App. Ser. No. 2008-556208, dated Jan. 22, 2013, 8 pages, with English translation.
Office Action for JP App. Ser. No. P2008-532141, dated May 21, 2013, 4 pages (with English translation).
Office Action for JP App. Ser. No. P2009-551518, dated Jun. 18, 2013, 5 pages (with English translation).
Office Action for JP2007-542863 dated May 29, 2012, 8 pages with English translation.
Office Action for KR App. Ser. No. 10-2008-7013685, dated May 20, 2013, 10 pages. (with English translation).
Office Action for PH App. Ser. No. 1-2011-502441 dated Oct. 1, 2013, 1 page.
Office Action for U.S. Appl. No. 12/039,381, dated Sep. 12, 2013, 15 pages.
Office Action for U.S. Appl. No. 13/083,338, dated Jan. 3, 2013, 9 pages.
Office Action for U.S. Appl. No. 13/238,085, dated Sep. 6, 2013, 10 pages.
Office Action for U.S. Appl. No. 12/439,339, dated May 23, 2013, 15 pages.
Office Action in AU App. Ser. No. 2006282456, dated Jun. 12, 2009, 1 pages.
Office Action in AU App. Ser. No. 2010285740, dated Aug. 22, 2014, 3 pages.
Office Action in AU App. Ser. No. 2011270165, dated Nov. 6, 2015, 3 pages.
Office Action in BD App. Ser. No. 184/2006, dated May 11, 2007, 2 pages.
Office Action in BR App. Ser. No. PI0418200-6, dated Jun. 16, 2015, 1 page.
Office Action in CA App. Ser. No. 2,704,000, dated Jan. 14, 2016, 3 pages.
Office Action in CA App. Ser. No. 2543859, dated Aug. 19, 2008, 5 pages.
Office Action in CA App. Ser. No. 2543861, dated Aug. 19, 2008, 4 pages.
Office Action in CA App. Ser. No. 2605854, dated Jul. 29, 2009, 2 pages.
Office Action in CA App. Ser. No. 2652442, dated Oct. 4, 2013, 2 pages.
Office Action in CA App. Ser. No. 2676796, dated Dec. 30, 2013, 5 pages.
Office Action in CA App. Ser. No. 2676796, dated Jan. 29, 2015, 5 pages.
Office Action in CA App. Ser. No. 2704000, dated Jul. 14, 2015, 3 pages.
Office Action in CA App. Ser. No. 2704000, dated Mar. 27, 2015, 3 pages.
Office Action in CA App. Ser. No. 2704000, dated Nov. 4, 2014, 3 pages.
Office Action in CA App. Ser. No. 2713930, dated Jan. 30, 2015, 5 pages.
Office Action in CA App. Ser. No. 2713930, dated Sep. 15, 2015, 3 pages.
Office Action in CA App. Ser. No. 2771403, dated Jul. 16, 2014, 3 pages.
Office Action in CA App. Ser. No. 2802644, dated Oct. 23, 2015, 6 pages.
Office Action in CA App. Ser. No. 2828946, dated Nov. 30, 2015, 4 pages.
Office Action in Chinese Application No. 200710007097.9, dated Mar. 6, 2009, 5 pages.
Office Action in CL App. Ser. No. 2012-00412, dated Jan. 28, 2015, 17 pages (with English translation).

(56) References Cited

OTHER PUBLICATIONS

Office Action in CL App. Ser. No. 2012-00412, dated Sep. 3, 2014, 22 pages (with English translation).
Office Action in CN App. Ser. No. 200680020317.5, dated Mar. 4, 2014, 13 pages.
Office Action in CN App. Ser. No. 200680020317.5, dated Nov. 28, 2013, 8 pages (with English translation).
Office Action in CN App. Ser. No. 200680021939.X, dated Mar. 30, 2011, 7 pages (with English translation).
Office Action in CN App. Ser. No. 200680021939.X, dated May 27, 2010, 9 pages (with English translation).
Office Action in CN App. Ser. No. 200680021939.X, dated Sep. 2, 2010, 10 pages (with English translation).
Office Action in CN App. Ser. No. 200780017371.9, dated Dec. 11, 2014, 9 pages (with English translation).
Office Action in CN App. Ser. No. 200780017371.9, dated May 15, 2015, 17 pages (with English translation).
Office Action in CN App. Ser. No. 200780019200.X, dated Apr. 6, 2012, 9 pages (with English translation).
Office Action in CN App. Ser. No. 200780019520.5, dated Dec. 21, 2010, 7 pages (with English translation).
Office Action in CN App. Ser. No. 200780019520.5, dated Sep. 27, 2010, 8 pages (with English translation).
Office Action in CN App. Ser. No. 2008800045113, dated Jul. 5, 2011, 10 pages (with English translation).
Office Action in CN App. Ser. No. 201180030568.2, dated Mar. 24, 2014, 8 pages (with English translation).
Office Action in CN App. Ser. No. 201180030568.2, dated Oct. 12, 2013, 11 pages (with English translation.
Office Action in CN App. Ser. No. 201280010427.9, dated Mar. 31, 2014, 11 pages (with English translation).
Office Action in CN App. Ser. No. 201280010898.X, dated Aug. 11, 2014, 14 pages (with English translation).
Office Action in CN App. Ser. No. 201280010898.X, dated Mar. 30, 2015, 13 pages (with English translation).
Office Action in CO App. Ser. No. 12-022608, dated Dec. 17, 2013, 12 pages (with English translation).
Office Action in DB App. Ser. No. 60/2005, dated Jul. 25, 2006, 2 pages.
Office Action in EP App. Ser. No. 03791389.4, dated Dec. 2, 2014, 5 pages.
Office Action in EP App. Ser. No. 03791389.4, dated Jun. 10, 2014, 4 pages.
Office Action in EP App. Ser. No. 04807580.8, dated Mar. 18, 2014, 12 pages.
Office Action in EP App. Ser. No. 05719973.9, dated Feb. 11, 2011, 7 pages.
Office Action in EP App. Ser. No. 05719973.9, dated Nov. 2, 2011, 4 pages.
Office Action in EP App. Ser. No. 07793075.8, dated Mar. 1, 2011, 3 pages.
Office Action in EP App. Ser. No. 08704376.6, dated Feb. 24, 2014, 4 pages.
Office Action in EP App. Ser. No. 08846814.5, dated Jun. 4, 2014, 4 pages.
Office Action in EP App. Ser. No. 10809938.3, dated Oct. 16, 2014, 5 pages.
Office Action in EP App. Ser. No. 12774278.1, dated Mar. 9, 2015, 6 pages.
Office Action in EP App. Ser. No. 12786619.2, dated Dec. 8, 2015, 4 pages.
Office Action in EP Application No. 07743994.1, dated Sep. 9, 2014, 8 pages.
Office Action in EP Application No. 10809938.3, dated Feb. 10, 2015, 4 pages.
Office Action in HU App. Ser. No. P0302603, dated Apr. 7, 2015, 5 pages (with English translation).
Office Action in ID App. Ser No. W-00 2008 00601, dated Jan. 13, 2012, 4 pages (with English translation).
Office Action in IL App. Ser. No. 188670, dated Jul. 3, 2011, 2 pages (with English translation).
Office Action in IL App. Ser. No. 197002, dated Feb. 8, 2012, 2 pages (with English translation).
Office Action in IL App. Ser. No. 197141, dated Feb. 22, 2012, 18 pages (with English translation).
Office Action in IL App. Ser. No. 205512, dated Oct. 28, 2013, 5 pages (with English translation).
Office Action in IL App. Ser. No. 205512, dated Sep. 22, 2014, 5 pages (with English translation).
Office Action in IL App. Ser. No. 207089, dated Nov. 25, 2013, 6 pages (with English translation).
Office Action in IL App. Ser. No. 217197, dated Oct. 22, 2014, 4 pages (with English translation).
Office Action in IL App. Ser. No. 217197, dated Oct. 25, 2015, 4 pages (with English translation).
Office Action in IL App. Ser. No. 223695, dated Aug. 25, 2015, 6 pages.
Office Action in IL App. Ser. No. 223695, dated Feb. 16, 2015, 5 pages (with English translation).
Office Action in IL App. Ser. No. 227558, dated Aug. 2, 2015, 5 pages (with English translation).
Office Action in IL App. Ser. No. 227777, dated Mar. 12, 2014, 5 pages (with English translation).
Office Action in IL App. Ser. No. 238463, dated Oct. 28, 2015, 5 pages (with English translation).
Office Action in IN App. Ser. No. 1424/CHENP/2008, dated Sep. 19, 2011, 18 pages.
Office Action in IN App. Ser. No. 1571/CHENP/2007, dated Oct. 23, 2013, 2 pages.
Office Action in IN App. Ser. No. 1571/CHENP/2007, dated Dec. 9, 2013, 2 pages.
Office Action in JP App. Ser. No. 2008-530917, dated Oct. 23, 2012, 4 pages (with English translation).
Office Action in JP App. Ser. No. 2011-206481, dated Jun. 2, 2015, 7 pages (with English translation).
Office Action in JP App. Ser. No. 2012-521531, dated Sep. 29, 2015, 4 pages (with English translation).
Office Action in JP App. Ser. No. 2013-510994, dated Jun. 9, 2015, 6 pages (with English translation).
Office Action in JP App. Ser. No. P2009-510543, dated Sep. 29, 2009, 7 pages (with English translation).
Office Action in JP App. Ser. No. P2009-540099, dated Mar. 25, 2014, 6 pages (with English translation).
Office Action in JP App. Ser. No. P2012-521531, dated Mar. 3, 2015, 6 pages (with English translation).
Office Action in JP Application No. P2005-516605 dated Jun. 1, 2010, 3 pages.
Office Action in JP. App. Ser. No. 2013-510994, dated Jul. 28, 2015, 5 pages (with English translation).
Office Action in KR App. Ser. No. 10-2006-7013907, dated Jul. 28, 2007, 7 pages (with English translation).
Office Action in KR App. Ser. No. 10-2006-7013940, dated Jul. 31, 2007, 19 pages (with English translation).
Office Action in KR App. Ser. No. 10-2007-7026886, dated Aug. 27, 2009, 5 pages (with English translation).
Office Action in KR App. Ser. No. 10-2008-7027527, dated Dec. 9, 2013, 6 pages (with English translation).
Office Action in KR App. Ser. No. 10-2008-7029472, dated Mar. 28, 2014, 6 pages (with English translation).
Office Action in KR App. Ser. No. 10-2008-7029577, dated Dec. 30, 2013, 7 pages (with English translation).
Office Action in KR App. Ser. No. 10-2009-7005657, dated Mar. 28, 2014, 6 pages (with English translation.
Office Action in KR App. Ser. No. 10-2009-7013723, dated May 19, 2011, 10 pages (with English translation).
Office Action in KR App. Ser. No. 10-2009-7017694, dated Jan. 29, 2014, 26 pages (with English translation).
Office Action in KR App. Ser. No. 10-2010-7011023, dated Sep. 3, 2014, 14 pages (with English translation).
Office Action in KR App. Ser. No. 10-2010-7018835, dated Sep. 30, 2014, 6 pages (with English translation).

(56) References Cited

OTHER PUBLICATIONS

Office Action in KR App. Ser. No. 10-2012-7003846, dated Oct. 7, 2014, 7 pages.
Office Action in MX App. Ser. No. MX/a/2010/008187, dated Apr. 28, 2014, 4 pages (with English translation).
Office Action in MX App. Ser. No. MX/a/2010/008187, dated Dec. 5, 2013, 8 pages (with English translation).
Office Action in MX App. Ser. No. MX/a/2012/002011, dated Apr. 28, 2014, 10 pages (with English translation).
Office Action in MX App. Ser. No. MX/a/2012/002011, dated Nov. 21, 2013, 8 pages (with English translation).
Office Action in MX App. Ser. No. MX/a/2012/014776, dated Apr. 4, 2014, 22 pages (with English Translation).
Office Action in MX App. Ser. No. MX/a/2012/014776, dated Oct. 15, 2014, 15 pages (with English translation).
Office Action in MX App. Ser. No. MX/a/2013/009931, dated Apr. 9, 2015, 3 pages (with English translation).
Office Action in MX App. Ser. No. MX/a/2013/009931, dated Sep. 5, 2014, 15 pages (with English translation).
Office Action in MX App. Ser. No. MX/a/2014/010594, dated Oct. 13, 2015, 8 pages (with English translation).
Office Action in NO App. Ser. No. 20063383, dated Apr. 15, 2015, 2 pages (with English translation).
Office Action in NZ App. Ser. No. 566793, dated Dec. 4, 2009, 1 page.
Office Action in PH App. Ser. No. 1-2007-502319, dated Dec. 16, 2011, 1 page.
Office Action in PH App. Ser. No. 1-2011-502441, dated Feb. 19, 2014, 2 pages.
Office Action in PH App. Ser. No. 1-2011-502441, dated May 8, 2015, 2 pages.
Office Action in PK App. Ser. No. 1024/2006, dated Dec. 12, 2007, 3 pages.
Office Action in PK App. Ser. No. 1024/2006, dated Feb. 24, 2009, 2 pages.
Office Action in PK App. Ser. No. 1024/2006, dated Oct. 21, 2008, 2 pages.
Office Action in PK App. Ser. No. 155/2005, dated Nov. 17, 2007, 2 pages.
Office Action in PK App. Ser. No. 375/2008, dated Feb. 24, 2009, 1 page.
Office Action in PK App. Ser. No. 375/2008, dated Jul. 20, 2009, 2 pages.
Office Action in PK App. Ser. No. 375/2008, dated Oct. 21, 2008, 3 pages.
Office Action in RU App. Ser. No. 2006134254, dated Oct. 13, 2006, 4 pages (with English translation).
Office Action in RU App. Ser. No. 2006134254, dated Sep. 18, 2007, 9 pages (with English translation).
Office Action in RU App. Ser. No. 2008110932, dated Dec. 3, 2008, 6 pages (with English translation).
Office Action in RU App. Ser. No. 2012103471, dated May 20, 2014, 5 pages (with English translation).
Office Action in RU App. Ser. No. 2012103471, dated Sep. 16, 2014, 5 pages (with English translation).
Office Action in RU App. Ser. No. 2012158142, dated Feb. 12, 2015, 21 pages (with English translation).
Office Action in RU App. Ser. No. 2013139556, dated Dec. 2, 2013, 6 pages (with English translation).
Office Action in RU App. Ser. No. 2013140169, dated Nov. 6, 2015, 9 pages (with English.
Office Action in TW App. Ser. No. 095130665, dated Mar. 2, 2012, 8 pages (with English translation).
Office Action in TW App. Ser. No. 100104281, dated Dec. 9, 2014, 13 pages (with English translation).
Office Action in U.S. Appl. No. 12/039,381, dated Oct. 7, 2015, 22 pages.
Office Action in U.S. Appl. No. 11/508,322, dated Dec. 18, 2008, 19 pages.
Office Action in U.S. Appl. No. 11/508,322, dated May 29, 2009, 8 pages.
Office Action in U.S. Appl. No. 11/662,425, dated Feb. 27, 2014, 152 pages.
Office Action in U.S. Appl. No. 11/662,425, dated Jun. 5, 2014, 30 pages.
Office Action in U.S. Appl. No. 11/662,425, dated Sep. 17, 2014, 3 pages.
Office Action in U.S. Appl. No. 11/997,543, dated Mar. 11, 2014, 20 pages.
Office Action in U.S. Appl. No. 12/031,568, dated Aug. 13, 2010, 15 pages.
Office Action in U.S. Appl. No. 12/031,568, dated Feb. 5, 2010, 16 pages.
Office Action in U.S. Appl. No. 12/031,568, dated May 12, 2011, 26 pages.
Office Action in U.S. Appl. No. 12/039,381, dated Feb. 26, 2015, 13 pages.
Office Action in U.S. Appl. No. 12/039,381, dated Jan. 9, 2014, 16 pages.
Office Action in U.S. Appl. No. 12/039,381, dated May 29, 2014, 78 pages.
Office Action in U.S. Appl. No. 12/315,291, dated Jan. 12, 2011, 9 pages.
Office Action in U.S. Appl. No. 12/315,291, dated Jun. 7, 2010, 20 pages.
Office Action in U.S. Appl. No. 12/558,982, dated Apr. 5, 2011, 31 pages.
Office Action in U.S. Appl. No. 12/558,982, dated Aug. 29, 2011, 13 pages.
Office Action in U.S. Appl. No. 12/864,817, dated Aug. 15, 2014, 79 pages.
Office Action in U.S. Appl. No. 12/867,646, dated Oct. 26, 2011, 37 pages.
Office Action in U.S. Appl. No. 13/238,085, dated Nov. 12, 2013, 74 pages.
Office Action in U.S. Appl. No. 13/805,826, dated Apr. 2, 2014, 8 pages.
Office Action in U.S. Appl. No. 13/805,826, dated Jul. 1, 2014, 88 pages.
Office Action in U.S. Appl. No. 13/805,826, dated Sep. 23, 2014, 25 pages.
Office Action in U.S. Appl. No. 13/870,507, dated Apr. 1, 2015, 82 pages.
Office Action in U.S. Appl. No. 13/870,507, dated Dec. 12, 2014, 10 pages.
Office Action in U.S. Appl. No. 13/923,858, dated Apr. 18, 2014, 64 pages.
Office Action in U.S. Appl. No. 13/923,858, dated Dec. 5, 2014, 67 pages.
Office Action in U.S. Appl. No. 13/923,858, dated Jul. 29, 2015, 15 pages.
Office Action in U.S. Appl. No. 13/983,891, dated Jan. 22, 2014, 11 pages.
Office Action in U.S. Appl. No. 14/002,018, dated Apr. 14, 2014, 28 pages.
Office Action in U.S. Appl. No. 14/002,018, dated Jul. 25, 2014, 14 pages.
Office Action in U.S. Appl. No. 14/002,018, dated Jun. 9, 2014, 19 pages.
Office Action in U.S. Appl. No. 14/438,366, dated Sep. 28, 2015, 8 pages.
Office Action in U.S. Appl. No. 11/065,631, dated Feb. 28, 2008, 12 pages.
Office Action in VN App. Ser. No. 1-2008-00723, dated Mar. 11, 2010, 4 pages (with English translation).
Office Action in VN App. Ser. No. 1-2011-03484, dated Dec. 31, 2013, 2 pages (with English translation).
Office Action issued for CN 200880002425.9 dated Mar. 2, 2011, 10 pages with English translation.
Office Action issued for EP 06768437.3 (EPO Form1224) dated Oct. 28, 2010, 47 pages.

(56) References Cited

OTHER PUBLICATIONS

Office Action issued for European Search Report for European Application No. 06782407 dated Sep. 29, 2011, 6 pages.
Office Action issued for Japanese Application No. 2007-529565 dated Dec. 13, 2011, 7 pages with English full translation.
Office Action issued for JP Appl. No. 2007-529565 dated May 8, 2012, 6 pages with English translation.
Office Action issued in MX App. Ser. No. MX/a/2012/002011, dated Jul. 17, 2013, 6 pages (with English translation).
Office Action dated Jan. 7, 2011, in U.S. Appl. No. 12/092,539, 12 pages.
Office Action, U.S. Appl. No. 11/347,749 dated Feb. 9, 2009, 6 pages.
Office Communication dated Sep. 13, 2004 for U.S. Appl. No. 10/420,466, 7 pages.
Office Letter Confirmation of Amendment After Allowance dated Jan. 11, 2011 for CA App. Ser. No. 2426461, 1 pages.
Office Letter re Notice of Allowance dated May 25, 2012 for ZA App. Ser. No. 201108697, 3 pages.
Official Letter and Notice of Allowance for AU App. Ser. No. 2008211952, dated Jul. 10, 2012, 10 pages.
Official Letter and Notice of Allowance for AU App. Ser. No. 2008325608, dated Feb. 27, 2013, 7 pages.
Official Letter dated Jun. 27, 2013 in CA App. Ser. No. 2661333, 2 pages.
Official Letter in AU App. Ser. No. 2006282456, dated May 15, 2012, 1 page.
Official Letter in AU App. Ser. No. 2006282456, dated Sep. 24, 2012, 259 pages.
Official Letter in BD App. Ser. No. 184/2006, dated Feb. 2, 2012, 1 page.
Official Letter re Deficiencies in sequence listing in EP App. Ser. No. 06796594.7, dated Mar. 10, 2008, 3 pages.
Official Letter re Grant of Request for Correction of Specification for SG App. Ser. No. 201108602-2, dated Aug. 8, 2012, 2 pages.
Official Letter re Granting Patent in EP App. Ser. No. 06796594.7, dated Sep. 25, 2012, 270 pages.
Official Letter re Intention to Grant Patent in EP App. Ser. No. 05719973.9, dated Feb. 6, 2012, 553 pages.
Official Letter re invitation to declare maintenance in EP App. Ser. No. 06796594.7, dated Sep. 26, 2011, 1 page.
Official Letter re invitation to declare maintenance in EP App. Ser. No. 07793075.8, dated Sep. 27, 2010, 1 page.
Official Letter re invitation to declare maintenance in EP App. Ser. No. 07805959.9, dated Dec. 3, 2010, 1 page.
Official Letter re invitation to declare maintenance in EP App. Ser. No. 08711837.8, dated Apr. 14, 2011, 1 page.
Official Letter re invitation to declare maintenance in EP App. Ser. No. 09713617.0, dated May 17, 2011, 5 pages.
Official Notification in CA App. Ser. No. 2771403, dated Dec. 16, 2014, 1 page.
Official Notification in CO App. Ser. No. 12-022608, dated Jan. 6, 2015, 8 pages (with English translation).
Official Notification in EP App. Ser. No. 04807580.8, dated Jun. 16, 2014, 1 pages.
Official Notification in EP App. Ser. No. 04807580.8, dated Jun. 27, 2014, 17 pages.
Official Notification in HU App. Ser. No. P0302603, dated Nov. 26, 2015, 4 pages (with English translation).
Official Notification re Decision on Petition in U.S. Appl. No. 11/997,719, dated Sep. 23, 2014, 1 page.
Official Notification re Interview Summary in U.S. Appl. No. 13/805,826, dated Dec. 1, 2014, 3 pages.
Official Notification re Interview Summary in U.S. Appl. No. 14/002,018, dated Oct. 6, 2014, 2 pages.
Ohe et al.,"Randomized phase III study of cisplatin plus irinotecan versus carboplatin plus paclitaxel, cisplatin plus gemcitabine, and cisplatin plus vinorelbine for advanced non-small-cell lung cancer: Four-Arm Cooperative Study in Japan," *Ann Oncol.*, 18(2):317-323 (2007).
Okayama et al., "Activation of Eosinophils with Cytokines Produced by Lung Mast Cells," Int Arch Allergy Immunol., 114(suppl 1):75-77 (1997).
Okayama et al., "Human Lung Mast Cells are Enriched in the Capacity to Produce Granulocyte-Macrophage Colony-Stimulating Factor in Response to IgE-Dependent Stimulation," Eur. J. Immunol., 28:708-715 (1998).
Okura et al., "Effects of monoclonal anti-c-kit antibody (ACK2) on melanocytes in newborn mice," J. Invest. Dermatol., 105(3):322-328 (1995).
Olaso et al., "DDR2 receptor promotes MMP-2-mediated proliferation and invasion by hepatic stellate cells," J. Clin. Invest., 108(9):1369-1378 (2001).
O'Reilly et al., "Hydrolysis of tert-Butyl Methyl Ether (MTBE) in Dilute Aqueous Acid," Environ. Sci. Technol., 2001, 35:3954-3961.
Ozols et al., "Phase III trial of carboplatin and paclitaxel compared with cisplatin and paclitaxel in patients with optimally resected stage III ovarian cancer: a Gynecologic Oncology Group study," J. Clin. Oncol., 21(17):3194-3200 (2003).
Pacini, "38th Annual Meeting of the European Thyroid Association", European Thyroid Association, Santiago de Compostela, Spain, Aug. 15, 2014, p. 73-p. 226.
Pakistani Office Action for App. Ser. No. 94/2011, dated May 9, 2012, 2 pages.
Pandey et al., "Identification of Orally Active, Potent, and Selective 4-Piperazinylquinazolines as Antagonists of the Platelet-Derived Growth Factor Receptor Tyrosine Kinase Family", Journal of Medicinal Chemistry., 45, 3772-3793, 2002.
Park, "Serum Angiopoietin-2 as a Clinical Market for Lung Cancer," Chest, Jul. 2007, 132(1):200.
Partial European Search Report for App. Ser. No. 01976786.2, dated Apr. 6, 2004, 5 pages.
Patel et al., "The effect of excipients on the stability of levothyroxine sodium pentahydrate tablets," Int'l J Pharm., 2003, 264:35-43.
Paterson et al., "Preclinical studies of fibroblast growth factor receptor 3 as a therapeutic target in multiple myeloma," British Journal of Haematology, 124:595-603 (2004).
Paulus, "Preparation and Biomedical Applications of Bispecific Antibodies", Behring Inst. Mitt. 78: 118-132 (1985).
Payment of Final Fee and Amendment after Allowance in CA App. Ser. No. 2771403, dated Nov. 24, 2014, 3 pages.
Paz et al., "Development of angiogenesis inhibitors to vascular endothelial growth factor receptor 2. Current status and future perspective," Frontiers in Bioscience, 10:1415-1439 (May 1, 2005).
Pearson, "Rapid and Sensitive Sequence Comparison with FASTP and FASTA", Methods in Enzymology 183 :63-98 (1990).
Petition in JP App. Ser. No. 2007-532099, dated Dec. 25, 2007, 3 pages (with English translation).
Petition in JP App. Ser. No. 2007-532099, dated Sep. 25, 2007, 3 pages (with English translation).
Petition in JP App. Ser. No. 2009-554285, dated Aug. 19, 2010, 3 pages (with English translation).
Petti et al., "Temporal quantitation of mutant Kit tyrosine kinase signaling attenuated by a novel thiophene kinase inhibitor OSI-930", Molecular Cancer Therapeutics., 4:1186-1197, 2005.
Plowright et al., "Ectopic expression of fibroblast growth factor receptor 3 promotes myeloma cell proliferation and prevents apoptosis," Blood, 95:992-998 (2000).
Podar et al., "GW654652, the pan-inhibitor of VEGF receptors, blocks the growth and migration of multiple myeloma cells in the bone marrow microenvironment", Blood.,103, 3474-3479, 2004.
Polverino et al, "AMG 706, an Oral, Multikinase Inhibitor that Selectively Targets Vascular Endothelial Growth Factor, Platelet—Derived Growth Factor, and Kit Receptors, Potently inhibits Angiogenesis and Induces Regression in Tumor Xenografts," Cancer Research, 66(17):8715-8721 (2006).
Preliminary Amendment and Response to Restriction Requirement in U.S. Appl. No. 12/439,339, filed Aug. 10, 2011, 24 pages.
Preliminary Amendment and Response to Restriction Requirement in U.S. Appl. No. 13/083,338, filed Apr. 30, 2012, 16 pages.
Preliminary Amendment dated Apr. 26, 2013 for U.S. Appl. No. 13/870,507, 10 pages.

(56) References Cited

OTHER PUBLICATIONS

Preliminary Amendment filed in EP App. Ser. No. 12786619.2, dated Nov. 13, 2013, 7 pages.
Preliminary Amendment filed in U.S. Appl. No. 14/117,276, dated Nov. 12, 2013, 11 pages.
Preliminary Amendment filed in U.S. Appl. No. 14/122,339, dated Aug. 27, 2015, 7 pages.
Preliminary Amendment filed in U.S. Appl. No. 14/122,339, dated Nov. 26, 2013, 10 pages.
Preliminary Amendment filed on Apr. 18, 2003 for U.S. Appl. No. 10/420,466, 376 pages.
Preliminary Amendment filed on Dec. 2, 2005 for U.S. Appl. No. 10/420,466, 36 pages.
Preliminary Amendment filed on Feb. 3, 2006 for U.S. Appl. No. 11/293,785, 33 pages.
Preliminary Amendment filed on May 23, 2003 for KR App. Ser. No. 10-2003-7005506, 42 pages (with English translation).
Preliminary Amendment filed on Oct. 27, 2003 for U.S. Appl. No. 10/420,517, 41 pages.
Preliminary Amendment for U.S. Appl. No. 13/624,278, filed Sep. 21, 2012, 7 pages.
Preliminary Amendment in U.S. Appl. No. 10/577,043, dated Apr. 24, 2006, 12 pages.
Preliminary Amendment in U.S. Appl. No. 10/577,065, dated Apr. 24, 2006, 11 pages.
Preliminary Amendment in U.S. Appl. No. 11/508,322, dated May 15, 2007, 4 pages.
Preliminary Amendment in U.S. Appl. No. 11/508,322, dated May 19, 2008, 15 pages.
Preliminary Amendment in U.S. Appl. No. 11/508,322, dated Nov. 5, 2007, 28 pages.
Preliminary Amendment in U.S. Appl. No. 11/892,785, dated Apr. 7, 2008, 16 pages.
Preliminary Amendment in U.S. Appl. No. 12/031,568, dated Jun. 6, 2008, 7 pages.
Preliminary Amendment in U.S. Appl. No. 12/315,291, dated Mar. 19, 2009, 17 pages.
Preliminary Amendment in U.S. Appl. No. 12/527,633, dated Apr. 14, 2010, 58 pages.
Preliminary Amendment in U.S. Appl. No. 12/527,633, dated Aug. 18, 2009, 62 page.
Preliminary Amendment in U.S. Appl. No. 12/867,646, dated Aug. 13, 2010, 5 pages.
Prior Art Submission and List of Corresponding Applications in IL Office Action in IL App. Ser. No. 227558, dated Nov. 30, 2015, 3 pages (with English translation).
Pritzker, "Cancer Biomarkers: Easier Said Than Done," Clinical Chemistry, 48(8):1147-1150 (2002).
Reasons for Reexamination dated Sep. 11, 2012 for CN App. Ser. No. 200680020317.5, 7 pages (with English translation).
Rectification for a Voluntary Amendment in CN App. Ser. No. 201510031628.2, dated Oct. 10, 2015, 5 pages (with English translation).
Reexamination filed on May 25, 2004 for TW App. Ser. No. 90125928, 59 pages (with English translation).
Reexamination filed on Nov. 25, 2004 for TW App. Ser. No. 90125928, 59 pages (with English translation).
Registered dated Feb. 24, 2009 for PH App. Ser. No. 1-2003-500266, 3 pages.
Registry's Letter in MT App. Ser. No. 3723, dated Sep. 29, 2007, 1 page.
Rejection dated Apr. 26, 2004 for TW App. Ser. No. 90125928, 10 pages (with English translation).
Ren, Xiubao, "Advances in Medical Therapy for Melanoma," Journal of Practical Oncology, Dec. 2010, 2(25):137-140 (with English translation).
Reply to communication from the Examining Division for EP App. Ser. 06023078.6, dated Feb. 4, 2008, 97 pages.
Reply to communication from the Examining Division for EP App. Ser. 06023078.6, dated Sep. 11, 2007, 10 pages.
Reply to communication from the Examining Division for EP App. Ser. No. 01976786.2, dated Jan. 25, 2006, 36 pages.
Reply to communication from the Examining Division for EP App. Ser. No. 01976786.2, dated Jul. 19, 2006, 124 pages.
Reply to communication from the Examining Division for EP App. Ser. No. 04025700.8, dated Feb. 15, 2007, 2 pages.
Reply to communication from the Examining Division for EP Ser. Appl. No. 04025700.8, dated Jan. 26, 2007, 232 pages.
Reply to communication from the Examining Division for EP Ser. Appl. No. 04025700.8, dated Sep. 12, 2006, 21 pages.
Reply to Examination Report dated Feb. 8, 2013 for EP App. Ser. No. 07743994.1, 4 pages.
Reply to final office action in U.S. Appl. No. 13/805,826, dated Nov. 26, 2014, 7 pages.
Reply to Final Office Action in U.S. Appl. No. 14/002,018, dated Oct. 1, 2014, 6 pages.
Reply to Notice of Allowance in U.S. Appl. No. 11/662,425, dated Jan. 20, 2015, 5 pages.
Reply to Notice of Non-Compliant Amendment in U.S. Appl. No. 12/315,291, dated Nov. 2010, 3 pages.
Reply to official communication for EP App. Ser. No. 05783232.1, dated Apr. 30, 2008, 13 pages.
Reply to Restriction Requirement in U.S. Appl. No. 13/870,507, dated Jan. 27, 2015, 3 pages.
Reply to the invitation to remedy deficiencies for EP App. Ser. No. 06023078.6, dated Jan. 11, 2007, 3 pages.
Request for accelerated examination in KR App. Ser. No. 10-2012-7003846, dated Jun. 18, 2014, 29 pages (with English translation).
Request for amendment of the text intended for grant and translation of claims for EP App. Ser. No. 04025700.8, dated Feb. 1, 2008, 41 pages.
Request for amendment of the text intended for grant and translation of claims for EP App. Ser. No. 06023078.6, dated Nov. 5, 2008, 19 pages.
Request for Continued Examination (RCE) in U.S. Appl. No. 13/624,278, dated Sep. 24, 2014, 1 page.
Request for Continued Examination (RCE) in U.S. Appl. No. 11/997,719, dated Aug. 29, 2014, 1 page.
Request for Continued Examination (RCE) transmittal for U.S. Appl. No. 12/864,817, filed Dec. 22, 2011, 1 page.
Request for correction of errors in filed documents for EP App. Ser. No. 06023078.6, dated Feb. 2007, 4 pages.
Request for Examination filed in KR App. Ser. No. 10-2012-7033886, dated Aug. 26, 2015, 12 pages (with English translation).
Request for Examination filed in NO App. Ser. No. 20063383, dated Aug. 26, 2015, 8 pages (with English translation).
Request for Examination filed in NO App. Ser. No. 20063383, dated Jun. 19, 2015, 8 pages (with English translation).
Request for Examination in CA App. Ser. No. 2713930, dated Oct. 21, 2013, 8 pages.
Request for Re-Examination in CN App. Ser. No. 200780017371.9, dated Oct. 11, 2013, 9 pages (with English translation).
Request for Substantive Examination for ID App. Ser. No. W-00201201031, filed Jun. 3, 2013, 6 pages (with English translation).
Request for Substantive Examination for UA App. Ser. No. a201203132, filed Apr. 15, 2013, 14 pages (with English translation).
Request for Voluntary Amendments filed May 10, 2012, in Ukraine Patent Application No. a 2012 03132, 11 pages with English Abstract.
Request to Amend Complete Specification dated Feb. 15, 2013 for AU App. Ser. No. 2008325608, 23 pages.
Request to Amend Complete Specification dated May 9, 2013 for AU App. Ser. No. 2009210098, 22 pages.
Request to Enter PPH and Amended Claims in MX App. Ser. No. MX/a/2014/010594, dated Oct. 8, 2015, 10 pages (with English translation).
Response and Amended Claims filed in EP App. Ser. No. 08846814.5, filed Aug. 1, 2013, 14 pages.
Response and Amended Claims filed in EP App. Ser. No. 10809938.3, filed Jul. 19, 2013, 7 pages.
Response and Amendment for CA App. Ser. No. 2652442, dated Sep. 5, 2013, 17 pages.

(56) References Cited

OTHER PUBLICATIONS

Response filed in CA App. Ser. No. 2652442, dated Jan. 8, 2014, 5 pages.
Response filed in CA App. Ser. No. 2713930, dated Jun. 22, 2015, 8 pages.
Response filed in CN App. Ser. No. 201280010898.X, dated Jun. 15, 2015, 12 pages (with English translation).
Response filed in CO App. Ser. No. 12-022608, dated Nov. 13, 2013, 13 pages (with English translation).
Response filed in IL App. Ser. No. 195282, filed Jul. 11, 2013, 13 pages (with English translation).
Response filed in IN App. Ser. No. 1571/CHENP/2007, dated Oct. 30, 2013, 9 pages.
Response filed in KR App. Ser. No. 10-2009-7005657, dated Nov. 21, 2013, 46 pages (with English translation).
Response filed in MX App. Ser. No. MX/a/2010/008187, dated Nov. 4, 2013, 21 pages (with English translation).
Response filed in PH App. Ser. No. 1-2011-502441, dated Feb. 28, 2014, 4 pages.
Response filed in PH App. Ser. No. 1-2011-502441, dated May 22, 2015, 25 pages.
Response filed in PH App. Ser. No. 1-2011-502441, dated Nov. 4, 2013, 28 pages.
Response filed in U.S. Appl. No. 10/797,903, dated Dec. 29, 2010, 13 pages.
Response filed in U.S. Appl. No. 13/870,507, dated Jun. 18, 2015, 13 pages.
Response filed in VN App. Ser. No. 1-2011-03484, dated Feb. 28, 2014, 40 pages (with English translation).
Response filed on Apr. 11, 2006 for CN App. Ser. No. 01819710.8, 4 pages (with English translation).
Response filed on Apr. 17, 2007 for PH App. Ser. No. 1-2003-500266, 1 page.
Response filed on Apr. 27, 2006 for AU App. Ser. No. 2001295986, 22 pages.
Response filed on Apr. 30, 2008 for PH App. Ser. No. 1-2003-500266, 1 page.
Response filed on Aug. 13, 2009 for CA App. Ser. No. 2426461, 4 pages.
Response filed on Aug. 14, 2006 for PH App. Ser. No. 1-2003-500266, 1 page.
Response filed on Aug. 18, 2008 for NO App. Ser. No. 20031731, 2 pages (with English translation).
Response filed on Aug. 21, 2006 for MX App. Ser. No. PA/a/2003/003362, 5 pages (with English translation).
Response filed on Aug. 26, 2004 for NZ App. Ser. No. 525324, 3 pages.
Response filed on Aug. 5, 2003 for PH App. Ser. No. 1-2003-500266, 1 page.
Response filed on Dec. 11, 2007 for TW App. Ser. No. 90125928, 54 pages (with English translation).
Response filed on Dec. 15, 2005 for MX App. Ser. No. PA/a/2003/003362, 9 page (with English translation).
Response filed on Dec. 4, 2007 for IL App. Ser. No. 155447, 35 pages (with English translation).
Response filed on Feb. 23, 2009 for CA App. Ser. No. 2426461, 31 pages.
Response filed on Feb. 26, 2008 for U.S. Appl. No. 11/293,785, 16 pages.
Response filed on Jan. 11, 2010 for CN App. Ser. No. 200580026468.7, 4 pages (with English translation).
Response filed on Jan. 21, 2005 for NZ App. Ser. No. 525324, 2 pages.
Response filed on Jan. 26, 2010 for CN App. Ser. No. 200710007097.9, 3 pages (with English translation).
Response filed on Jan. 26, 2011 for IL App. Ser. No. 181697, 5 pages (with English translation).
Response filed on Jul. 1, 2005 for U.S. Appl. No. 10/420,466, 14 pages.
Response filed on Jul. 2, 2009 for CN App. Ser. No. 200710007097.9, 4 pages (with English translation).
Response filed on Jul. 26, 2006 for AU App. Ser. No. 2001295986, 11 pages.
Response filed on Jul. 31, 2007 for PH App. Ser. No. 1-2003-500266, 1 page.
Response filed on Jun. 22, 2010 for CN App. Ser. No. 200710007097.9, 3 pages (with English translation).
Response filed on Mar. 17, 2005 for RU App. Ser. No. 2003114740, 75 pages (with English translation).
Response filed on May 13, 2009 for IL App. Ser. No. 189677, 125 pages (with English translation).
Response filed on May 16, 2008 for CA App. Ser. No. 2426461, 79 pages.
Response filed on May 20, 2010 for CA App. Ser. No. 2426461, 23 pages.
Response filed on May 7, 2008 for NO App. Ser. No. 20031731, 2 pages (with English translation).
Response filed on May 8, 2008 for AU App. Ser. No. 2006236039, 2 pages.
Response filed on Nov. 19, 2009 for CN App. Ser. No. 200710007097.9, 9 pages (with English translation).
Response filed on Nov. 30, 2004 for RU App. Ser. No. 2003114740, 90 pages (with English translation).
Response filed on Oct. 13, 2008 for NO App. Ser. No. 20031731, 400 pages (with English translation).
Response filed on Oct. 15, 2007 for PH App. Ser. No. 1-2003-500266, 1 page.
Response filed on Oct. 8, 2004 for U.S. Appl. No. 10/420,466, 19 pages.
Response filed on Oct. 9, 2006 for CN App. Ser. No. 01819710.8, 2 pages (with English.
Response filed on Sep. 10, 2007 for NO App. Ser. No. 20031731, 60 pages (with English translation).
Response filed on Sep. 13, 2005 for CN App. Ser. No. 01819710.8, 7 pages (with English translation).
Response filed on Sep. 15, 2003 for PH App. Ser. No. 1-2003-500266, 1 page.
Response filed on Sep. 21, 2011 for CA App. Ser. No. 2579810, 16 pages.
Response filed on Sep. 23, 2009 for CN Patent Application No. 200580026468.7, 4 pages with English translation.
Response filed on Sep. 8, 2003 for PH App. Ser. No. 1-2003-500266, 1 page.
Response in AU App. Ser. No. 2011270165, dated Dec. 4, 2015, 5 pages.
Response in EP App. Ser. No. 06796594.7, dated Mar. 31, 2008, 3 pages.
Response in EP App. Ser. No. 12774278.1, dated Oct. 13, 2014, 4 pages.
Response in Reexamination and Invalidation Procedure in CN App. Ser. No. 200780017371.9, dated Jan. 19, 2015, 8 pages (with English translation).
Response to Advisory Action in U.S. Appl. No. 12/315,291, dated Mar. 31, 2011, 6 pages.
Response to AU OA for AU 2008211952 filed on Jun. 28, 2012, 36 pages.
Response to Australian Office Action filed on Apr. 29, 2010 for corresponding AU Application No. 2006285673, 11 pages.
Response to Australian Office Action filed on Jul. 28, 2010 for corresponding AU Application No. 2006285673, 6 pages.
Response to Australian Office Action filed on Oct. 16, 2009 for corresponding AU Application No. 2006285673, 14 pages.
Response to Canadian Office Action filed Feb. 13, 2012, in Canadian Application No. 2,620,594, 8 pages.
Response to Canadian Office Action filed on Apr. 12, 2011 for corresponding CA Application No. 2,620,594, 4 pages.
Response to Canadian Office Action filed on Apr. 26, 2011 for corresponding CA Application No. 2,620,594.
Response to Canadian Office Action filed on Jun. 21, 2010 for corresponding CA Application No. 2,620,594, 18 pages.

(56) References Cited

OTHER PUBLICATIONS

Response to Chinese Office Action filed on Jul. 11, 2012 for Chinese Patent Application No. 200680036592.6, 17 pages with English translation.
Response to Chinese Office Action filed on Mar. 5, 2010 for corresponding CN Application No. 200680036592.6, 11 pages (with English translation).
Response to Chinese Office Action for CN 200680020317.5 dated Sep. 11, 2012, 7 pages with English translation.
Response to CN OA for CN200880003336.6 filed on May 3, 2012, 15 pages.
Response to Communication in EP App. Ser. 07743994.1, dated Dec. 22, 2014, 62 pages.
Response to EESR in EP App. Ser. No. 09713617.0, dated Sep. 2, 2011, 12 pages.
Response to EP OA for EP 07806561.2 filed on Apr. 18, 2012, 8 pages.
Response to Examination Report in AU App. Ser. No. 2005217325, dated Oct. 26, 2007, 33 pages.
Response to Examination Report in AU App. Ser. No. 2005217328, dated Sep. 20, 2007, 6 pages.
Response to Examination Report in AU App. Ser. No. 2007288793, dated Mar. 30, 2012, 5 pages.
Response to Examiner's Report in CL App. Ser. No. 2012-00412, dated Mar. 30, 2015, 16 pages (with English translation).
Response to Examiner's Substantive Report in CL App. Ser. No. 2012-00412, dated Nov. 28, 2014, 39 pages (with English translation).
Response to Extended European Search Report in EP App. Ser. No. 07793075.8, dated Nov. 8 2010, 11 pages.
Response to Extended European Search Report in EP App. Ser. No. 07805959.9, dated Mar. 29, 2011, 2 pages.
Response to Final Rejection in U.S. Appl. No. 12/039,381, dated Dec. 22, 2015, 10 pages.
Response to Hearing Notice in IN App. Ser. No. 1424/CHENP/2008, dated Sep. 11, 2012, 14 pages.
Response to IL OA for IL 195282 filed on May 28, 2012, 5 pages.
Response to Indian Office Action dated Feb. 2, 2012, dated Jun. 22, 2012, for Application No. 1908/DELNP/2008, 27 pages.
Response to Israeli Office Action filed on Sep. 7, 2010 for the corresponding Israeli Application No. 189589, 9 pages.
Response to Israeli Office Action, filed Jul. 24, 2012 for corresponding Israeli Patent Application No. 189589, 7 pages.
Response to Japanese Office Action dated Jul. 17, 2012 for Japanese Application No. 2007-533350, 12 pages with English translation.
Response to Japanese Office Action filed on Jan. 9, 2013 for corresponding Japanese Application JP-2007-533350, 6 pages.
Response to Korean Office Action filed on Feb. 24, 2010 for corresponding KR Application No. 10-2008-7005195, 31 pages with English translation.
Response to Korean Office Action filed on Jul. 29, 2010 for corresponding KR Application No. 10-2008-7005195, 26 pages with English translation.
Response to Notice of Allowability filed on Dec. 13, 2007 for PH App. Ser. No. 1-2003-500266, 1 page.
Response to Notice of Allowance in U.S. Appl. No. 13/205,328, dated Jul. 8, 2014, 7 pages.
Response to Notice of Incomplete Reply in U.S. Appl. No. 11/892,785, dated Apr. 17, 2008, 7 pages.
Response to Notice of Missing Parts and Preliminary Amendment in U.S. Appl. No. 11/892,785, dated Mar. 17, 2008, 4 pages.
Response to Notice Prior to Examination filed in IL App. Ser. No. 217197, filed Jul. 31, 2013, 9 pages (with English translation).
Response to Notice Prior to Examination filed on Apr. 22, 2009 for IL App. Ser. No. 181697, 11 pages (with English translation).
Response to Notice Prior to Examination filed on Jan. 11, 2009 for IL App. Ser. No. 189677, 7 pages (with English translation).
Response to Notice Prior to Examination in IL App. Ser. No. 188670, dated Nov. 22, 2009, 29 pages (with English translation).
Response to Notice Prior to Examination in IL App. Ser. No. 197002, dated Oct. 13, 2010, 18 pages (with English translation).
Response to Notice Prior to Examination in IL App. Ser. No. 197141, dated Jun. 1, 2010, 22 pages (with English translation).
Response to OA for EP 10015141 filed on Mar. 5, 2012, 47 pages.
Response to Office Action dated Feb. 7, 2013 for CN App. Ser. No. 201080030508.6, 17 pages (with English translation).
Response to Office Action dated Jul. 5, 2012 for CN App. Ser. No. 200880115011.7, 24 pages (with English translation).
Response to Office Action dated Nov. 30, 2012 for CN App. Ser. No. 200780017371.9, 4 pages (with English translation).
Response to Office Action directed at Australian Appl. No. 2006309551 filed on Mar. 28, 2012, 27 pages.
Response to Office Action filed in EP App. Ser. No. 04807580.8, dated May 16, 2014, 13 pages.
Response to Office Action filed on Jan. 25, 2013 for CA App. Ser. No. 2627598, 9 pages.
Response to Office Action filed on Jul. 11, 2012 for CN App. Ser. No. 200880003336.6 (with English translation), 10 pages.
Response to Office Action filed on May 29, 2012 for RU App. Ser. No. 2012103471 (with English translation), 7 pages.
Response to Office Action for Australian App. Ser. No. 2006309551, filed on Mar. 28, 2012.
Response to Office Action for CA App. Ser. No. 2661702, filed Jul. 16, 2013, 13 pages.
Response to Office Action for EP 08704376.6 dated Jan. 2, 2013, 22 pages.
Response to Office Action for IL 199907 filed on Oct. 11, 2010, 4 pages (with English translation).
Response to Office Action for Israeli App. Ser. No. 205512, filed on Mar. 11, 2012 (with English translation), 12 pages.
Response to Office Action for Israeli App. Ser. No. 207089, filed on Mar. 11, 2012, with English translation, 13 pages.
Response to Office Action for MX App. Ser. No. MX/a/2012/002011, dated Aug. 29, 2013, 12 pages (with English translation).
Response to Office Action for U.S. Appl. No. 13/322,961, dated Jan. 25, 2013, 22 pages.
Response to Office Action for U.S. Appl. No. 10/420,466 dated Jun. 29, 2005, 14 pages.
Response to Office Action in AU App. Ser. No. 2006282456, dated Jul. 16, 2009, 2 pages.
Response to office action in AU App. Ser. No. 2007289787, dated Feb. 16, 2012, 27 pages.
Response to office action in AU App. Ser. No. 2010285740, dated Oct. 28, 2014, 14 pages.
Response to Office Action in BD App. Ser. No. 184/2006, dated Dec. 13, 2007, 2 pages.
Response to Office Action in CA App. Ser. No. 2605854, dated Oct. 8, 2009, 18 pages.
Response to Office Action in CA App. Ser. No. 2661333, dated Nov. 12, 2013, 18 pages.
Response to Office Action in CA App. Ser. No. 2676796, dated Jun. 27, 2014, 18 pages.
Response to Office Action in CA App. Ser. No. 2704000, dated Dec. 19, 2014, 13 pages.
Response to Office Action in CA App. Ser. No. 2771403, dated Sep. 10, 2014, 11 pages.
Response to Office Action in CN App. Ser. No. 200680020317.5 filed on Jan. 9, 2014, 7 pages (with English translation).
Response to Office Action in CN App. Ser. No. 200680021939.X, dated Jul. 27, 2010, 44 pages (with English translation).
Response to Office Action in CN App. Ser. No. 200680021939.X, dated May 20, 2011, 39 pages (with English translation).
Response to Office Action in CN App. Ser. No. 200680021939.X, dated Oct. 28, 2010, 40 pages (with English translation).
Response to office action in CN App. Ser. No. 200780019200.X, dated Jul. 24, 2012, 49 pages (with English translation).
Response to office action in CN App. Ser. No. 200780019520.5, dated Dec. 3, 2010, 28 pages (with English translation).
Response to office action in CN App. Ser. No. 200780019520.5, dated Feb. 21, 2011, 7 pages (with English translation).
Response to Office Action in CN App. Ser. No. 201180030568.2 filed on Jan. 13, 2014, 46 pages (with English translation).

(56) References Cited

OTHER PUBLICATIONS

Response to Office Action in CN App. Ser. No. 201180030568.2 filed on May 14, 2014, 10 pages (with English translation).
Response to Office Action in CN App. Ser. No. 201280010427.9, dated Jun. 12, 2014, 13 pages (with English translation).
Response to office action in CN App. Ser. No. 201280010898.X, dated Nov. 25, 2014, 7 pages (with English translation).
Response to Office Action in EP App. Ser. No. 03791389.4, dated Jul. 25, 2014, 75 pages.
Response to office action in EP App. Ser. No. 05719973.9, dated Dec. 21, 2011, 150 pages.
Response to office action in EP App. Ser. No. 05719973.9, dated May 24, 2011, 26 pages.
Response to office action in EP App. Ser. No. 07793075.8, dated May 27, 2011, 17 pages.
Response to Office Action in EP App. Ser. No. 08704376.6, dated Apr. 30, 2014, 73 pages.
Response to Office Action in EP App. Ser. No. 08846814.5, dated Jul. 24, 2014, 71 pages.
Response to Office Action in EP App Ser. No. 10809938.3, dated Apr. 13, 2015, 12 pages.
Response to office action in EP App. Ser. No. 12786619.2, dated May 12, 2015, 99 pages.
Response to office action in ID App. Ser No. W-00 2008 00601, dated Jun. 18, 2012, 3 pages (with English translation).
Response to office action in IL App. Ser. No. 188670, dated Aug. 15, 2011, 43 pages (with English translation).
Response to office action in IL App. Ser. No. 197002, dated Feb. 29, 2012, 7 pages (with English translation).
Response to office action in IL App. Ser. No. 197141, dated Jun. 6, 2012, 10 pages (with English translation).
Response to office action in IL App. Ser. No. 217197, dated Nov. 26, 2014, 7 pages (with English translation).
Response to office action in IN App. Ser. No. 1424/CHENP/2008, dated Jan. 18, 2012, 17 pages.
Response to office action in JP App. Ser. No. 2008-530917, dated Dec. 13, 2012, 9 pages (with English translation).
Response to office action in JP App. Ser. No. P2009-510543, dated Nov. 9, 2009, 12 pages (with English translation).
Response to Office Action in JP App. Ser. No. P2009-540099, dated Apr. 28, 2014, 9 pages (with English Translation).
Response to office action in KR App. Ser. No. 10-2006-7013907, dated Sep. 28, 2007, 10 pages (with English translation).
Response to office action in KR App. Ser. No. 10-2006-7013940, dated Oct. 1, 2007, 20 pages (with English translation).
Response to Office Action in MX App. Ser. No. MX/a/2010/008187, dated Feb. 17, 2014, 7 pages (with English translation).
Response to Office Action in MX App. Ser. No. MX/a/2010/008187, dated Jun. 25, 2014, 5 pages (with English translation).
Response to Office Action in MX App. Ser. No. MX/a/2012/002011 filed on Jan. 16, 2014, 20 pages (with English translation).
Response to Office Action in MX App. Ser. No. MX/a/2012/014776, dated Jan. 7, 2015, 20 pages (with English translation).
Response to Office Action in MX App. Ser. No. MX/a/2012/014776, dated Jun. 20, 2014, 9 pages (with English translation).
Response to Office Action in MX App. Ser. No. MX/a/2013/009931, dated Dec. 9, 2014, 24 pages (with English translation).
Response to office action in NZ App. Ser. No. 566793, dated Jan. 17, 2010, 17 pages.
Response to office action in PH App. Ser. No. 1-2007-502319, dated Feb. 6, 2012, 19 pages.
Response to office action in PK App. Ser. No. 1024/2006, dated Apr. 20, 2009, 14 pages.
Response to office action in PK App. Ser. No. 1024/2006, dated Apr. 7, 2008, 17 pages.
Response to office action in PK App. Ser. No. 1024/2006, dated Jan. 29, 2009, 6 pages.
Response to office action in PK App. Ser. No. 155/2005, dated Jan. 4, 2008, 34 pages.
Response to office action in PK App. Ser. No. 375/2008, dated Apr. 8, 2009, 19 pages.
Response to office action in PK App. Ser. No. 375/2008, dated Dec. 20, 2008, 1 page.
Response to office action in PK App. Ser. No. 375/2008, dated Sep. 1, 2009, 20 pages.
Response to office action in RU App. Ser. No. 2006134254, dated Dec. 15, 2006, 23 pages (with English translation).
Response to office action in RU App. Ser. No. 2006134254, dated Nov. 20, 2007, 32 pages (with English translation).
Response to office action in RU App. Ser. No. 2008110932, dated Jan. 26, 2009, 29 pages (with English translation).
Response to Office Action in RU App. Ser. No. 2012103471, dated Jul. 21, 2014, 7 pages (with English translation).
Response to office action in RU App. Ser. No. 2012103471, dated Nov. 18, 2014, 17 pages (with English translation).
Response to Office Action in RU App. Ser. No. 2012158142, dated Apr. 13, 2015 (with English translation).
Response to Office Action in RU App. Ser. No. 2013139556, dated Dec. 25, 2013, 10 pages (with English translation).
Response to Office Action in SG App. Ser. No. 201108602-2, dated May 22, 2014, 37 pages.
Response to office action in TW App. Ser. No. 095130665, dated May 28, 2012, 379 pages (with English translation).
Response to Office Action in U.S. Appl. No. 13/923,858, filed Apr. 1, 2015, 12 pages.
Response to office action in U.S. Appl. No. 11/508,322, dated Aug. 31, 2009, 11 pages.
Response to office action in U.S. Appl. No. 11/508,322, dated Mar. 18, 2009, 20 pages.
Response to Office Action in U.S. Appl. No. 11/662,425, filed May 20, 2014, 8 pages.
Response to office action in U.S. Appl. No. 12/031,568, dated Aug. 12, 2011, 12 pages.
Response to office action in U.S. Appl. No. 12/031,568, dated Jun. 2, 2010, 13 pages.
Response to Office Action in U.S. Appl. No. 12/039,381, dated Apr. 3, 2014, 7 pages.
Response to office action in U.S. Appl. No. 12/315,291, dated Aug. 18, 2010, 8 pages.
Response to office action in U.S. Appl. No. 12/315,291, dated Feb. 28, 2011, 8 pages.
Response to office action in U.S. Appl. No. 12/558,982, dated Jul. 5, 2011, 21 pages.
Response to Office Action in U.S. Appl. No. 13/805,826, dated Aug. 8, 2014, 9 pages.
Response to Office Action in U.S. Appl. No. 13/923,858, dated Aug. 8, 2014, 24 pages.
Response to Office Action in U.S. Appl. No. 13/983,891, dated Feb. 27, 2014, 6 pages.
Response to Office Action in U.S. Appl. No. 14/002,018, dated Jul. 18, 2014, 8 pages.
Response to Office Action in U.S. Appl. No. 14/002,018, filed May 28, 2014, 7 pages.
Response to office action in VN App. Ser. No. 1-2008-00723, dated May 10, 2010, 7 pages (with English translation).
Response to Office Action under 37 C.F.R. §1.111 for U.S. Appl. No. 12/523,495, filed Dec. 7, 2011, 13 pages.
Response to Office Action under 37 C.F.R. §1.111 for U.S. Appl. No. 13/083,338, filed Apr. 8, 2011, 6 pages.
Response to Office Action under 37 C.F.R. §1.111 for U.S. Appl. No. 13/083,338, filed Sep. 6, 2012, 8 pages.
Response to Office Action under 37 C.F.R.S 1.111 and Information Disclosure Statement for U.S. Appl. No. 11/997,719, filed Jul. 3, 2013, 26 pages.
Response to Official Action in CA App. Ser. No. 2,704,000, dated Dec. 24, 2015, 11 pages.
Response to Restriction Requirement for U.S. Appl. No. 11/997,543, filed Mar. 22, 2011, 4 pages.
Response to Restriction Requirement for U.S. Appl. No. 12/301,353, filed Nov. 23, 2010, 4 pages.
Response to Restriction Requirement for U.S. Appl. No. 12/524,754, filed Dec. 1, 2011, 2 pages.

(56) References Cited

OTHER PUBLICATIONS

Response to Restriction Requirement in U.S. Appl. No. 11/892,785, dated Oct. 30, 2009, 16 pages.
Response to Restriction Requirement in U.S. Appl. No. 13/238,085, dated Oct. 4, 2013, 3 pages.
Response to Restriction Requirement in U.S. Appl. No. 11/065,631, dated Nov. 26, 2007, 16 pages.
Response to Restriction Response in U.S. Appl. No. 13/805,826, dated Jun. 2, 2014, 2 pages.
Response to the European Search Report for European Application No. 06782407 filed on Nov. 8, 2010, 105 pages.
Response to the Office Action for European Application No. 06782407 filed on Jan. 23, 2012, 17 pages.
Response to the Office Action issued for IN App. Ser. No. 6415/CHENP/2008 filed on Jan. 17, 2014, 16 pages.
Response to the Office Action issued for Japanese Application No. 2007-529565 filed on Feb. 3, 2012, 44 pages with English full translation.
Restriction Requirement for U.S. Appl. No. 11/997,543, dated Feb. 23, 2011, 9 pages.
Restriction Requirement for U.S. Appl. No. 12/092,539, dated Oct. 29, 2010, 8 pages.
Restriction Requirement for U.S. Appl. No. 12/301,353, dated Oct. 29, 2010, 11 pages.
Restriction Requirement for U.S. Appl. No. 12/439,339, dated Jul. 29, 2011, 10 pages.
Restriction Requirement for U.S. Appl. No. 12/524,754, dated Nov. 3, 2011, 11 pages.
Restriction Requirement in U.S. Appl. No. 11/892,785, dated Oct. 7, 2009, 5 pages.
Restriction Requirement in U.S. Appl. No. 12/359,475, dated Mar. 7, 2011, 5 pages.
Restriction Requirement in U.S. Appl. No. 12/527,633, dated Aug. 13, 2012, 10 pages.
Restriction Requirement in U.S. Appl. No. 11/065,631, dated Oct. 25, 2007, 8 pages.
Roberts et al., "Antiangiogenic and Antitumor Activity of a Selective PDGFR Tyrosine Kinase Inhibitor, CP-673,451", Cancer Research., 65, 957-966, 2005.
Robinson et al, "Characterization of Tumor Size Changes Over Time From the Phase 3 Study of (E7080) Lenvatinib in Differentiated Cancer of the Thyroid (Select)", The Poster, No.1031P, presented at European Society for Medical Oncology 2014 Congress, Sep. 26-30, 2014, 1 page.
Rosen and Goldberg, "Scatter Factor and Angiogenesis," *Advances in Cancer Research*, 1995, 67:257-279.
Rowe, R.C. et al. (ed.), Handbook of Pharmaceutical Excipients, 5th ed. Pharmaceutical Press, London, 2006, pp. 336-343.
Ruggeri et al., "CEP-7055: A Novel, Orally Active Pan Inhibitor of Vascular Endothelial Growth Factor Receptor Tyrosine Kinases with Potent Antiangiogenic Activity and Antitumor Efficacy in Preclinical Models1", Cancer Research., 63, 5978-5991, 2003.
Ruggeri et al., "CEP-7055: An orally-active VEGF-R kinase inhibitor with potent anti-angiogenic activity and anti-tumor efficacy against human tumor xenograft growth," AACR American Association Cancer Research., 93rd Annual Meeting, 43:1080, Apr. 6-10, 2002, San Francisco, CA, USA, abstract 5347, 2 pages.
Russian Decision of Grant directed at Appl. No. 2008149948115(065561), 16 pages with English translation.
Russian Office Action dated Apr. 11, 2012 for Appl. No. 2012103471, 6 pages (with English translation).
Russian Office Action dated Jan. 19, 2005 for App. Ser. No. 2003114740 (with English translation), 3 pages.
Russian Office Action dated Jun. 29, 2004 for App. Ser. No. 2003114740 (with English translation), 16 pages.
Russian Office Action directed at Appl. No. 2008149948115(065561) dated May 24, 2011, 8 pages with English translation.
Russian Response to Office Action directed at Appl. No. 2008149948115(065561) filed on Jul. 27, 2011, 14 pages with English translation.
Saeki et al., "Concurrent overexpression of Ets-1 and c-Met correlates with a phenotype of high cellular motility in human esophageal cancer," International J Cancer, 2002, 98(1):8-13.
Salassidis et al., "Translocation t(1 0; 14) (q 11.2; q22.1) Fusing the Kinectin to the RET Gene Creates a Novel Rearranged Form (PTC8) of the RET Proto-Oncogene in Radiation-induced Childhood Papillary Thyroid Carcinoma", Cancer Research, 60: 2786-2789 (2000).
Salmon et al., "Anti-angiogenic treatment of gastrointestinal malignancies," Cancer Invest., 23(8):712-726 (2005).
Salvatore et al., "Molecular profile of hyalinizing trabecular tumours of the thyroid: High prevalence of RET/PTC rearrangements and absence of B-raf and N-raspoint mutations", European Journal of Cancer, 41: 816-821 (2005).
Sandler et al., "Phase III trial of gemcitabine plus cisplatin versus cisplatin alone in patients with locally advanced or metastatic non-small-cell lung cancer," J. Clin. Oncol., 18(1):122-130 (200).
Sanger et al., "DNA sequencing with chain-terminating inhibitors", Proc. Natl. Acad. Sci. USA 74:5463 (1977).
Santoro et al., "Drug insight: Small-molecule inhibitors of protein kinases in the treatment of thyroid cancer," Nat. Clin. Pract. Endocrinol. Metab., 2(1):42-52 (2006).
Santoro et al., "Minireview: RET: normal and abnormal functions," Endocrinology, 145:5448-5451 (2004).
Santoro et al., "Molecular Mechanisms of RET Activation in Human Cancer," Ann. N.Y. Academy of Sciences, 963:116-121 (2002).
Sattler et al., "Targeting c-Kit mutations: basic science to novel therapies," Leukemia Research, 2004, 28S1:S11-S20.
Scheijen et al., "Tryosine Kinase Oncogenes in Normal Hematopoiesis and Hematological Disease," Oncogene, 21:3314-3333 (2002).
Schlumberger et al., "A phase 3, multicenter, double-blind, placebo-controlled trial of lenvatinib (E7080) in patients with $^{131}$I-refractory differentiated thyroid cancer (SELECT)," Am Soc Clin Oncol., Annual Meeting Abstract LBA6008, 2012, 4 pages.
Schlumberger et al., "A Phase 2 Trial of the Multi-Targeted Kinase Inhibitor Lenvatinib (E7080) in Advanced Medullary Thyroid Cancer (MTC)," 2012 ASCO Annual Meeting, Poster Presentation, Jun. 1-5, 2012.
Schlumberger et al., "Lenvatinib versus Placebo in Radioiodine-Refractory Thyroid Cancer," N Engl J Med., 372(7):621-630, Feb. 12, 2015.
Schoepp and Conn, "Metabotropic glutamate receptors in brain function and pathology," Trends in Pharmacological Sciences, 1993, pp. 13-20.
Search Report in EP App. Ser. No. 09705712.9, dated Aug. 7, 2014, 6 pages.
Search Report in EP App. Ser. No. 11798224.9, dated Mar. 21, 2014, 1 page.
Search Report in EP App. Ser. No. 11798224.9, dated Mar. 4, 2014, 6 pages.
Search Report in EP App. Ser. No. 12774278.1, dated Aug. 14, 2014, 8 pages.
Search Report in EP App. Ser. No. 12786619.2, dated Dec. 15, 2014, 6 pages.
Search Report in EP App. Ser. No. 12793322.4, dated May 26, 2015, 9 pages.
Search Report in EP App. Ser No. 12793322.4, dated Sep. 10, 2015, 13 pages.
Second Preliminary Amendment and Response to Restriction Requirement for U.S. Appl. No. 12/092,539, filed Nov. 22, 2010, 5 pages.
Section 18 Submission in IL App. Ser. No. 223695, dated May 4, 2015, 4 pages (with English translation).
Sekido et al., "Preferential Expression of c-kit Protooncogene Transcripts in Small Cell Lung Cancer," Cancer Res., 51:2416-2418 (1991).
Sennino and McDonald, "Controlling escape from angiogenesis inhibitors", Nature Rev Cancer, 12:699-709, Oct. 2012.
Sharma et al., "Thyroid Cancer," Feb. 18, 2015, pp. 1-16.
Shiang et al., "Mutations in the transmembrane domain of FGFR3 cause the most common genetic form of dwarfism, achondroplasia," Cell., 78:335-342 (1994).

(56) References Cited

OTHER PUBLICATIONS

Shibata et al., "Rapid Communication Association of Epstein-Barr Virus with Undifferentiated Gastric Carcinomas with Intense Lymphoid Infiltration", American Journal of Pahthology 139(3):469-473 (1991).
Shimizu et al., "Orally active anti-proliferation agents: novel diphenylamine derivatives as FGF-R2 autophosphorylation inhibitors," Bioorganic and Medicinal Chemistry Letters, 14(4):875-879 (2004).
Shirai, et al., ""Role of low-substituted hydroxypropylcellulose in dissociation and bioavalability of novel fine granule system for masking bitter taste,"" Biol. Pharm. Bull, 17(3): 427-431 (1994).
Shumaker et al., "Effect of lenvatinib (E7080) on the QTc interval: results from a thorough QT study in healthy volunteers," Cancer Chemother Pharmacol., published online Mar. 23, 2014, 9 pages (with English abstract).
Siegel et al., "Sorafenib: Where Do We Go from Here," *Hepatology*, 52:360-369 (2010).
Siemeister et al., "ZK304709, the oral Multitarget Tumor Growth Inhibitor™, acts via inihibition of cell cycle progression and tumor-induced angiogenesis," Proceedings of the American Association for Cancer Research, 46, (Abstract 5842), 2005, 3 pages.
Sihto et al., "KIT and platelet-derived growth factor receptor alpha tyrosine kinase gene mutations and KIT amplifications in human solid tumors," Journal of Clinical Oncology, 23(1):49-57 (2005).
Sondergaard et al., Differential sensitivity of melanoma cell lines with BRAF$^{V600E}$ mutation to the specific RAF inhibitor PLX4032, J Translational Med., 2010, 8:39, 11 pages.
Spacey et al., "Indolocarbazoles, Potent and Selective Inhibitors of Platelet-Derived Growth Factor Receptor Autophosphorylation," *Biochemical Pharmacology*, 55:261-271 (1998).
St. Bernard et al., "Fibroblast Growth Factor Receptors as Molecular Targets in Thyroid Carcinoma," Endocrinology, Mar. 2005, 146(3):1145-1153.
Stahl and Wermuth, "Handbook of Pharmaceutical Salts: Properties, selection, and use," 2002, pp. 117-122.
Stjepanovic and Capdevila, "Multikinase inhibitors in the treatment of thyroid cancer: specific role of lenvatinib," Biologics: Targets and Therapy, 8:129-139, Aug. 2014.
Strohmeyer et al., "Expression of the hst-1 and c-kit Protoonocogenes in Human Testicular Germ Cell Tumors," *Cancer Res.*, 51:1811-1816 (1991).
Submission Document(s) Before the Patent Office for IL App. Ser. No. 200090, dated Dec. 23, 2012, 16 pages, with English translation.
Submission Document Before the Patent Office dated Apr. 22, 2013 for IL App. Ser. No. 207089, 7 pages (with English translation).
Submission Document Before the Patent Office dated Mar. 14, 2013 for IL App. Ser. No. 205512, 12 pages (with English translation).
Submission Document Before the Patent Office for CL App. Ser. No. 2012-00412, dated Aug. 31, 2012, 6 pages (with English translation).
Submission Document Before the Patent Office for EP App. Ser. No. 03791389.4, dated Dec. 20, 2012, 4 pages.
Submission Document Before the Patent Office for EP App. Ser. No. 08846814.5, dated Jan. 3, 2013, 102 pages.
Submission Document Before the Patent Office for EP App. Ser. No. 8704376.6, dated Jan. 2, 2013, 22 pages.
Submission Document Before the Patent Office re Observation dated Feb. 16, 2013 for CN App. Ser. No. 200980103218.7, 8 pages (with English translation).
Submission Document in CL App. Ser. No. 2012-00412, dated Aug. 12, 2014, 2 pages (with English translation).
Submission Document in EP App. Ser. No. 09705712.9, dated Feb. 24, 2015, 196 pages.
Submission Document in HU App. Ser. No. P0302603, dated Jul. 7, 2015, 45 pages (with English translation).
Submission Document in MX App. Ser. No. MX/a/2014/010594, dated Sep. 4, 2014, 70 pages (with English translation).
Submission document in MX App. Ser. No. MX/a/2014/010594, dated Sep. 24, 2015, 12 pages (with English translation).
Submission Document in MY App. Ser. No. PI2011700172, dated Nov. 4, 2014, 3 pages.
Submission Document in PH App Ser. No. 1-2011-502441, dated May 22, 2015, 25 pages.
Submission Document re figures in AR App. Ser. No. P110100513, dated Oct. 22, 2014, 3 pages.
Submission Document re Petition on Oct. 2, 2013 in CL App. Ser. No. 2012-00412, 22 pages (with English translation).
Submission Document re RCE and Amendment in U.S. Appl. No. 12/031,568, dated Oct. 26, 2010, 23 pages.
Submission Document re RCE and Information Disclosure Statement in U.S. Appl. No. 11/065,631, dated Oct. 8, 2008, 7 pages.
Submission Document RCE and Information Disclosure Statement in U.S. Appl. No. 12/558,982, dated May 9, 2012, 36 pages.
Submission Document re RCE and Information Disclosure Statement dated Oct. 18, 2013, in U.S. Appl. No. 12/524,754, 17 pages.
Submission Document re RCE and Information Disclosure Statement dated Sep. 19, 2013 in U.S. Appl. No. 12/741,682, 19 pages.
Submission Document re RCE in U.S Appl. No. 12/031,568, dated Aug. 30, 2012, 12 pages.
Submission Document re RCE in U.S. Appl. No. 12/031,568, dated Jan. 18, 2012, 11 pages.
Submission Document re RCE in U.S Appl. No. 12/558,982, dated Nov. 29, 2011, 13 pages.
Submission Document re RCE in U.S. Appl. No. 12/741,682, dated Aug. 14, 2014, 1 page.
Submission Document re RCE in U.S. Appl. No. 13/205,328, dated Sep. 10, 2013, 12 pages.
Submission Documents Before the Patent Office for CN App. Ser. No. 201080030508.6, dated May 27, 2013, 7 pages (with English translation).
Submission Documents Before the Patent Office for KR App. Ser. No. 10-2009-7017694, dated Jan. 18, 2013, 22 pages, with English translation.
Submission Documents Before the Patent Office for U.S. Appl. No. 12/741,682, dated May 17, 2013, 16 pages.
Submission Documents in EG App. Ser. No. PCT 283/2012, dated Jan. 18, 2015, 26 pages (with English translation).
Submission Documents in TW App. Ser. No. 100104281, dated Mar. 9, 2015, 12 pages (with English translation).
Submission Documents New Claim Set Before the Patent Office for AR App. Ser. No. P110100513, dated Aug. 27, 2013, 8 pages (with English translation).
Submission Documents re Preliminary Amendment Before the Patent Office U.S. Appl. No. 14/002,018, dated Aug. 28, 2013, 9 pages.
Submission Documents re RCE Before the Patent Office for U.S. Appl. No. 13/083,338, dated Aug. 28, 2013, 20 pages.
Submission Documents re RCE Before the Patent Office for U.S. Appl. No. 12/524,754, dated Apr. 15, 2013, 17 pages.
Submission documents re RCE filed in U.S. Appl. No. 11/997,719, dated Dec. 11, 2013, 10 pages.
Submission Documents re RCE filed in U.S. Appl. No. 12/524,754, dated May 13, 2014, 1 page.
Submission documents re RCE filed in U.S. Appl. No. 12/741,682, dated Jan. 17, 2014, 1 page.
Submission documents re RCE filed in U.S. Appl. No. 13/083,338, dated Dec. 2, 2013, 5 pages.
Submission documents re RCE filed in U.S. Appl. No. 13/205,328, dated Dec. 30, 2013, 1 page.
Submission documents re RCE filed in U.S. Appl. No. 13/624,278, dated Dec. 13, 2013, 10 pages.
Submission documents re RCE in U.S. Appl. No. 12/439,339, dated Jan. 27, 2014, 1 page.
Submission documents re RCE in U.S. Appl. No. 12/524,754, filed Feb. 3, 2014, 1 page.
Submission Documents re Request for Continued Examination filed in U.S. Appl. No. 12/741,682, dated May 6, 2014, 1 page.
Submission Documents re Request for Continued Examination filed in U.S. Appl. No. 13/083,338, dated May 6, 2014, 1 page.

(56) References Cited

OTHER PUBLICATIONS

Submission documents re Request for Continued Examination in U.S. Appl. No. 13/205,328, dated Apr. 28, 2014, 1 page.
Submission in EP App. Ser. No. 04807580.8, dated Jun. 13, 2014, 18 pages.
Submission of Amended Claims in IL App. Ser. No. 223695, dated Dec. 24, 2015, 6 pages (with English translation).
Submission of Amended specification in IL App. Ser. No. 217197, dated Dec. 24, 2015, 5 pages (with English translation).
Submission of Amendments and Complete Specification dated Apr. 10, 2013 for IN App. Ser. No. 1571/CHENP/2007, 15 pages.
Submission of claims and abstract in MX App. Ser. No. MX/a/2014/010594, dated Oct. 8, 2015, 10 pages (with English translation).
Submission of Claims in IL App. Ser. No. 223695, dated Jan. 17, 2015, 16 pages.
Submission of Document Before the Patent Office re Request for Voluntary Amendments dated Jan. 30, 2013 for NZ App. Ser. No. 598291, 8 pages.
Submission of Document re Claims filed in Response to Second Office Action for CN App. Ser. No. 200880115011.7, filed on Nov. 20, 2012, 16 pages.
Submission of Document re Request for Examination in CO App. Ser. No. 12-022608, submitted on Jun. 12, 2012, 6 pages.
Submission of Documents before the Patent Office for CN App. Ser. No. 200880115011.7, dated Apr. 11, 2013, 10 pages (with English translation).
Submission of Documents before the Patent Office for CN App. Ser. No. 200980103218.7, dated Mar. 13, 2013, 6 pages (with English translation).
Submission of Documents Before the Patent Office for IL App. Ser. No. 175363, dated Feb. 27, 2013, 22 pages.
Submission of Documents re Amendment in UA App. Ser. No. a2012 03132, dated May 22, 2012, 11 pages (with English translation).
Submission of Documents re Claim 3 and Figure 3 for KR App. Ser. No. 10-2009-7005657, filed on Jul. 13, 2012, 5 pages.
Submission of Reference Materials in KR App. Ser. No. 10-2008-7013685, filed Jul. 5, 2013, 43 pages, (with English translation).
Submission of Relevant Patent in MX App. Ser. No. MX/a/2014/010594, dated Sep. 24, 2015, 2 pages (with English translation).
Submission of Voluntary Amendment and Request for Examination in TH App. Ser. No. 0401005163, dated Aug. 21, 2015, 29 pages (with English translation).
Sun et al., " Design, synthesis, and evaluations of substituted 3-[(3-or 4-carboxyethylpyrrol-2-yl)methylidenyl]indolin-2-ones as inhibitors of VEGF, FGF, and PDGF receptor tyrosine kinases", Journal of Medicinal Chemistry., 42:5120-5130 (1999).
Sun et al., "Discovery of 5[5-Fluoro-2-oxo-1,2-dihydroindol-(3Z)-ylidenemethyl]-2,4-dimethyl-1H-pyrrole-3carboxylic acid . . . Tyrosine Kinase", Journal of Medicinal Chemistry., 46:1116-1119 (2003).
Sun et al., "Synthesis and Biological Evaluations of 3-Substituted Indolin-2-ones: A novel class of Tyrosine kinase inhibitors that exhibit selectivity toward particular receptor tyrosine kinases", Journal of Medicinal Chemistry., 41:2588-2603 (1998).
Supplemental Search Report in EP App. Ser. No. 05719973.9, dated Dec. 6, 2007, 3 pages.
Supplemental Search Report in EP App. Ser. No. 05719976.2, dated Dec. 6, 2007, 3 pages.
Supplementary European Search Report for App. Ser. No. 01976786.2, dated Jul. 6, 2004, 6 pages.
Supplementary European Search Report for App. Ser. No. 08 70 4376, dated Jun. 14, 2012.
Supplementary European Search Report for App. Ser. No. 08846814.5, dated Jun. 18, 2012.
Supplementary European Search Report dated Jul. 5, 2012, in European Patent Application No. 08846814.5, 1 page.
Suzuki et al., "MP-412, a dual EGFR/HER2 tyrosine kinase inhibitor: 1. In vivo kinase inhibition profiled," Am. Assoc. Cancer Research, A3405, 2005, 2 pages.

Taguchi et al., "A novel orally active inhibitor of VEGF receptor tyrosine kinases KRN951: Anti-angiogenic and anti-tumor activity against human solid tumors," Proc Am Assoc Cancer Res., 45:1070-1071, Abstract 2575, 2004.
Tahara et al, "Comprehensive Analysis of Serum Biomarkers and Tumor Gene Mutations Associated With Clinical Outcomes in the Phase 3 Study of (E7080) Lenvatinib in Differentiated Cancer of the Thyroid (SELECT)", The presentation document, presented at European Society for Medical Oncology 2014 Congress, Sep. 26-30, 2014, 18 pages.
Tahara et al., "Comprehensive Analysis of Serum Biomarkers and Tumor Gene Mutations Associated With Clinical Outcomes in the Phase 3 Study of (E7080) Lenvatinib in Differentiated Cancer of the Thyroid (SELECT),", 12th Annual Meeting of Japanese Society of Medical Oncology, Jul. 17, 2014, Abstract (Document is 6 total pages).
Takahashi et al, "Phase II Study of Lenvatinib, A Multitargeted Tyrosine Kinase Inhibitor, In Patients With All Histologic Subtypes of Advanced Thyroid Cancer (Differentiated, Medullary, and Anaplastic)", The Poster, presented at the European Society for Medical Oncology 2014 Congress, Sep. 26-30, 2014, 1 page.
Takahashi et al., "A case of inoperable scirrhous gastric cancer that responded remarkably to a combination of TS-1+paclitaxel and showed complete loss of ascites," *Japanese Journal of Cancer and Chemotherapy*, 31(7):1093-1095 (2004).
Takeda et al., "AZD2171 shows potent anti-tumor activity against gastric cancer expressing variant K-SAM/FGFR2," Abstract #3785, *Proceeding of the American Association for Cancer Research*, 47:890 (2006).
Tamura et al., "Molecular Characterization of Undifferentiated-Type Gastric Carcinoma," Laboratory Investigation, 81(4):593-598, Apr. 2001.
Tan et al., "Randomized study of vinorelbine—gemcitabine versus vinorelbine—carboplatin in patients with advanced non-small cell lung cancer," *Lung Cancer*, 49(2):233-240 (2005).
Taniguchi et al., "Effect of c-kit Mutation on Prognosis of Gastrointestinal Stromal Tumors," *Cancer Res.*, 59:4297-4300 (1999).
The Pharmacology of Monoclonal Antibody, vol. 113, Chapter 11, Rosenburg and Moore ed., Springer Verlag (1994) pp. 269-315.
Third Office Action dated Feb. 25, 2013 for CN App. Ser. No. 200880115011.7, 6 pages (with English translation).
Thomas et al., "The Eosinophil and its Role in Asthma," Gen. Pharmac., 27(4)593-597 (1996).
Thyroid Cancers, Endocrine and Metabolic Disorders, http://www.merkmanuals.com/professional/print/sec12/ch152/ch152j.html Mar. 16, 2011, 4 pages.
Tian et al., "Activating c-kit Gene Mutations in Human Germ Cell Tumors," *American Journal of Pathology*, 154(6):1643-1647 (1999).
To and Tsao, "The roles of hepatocyte growth factor/scatter factor and Met receptor in human cancers (Review)," *Oncology Reports*, 1998, 5:1013-1024.
Tohyama et al, "Antitumor Activity of Lenvatinib (E7080): An Angiogenesis Inhibitor That Targets Multiple Receptor Tyrosine Kinases in Preclinical Human Thyroid Cancer Models," J Thyroid Res, 2014:1-13, Sep. 10, 2014.
Tohyama et al., "P-3111, Preclinical effect of lenvatinib on human thyroid cancer targeting angiogenesis and receptor tyrosine kinase signaling," The 71$^{st}$ Annual Meeting of the Japanese Cancer Association, Sep. 19-21, 2012, p. 502.
Tonary et al., "Lack of expression of c-KIT in ovarian cancers is associated with poor prognosis,"Int. J. Cancer, 89:242-250 (2000).
Tong et al., "Vascular normalization by vascular endothelial growth factor receptor 2 blockade induces a pressure gradient across the vasculature and improves drug penetration in tumors," Cancer Res., 64:3731-3736 (2004).
Toshiyuki et al., "Thermal recording materials with improved background stability," Database CA (Online) Chemical Abstracts Service, Columbus, OH, US (Feb. 20, 1996) (XP002443195), 1 page.
Transmittal of Information Disclosure Statement, Terminal Disclaimer, Request for Continued Examination, and Response to Office Action under 37 C.F.R. §1.116 for U.S. Appl. No. 11/997,719, filed Jul. 6, 2011, 15 pages.

(56) References Cited

OTHER PUBLICATIONS

Traxler et al., "AEE788; A dual family epidermal growth factor receptor/ErbB2 and vascular endothelial growth factor receptor tyrosine kinase inhibitor with antitumor and antiangiogenic activity," Cancer Res., 64:4931-4941 (2004).

Trudel et al., "CHIR-258, a novel, multitargeted tyrosine kinase inhibitor for the potential treatment of t(4;14) multiple myeloma," Blood, 105:2941-2948 (2005).

Trudel et al., "Inhibition of fibroblast growth factor receptor 3 induces differentiation and apoptosis in t(4;14) myeloma," Blood, 103:3521-3528 (2004).

Tsou et al., "Optimization of 6,7-Disubstituted-4-(arylamino)quinoline-3-carbonitriles as Orally Active, Irreversible Inhibitors of Human Epidermal Growth Factor Receptor-2 Kinase Activity", Journal of Medicinal Chemistry., 48, 1107-1131, 2005.

Turner et al., "Fibroblast growth factor signaling: from development to cancer," Nature Reviews, Cancer, 10:116-129 (2010).

U.S. Certificate of Correction in U.S. Appl. No. 12/524,754, dated Aug. 11, 2015, 1 page.

U.S. Certificate of Correction in U.S. Appl. No. 13/624,278, dated Aug. 18, 2015, 1 page.

U.S. Final Office Action in U.S. Appl. No. 10/797,903, dated Jul. 23, 2008, 11 pages.

U.S. Notice of Allowance for U.S. Appl. No. 12/244,227, dated Oct. 22, 2010, 32 pages.

U.S. Office Action for U.S. Appl. No. 10/797,903, dated Aug. 20, 2009, 10 pages.

U.S. Office Action for U.S. Appl. No. 10/420,466, dated Apr. 13, 2005, 16 pages.

U.S. Office Action for U.S. Appl. No. 10/577,531, dated Sep. 23, 2008, 17 pages.

U.S. Office Action for U.S. Appl. No. 10/797,903, dated Apr. 1, 2010, 11 pages.

U.S. Office Action for U.S. Appl. No. 10/797,903, dated Dec. 11, 2007, 12 pages.

U.S. Office Action for U.S. Appl. No. 10/797,903, dated Sep. 1, 2010, 7 pages.

U.S. Office Action for U.S. Appl. No. 11/293,785, dated Sep. 4, 2007, 18 pages.

U.S. Office Action for U.S. Appl. No. 11/347,749, dated Feb. 9, 2009.

U.S. Office Action for U.S. Appl. No. 11/662,425, dated May 3, 2010, 16 pages.

U.S. Office Action for U.S. Appl. No. 11/662,425, dated Sep. 28, 2010, 35 pages.

U.S. Office Action for U.S. Appl. No. 11/997,543, dated Feb. 23, 2011, 9 pages.

U.S. Office Action for U.S. Appl. No. 11/997,543, dated May 19, 2011, 38 pages.

U.S. Office Action for U.S. Appl. No. 11/997,543, dated Nov. 9, 2011, 12 pages.

U.S. Office Action for U.S. Appl. No. 11/997,719, dated Apr. 6, 2011, 6 pages.

U.S. Office Action for U.S. Appl. No. 11/997,719, dated Sep. 3, 2010, 10 pages.

U.S. Office Action for U.S. Appl. No. 12/092,539, dated Jan. 7, 2011.

U.S. Office Action for U.S. Appl. No. 12/092,539, dated Jun. 28, 2011, 3 pages.

U.S. Office Action for U.S. Appl. No. 12/092,539, dated May 9, 2011, 10 pages.

U.S. Office Action for U.S. Appl. No. 12/094,492, dated Mar. 24, 2011, 16 pages.

U.S. Office Action for U.S. Appl. No. 12/301,353, dated Jan. 24, 2011, 10 pages.

U.S. Office Action for U.S. Appl. No. 12/400,562, dated Mar. 31, 2010, 11 pages.

U.S. Office Action for U.S. Appl. No. 12/439,339, dated Mar. 30, 2012, 6 pages.

U.S. Office Action for U.S. Appl. No. 12/439,339, dated Nov. 14, 2011, 44 pages.

U.S. Office Action for U.S. Appl. No. 12/523,495, dated Dec. 27, 2011, 11 pages.

U.S. Office Action for U.S. Appl. No. 12/523,495, dated Sep. 27, 2011, 37 pages.

U.S. Office Action for U.S. Appl. No. 12/524,754, dated Dec. 19, 2011, 53 pages.

U.S. Office Action for U.S. Appl. No. 12/741,682, dated Apr. 30, 2012, 50 pages.

U.S. Office Action for U.S. Appl. No. 12/864,817, dated Dec. 16, 2011, 4 pages.

U.S. Office Action for U.S. Appl. No. 12/864,817, dated May 19, 2011, 11 pages.

U.S. Office Action for U.S. Appl. No. 12/864,817, dated Nov. 3, 2011, 11 pages.

U.S. Office Action for U.S. Appl. No. 13/083,338, dated Apr. 12, 2012, 8 pages.

U.S. Office Action for U.S. Appl. No. 13/083,338, dated Jun. 8, 2012, 55 pages.

U.S. Office Action for U.S. Appl. No. 13/083,338, dated Nov. 23, 2012, 38 pages.

U.S. Office Action for U.S. Appl. No. 13/205,328, dated Jan. 12, 2012, 37 pages.

U.S. Office Action for U.S. Appl. No. 13/205,328, dated May 1, 2012, 21 pages.

U.S. Office Action for U.S. Appl. No. 13/322,961, dated Sep. 25, 2012, 62 pages.

U.S. Supplemental Notice of Allowance in U.S. Appl. No. 12/315,291, dated Jul. 21, 2011, 4 pages.

Ueda et al., "VGA1155, a Novel Binding Antagonist of VEGF, Inhibits Angiogenesis In Vitro and In Vivo", Anticancer Research., 24, 3009-3017, 2004.

Ueda et al., "Deletion of the carboxyl-terminal exons of K-sam/FGFR2 by short homology-mediated recombination, generating preferential expression of specific messenger RNAs," Cancer Res., 59(24):6080-6086 (1999).

U.S. Office Action for U.S. Appl. No. 11/997,543, dated Sep. 30, 2013, 88 pages.

U.S. Response to Notice of Non-Compliant Amendment dated Jan. 13, 2005 for U.S. Appl. No. 10/420,466, 17 pages.

U.S. Response to Notice of Non-Compliant Amendment dated Jan. 18, 2005 for U.S. Appl. No. 10/420,466.

Van Dijk et al. "Induction of Tumor-Cell Lysis by B-Specific Monoclonal Antibodies Recognizing Renal-Cell Carcinoma and CD3 Antigen", Int. J. Cancer 43: 344-9, 1989.

Van Oers et al., "A simple and fast method for the simultaneous detection of nine fibroblast growth factor receptor 3 mutations in bladder cancer and voided urine," Clin. Cancer Res., 11:7743-7748 (2005).

Varvoglis et al., "Chemical Transformations Induced by Hypervalent Iodine Reagents," Tetrahedron, 1997, 53(4):1179-1255.

Vergote et al., "Prognostic and predictive role of circulating angiopoietin-2 in multiple solid tumors: An analysis of approximately 500 patients treated with lenvatinib across tumor types," Abstract of the presentation #4 (abstract 11061), Retrieved from the website http://meetinglibrary.asco.org/content/132299-144, 2014, 2 pages.

Vergote et al., "Prognostic and predictive role of circulating angiopoietin-2 in multiple solid tumors: An analysis of approximately 500 patients treated with lenvatinib across tumor types," Poster for a presentation on May 30, 2014 at ASCO Annual Meeting (Chicago, IL May 30-Jun. 3, 2014), May 2014, 1 page.

Vergote et al., "Phase II trial of lenvatinib in patients with advanced or recurrent endometrial cancer: Angiopoiryin-2 as a predictive marker for clinical outcomes," Presentation slides presented on May 31, 2013 at ASCO Annual Meeting (Chicago, IL, May 31-Jun. 4, 2013), May 31, 2013, 12 pages.

Vianna et al., "The histological rarity of thyroid cancer", Brazilian Journal of Otorhinolaryngology, 2012, 78(4):48-51.

Vippagunta et al., "Crystalline solids," Advanced Drug Delivery Reviews, 48:3-26 (2001).

(56) References Cited

OTHER PUBLICATIONS

Vogel et al., "Sensing extracellular matrix: an update on discoidin domain receptor function," Cell Signaling, 18:1108-1116 (2006).
Voluntary Amendment (Specification) in AU App. Ser. No. 2010285740, dated Nov. 20, 2015, 11 pages.
Voluntary Amendment filed in CA App. Ser. No. 2704000, filed Aug. 6, 2013, 6 pages.
Voluntary Amendment filed in CA App. Ser. No. 2802644, dated Nov. 22, 2013, 25 pages.
Voluntary Amendment filed on Aug. 11, 2010 for CN App. Ser. No. 200710007097.9, 12 pages (with English translation).
Voluntary Amendment filed on Aug. 19, 2010 for CA App. Ser. No. 2426461, 2 pages.
Voluntary Amendment filed on Aug. 30, 2006 for AU App. Ser. No. 2006203099, 16 pages.
Voluntary Amendment filed on Feb. 16, 2012 for BR Patent App. No. BR112012003592-4, 18 pages (with partial English translation).
Voluntary Amendment filed on Feb. 21, 2007 for AU App. Ser. No. 2006203099.
Voluntary Amendment filed on Feb. 27, 2007 for AU App. Ser. No. 2006236039, 10 pages.
Voluntary Amendment filed on Feb. 9, 2010 for AU App. Ser. No. 2005283422, 12 pages.
Voluntary Amendment filed on Jul. 6, 2010 for AU App. Ser. No. 2005283422, 21 pages.
Voluntary Amendment filed on Sep. 10, 2010 for HU App. Ser. No. P0302603, 36 pages (with English translation).
Voluntary Amendment for Australian App. Ser. No. 2010285740, filed on Nov. 21, 2011, 3 pages.
Voluntary Amendment for Chinese counterpart of App. No. PCT/JP2010/063804, filed on Jan. 5, 2012, 8 pages (with English translation).
Voluntary Amendment for counterpart Canadian patent application, filed on Feb. 16, 2012, 3 pages.
Voluntary Amendment for Russian App. Ser. No. 2012103471, filed on Feb. 1, 2012, 3 pages (with English translation).
Voluntary Amendment for Thailand App. Ser. No. 1201000221, filed on Feb. 17, 2012, 8 pages.
Voluntary Amendment in BR App. Ser. No. P10616799/3, dated May 29, 2009, 21 pages.
Voluntary Amendment in CA App. Ser. No. 2605854, dated Oct. 23, 2007, 14 pages.
Voluntary Amendment in CA App. Ser. No. 2661702, dated Feb. 24, 2009, 4 pages.
Voluntary Amendment in CA App. Ser. No. 2679602, dated Aug. 20, 2009, 6 pages.
Voluntary Amendment in ID App. Ser. No. W-00201201031, dated Nov. 5, 2014, 2 pages (with English translation).
Voluntary Amendment in IN App. Ser. No. 1424/CHENP/2008, dated Mar. 24, 2008, 257 pages.
Voluntary Amendment in IN App. Ser. No. 5625/CHENP/2009, dated Sep. 23, 2009, 147 pages.
Voluntary Amendment in LK App. Ser. No. 14703, dated Mar. 31, 2011, 256 pages.
Voluntary Amendment in MX App. Ser. No. MX/a/2014/010594, dated Oct. 23, 2014, 4 pages (with English translation).
Voluntary Amendment in TW App. Ser. No. 095130665, dated Mar. 20, 2009, 36 pages (with English translation).
Voluntary Amendments in AU App. Ser. No. 2007288793, dated May 29, 2009, 9 pages.
Voluntary Amendments in AU App. Ser. No. 2008217931, dated Nov. 18, 2009, 17 pages.
Voluntary Brief Amendments for Venezuelan App. Ser. No. 2011-000193, filed on Dec. 21, 2011, 8 pages (with English translation).
Wakeling et al., "ZD1839 (Iressa): an orally active inhibitor of epidermal growth factor signaling with potential for cancer therapy," Cancer Res., 62(20)5749-5754 (2002).
Wakui, "Chemotherapy of scirrhous gastric cancer," Japanese Journal of Cancer and Chemotherapy, 21(14):2398-2406 (1994) (English abstract).
Wang et al., "KRAS, BRAF, PIK3CA mutations and Pten Expression in Human Colorectal Cancer-Relationship with Metastatic Colorectal Cancer," Ann Oncol., 2010, 21(Supp 6):V164.
Wang et al., "A Convenient Set of Bidentate Pyridine Ligands for Combinatorial Synthesis," Tetrahedron Lett., 40:4779-1478 (1999).
Wang et al., "Phase II study of gemcitabine and carboplatin in patients with advanced non-small-cell lung cancer," Cancer Chemother Pharmacol., 60(4):601-607 (2007).
Wang et al., "The Expression of the Proto-Oncogene C-Kit in the Blast Cells of Acute Myeloblastic Leukemia," Leukemia, 3(10):699-702 (1989).
Wang, "Everolimus in renal cell carcinoma," Drugs of Today, Aug. 2010, 46(8), abstract, 1 page.
Waterman, M., "Computer Analysis of Nucleic Acid Sequences", Methods in Enzymology, 164:765-793 (1988).
Watson et al., "Inhibition of c-Met as a therapeutic strategy for esophageal adenocarcinoma," Neoplasia, 2006, 8(11):949-955.
Wedge et al., "ZD4190: An Orally Active Inhibitor of Vascular Endothelial Growth Factor Signaling with Broad-Spectrum Antitumor Efficacy", Cancer Research., 60, 970-975, 2000.
Wedge et al., "AZD2171: a highly potent, orally bioavailable, vascular endothelial growth factor receptor-2 tyrosine kinase inhibitor for the treatment of cancer," Cancer Res., 65(10):4389-4400 (2005).
Wedge et al., "Pharmacological Efficacy of ZD6474, a VEGF Receptor Tyrosine Kinase Inhibitor, in Rat," AACR American Association Cancer Research, 92nd Annual Meeting, 42:583, Mar. 2428, 2001, New Orleans, LA, USA, abstract 3126, 2 pages.
Wells et al., "Targeting the RET Pathway in Thyroid Cancer," Clin. Cancer Res., 15:7119-7123 (2009).
Wells Jr et al, "Vandetanib in Patients With Locally Advanced or Metastatic Medullary Thyroid Cancer: A Randomized, Double-Blind Phase III Trial", J Clinical Oncol., 30(2):134-141, Jan. 10, 2012, corrections published Aug. 20, 2013, p. 3049.
Werner et al., "Gastric adenocarcinoma: pathomorphology and molecular pathology," J. Cancer Res. Clin. Oncology, 127:207-216 (2001) (English abstract).
Wickman et al., "Further characterization of the potent VEGF/PDGF receptor tyrosine kinase inhibitor AG-013736 in preclinical tumor models for its antiangiogenesis and antitumor activity," Proceedings of the American Association for Cancer Research, 44, 865, (Abstract 3780), 2003, 1 page.
Wilbur, W.J. and Lipman, DJ., "Rapid similarity searches of nucleic acid and protein data banks", Natl. Acad. Sci, U.S.A. 80:726-730 (1983).
Wilhelm et al., "BAY 43/9006 Exhibits Broad Spectrum Oral Antitumor Activity and Targets the RAF/MEK/ERK Pathway and Receptor Tyrosine Kinases Involved in Tumor Progression and Angiogenesis", Cancer Research., 64:7099-7109 (2004).
Willett et al., "Direct evidence that the VEGF-specific antibody bevacizumab has antivascular effects in human rectal cancer," Nat. Med., 10(2):145-1147 (2004).
Winkler et al., "Kinetics of vascular normalization by VEGFR2 blockade governs brain tumor response to radiation: Role of oxygenation, angiopoietin-1, and matrix metalloproteinases," Cancer Cell, Dec. 2004, 6:553-563.
Wirth et al, "Treatment-Emergent Hypertension and Efficacy in the Phase 3 Study of (E7080) Lenvatinib in Differentiated Cancer of the Thyroid (Select)", The Poster, No. 1030P, presented at the European Society for Medical Oncology 2014 Congress, Sep. 26-30, 2014, 1 page.
Wisniewski et al.,"Characterization of Potent Inhibitors of the Bcr-Abl and the c-Kit Receptor Tyrosine Kinases", Cancer Research., 62, 4244-4255, 2002.
Wood et al., "A Unique Structure for Epidermal Growth Factor Receptor Bound to GW572016 (Lapatinib): Relationships among Protein Conformation, Inhibitor Off-Rate, and Receptor Activity in Tumor Cells", Cancer Research, 64, 6652-6659. 2004.
Wood et al., "PTK787/ZK 222584, a Novel and Potent Inhibitor of Vascular Endothelial Growth Factor Receptor Tyrosine Kinases,

(56) References Cited

OTHER PUBLICATIONS

Impairs Vascular Endothelial Growth Factor-Induced Responses and Tumor Growth after Oral Administration", Cancer Research., 60, 2178-2189, 2000.
Wozniak et al., "Randomized trial comparing cisplatin with cisplatin plus vinorelbine in the treatment of advanced non-small-cell lung cancer: a Southwest Oncology Group study," *J. Clin. Oncol.*, 16(7):2459-2465 (1998).
Written Amendment filed on Jun. 16, 2009 for JP App. Ser. No. 2009-123432, 12 pages (with English translation).
Written Amendment filed on Sep. 21, 2011 for JP App. Ser. No. 2011-527665, 2 pages (with English translation).
Written Statement filed on Jun. 16, 2009 for JP App. Ser. No. 2009-123432, 32 pages (with English translation).
Written Statement filed on Sep. 21, 2011 for JP App. Ser. No. 2011-527665, 2 pages (with English translation).
Written Submission regarding hearing in IN App. Ser. No. 1571/CHENP/2007 filed on Jan. 23, 2014, 8 pages.
Written Verdict in SA App. Ser. No. 06270287, dated Feb. 17, 2013, 11 pages (with English translation).
Wu et al., "A fully human monoclonal antibody against VEGFR-1 inhibits growth of human breast cancers," Proceedings of the American Association for Cancer Research, 45, 694, (Abstract 3005), 2004, 3 pages.
Wulff et al., "Luteal Angiogenesis: Prevention and Intervention by Treatment with Vascular Endothelial Growth Factor TrapA40", The Journal of Clinical Endocrinology & Metabolism. 86(7), 3377-3386, 2001.
Yamada et al., "Phase 1 Dose-Escalation Study and Biomarker Analysis of E7080 in Patients with Advanced Solid Tumors," Clinical Cancer Research, Mar. 2011, 17(8):2528-2537 (with supplementary data).
Yamada et al., "New technique for staining," Monthly Medical Technology Supplementary Volume (Apr. 1999) (with English translation), 13 pages.
Yamamoto et al., "E7080 (ER-203492-00), a Novel VEGF Receptor Tyrosine Kinase Inhibitor-III. Significant prolongation of life span in mice transplanted with human ovarian carcinoma based on inhibition of VEGF signaling," Abstract #50, *AACR*, Toronto, Canada (Apr. 5-9, 2003).
Yamamoto et al., "E7080 a novel multitargeted tyrosine kinase inhibitor, has direct anti-tumor activity via inhibition of KIT signaling in small cell lung cancer," Abstract #4636, AACR, Orlando, FL, (Mar. 27-31, 2004).
Yamamoto et al., "E7080, an oral multi-targeted tyrosine kinase inhibitor, has direct anti-tumor efficacy via inhibition of KIT signaling in gastrointestinal stromal tumor (GIST)," Abstract #4038, *97th Annual Meeting AACR*, Washington, DC (Apr. 1-5, 2006).
Yamamoto et al., "E7080, an oral multi-targeted tyrosine kinase inhibitor, has direct anti-tumor efficacy via inhibition of KIT signaling in small cell lung cancer," *Proceedings of the American Association for Cancer Research*,45:1070-1071 (Mar. 2004).
Yamamoto et al., "Lenvatinib, an angiogenesis inhibitor targeting VEGFR/FGFR, shows broad antitumor activity in human tumor xenograft models associated with microvessel density and pericyte coverage," Vascular Cell, 6(18):1-13, 2014.
Yamori et al., "Current Treatment of Solid Tumors New Approaches of Treatment, Drug Treatment, Kinase Inhibitors/Kokeigan no Saishin Chiryo Chiryo no Aratana Torikumi Yakubutsu Ryoho Kinase Inhibitors," JP J Clin Med., Jun. 1, 2010, 68(6):1059-1066 (with English translation).
Yanagihara et al., "Development and biological analysis of peritoneal metastasis mouse models for human scirrhous stomach cancer," Cancer Sci., 96(6):323-332 (2005).
Yang et al., "RG7204 (PLX4032), a Selective BRAF V600E Inhibitor, Displays Potent Antitumor Activity in Preclinical Melanoma Models," Cancer Res., 2010, 70(13):5518-5527.
Yigitbasi et al., "Tumor Cell and Endothelial Cell Therapy of Oral Cancer by Dual Tyrosine Kinase Receptor Blockade", Cancer Research, 64, 7977-7984, 2004.
Yokota, "ASCO report: Gastrointestinal Cancer field/ASCO Hokoku Shokakigan Ryoiki," Gan Bunshi Hyoteki Chiryo, 2010, 8(4):271-283.
Yu, "Amorphous Pharmaceutical Solids:Preparation Characterization and Stabilization," Advanced Drug Delivery Reviews, 48:27-42 (2001) (XP009065056).
Zhang et al., "Induction of apoptosis in EMT-6 breast cancer cell in line by a Sigma-2 selective ligand," Am. Assoc. Cancer Research, Abstract 5353, 2005, 2 pages.
Zhang et al., "Inhibition of both autocrine and paracrine growth and propagation of human myeloid leukemia with antibodies directed against VEGF receptor 2," Proceedings of the American Association for Cancer Research, 44, 1479, (Abstract 6454), 2003, 2 pages.
Zhang et al., "Overexpression of Platelet-Derived Growth Factor Receptor a in Endothelial Cells of Hepatocellular Carcinoma Associated with High Metastatic Potential," Clin. Cancer Res., 11(24):8557-8563 (2005).
Zhang et al., "Synergic antiproliferative effect of DNA methyltransferase inhibitor in combination with anticancer drugs in gastric carcinoma," Cancer Sci., Sep. 2006, 97(9):938-944.
Zhong et al., "Mechanisms underlying the synergistic effect of SU5416 and cisplatin on cytotoxicity in human ovarian tumor cells," Inter'l J Oncol., 25(2):445-451, 2004.
Zhou et al., "Correlation Research on VEGF Testing in Primary Gastric Cancer and Clinical Pathology Factor," Journal of Practical Oncology, 20(2):103-105 (Apr. 25, 2006) with English translation.
Zhu et al., "Fibroblast growth factor receptor 3 inhibition by short hairpin RNAs leads to apoptosis in multiple myeloma," Mol. Cancer Ther., 4(5):787-798 (2005).
Zhu et al., "Inhibition of human leukemia in an animal model with human antibodies directed against vascular endothelial growth factor receptor 2. Correlation between antibody affinity and biological activity," Leukemia, 17:604-611 (2003).
Zieger et al., "Role of activating fibroblast growth factor receptor 3 mutations in the development of bladder tumors," Clin. Cancer Res., 11:7709-7719 (2005).
Zimmermann et al., "Potent and Selective Inhibitors of the Abl-Kinase:Phenylamino-Pyrimidine (PAP) Derivatives", Bioorganic and Medicinal Chemistry Letters., 7(2):187-192, 1997.
Zimmermann, "Electrical Breakdown, Electropermeabilization and Electrofusion", Rev. Physiol. Biochem. Pharmacol. 105:176-260 (1986).
Zurita et al., "A cytokine and angiogenic factor (CAF) analysis in—plasma for selection of sorafenib therapy in patients with metastatic renal cell carcinoma," Annals of oncology, Apr. 2011, 23(1):46-52.
Zurita et al., "Circulating biomarkers for vascular-endothelial growth factor inhibitors in renal cell carcinoma," Cancer, May 2009, 115(S10):2346-2354.
Amendment in European Patent Application No. 12793322.4, dated Sep. 15, 2017, 20 pages.
Auburn University, "Thyroid Cancer," (as of Feb. 25, 2006, using Wayback machine), Feb. 25, 2006, 8 pages.
Board of Appeal of the European Patent Office, "Decision—T1212/01 3.3.2," dated Feb. 3, 2015, 55 pages.
Chemical & Engineering News, "The Top Pharmaceuticals That Changed the World," 83, [cited: Mar. 29, 2016], Jun. 20, 2005, 3 pages.
European Search Report in Application No. 13865671.5, dated May 23, 2016, 7 pages.
Ferrara, "Vascular Endothelial Growth Factor: Basic Science and Clinical Progress," Endocrine Reviews, 25(4):581-611, Aug. 2004.
Folkman, "What is the evidence that tumors are angiogenesis dependent," J Nat Can Inst 82(1), 1990.
Gong et al., "Expression of CC Chemokine Receptor 4 in Human Follicular Thyroid Carcinoma," Academic Journal of Military Medical University, 28:701-703, 2007 English Translation.
Herbst and Khuri et al., "Mode of action of docetaxel—a basis for combination with novel anticancer agents," Cancer Treat Rev, 29:407-415, 2003.

(56) References Cited

OTHER PUBLICATIONS

International Adjuvant Lung Cancer Trial Collaborative Group, "Cisplatin-Based Adjuvant Chemotherapy in Patients with Completely Resec," The New England Journal of Medicine, 350(4):351-360, Jan. 22, 2004.
International Preliminary Report on Patentability in International Application No. PCT/JP2016/055268, dated Sep. 8, 2017, 9 pages.
Jain, "Normalizing tumor vasculature with anti-angiogenic therapy: A new paradigm for combination therapy," Nature Medicine 7(9):987-989, Sep. 2001.
Johnson et al., "Randomized phase II trial comparing bevacizumab plus carboplatin and paclitaxel with carboplatin and paclitaxel alone in previously untreated locally advanced or metastatic non-small-cell lung cancer," J Clin Oncol 22(11):2184-2191, Jun. 1, 2004.
Klein et al, "Vascular endothelial growth factor gene and protein: strong expression in thyroiditis and thyroid carcinoma", Journal of endocrinology, Nov. 30, 1999, 41-49.
Konno, "Physical and Chemical Changes of Medicinals in Mixtures with Adsorbents in the Solid State IV," Study on Reduced-Pressure Mixing for Practical Use of Amorphous Mixtures of Flufenamic Acid, Chem. Pharm Bull, 1990, p. 2003.
Matsui et al, "a novel multi-targeted tyrosine kinase inhibitor, exhibits anti-angiogenic activity via inhibition of KIT signaling in a small cell lung cancer xenograft model", European Journal of Cancer, Sep. 29, 2004, p. 47.
Nakamura et al., "In Vitro selectivity and potency of KRN951, a novel inhibitor of VEGF receptor tyrosine kinases", Cancer Research, cited Jul. 13, 2016, 2 pages.
Notice of Allowance in Australian Patent Application No. 2012246490, dated Jul. 25, 2016, 4 pages.
Notice of Allowance in Canadian Patent Application No. 2704000, dated Jul. 7, 2016, 1 page.
Notice of Allowance in Canadian Patent Application No. 2802644, dated Aug. 5, 2016, 1 page.
Notice of Allowance in Canadian Patent Application No. 2828946, dated Feb. 22, 2016, 1 page.
Notice of Allowance in Chinese Patent Application No. 201480026871.9, dated Jun. 28, 2017, 8 pages (English Translation).
Notice of Allowance in European Patent Application No. 12786619.2, dated Sep. 30, 2016, 155 pages.
Notice of Allowance in Indonesian Patent Application No. W-00201201031, dated Dec. 28, 2016, 5 pages (English Translation).
Notice of Allowance in Israeli Patent Application No. 217197, dated Jun. 26, 2016, 3 pages, (English translation).
Notice of Allowance in Israeli Patent Application No. 223695, dated Apr. 4, 2017, 3 pages (English Translation).
Notice of Allowance in Israeli Patent Application No. 227558, dated May 8, 2017, 6 pages (English Translation).
Notice of Allowance in Japanese Patent Application No. P2012-521531, dated Mar. 1, 2016, 6 pages (English Translation).
Notice of Allowance in Japanese Patent Application No. P2013-515178, dated May 17, 2016, 6 pages (English Translation).
Notice of Allowance in Japanese Patent Application No. P2014-513691, dated Oct. 4, 2016, 6 pages (English Translation).
Notice of Allowance in Jordan Patent Application No. 55/2011, dated Apr. 16, 2017, 2 pages (English Translation).
Notice of Allowance in Korean Patent Application No. 10-2012-7033886, dated Oct. 18, 2016, 3 pages (English Translation).
Notice of Allowance in Korean Patent Application No. 10-2013-7020616, dated Jun. 29, 2017, 3 pages (English Translation).
Notice of Allowance in Mexican Patent Application No. MX/a/2014/010594, dated Nov. 17, 2016, 3 pages (English Translation).
Notice of Allowance in Singapore Patent Application No. 11201509278X, dated Nov. 22, 2017, 5 pages (English Translation).
Notice of Allowance in U.S. Appl. No. 13/870,507, dated Jul. 26, 2016, 13 pages.
Notice of Appeal in European Patent Application No. 08846814.5, dated Jul. 5, 2017, 3 pages.
Office Action in Australian Patent Application No. 2012246490, dated Apr. 20, 2016, 3 pages.
Office Action in Australian Patent Application No. 2012246490, dated Feb. 5, 2016, 3 pages.
Office Action in Australian Patent Application No. 2013364953, dated Apr. 19, 2017, 3 pages.
Office Action in Australian Patent Application No. 2013364953, dated Feb. 16, 2017, 3 pages.
Office Action in Canadian Patent Application No. 2713930, dated Mar. 7, 2016, 5 pages.
Office Action in Chilean Patent Application No. 2012-00412, dated Jan. 23, 2017, 4 pages (English Translation).
Office Action in Chinese Patent Application No. 201380054667.3 dated Aug. 9, 2017, 11 pages (English Translation).
Office Action in Chinese Patent Application No. 201380054667.3, dated Feb. 14, 2017, 9 pages (English Translation.
Office Action in Chinese Patent Application No. 201380054667.3, dated Jul. 18, 2016, 18 pages (English Translation).
Office Action in Chinese Patent Application No. 201480026871.9, dated Feb. 21, 2017, 10 pages (English Translation).
Office Action in Chinese Patent Application No. 201510031628.2, dated Apr. 5, 2017, 8 pages (English Translation).
Office Action in Chinese Patent Application No. 201510031628.2, dated Jun. 2, 2016, 11 pages (English Translation).
Office Action in European Patent Application No. 07743994.1, dated Apr. 18, 2017, 5 pages.
Office Action in European Patent Application No. 07743994.1, dated Mar. 8, 2017, 5 pages.
Office Action in European Patent Application No. 08846814.5, dated Apr. 29, 2016, 28 pages.
Office Action in European Patent Application No. 08846814.5, dated Sep. 28, 2016, 14 pages.
Office Action in European Patent Application No. 08846814.5, dated Sep. 13, 2017, 19 pages.
Office Action in European Patent Application No. 12793322.4, dated May 19, 2017, 4 pages.
Office Action in European Patent Application No. 13865671.5, dated Mar. 7, 2017, 4 pages.
Office Action in European Patent Application No. 14727633.1, dated Oct. 13, 2016, 4 pages.
Office Action in Indian Patent Application No. 1511/CHENP/2009, dated Feb. 27, 2017, 7 pages (English Translation).
Office Action in Indian Patent Application No. 2371/CHENP/2012, dated Jul. 27, 2017, 5 pages (English Translation).
Office Action in Indian Patent Application No. 2793/CHENP/2013, dated Sep. 13, 2017, 12 pages (English Translation).
Office Action in Indian Patent Application No. 3334/CHENP/2010, dated Feb. 6, 2017, 13 pages (English Translation).
Office Action in Indian Patent Application No. 5022/CHENP/2009, dated Jun. 28, 2016, 7 pages.
Office Action in Indian Patent Application No. 5022/CHENP/2009, dated Jun. 29, 2017, 3 pages (English Translation).
Office Action in Indian Patent Application No. 5287/CHENP/2010, dated Mar. 15, 2017, 8 pages (English Translation).
Office Action in Indian Patent Application No. 6415/CHENP/2008, dated Jan. 19, 2017, 5 pages (English Translation).
Office Action in Indonesian Patent Application No. W-00201201031, dated Mar. 14, 2016, 4 pages (English translation).
Office Action in Israeli Patent Application No. 227558, dated Mar. 13, 2016, 5 pages (English Translation).
Office Action in Israeli Patent Application No. 242519, dated Aug. 9, 2017, 7 pages (English Translation).
Office Action in Japanese Application No. P2014-553200, dated Jun. 6, 2017, 6 pages (with English Translation).
Office Action in Japanese Patent Application No. P2014-513691, dated Mar. 8, 2016, 6 pages (English Translation).
Office Action in Japanese Patent Application No. P2014-513691, dated Jun. 21, 2016, 4 pages, (English Translation).
Office Action in Japanese Patent Application No. P2016-214593, dated Oct. 17, 2017, 9 pages (English Translation).
Office Action in Jordan Patent Application No. 55/2011, dated Feb. 16, 2017, 2 pages (English Translation).

(56) References Cited

OTHER PUBLICATIONS

Office Action in Korean Patent Application No. 10-2013-7020616, dated Dec. 19, 2016, 12 pages (English Translation).
Office Action in Mexican Patent Application No. MX/a/2014/010594, dated Aug. 17, 2016, 10 pages (English Translation).
Office Action in Norwegian Patent Office Application No. 20063383, dated Mar. 15, 2016, 6 pages (English Translation).
Office Action in Peruvian Patent Application No. 2081-2011, dated Jul. 15, 2016, 12 pages (English Translation).
Office Action in Russian Patent Application No. 2015148193, dated May 10, 2016, 3 pages (English Translation).
Office Action in Russian Patent Application No. 2015148193, dated Jan. 27, 2016, 4 pages, (English Translation).
Office Action in Russian Patent Application No. 2015115397, dated Oct. 26, 2017, 16 pages (English Translation).
Office Action in U.S. Appl. No. 13/870,507, dated Feb. 17, 2016, 28 pages.
Office Action in U.S. Appl. No. 13/923,858, dated May 4, 2017, 31 pages.
Office Action in U.S. Appl. No. 14/117,276, dated May 20, 2016, 11 pages.
Office Action in U.S. Appl. No. 14/122,339, dated Aug. 10, 2017, 10 pages.
Office Action in U.S. Appl. No. 14/122,339, dated Jul. 8, 2016, 12 pages.
Office Action in Yemen Patent Application No. 592/2011, dated Jan. 16, 2017, 2 pages (English Translation).
Official Notification in Australian Patent Application No. 2005283422, dated Jul. 14, 2016, 8 pages.
Official Notification in Australian Patent Application No. 2005283422, dated Oct. 20, 2016, 1 pages.
Official Notification in Indian Patent Application No. 6415/CHENP/2008, dated Apr. 28, 2017, 5 pages (English Translation).
Official Notification in Israeli Patent Application No. 223695, dated May 29, 2017, 1 page (English Translation).
Office Action in Peruvian Patent Application No. 2081-2011, dated Mar. 23, 2016, 12 pages, (English Translation).
Pisters et al, "Induction chemotherapy before surgery for early-stage lung cancer: A novel approach," J Thoracic Cardiovasc Surg 119(3):429-439, Mar. 2000.
Remington, "The Science and Practice of Pharmacy," Remington, 20th Edition, 2000, pp. 1123-1124.
Response in Chinese Patent Application No. 201510031628.2, dated Aug. 11, 2017, 8 pages (English Translation).
Response in Indian Patent Application No. 5287/CHENP/2010, dated Sep. 12, 2017, 6 pages (English Translation).
Response in U.S. Appl. No. 13/923,858 dated Oct. 3, 2017, 29 pages.
Response to Examination Report in Australian Patent Application No. 2012246490, dated Jul. 15, 2016, 30 pages.
Response to Office Action in Canadian Patent Application No. 2704000, dated May 19, 2016, 11 pages.
Response to Office Action in European Patent Application No. 12786619.2, dated Apr. 15, 2016, 41 pages.
Response to Office Action in European Patent Application No. 12793322.4, dated Apr. 8, 2016, 10 pages.
Response to Office Action in U.S. Appl. No. 13/870,507, dated May 17, 2016, 12 pages.
Sandler et al, "Paclitaxel-carboplatin alone or with bevacizumab for non-small-cell lung cancer," N Engl J Med, 355(24):2542-2550, Dec. 14, 2006.
Stinchcombe "Targeted therapy of advanced non-small cell lung cancer: the role of bevacizumab," Biologics: Targets & Therapy 1(3):185-194, 2007.
Stinchcombe and Scoinski, "Bevacizumab in the treatment of non-small-cell lung cancer," Oncogene 26:3691-3698, May 28, 2007.
Submission Documents in Australian Patent Application No. 2013364953, dated Apr. 13, 2017, 15 pages.
Submission Documents in Canadian Patent Application No. 201380054667.3, dated Apr. 12, 2017, 9 pages.
Submission Documents in Chilean Patent Application No. 2012-00412, dated Mar. 6, 2017, 9 pages (English Translation).
Submission Documents in Chinese Patent Application No. 201380054667.3, dated Nov. 17, 2016, 8 pages (English Translation).
Submission Documents in Chinese Patent Application No. 201480026871.9, dated May 8, 2017, 10 pages (English Translation).
Submission Documents in Chinese Patent Application No. 201480026871.9, dated Nov. 14, 2016, 11 pages (English Translation).
Submission Documents in Chinese Patent Application No. 201510031628.2, dated Nov. 29, 2016, 8 pages (English Translation).
Submission Documents in European Patent Application No. 08846814.5, dated Mar. 31, 2017, 45 pages.
Submission Documents in European Patent Application No. 08846814.5, dated Mar. 2, 2017, 18 pages.
Submission Documents in European Patent Application No. 13865671.5, dated Jul. 7, 2016, 3 pages.
Submission Documents in European Patent Application No. 14727633.1, dated Feb. 2, 2017, 12 pages.
Submission Documents in European Patent Application No. 14727633.1, dated Jul. 18, 2016, 8 pages.
Submission Documents in Indian Patent Application No. 1511/CNENP/2009, dated Aug. 18, 2017, 55 pages (English Translation).
Submission Documents in Indian Patent Application No. 3334/CHENP/2010, dated Jul. 26, 2017, 59 pages (English Translation).
Submission Documents in Indian Patent Application No. 5022/CHENP/2009, dated Sep. 23, 2016, 9 pages (English Translation).
Submission Documents in Indian Patent Application No. 6415/CHENP/2008, dated Apr. 18, 2017, 317 pages (English Translation).
Submission Documents in Indonesia Patent Application No. W-00201201031, dated Aug. 11, 2016, 13 pages (English Translation).
Submission Documents in Indonesia Patent Application No. W-00201201031, dated Dec. 9, 2016, 4 pages (English Translation).
Submission Documents in Israel Patent Application No. 223695, dated Dec. 22, 2016, 5 pages (English Translation).
Submission Documents in Israel Patent Application No. 227558, dated Jul. 12, 2016, 6 pages (English Translation).
Submission Documents in Israel Patent Application No. 242519, dated Apr. 13, 2016, 4 pages (English Translation).
Submission Documents in Jordan Patent Application No. 55/2011, dated Apr. 9, 2017, 7 pages (English Translation).
Submission Documents in Jordan Patent Application No. 55/2011, dated Mar. 29, 2017, 5 pages (English Translation).
Submission Documents in Korean Patent Application No. 10-2013-7020616, dated Feb. 13, 2017, 47 pages (English Translation).
Submission Documents in Mexican Patent Application No. MX/a/2014/010594, dated Oct. 20, 2016, 15 pages (English Translation).
Submission Documents in Norwegian Patent Application No. 20063383, dated Jun. 15, 2016, 181 pages.
Submission Documents in Russian Patent Application No. 2015148193, dated Aug. 5, 2016, 16 pages (English Translation).
Submission Documents in U.S. Appl. No. 13/870,507, dated Apr. 11, 2017, 4 pages.
Submission Documents in U.S. Appl. No. 14/117,276, dated Jul. 18, 2016, 3 pages.
Submission Documents in U.S. Appl. No. 14/122,339, dated Jun. 12, 2017, 5 pages.
Submission Documents in U.S. Appl. No. 14/122,339, dated Mar. 27, 2017, 14 pages.
Tanaka et al., "Biological Equivalence Test on Tandospirone Citrate 10 mg Tablet "AMEL"," Journal of New Remedies & Clinics, 57(6):936-951 (Jun. 2008) (Partial English Translation).
Vergote et al., "A phase II trial of lenvatinib in patients with advanced or recurrent endometrial cancer: Angiopoietin-2 as a predictive marker for clinical outcomes.", J. Clin. Oncol, vol. 31, No. 15 supplement, 5520, May 20, 2013, XP002728918.

(56) References Cited

OTHER PUBLICATIONS

Vieira et al, "Expression of vascular endothelial growth factor (VEGF) and its receptors in thyroid carcinomas of follicular origin: a potential autocrine loop", European Journal of Endocrinology, 2005;153:701-709.
Went et al, "Prevalence of KIT Expression in Human Tumor", Journal of Clinical Oncology, Nov. 15, 2004, 4514-4522.
Written Submission in Indian Patent Application No. 5022/CHENP/2009, dated Aug. 8, 2017, 16 pages (English Translation).
Yamamoto et al., "Plasma biomarkers predictive for disease control duration in the phase I study of E7080, a multitarget kinase inhibitor," ASCO Annual Meeting Proceedings(Post Meeting Edition), Journal of Clinical Oncology, 27:15S, 2009, 1 page.
"Impurities in New Drug Substances Q3A (R2)", ICH Harmonized—Tripartite Guideline, Oct. 25, 2006.
"IN 1571/CHENP/2007", Aug. 31, 2007, 50 pages (English Translation).
"IN 2045/CHENP/2006", Jun. 1, 2007, 13 pages (English Translation).
"IN 2572/CHENP/2006", Jun. 8, 2007, 74 pages (English Translation).
"IN 383/CHENP/2008", Sep. 19, 2008, 26 pages (English Translation).
"Mix: Merriam-Webster Dictionary (Year: 2018)," 2018.
Ang, "Role of the fibroblast growth factor receptor axis in cholangiocarcinoma", Journal of Gastroenterology and Hepatology, 2015 vol. 30, p. 1116-p. 1122.
Eisai Co., Ltd., "Phase II Study Results Showed Eisai's Lenvatinib (E7080) Demonstrated an Objective Response Rate of 59% in Advance Radioiodine-Refractory Differentiated Thyroid Cancer", News Release: 2011 PR Department, Eisai Co., Ltd.,No. 11-44, https://www.eisai.co.jp.news/news201144.html, Jun. 2, 2011, p. 11-p. 44.
Extended European Search Report in Application No. 16755489.8, dated Jul. 30, 2018, 8 pages.
Gaspar et al., "Single-agent Dose-finding Cohort of a Phase 1/2 Study of Lenvatinib in Children and Adolescents With Refractory or Relapsed Solid Tumors", ASCO 2017 Poster 301, ITCC-50 Study, Jun. 2-6, 2017.
Gentet et al., "Ifosfamide and etoposide in childhood osteosarcoma. A phase II study of the French Society of Paediatric Oncology", European Journal of Cancer, vol. 33, 1997, p. 232-p. 237.
Grier et al., "Addition of Ifosfamide and Etoposide to Standard Chemotherapy for Ewing's Sarcoma and Primitive Neuroectodermal Tumor of Bone", The New England Journal of Medicine, vol. 348, 2003, p. 694-p. 701.
Ikeda et al., "A Phase 2 Study of Lenvatinib Monotherapy as Second-line Treatment in Unresectable Biliary Tract Cancer: Primary Analysis Results", ESMO 2017 Congress, Sep. 8-12, 2017.
Indian Office Action in Application No. 2365/CHENP/2015, dated Sep. 6, 2018, 6 pages (with English Translation).
International Preliminary Report on Patentability for Application No. PCT/JP2018/018810, dated Aug. 7, 2018, 10 pages.
International Preliminary Report on Patentability in International Patent Application No. PCT/JP2015/073946, dated Mar. 9, 2017, 8 pages (English Translation).
International Preliminary Report on Patentability in International Patent Application No. PCT/JP2016/074017, dated Mar. 1, 2018, 8 pages (English Translation).
International Preliminarty Report on Patentability in International Patent Application No. PCT/JP2016/074090, dated Mar. 1, 2018, 6 pages (English Translation).
Japanese Office Action dated Jun. 19, 2018 for Application No. P2016-214593, 7 pages (with English translation).
Molina et al.,"'A phase 1b clinical trial of the multitargeted tyrosine kinase inhibitor lenvatinib (E7080) in combination with everolimus for treatment of metastatic renal cell carcinoma (RCC)'", Cancer Chemotherapy and Pharmacology, Jan. 2014, vol. 73, No. 1, p. 181-p. 189.
Nakagawa, Takayuki et al., "Lenvatinib in combination with golvatinib oversomes hepatocyte growth factor pathway-induced resistance to vascular endothelial growth factor receptor inhibitor", Cancer Science, Jun. 2014, vol. 105, No. 6, p. 723-p. 730.
Nakazawa et al., "Multitargeting strategy using lenvatinib and golvatinib: Maximizing anti-angiogenesis activity in a preclinical cancer model", Cancer Science, Feb. 2015, vol. 106, No. 2, p. 201-p. 207.
Notice of Allowance in European Patent Application No. 12793322.4, dated Feb. 14, 2018, 82 pages.
Notice of Allowance in European Patent Application No. 12793322.4, dated Jun. 4, 2018, 7 pages.
Notice of Allowance in European Patent Application No. 14727633.1, dated Feb. 9, 2018, 72 pages.
Notice of Allowance in Israeli Patent Application No. 242519, dated Dec. 13, 2017, 6 pages (English Translation).
Notice of Allowance in Russian Patent Application No. 2015148193, dated Apr. 23, 2018, 15 pages (English Translation).
Notice of Allowance in U.S. Appl. No. 14/122,339, dated Dec. 21, 2017, 8 pages.
Notice of Allowance in U.S. Appl. No. 15/503,108, dated Apr. 11, 2018, 7 pages.
Office Action in Algerian Patent Application No. 120036, dated Dec. 31, 2017, 2 pages (English Translation).
Office Action in Chinese Patent Application No. 201510031628.2, dated Dec. 12, 2017, 11 pages (English Translation).
Office Action in Chinese Patent Application No. 201510031628.2, dated Jul. 19, 2018, 11 pages (English Translation).
Office Action in Egyptian Patent Application No. PCT 283/2012, dated Feb. 19, 2018, 10 pages (English Translation).
Office Action in European Patent Application No. 09705712.9, dated Apr. 11, 2018, 5 pages.
Office Action in European Patent Application No. 15836577.5, dated Mar. 23, 2018, 9 pages.
Office Action in Gulf Cooperation Council Patent Application No. GC2011-17812, dated Aug. 2, 2018, 8 pages (English Translation).
Office Action in Gulf Cooperation Council Patent Application No. GC2015-29939, dated Feb. 22, 2018, 16 pages (English Translation).
Office Action in Indian Patent Application No. 10502/CHENP/2012, dated Dec. 29, 2017, 5 pages (English Translation).
Office Action in Indian Patent Application No. 2371/CHENP/2012, dated Jun. 15, 2018, 3 pages (English Translation).
Office Action in Indian Patent Application No. 2793/CHENP/2013, dated Feb. 28, 2018, 2 pages (English Translation).
Office Action in Indian Patent Application No. 5287/CHENP/2010, dated Mar. 22, 2018, 2 pages (English Translation).
Office Action in Indian Patent Application No. 7026/CHENP/2013, dated Mar. 8, 2018, 7 pages (English Translation).
Office Action in Israeli Patent Application No. 238463, dated Feb. 1, 2018, 6 pages (English Translation).
Office Action in Israeli Patent Application No. 250454, dated Feb. 11, 2018, 4 pages (English Translation).
Office Action in Japanese Patent Application No. P2015-555882, dated Mar. 27, 2018, 4 pages (English Translation).
Office Action in Japanese Patent Application No. P2016-214593, dated Jun. 19, 2018, 7 pages (English Translation).
Office Action in Pakistan Patent Application No. 548/2015, dated Oct. 18, 2017, 2 pages (English Abstract).
Office Action in Russian Patent Application No. 2015148193, dated Dec. 25, 2017, 13 pages (English Translation).
Office Action in Singaporean Patent Application No. 11201706630U, dated Apr. 30, 2018, 8 pages. (English Translation).
Office Action in U.S. Appl. No. 13/923,858, dated Feb. 22, 2018, 16 pages.
Office Action in U.S. Appl. No. 14/122,339, dated Jan. 2, 2018, 3 pages.
Office Action in U.S. Appl. No. 15/503,108, dated Nov. 14, 2017, 12 pages.
Office Action in U.S. Appl. No. 15/503,108, dated Sep. 5, 2018, 8 pages.
Office Action in U.S. Appl. No. 15/550,124, dated Jan. 26, 2018, 12 pages.

(56) References Cited

OTHER PUBLICATIONS

Office Action in U.S. Appl. No. 15/550,124, dated May 3, 2018, 124 pages.
Official Notification in European Patent Application No. 14727633.1, dated Jun. 21, 2018, 2 pages.
Official Notification in Indian Patent Application No. 201747004829, dated Mar. 20, 2018, 87 pages (English Translation).
Official Notification in Indian Patent Application No. 2371/CHENP/2012, dated Jan. 25, 2018, 3 pages (English Translation).
Official Notification in Indian Patent Application No. 2793/CHENP/2013, dated Mar. 19, 2018, 2 pages (English Translation).
Official Notification in Indian Patent Application No. 5287/CHENP/2010, dated Apr. 6, 2018, 2 pages (English Translation).
Official Notification in Jordan Patent Application No. 55/2011, dated Feb. 12, 2018, 2 pages (English Translation).
Official Notification in U.S. Appl. No. 13/92,358, dated Jul. 23, 2018, 15 pages.
Okusaka et al., "Chemotherapy for biliary tract cancer", biliary tract, 2013 vol. 27 No. 1, p. 124-p. 134 (Machine Translation).
Papai et al., "The efficacy of a combination of etoposide, ifosfamide, and cisplatin in the treatment of patients with soft tissue sarcoma", Cancer, 2000.07, vol. 89, No. 1, p. 177-p. 180.
Pilaniya et al., "Recent trends in the impurity profile of pharmaceuticals", J Adv Pharm Technol Res.; 1(3): 302-310, Jul.-Sep. 2010.
Search Report in European Patent Application No. 15836577.5, dated Jun. 28, 2018, 9 pages.
Singaporean Submission Documents in Application No. 11201706630U, dated Aug. 21, 2018, 9 pages.
Submission Document in Algerian Patent Application No. 120036, dated Feb. 22, 2018, 16 pages (English Translation).
Submission Document in Chinese Patent Application No. 201510031628.2, dated Feb. 27, 2018, 7 pages (English Translation).
Submission Document in Egyptian Patent Application No. PCT 283/2012, dated May 9, 2018, 13 pages (English Translation).
Submission Document in European Patent Application No. 12793322.4, dated Apr. 19, 2018, 8 pages.
Submission Document in Gulf Cooperation Council Patent Application No. GC2015-29939, dated May 21, 2018, 6 pages (English Translation).
Submission Document in Indian Patent Application No. 10502/CHENP/2012, dated May 3, 2018, 10 pages (English Translation).
Submission Document in Indian Patent Application No. 2371/CHENP/2012, dated Jun. 15, 2018, 14 pages (English Translation).
Submission Document in Indian Patent Application No. 2371/CHENP2012, dated Jan. 8, 2018, 10 pages (English Translation).
Submission Document in Indian Patent Application No. 2793/CHENP/2013, dated Apr. 20, 2018, 4 pages (English Translation).
Submission Document in Indian Patent Application No. 2793/CHENP/2013, dated Dec. 13, 2017, 10 pages (English Translation).
Submission Document in Indian Patent Application No. 2793/CHENP/2013, dated Mar. 8, 2018, 1 page (English Translation).
Submission Document in Indian Patent Application No. 7026/CHENP/2013, dated Jul. 9, 2018, 15 pages.
Submission Document in Israeli Patent Application No. 242519, dated Nov. 29, 2017, 13 pages (English Translation).
Submission Document in Russian Patent Application No. 2015148193, dated Mar. 23, 2018, 17 pages (English Translation).
Submission Document in Thailand Patent Application No. 1201000221, dated Mar. 12, 2018, 3 pages (English Translation).
Submission Document in U.S. Appl. No. 14/122,339, dated Mar. 1, 2018, 15 pages.
Submission Document in U.S. Appl. No. 15/503,108, dated Apr. 17, 2018, 5 pages.
Submission Document in U.S. Appl. No. 15/503,108, dated Aug. 9, 2018, 15 pages.
Submission Document in U.S. Appl. No. 15/550,124, dated Mar. 14, 2018, 3 pages.
Submission Document in U.S. Appl. No. 15/934,242, dated Mar. 23, 2018, 10 pages.
Takahashi et al., "Preclinical Study of VEGFR and EGFR Inhibitor— Are They Potential Therapeutic Targets in Biliary Tract Carcinoma?", The Biliary Tract & Pancreas, Feb. 2015 vol. 36 No. 2, p. 153-p. 160 (Machine Translation).
Tamai et al., "Developmental strategy of Lenvatinib and developmental status in gastrointestinal cancer", BIO Clinica, 2014 vol. 29 No. 2, p. 61-p. 65 (Machine Translation).
"The ESMO/European Sarcoma Network Working Group, ""Bone sarcomas: ESMO Clinical Practice Guideline for diagnosis, treatment and follow-up""", Annals of Oncology, vol. 23, supplement 7, 2012, pvii100-pvii109".
Valle et al., Cisplatin plus Gemcitabine versus Gemcitabine for Biliary Tract Cancer, The New England Journal of Medicine, Apr. 8, 2010 vol. 362, p. 1273-p. 1281.
Zhang et al., "Stage 1 in vivo evaluation of multi-receptor tyrosine-kinase inhibitor lenvatinib in osteosarcoma patient derived mouse xenograft models", AACR 2017, Abstract 697, Jul. 2017.
Gayed et al., "Prospective evaluation of plasma levels of ANGPT2, TuM2PK, and VEGF in patients with renal cell carcinoma", BMC Urology, Biomed Central, London, GB, vol. 15, No. 1, Apr. 3, 2015, p. 24, XP021217372.
Glen et al., "432 Correlative analyses of serum biomarkers and clinical outcomes in the phase 2 study of lenvatinib, everolimus, and the combination, in patients with metastatic renal cell carcinoma following 1 VEGF-targeted therapy", European Journal of Cancer, vol. 51, Sep. 1, 2015, p. S89, XP055510094.
Glen et al., "Correlative Analyses of Serum Biomarkers and Clinical Outcomes in the Phase 2 Study of Lenvatinib, Everolimus, and the Combination, in Patients With a Metastatic Renal Cell Carcinoma Following 1 VEGF-Targeted Therapy", Poster presentation at 18th ECCO—40th ESMO European Cancer Congress, Vienna, Sep. 25-29, 2015.
International Preliminary Report on Patentability in International Patent Application No. PCT/JP2016/002562, dated Aug. 9, 2016, 4 pages (English Translation).
Leow et al. "MEDI3617, a human anti-angiopoietin 2 monoclonal antibody, inhibits angiogenesis and tumor growth in human tumor xenograft models", International Journal of Oncology, Demetrios A. Spandidos ED. & Pub, GR, vol. 40, No. 5, May 1, 2012, p. 1321-p. 1330, XP002721374.
Motzer et al., "Investigation of novel circulating proteins, germ line single nucleotide polymorphisms, and molecular tumor markers as potential efficacy biomarkers of first-line sunitinib therapy for advanceed renal cell carcinoma," Cancer Chemotherapy and Pharmacology, Aug. 7, 2014, vol. 74 No. 4, p. 739-p. 750.
Motzer et al., "Randomized phase 2 three-arm trial of lenvatinib (LEN), everolimus (EVE), and LEN+EVE in patients (pts) with metastatic renal cell carcinoma (mRCC)," Oral presentation at ASCO Annual Meeting, Chicago, May 29-Jun. 2, 2015.
Motzer et al., "Randomized phase II, three-arm trial of lenvatinib (LEN), everolimus (EVE), and LEN+EVE in patients pts) with metastatic renal cell carcinoma (mRCC)," Journal of Clinical Oncology, May 20, 2015, vol. 33, Issue 15S, p. 248.
Office Action in Israeli Application No. 255564, dated Aug. 15, 2018, 5 pages (English Translation).
Search Report in EP Application No. 16802790.2, dated Oct. 9, 2018, 10 pages.
Submission Document in Korean Patent Application 10-2017-7032771, dated Jan. 8, 2018, 11 pages (English Translation).
Submission Document in U.S. Appl. No. 15/573,197, dated Dec. 5, 2018, 4 pages.
Wang et al., "The Role of Angiopoietins as Potential Therapeutic Targets in Renal Cell Carcinoma", Translational Oncology, vol. 7, No. 2, Apr. 1, 2014, p. 188-p. 195, XP055218621.

\* cited by examiner

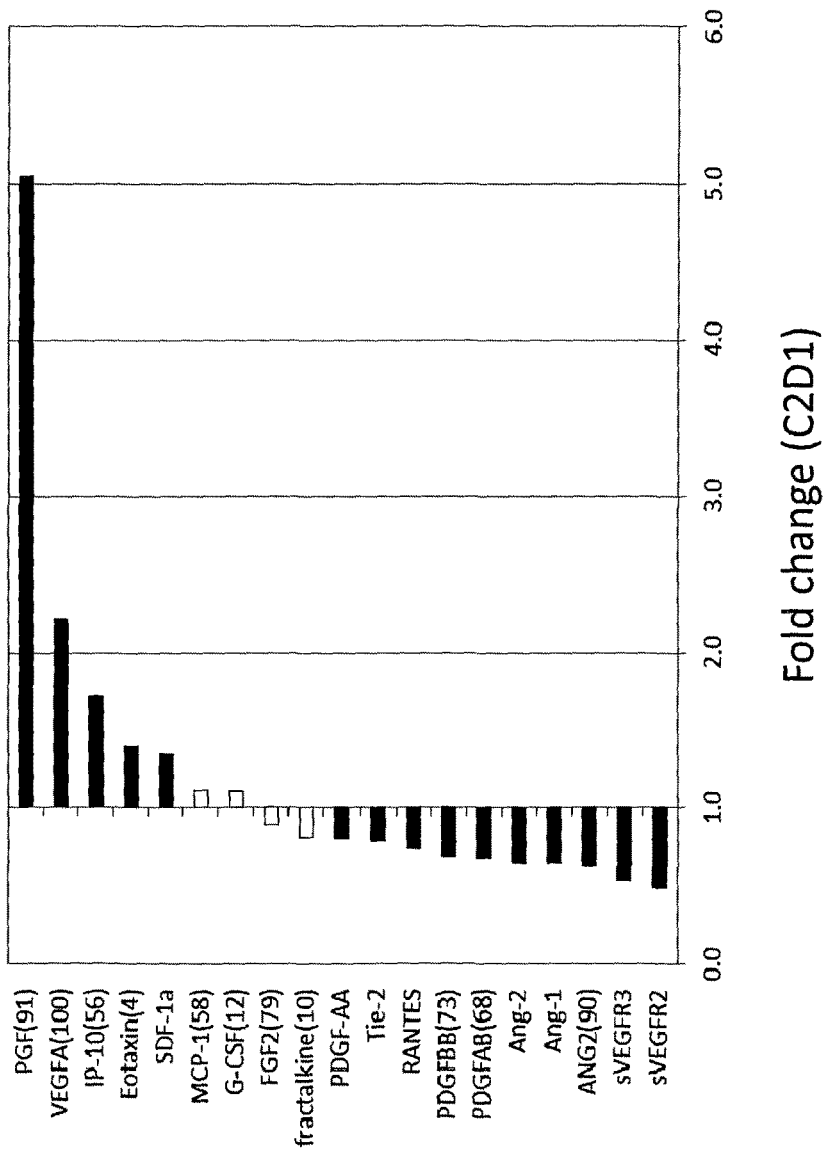

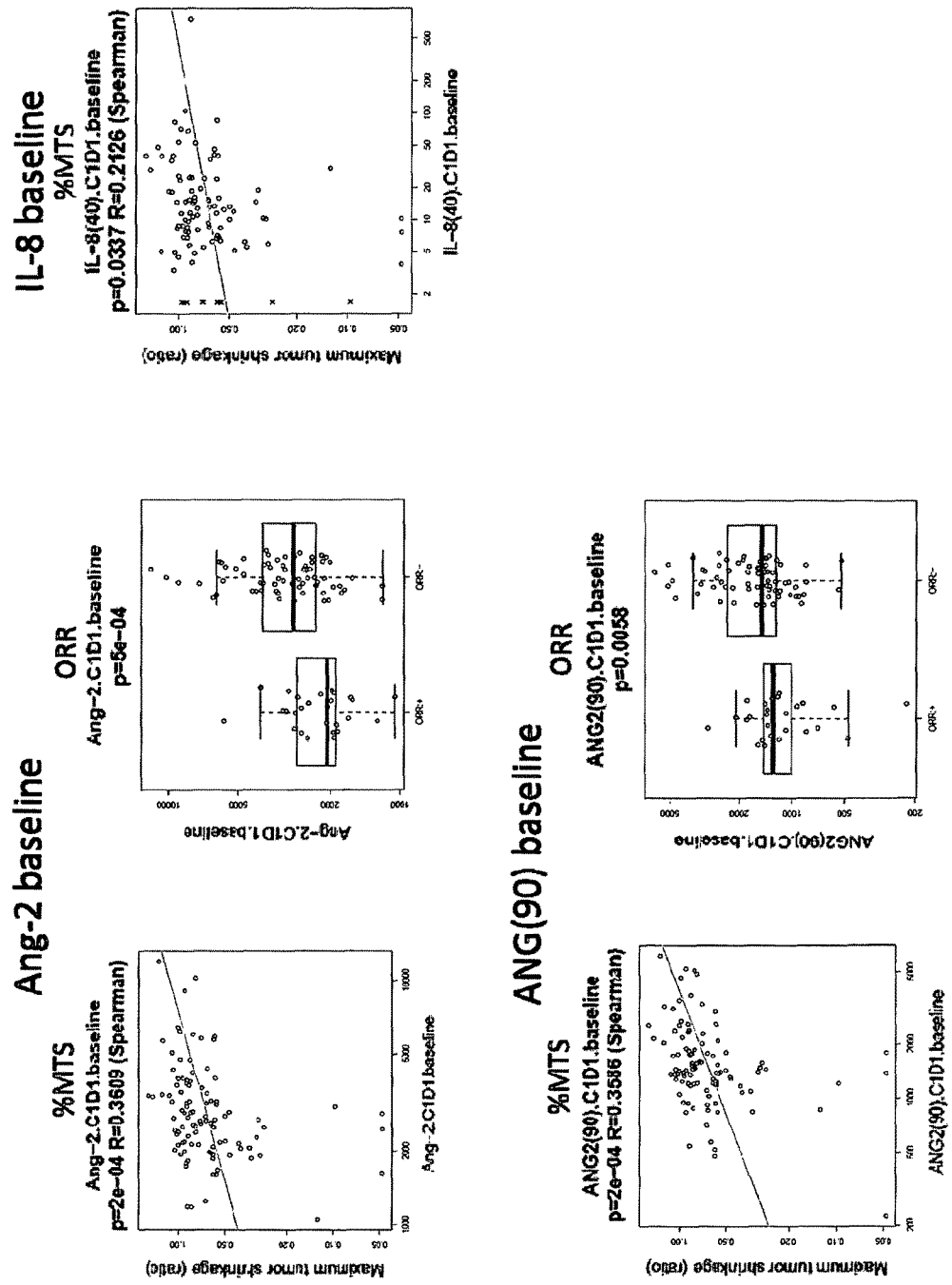

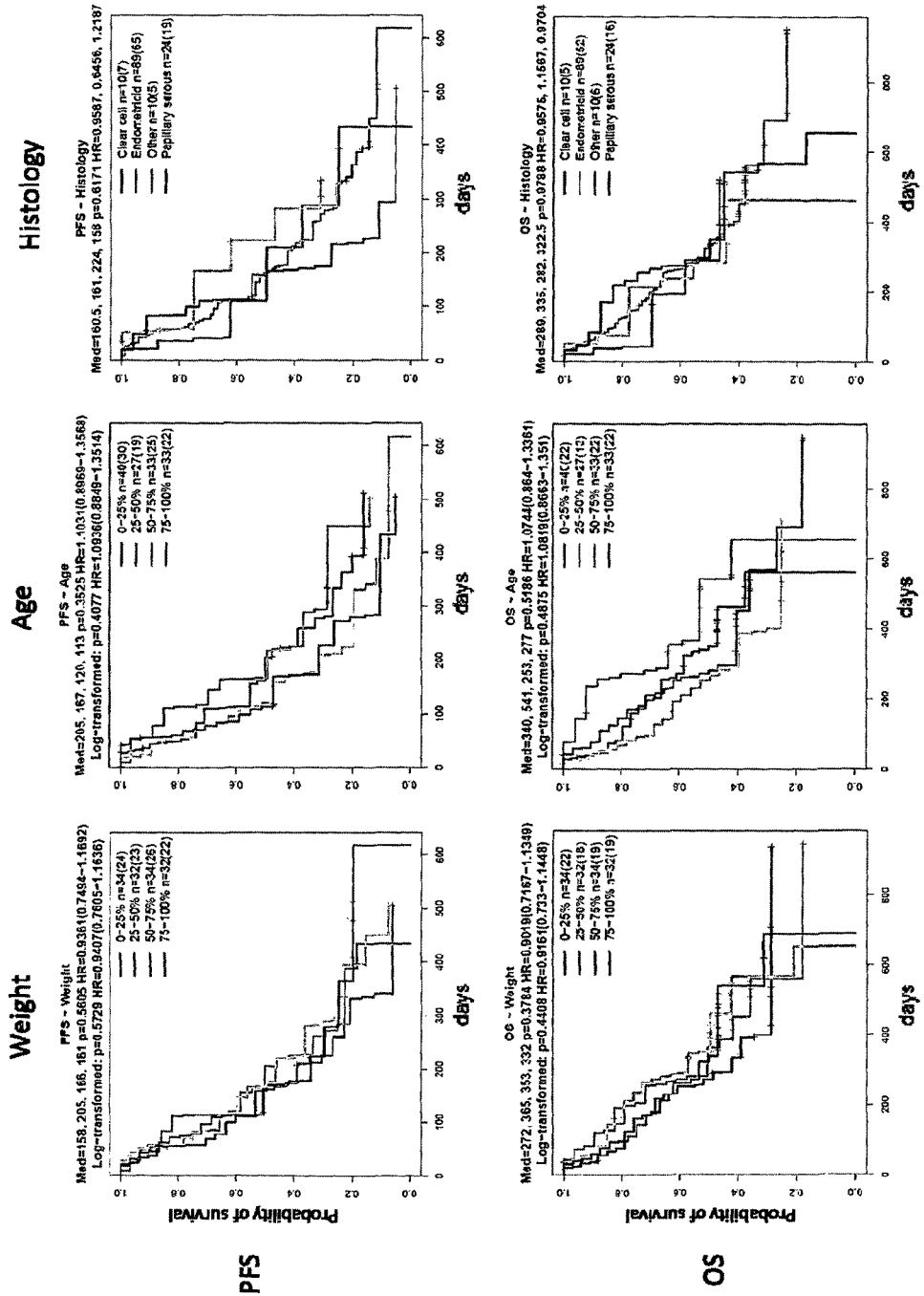
Fig. 3 No significant correlation of weight, age and histology with PFS and OS

Fig. 4 Multivariate analysis does not identify potential combination factors with Ang-2

MTS

|  | Estimate | Std. Error | t value | Pr(>|t|) |  |
|---|---|---|---|---|---|
| (Intercept) | -23.269 | 2.850 | -8.163 | 1.14e-12 | *** |
| `Ang-2.C1D1.baseline` | 12.517 | 3.592 | 3.485 | 0.000738 | *** |

ORR

|  | bbEstimate | Std. Error | z value | Pr(>|z|) |  |
|---|---|---|---|---|---|
| (Intercept) | -1.4782 | 0.3643 | -4.057 | 4.96e-05 | *** |
| `Ang-2.C1D1.baseline` | -1.6398 | 0.6193 | -2.648 | 0.00811 | ** |

PFS

|  | coef | exp(coef) | se(coef) | z | Pr(>|z|) |  |
|---|---|---|---|---|---|---|
| `Ang-2.C1D1.baseline` | 0.6422 | 1.9007 | 0.1099 | 5.846 | 5.04e-09 | *** |

OS

|  | coef | exp(coef) | se(coef) | z | Pr(>|z|) |  |
|---|---|---|---|---|---|---|
| `Ang-2.C1D1.baseline` | 0.53042 | 1.69964 | 0.11519 | 4.605 | 4.13e-06 | *** |
| `FGF-2(6).C1D1.baseline` | 0.33595 | 1.39927 | 0.11400 | 2.947 | 0.00321 | ** |
| `PGF(91).C1D1.baseline` | 0.19499 | 1.21530 | 0.08356 | 2.334 | 0.01962 | * |
| `HGF(86).C1D1.baseline` | 0.18837 | 1.20728 | 0.09339 | 2.017 | 0.04369 | * |

Variables use in analyses
- WEIGHT
- AGE
- Ang-1
- Ang-2
- ANG2(90)
- FGF-2(6)
- FGF4(75)
- HGF(86)
- IL-8(40)
- PDGF-AA
- PDGFAB(68)
- PDGFBB(73)
- PGF(91)
- Tie-2
- VEGF(86)
- VEGFA(100)
- VEGFD(78)

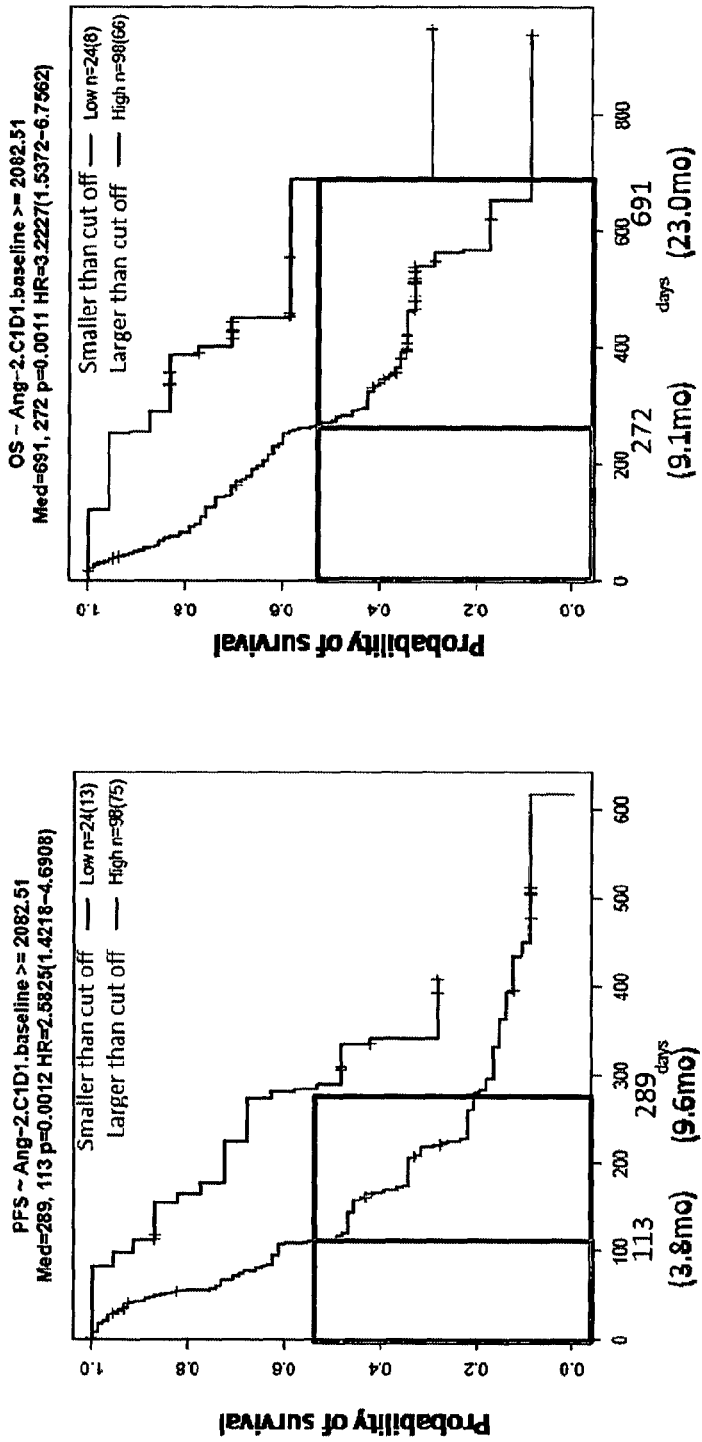
Fig. 5 mPFS and mOS of sub-groups stratified by baseline Ang-2 level
PFS and OS: based on cut off (2082.5 pg/ml)

Fig. 6 Enrichment of patients population with better ORR based on baseline Ang-2 level
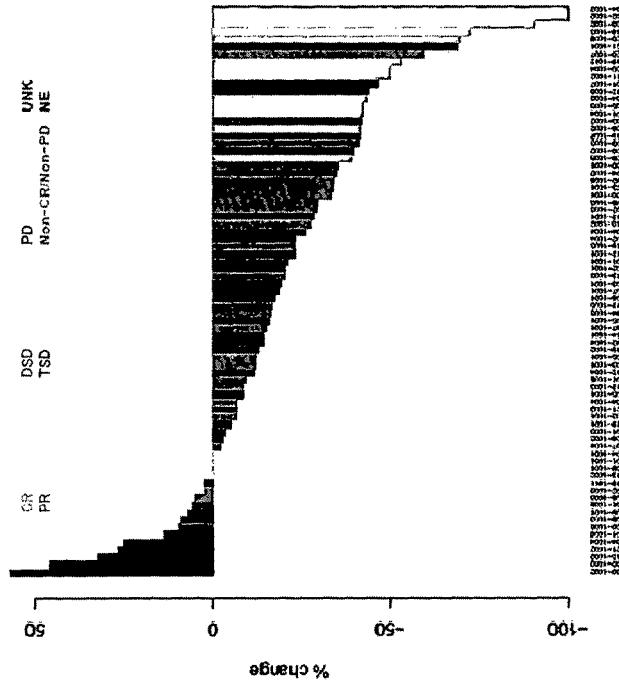
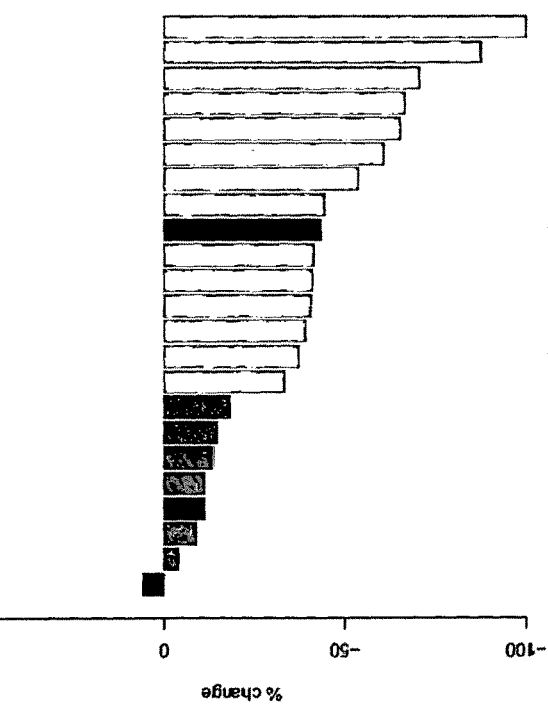

BIOMARKERS FOR PREDICTING AND ASSESSING RESPONSIVENESS OF ENDOMETRIAL CANCER SUBJECTS TO LENVATINIB COMPOUNDS

CROSS-REFERENCE TO RELATED APPLICATION

This application claims the benefit of U.S. provisional application No. 61/823,034 filed on May 14, 2013, the disclosure of which is herein incorporated by reference in its entirety.

TECHNICAL FIELD

The present invention relates generally to biomarkers and endometrial cancer.

BACKGROUND ART

A number of kinase inhibitors have been developed as antitumor agents. For example, a group of compounds having inhibitory activity against receptor tyrosine kinases, such as vascular endothelial growth factor receptor (VEGFR), are known to inhibit angiogenesis and are regarded as a new class of antitumor agents. Lenvatinib mesylate (also known as E7080) is an oral tyrosine kinase inhibitor targeting VEGFR1-3, fibroblast growth factor receptor (FGFR) 1-4, rearranged during transfection receptor (RET), KIT, and platelet-derived growth factor receptor (PDGFR). In phase I clinical studies of lenvatinib mesylate, response to treatment was observed in various tumor types, e.g., endometrial cancers.

Unfortunately, most anti-tumor treatments are associated with undesirable side effects, such as profound nausea, vomiting, or severe fatigue. Also, while anti-tumor treatments have been successful, they do not produce significant clinical responses in all patients who receive them, resulting in undesirable side effects, delays, and costs associated with ineffective treatment. Therefore, biomarkers that can be used to predict the response of a subject to an antitumor agent prior to administration thereof are greatly needed.

WO 2012/157672 discloses that, in a sub-group of melanoma patients who either have wild type B-raf and PTEN or mutated B-raf and PTEN, high levels of Ang2, IL6, CXCR4, COL4A3, MEIS1, FGF9, FGFR1, FGFR2, FGFR3, FGFR4, or VEGFR1 and low levels of SHC1, NRP2, ARHGAP22, SCG2, or PML are predictive of responsiveness to lenvatinib compounds.

WO 2012/166899 discloses that, in subjects having thyroid or kidney cancer, low levels of Ang2, VEGFA, IFNG, or soluble KDR or high levels of IL-6, IL-13, PDGFAB, CSF3, CCL3, CCL4, FLT4, or FGF2 are predictive of responsiveness to lenvatinib compounds. However, WO 2012/166899 does not disclose or suggest that Ang2 can be used as predictive of responsiveness to lenvatinib compounds in endometrial cancer patients.

Llovet et al. *Clin Cancer Res.*, 18(8):2290-2300 (2012), reports that in patients with advanced hepatocellular carcinoma, while the angiogenesis biomarkers Ang2 and VEGF were predictors of survival, these biomarkers were not predictive of responsiveness to the angiogenesis inhibitor, sorafenib.

Thus, an angiogenesis biomarker like Ang2 is not expected to serve as a biomarker for responsiveness to angiogenesis inhibitors in all cancers.

SUMMARY OF INVENTION

The present application is based, at least in part, on the identification of biomarkers that are predictive of an endometrial cancer subject's responsiveness to a therapy comprising lenvatinib or a pharmaceutically acceptable salt thereof (e.g., lenvatinib mesylate). The expression level of certain genes (e.g., the proteins and mRNA of the genes listed in Table 1) prior to treatment is identified as a useful predictor of responsiveness (e.g., survival and/or tumor response) to a therapy comprising lenvatinib or a pharmaceutically acceptable salt thereof (e.g., lenvatinib mesylate). Thus, the biomarkers and compositions described herein are useful, for example, in identifying, stratifying, and/or selecting a patient or a subset of patients having endometrial cancer that could benefit from treatment with lenvatinib or a pharmaceutically acceptable salt thereof (e.g., lenvatinib mesylate). In addition, the methods described herein are useful, for example, in selecting appropriate treatment modalities (e.g., therapy comprising lenvatinib or a pharmaceutically acceptable salt thereof (e.g., lenvatinib mesylate) or an alternative endometrial cancer therapy) for a subject suffering from, suspected of having, or at risk of developing an endometrial cancer.

In one aspect, the disclosure provides a method of predicting the response of a subject having, suspected of having, or at risk of developing, an endometrial cancer to a therapy comprising lenvatinib or a pharmaceutically acceptable salt thereof. The method involves assaying a biological sample obtained from the subject and determining that the concentration of Ang2 protein in the biological sample is low, as compared to a control. The subject having a low concentration of Ang2 protein in the biological sample is identified as likely to respond to the therapy comprising lenvatinib or a pharmaceutically acceptable salt thereof.

In addition, the disclosure provides a method of predicting the response of a subject having, suspected of having, or at risk of developing, an endometrial cancer to a therapy comprising lenvatinib or a pharmaceutically acceptable salt thereof. The method involves assaying a biological sample obtained from the subject and determining that the concentration of HGF, IL-8, IP-10, MCP-1, MIP-1α, PGF, sIL-2Rα, Tie-2, TNF-α, or VEGFA protein in the biological sample is low, as compared to a control. The subject having a low concentration of HGF, IL-8, IP-10, MCP-1, MIP-1α, PGF, sIL-2Rα, Tie-2, TNF-α, or VEGFA protein in the biological sample is identified as likely to respond to the therapy comprising lenvatinib or a pharmaceutically acceptable salt thereof.

In a second aspect, the disclosure provides a method of predicting the response of a subject having, suspected of having, or at risk of developing, an endometrial cancer to a therapy comprising lenvatinib or a pharmaceutically acceptable salt thereof. The method involves assaying a biological sample obtained from the subject and determining that the concentration of Ang2 protein in the biological sample is high, as compared to a control. The subject having a high concentration of Ang2 protein in the biological sample is identified as unlikely to respond to the therapy comprising lenvatinib or a pharmaceutically acceptable salt thereof.

In addition, the disclosure provides a method of predicting the response of a subject having, suspected of having, or at risk of developing, an endometrial cancer to a therapy comprising lenvatinib or a pharmaceutically acceptable salt thereof. The method involves assaying a biological sample obtained from the subject and determining that the concentration of HGF, IL-8, IP-10, MCP-1, MIP-1α, PGF, sIL- 2Rα, Tie-2, TNF-α, or VEGFA protein in the biological sample is high, as compared to a control. The subject having a high concentration of HGF, IL-8, IP-10, MCP-1, MIP-1α, PGF, sIL-2Rα, Tie-2, TNF-α, or VEGFA protein in the biological sample is identified as unlikely to respond to the therapy comprising lenvatinib or a pharmaceutically acceptable salt thereof.

In a third aspect, the disclosure provides a method of selecting a subject having, suspected of having, or at risk of developing, an endometrial cancer for a therapy comprising lenvatinib or a pharmaceutically acceptable salt thereof. This method involves assaying a biological sample obtained from the human subject and determining that the concentration of Ang2 protein in the biological sample is low, as compared to a control. The method further involves selecting the human subject having a low concentration of Ang2 protein in the biological sample for the therapy comprising lenvatinib or a pharmaceutically acceptable salt thereof.

In addition, the disclosure provides a method of selecting a subject having, suspected of having, or at risk of developing, an endometrial cancer for a therapy comprising lenvatinib or a pharmaceutically acceptable salt thereof. This method involves assaying a biological sample obtained from the human subject and determining that the concentration of HGF, IL-8, IP-10, MCP-1, MIP-1α, PGF, sIL-2Rα, Tie-2, TNF-α, or VEGFA protein in the biological sample is low, as compared to a control. The method further involves selecting the human subject having a low concentration of HGF, IL-8, IP-10, MCP-1, MIP-1α, PGF, sIL-2Rα, Tie-2, TNF-α, or VEGFA protein in the biological sample for the therapy comprising lenvatinib or a pharmaceutically acceptable salt thereof.

In a fourth aspect, the disclosure provides a method of treating an endometrial cancer. The method involves providing a biological sample obtained from a subject that has endometrial cancer; measuring, in the biological sample, an Ang2 protein expression level that is low as compared to a control; and administering to the subject a therapeutically effective amount of lenvatinib or a pharmaceutically acceptable salt thereof.

In addition, the method involves providing a biological sample obtained from a subject that has endometrial cancer; measuring, in the biological sample, an HGF, IL-8, IP-10, MCP-1, MIP-1α, PGF, sIL-2Rα, Tie-2, TNF-α, or VEGFA protein expression level that is low as compared to a control; and administering to the subject a therapeutically effective amount of lenvatinib or a pharmaceutically acceptable salt thereof.

In a fifth aspect, the disclosure provides a method of treating an endometrial cancer. The method involves administering to the subject that has an endometrial cancer a therapeutically effective amount of lenvatinib or a pharmaceutically acceptable salt thereof, wherein the subject has been identified as having an Ang2 protein expression level that is low as compared to a control. In certain embodiments, the subject has been identified as having a low concentration of Ang2 protein in a biological sample obtained from the human subject.

In addition, the method involves administering to the subject that has an endometrial cancer a therapeutically effective amount of lenvatinib or a pharmaceutically acceptable salt thereof, wherein the subject has been identified as having an HGF, IL-8, IP-10, MCP-1, MIP-1α, PGF, sIL-2Rα, Tie-2, TNF-α, or VEGFA protein expression level that is low as compared to a control. In certain embodiments, the subject has been identified as having a low concentration of HGF, IL-8, IP10, MCP-1, MIP-1α, PGF, sIL-2Rα, Tie-2, TNF-α, or VEGFA protein in a biological sample obtained from the human subject.

The following embodiments are envisaged for all of the above aspects.

In one embodiment the lenvatinib or a pharmaceutically acceptable salt thereof is lenvatinib mesylate.

In one embodiment, the endometrial cancer is an advanced endometrial cancer. In another embodiment, the endometrial cancer is a recurrent endometrial cancer. In one embodiment, the endometrial cancer is a stage III endometrial cancer. In one embodiment, the endometrial cancer is a stage IV endometrial cancer. In one embodiment, the endometrial cancer is an unresectable form of stage III or stage IV endometrial cancer.

In some embodiments, the biological sample is selected from the group consisting of a blood sample, a serum sample, a plasma sample, a uterine fluid sample, a urine sample, an endometrial archived tumor sample, and an endometrial biopsy sample.

In some embodiments, the control is a pre-established cut-off value. In one embodiment, the pre-established cut-off value is an Ang2 protein concentration that is determined based on receiver operating characteristic (ROC) analysis predicting tumor response with a higher positive predictive value compared to no cut-off, and wherein a concentration of Ang2 protein equal to or below the pre-established cut-off value is a low concentration of Ang2 and a value higher than the pre-established cut-off value is a high concentration of Ang2. The tumor response is an objective response rate (ORR), a clinical benefit rate (CBR), or % of maximum tumor shrinkage. In another embodiment, the pre-established cut-off value is an Ang2 protein concentration that is determined based on simulation models predicting survival, and wherein a concentration of Ang2 protein equal to or below the pre-established cut-off value is a low concentration of Ang2 and a value higher than the pre-established cut-off value is a high concentration of Ang2. In this context, survival is progression free survival (PFS) or overall survival (OS). In a particular embodiment, the pre-established cut-off value is an Ang2 protein concentration that is within the range of 1866.5 to 6024.5 (e.g., 2082.5 pg/ml), and wherein a concentration of Ang2 protein equal to or below the pre-established cut-off value is a low concentration of Ang2 and a value higher than the pre-established cut-off value is a high concentration of Ang2.

In some embodiments, the method further includes communicating the test results to the subject's health care provider. In certain embodiments, the method further includes modifying the subject's medical record to indicate that the subject is likely or not likely to respond to a therapy comprising lenvatinib or a pharmaceutically acceptable salt thereof. In specific embodiments, the record is created on a computer readable medium. In certain embodiments, the method further includes prescribing a therapy comprising lenvatinib or a pharmaceutically acceptable salt thereof for the subject if the biomarker expression profile is predictive that the subject will respond to a therapy comprising lenvatinib or a pharmaceutically acceptable salt thereof. In certain embodiments, the method further includes prescribing a therapy not comprising lenvatinib or a pharmaceutically acceptable salt thereof for the subject if the biomarker expression profile is predictive that the subject will not respond to a therapy comprising lenvatinib or a pharmaceutically acceptable salt thereof. In some embodiments, the method further includes administering to the subject a therapy comprising lenvatinib or a pharmaceutically acceptable salt thereof if the biomarker expression profile is predictive that the subject will respond to a therapy comprising lenvatinib or a pharmaceutically acceptable salt thereof. In some embodiments, the method further includes administering to the subject a therapy that does not comprise lenvatinib or a pharmaceutically acceptable salt thereof if the biomarker expression profile is predictive that the subject will not respond to a therapy comprising lenvatinib or a pharmaceutically acceptable salt thereof.

In one embodiment, the concentration of the protein is measured by an immunological method. In some embodiments, the immunological method is selected from the group consisting of enzyme immunoassay, radioimmunoassay, chemiluminescent immunoassay, electrochemiluminescence immunoassay, latex turbidimetric immunoassay, latex photometric immunoassay, immuno-chromatographic assay, and western blotting. In another embodiment, the concentration of the protein is measured by mass spectrometry.

In a sixth aspect, this disclosure provides lenvatinib or a pharmaceutically acceptable salt thereof for use in treating an endometrial cancer in a human subject, wherein the human subject is identified by the methods described above as a subject that is likely to respond to a therapy comprising lenvatinib or a pharmaceutically acceptable salt thereof. In some embodiments, the pharmaceutically acceptable salt of lenvatinib is lenvatinib mesylate. In one embodiment, the endometrial cancer is an advanced endometrial cancer. In another embodiment, the endometrial cancer is a recurrent endometrial cancer. In one embodiment, the endometrial cancer is a stage III endometrial cancer. In one embodiment, the endometrial cancer is a stage IV endometrial cancer. In one embodiment, the endometrial cancer is an unresectable form of stage III or stage IV endometrial cancer.

In a seventh aspect, the disclosure provides an Ang2 protein detection agent for use in predicting the response of a human subject having, suspected of having, or at risk of developing, an endometrial cancer to a therapy comprising lenvatinib or a pharmaceutically acceptable salt thereof. In one embodiment, the Ang2 protein detection agent is an anti-Ang2 antibody.

In addition; the disclosure provides an HGF, IL-8, IP-10, MCP-1, MIP-1α, PGF, sIL-2Rα, Tie-2, TNF-α, or VEGFA protein detection agent for use in predicting the response of a human subject having, suspected of having, or at risk of developing, an endometrial cancer to a therapy comprising lenvatinib or a pharmaceutically acceptable salt thereof. In one embodiment, the HGF, IL-8, IP-10, MCP-1, MIP-1α, PGF, sIL-2Rα, Tie-2, TNF-α, or VEGFA protein detection agent is an anti-HGF, IL-8, IP10, MCP-1, MIP-1α, PGF, sIL-2Rα, Tie-2, TNF-α, or VEGFA antibody.

In an eighth embodiment, the disclosure features a kit comprising an Ang2 protein detection agent for use in predicting the response of a human subject having, suspected of having, or at risk of developing, an endometrial cancer to a therapy comprising lenvatinib or a pharmaceutically acceptable salt thereof. In certain embodiments, the Ang2 protein detection agent is an anti-Ang2 antibody. In certain embodiments, the anti-Ang2 antibody is a monoclonal antibody. In other embodiments, the anti-Ang2 antibody is a polyclonal antibody. In certain embodiments, the antibody is conjugated with a detectable agent. In one embodiment, the detectable agent is horse radish peroxidase, biotin, a fluorescent moiety, a radioactive moiety, a histidine tag, or a peptide tag. In one embodiment, the detectably labeled antibody is coated on a microplate. In certain embodiments, the microplate is a 96 well microplate. In certain embodiments, the kit optionally includes one or more concentration standards, one or more buffers (e.g., wash buffers), one or more diluents (e.g., assay and/or calibration diluents), and one or more reagents that facilitate detecting whether the Ang2 protein detection agent specifically binds Ang2 in a biological sample obtained from the subject (e.g., color reagents, stop solutions).

In addition, the disclosure features a kit comprising an HGF, IL-8, IP-10, MCP-1, MIP-1α, PGF, sIL-2Rα, Tie-2, TNF-α, or VEGFA protein detection agent for use in predicting the response of a human subject having, suspected of having, or at risk of developing, an endometrial cancer to a therapy comprising lenvatinib or a pharmaceutically acceptable salt thereof. In certain embodiments, the HGF, IL-8, IP-10, MCP-1, MIP-1α, PGF, sIL-2Rα, Tie-2, TNF-α, or VEGFA protein detection agent is an anti-HGF, IL-8, IP-10, MCP-1, MIP-1α, PGF, sIL-2Rα, Tie-2, TNF-α, or VEGFA antibody. In certain embodiments, the antibody is a monoclonal antibody. In other embodiments, the antibody is a polyclonal antibody. In certain embodiments, the antibody is conjugated with a detectable agent. In one embodiment, the detectable agent is horse radish peroxidase, biotin, a fluorescent moiety, a radioactive moiety, a histidine tag, or a peptide tag. In one embodiment, the detectably labeled antibody is coated on a microplate. In certain embodiments, the microplate is a 96 well microplate. In certain embodiments, the kit optionally includes one or more concentration standards, one or more buffers (e.g., wash buffers), one or more diluents (e.g., assay and/or calibration diluents), and one or more reagents that facilitate detecting whether the protein detection agent specifically binds HGF, IL-8, IP-10, MCP-1, MIP-1α, PGF, sIL-2Rα, Tie-2, TNF-α, or VEGFA in a biological sample obtained from the subject (e.g., color reagents, stop solutions).

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, the exemplary methods and materials are described below. All publications, patent applications, patents, and other references mentioned herein are incorporated by reference in their entirety. In case of conflict, the present application, including definitions, will control. The materials, methods, and examples are illustrative only and not intended to be limiting.

Other features and advantages of the invention will be apparent from the following detailed description, and from the claims.

BRIEF DESCRIPTION OF DRAWINGS

FIG. 1 is a graphical depiction of the change in levels of blood biomarkers after E7080 treatment.

FIG. 2 is a series of graphs showing the correlation of baseline cytokine, chemokine, and angiogenic factors (CAFs) with tumor response.

FIG. 3 is a series of graphs showing that there is no significant correlation of weight, age, and histology with progression free survival (PFS) and overall survival (OS).

FIG. 4 shows the results of a multivariate analysis that does not identify potential combination factors with Ang-2 as improving predictions of clinical outcome.

FIG. 5 includes two graphs showing the median PFS and median OS of sub-groups of endometrial cancer patients stratified by baseline Ang-2 levels.

FIG. 6 includes two graphs showing the enrichment of patient populations with better objective response rate (ORR) based on baseline Ang-2 level.

DESCRIPTION OF EMBODIMENTS

This disclosure provides methods and compositions for predicting the response of an endometrial cancer subject (such as a human patient) to a therapy comprising lenvatinib or a pharmaceutically acceptable salt thereof (e.g., lenvatinib mesylate). The disclosure provides predictive biomarkers (e.g., protein or RNA expression levels) to identify those subjects having, suspected of having, or at risk of developing, endometrial cancer (e.g., advanced or recurrent endometrial cancer) for whom administering a therapy comprising lenvatinib or a pharmaceutically acceptable salt thereof (e.g., lenvatinib mesylate) is likely to be effective or ineffective. The biomarkers, compositions, and methods described herein are useful in selecting appropriate therapeutic modalities (e.g., a lenvatinib or a pharmaceutically acceptable salt thereof (e.g., lenvatinib mesylate) therapy or an alternative therapy) for subjects suffering from, suspected of having or at risk of developing endometrial cancer. Furthermore, this application provides methods of selecting patients having, suspected of having, or at risk of developing, endometrial cancer that could benefit from a therapy comprising lenvatinib or a pharmaceutically acceptable salt thereof (e.g., lenvatinib mesylate) as well as methods of treatment.

Definitions

The term "decreased/reduced expression level" means an expression level (amount) that is lower than the expression level in a control.

The term "elevated expression level" means an expression level (amount) that is higher than the expression level in a control.

The term "expression level of a gene" means expression level (amount) of the protein encoded by the gene or the RNA transcribed from the gene.

The term "low concentration" means a concentration of the substance being analyzed that is lower than the concentration of that substance in a control.

The term "high concentration" means a concentration of the substance being analyzed that is higher than the concentration of that substance in a control.

The term "lenvatinib" refers to 4-(3-chloro-4-(cyclopropylaminocarbonyl)aminophenoxy)-7-methoxy-6-quinolinecarboxamide. This compound is disclosed in Example 368 (see, column 270) of U.S. Pat. No. 7,253,286. U.S. Pat. No. 7,253,286 is incorporated by reference in its entirety herein. The term "lenvatinib compound" refers to "lenvatinib or a pharmaceutically acceptable salt thereof." An example of a pharmaceutically acceptable salt of lenvatinib is lenvatinib mesylate. Lenvatinib mesylate is also referred to as E7080.

The term "phamaceutically acceptable salt" is not particularly restricted as to the type of salt. Examples of such salts include, but are not limited to, inorganic acid addition salt such as hydrochloric acid salt, sulfuric acid salt, carbonic acid salt, bicarbonate salt, hydrobromic acid salt and hydriodic acid salt; organic carboxylic acid addition salt such as acetic acid salt, maleic acid salt, lactic acid salt, tartaric acid salt and trifluoroacetic acid salt; organic sulfonic acid addition salt such as methanesulfonic acid salt, hydroxymethanesulfonic acid salt, hydroxyethanesulfonic acid salt, benzenesulfonic acid salt, toluenesulfonic acid salt and taurine salt; amine addition salt such as trimethylamine salt, triethylamine salt, pyridine salt, procaine salt, picoline salt, dicyclohexylamine salt, N,N'-dibenzylethylenediamine salt, N-methylglucamine salt, diethanolamine salt, triethanolamine salt, tris(hydroxymethylamino)methane salt and phenethylbenzylamine salt; and amino acid addition salt such as arginine salt, lysine salt, serine salt, glycine salt, aspartic acid salt and glutamic acid salt. In one embodiment, the pharmaceutically acceptable salt is a methanesulfonic acid salt ("mesylate"). The methanesulfonic acid salt form (i.e., the mesylate) of 4-(3-chloro-4-(cyclopropylaminocarbonyl)aminophenoxy)-7-methoxy-6-quinolinecarboxamide is disclosed in U.S. Pat. No. 7,612,208, which is incorporated by reference herein in its entirety.

"Polypeptide" and "protein" are used interchangeably herein and mean any peptide-linked chain of amino acids, regardless of length or post-translational modification. Typically, a polypeptide described herein is "isolated" when it constitutes at least 60%, by weight, of the total protein in a preparation, e.g., 60% of the total protein in a sample. In some embodiments, a polypeptide described herein consists of at least 75%, at least 90%, or at least 99%, by weight, of the total protein in a preparation.

The term "responds/responsive to a therapy" means that the subject administered with the therapy shows a positive response to the therapy provided. Non-limiting examples of such a positive response are: a decrease in tumor size, a decrease in metastasis of a tumor, or an increased period of survival after treatment.

The term "subject" means a mammal, including but not limited to, a human, a chimpanzee, an orangutan, a gorilla, a baboon, a monkey, a mouse, a rat, a pig, a horse, a dog, and a cow.

Endometrial Cancer

Endometrial cancer refers to several types of malignancies that arise from the endometrium, or lining, of the uterus. Most endometrial cancers are carcinomas (generally adenocarcinomas). In other words, they originate from the single layer of epithelial cells that line the endometrium and form the endometrial glands. Endometrial carcinomas are sometimes classified into two groups: Type I includes the cancers found in pre- and peri-menopausal women and are generally minimally invasive; Type II includes the cancers that occur in older, post-menopausal women and carry a poorer prognosis than Type I. In contrast to endometrial carcinomas, the uncommon endometrial stromal sarcomas are cancers that originate in the non-glandular connective tissue of the endometrium.

In order to choose a treatment plan for patients, doctors need to determine how the endometrial cancer has spread in a patient, or in other words "stage" the endometrial cancer. Endometrial cancer is staged based on examination of tissue removed during an operation (surgical staging). The staging system looks at how far the cancer has spread. Endometrial cancer can spread locally to the cervix and other parts of the uterus. It can also spread regionally to nearby lymph nodes. In addition, this cancer can metastasize to distant lymph nodes, the upper abdomen, the omentum, or other organs such as lung, liver, bone, and brain.

The two systems used to stage endometrial cancer are the FIGO (International Federation of Gynecology and Obstetrics) system and the American Joint Committee on Cancer (AJCC) staging system. These systems are basically the same; the difference between the AJCC system and the FIGO system is that the FIGO system does not include stage 0. Both staging systems classify endometrial cancer on the basis of three factors: the extent of the tumor (T), whether the cancer has spread to lymph nodes (N) and whether it has spread to distant sites (M). Information about the tumor, lymph nodes, and any cancer spread is then combined to assign the stage of disease, a process called stage grouping. The stages are described using the number 0 and Roman numerals from I to IV. Some stages are divided into sub-stages indicated by letters and numbers.

Stage 0: Tis, N0, M0—This stage is also known as carcinoma in situ. Cancer cells are only found in the surface layer of cells of the endometrium, without growing into the layers of cells below. The cancer has not spread to nearby lymph nodes or distant sites. This is a pre-cancerous lesion. This stage is not included in the FIGO staging system.

Stage I: T1, N0, M0—The cancer is only growing in the body of the uterus. It may also be growing into the glands of the cervix, but is not growing into the supporting connective tissue of the cervix. The cancer has not spread to lymph nodes or distant sites.

Stage IA: T1a, N0, M0—In this earliest form of stage I, the cancer is in the endometrium and may have grown from the endometrium less than halfway through the underlying muscle layer of the uterus (the myometrium). It has not spread to lymph nodes or distant sites.

Stage IB: T1b, N0, M0—The cancer has grown from the endometrium into the myometrium, growing more than halfway through the myometrium. The cancer has not spread beyond the body of the uterus.

Stage II: T2, N0, M0—The cancer has spread from the body of the uterus and is growing into the supporting connective tissue of the cervix (the cervical stroma). The cancer has not spread outside of the uterus. The cancer has not spread to lymph nodes or distant sites.

Stage III: T3, N0, M0—Either the cancer has spread outside of the uterus or into nearby tissues in the pelvic area.

Stage IIIA: T3a, N0, M0—The cancer has spread to the outer surface of the uterus (called the serosa) and/or to the fallopian tubes or ovaries (the adnexa). The cancer has not spread to lymph nodes or distant sites.

Stage IIIB: T3b, N0, M0—The cancer has spread to the vagina or to the tissues around the uterus (the parametrium). The cancer has not spread to lymph nodes or distant sites.

Stage IIIC1: T1 to T3, N1, M0—The cancer is growing in the body of the uterus. It may have spread to some nearby tissues, but is not growing into the inside of the bladder or rectum. The cancer has spread to pelvic lymph nodes but not to lymph nodes around the aorta or distant sites.

Stage IIIC2: T1 to T3, N2, M0—The cancer is growing in the body of the uterus. It may have spread to some nearby tissues, but is not growing into the inside of the bladder or rectum. The cancer has spread to lymph nodes around the aorta (peri-aortic lymph nodes) but not to distant sites.

Stage IV: The cancer has spread to the inner surface of the urinary bladder or the rectum to lymph nodes in the groin, and/or to distant organs, such as the bones, omentum or lungs.

Stage IVA: T4, any N, M0—The cancer has spread to the inner lining of the rectum or urinary bladder (called the mucosa). It may or may not have spread to nearby lymph nodes but has not spread to distant sites.

Stage IVB: any T, any N, M1—The cancer has spread to distant lymph nodes, the upper abdomen, the omentum, or to organs away from the uterus, such as the bones, omentum, or lungs. The cancer can be any size and it may or may not have spread to lymph nodes.

Methods of Predicting Responsiveness to Therapy Comprising a Lenvatinib Compound A number of genes have been identified whose expression levels (e.g., mRNA or protein expression levels) are useful in predicting responsiveness of a subject having an endometrial cancer to a therapy comprising a lenvatinib compound (e.g., lenvatinib mesylate). These genes as identified by Gene ID, related URL, protein ID and UniProtKB Accession Nos. are listed in Table 1.

TABLE 1

List of Biomarkers

| Official Gene Symbol | Gene ID | URL | Alternative Symbol | UniProtKB Accession No. |
|---|---|---|---|---|
| Ang2 | 285 | www.ncbi.nlm.nih.gov/gene/285 | Ang-2/ANG-2/ANG2 (90)/ANG290/ANGPT2 | O15123 |
| HGF | 3082 | www.ncbi.nlm.nih.gov/gene/3082 | HGF (86) | P14210 |
| IL-8 | 3576 | www.ncbi.nlm.nih.gov/gene/3576 | IL-8 (40) | P10145 |
| IP-10 | 3627 | www.ncbi.nlm.nih.gov/gene/3627 | CXCL10 | P02778 |
| MCP-1 | 6347 | www.ncbi.nlm.nih.gov/gene/6347 | CCL2 | P13500 |
| MIP-1a | 6348 | www.ncbi.nlm.nih.gov/gene/6348 | CCL3/MIP1a/MIP-1α | P10147 |
| PGF | 5228 | www.ncbi.nlm.nih.gov/gene/5228 | PGF (91) | P49763 |
| sIL2-Ra | 3559 | www.ncbi.nlm.nih.gov/gene/3559 | sIL2-Ra(76) | P01589 |
| TIE-2 | 7010 | www.ncbi.nlm.nih.gov/gene/7010 | TEK/CD202B/TIE2/VMCM/VMCM1 | Q02763 |
| TNF | 7124 | www.ncbi.nlm.nih.gov/gene/7124 | TNFa/TNF-α | P01375 |
| VEGFA | 7422 | www.ncbi.nlm.nih.gov/gene/7422 | VEGF/VEGFA(100)/VEGFA100 | P15692 |

Angiopoietins are protein growth factors that promote angiogenesis (the formation of blood vessels from pre-existing blood vessels) and maturation of tumor blood vessels. Mouse knock out studies have shown that Angiopoietin 2 (Ang2) is required for the formation of mature blood vessels. Expression of Ang2 in the endothelial cells is sufficient to recruit myeloid cells and induce inflammation even in the absence of preceding proinflammatory stimuli.

Hepatocyte growth factor (HGF) is a paracrine cellular growth, motility and morphogenic factor. It is secreted by mesenchymal cells and targets and acts primarily upon epithelial cells and endothelial cells, but also acts on haemopoietic progenitor cells. It plays a major role in embryonic organ development, in adult organ regeneration and in wound healing. HGF regulates cell growth, cell motility, and morphogenesis by activating a tyrosine kinase signaling cascade after binding to the proto-oncogenic c-Met receptor.

Interleukin 8 (IL-8) is a chemokine produced by macrophages and other cell types such as epithelial cells and endothelial cells. Il-8 can bind several receptors including CXCR1, and CXCR2.

Interferon gamma-induced protein 10 (IP-10) is a small cytokine belonging to the CXC chemokine family. It is secreted by several cell types (e.g., monocytes, endothelial cells and fibroblasts) in response to IFN-γ. This protein has been attributed several roles, such as chemoattraction for monocytes/macrophages, T cells, NK cells, and dendritic cells, promotion of T cell adhesion to endothelial cells, antitumor activity, and inhibition of bone marrow colony formation and angiogenesis.

Monocyte chemotactic protein-1 (MCP-1) is a small cytokine that belongs to the CC chemokine family. It plays a role in recruiting monocytes, memory T cells, and dendritic cells to the sites of inflammation produced by either tissue injury or infection.

Macrophage Inflammatory Protein-1a (MIP-1a) belongs to the family of chemotactic cytokines. This protein is crucial for immune responses towards infection and inflammation. It activates granulocytes (neutrophils, eosinophils and basophils) which can lead to acute neutrophilic inflammation. In addition, it induces the synthesis and release of other pro-inflammatory cytokines such as interleukin 1 (IL-1), IL-6 and TNF-α from fibroblasts and macrophages.

Placental growth factor (PGF) is a member of the vascular endothelial growth factor sub-family. Placental growth factor-expression within human atherosclerotic lesions is associated with plaque inflammation and neovascular growth.

Soluble Interleukin-2 receptor alpha (sIL-2Ra) is the secreted extracellular domain of IL-2R alpha and is expressed by leukemia cells, lymphoma cells, a fraction of NK cells, as well as recently activated T and B cells.

Tie-2 is a cell surface receptor tyrosine kinase that binds and is regulated by the angiopoietins (Ang1, Ang2, Ang3, Ang4). This receptor is expressed mainly in endothelial cells in humans. It possesses a unique extracellular domain containing two immunoglobulin-like loops separated by three epidermal growth factor-like repeats that are connected to three fibronectin type III-like repeats. The TIE-2 signaling pathway appears to be critical for endothelial cell-smooth muscle cell communication in venous morphogenesis. Defects in TIE-2 are associated with inherited venous malformations.

Tumor necrosis factor alpha (TNF-α) is a monocyte-derived cytotoxin that has been implicated in tumor regression, septic shock, and cachexia.

Vascular endothelial growth factor A (VEGF-A) is a glycosylated mitogen that specifically acts on endothelial cells and has various effects, including mediating increased vascular permeability, inducing angiogenesis, vasculogenesis and endothelial cell growth, promoting cell migration, and inhibiting apoptosis.

A low expression (e.g., protein or mRNA expression) level compared to a control of one or more (e.g., 2, 3, 4, 5, 6, 7, 8, 9, 10, or 11) genes listed in Table 1 is indicative/predictive that a subject will respond to a therapy comprising a lenvatinib compound (e.g., lenvatinib mesylate). For example, low concentrations (compared to a control) of Ang2 protein in a biological sample obtained from a subject prior to treatment with the therapy comprising a lenvatinib compound are predictive that the subject will respond to a therapy comprising a lenvatinib compound (e.g., lenvatinib mesylate).

In certain embodiments, a subject is determined to respond to a therapy comprising a lenvatinib compound (e.g., lenvatinib mesylate), if the subject shows a partial response following treatment with the therapy. "Partial Response" means at least 30% decrease in the sum of the longest diameter (LD) of target lesions, taking as reference the baseline summed LD. In some embodiments, a subject is determined to respond to a therapy comprising a lenvatinib compound, if the subject shows tumor shrinkage post-treatment with the therapy. "% of maximum tumor shrinkage" (MTS) means percent change of sum of diameters of target lesions, taking as reference the baseline sum diameters. In other embodiments, a subject is determined to respond to a therapy comprising a lenvatinib compound, if the subject shows progression free survival. "Progression Free Survival" (PFS) refers to the period from start date of treatment to the last date before entering Progressive Disease (PD) status. PD means at least 20% increase in the sum of the LD of target lesions, taking as reference the smallest summed LD recorded since the treatment started, or the appearance of one or more new lesions. In some embodiments, a subject is determined to respond to a therapy comprising a lenvatinib compound, if the subject shows both progression free survival and tumor shrinkage.

This disclosure provides methods of identifying a subject having endometrial cancer who is likely to have both survival benefits (e.g., PFS) and tumor shrinkage following a therapy comprising a lenvatinib compound (e.g., lenvatinib mesylate). In this method, a biological sample of the subject, obtained prior to treatment with the therapy comprising a lenvatinib compound, is assayed and the level of Ang2 protein is measured. A low concentration of the Ang2 protein compared to a control indicates that the subject will likely have both survival benefits (e.g., PFS) and tumor shrinkage following therapy comprising a lenvatinib compound. Conversely, a high concentration of the Ang2 protein compared to a control indicates that the subject will likely not have both survival benefits (e.g., PFS) and tumor shrinkage following therapy comprising a lenvatinib compound.

The methods described herein also permit identification of a subject having endometrial cancer who is likely to have survival benefits (e.g., PFS) following a therapy comprising a lenvatinib compound (e.g., lenvatinib mesylate). In this method, a biological sample of the subject, obtained prior to treatment with the therapy comprising a lenvatinib compound, is assayed and the level of at least one, at least two, at least three, at least four, at least five, at least six, at least seven, at least eight, at least nine, at least ten, or one, two, three, four, five, six, seven, eight, nine, ten or eleven of Ang2, HGF, IP-10, MCP-1, MIP-1a, PGF, sIL-2Ra, Tie-2, TNFα, and VEGFA protein is measured. A low concentration of any of these proteins (either alone or in combination with the others listed above) compared to a control indicates that the subject will likely have survival benefits (e.g., PFS) following therapy comprising a lenvatinib compound. Conversely, a high concentration of any of these proteins (either alone or in combination with the others listed above) compared to a control indicates that the subject will likely not have survival benefits (e.g., PFS) following therapy comprising a lenvatinib compound. In certain embodiments, the subject with a low concentration of one or more of the proteins listed above is likely to have a progression free survival of one, two, three, four, five, six, seven, eight, nine, ten, eleven, twelve, thirteen, fourteen, fifteen, sixteen, seventeen, eighteen, nineteen, twenty, twenty one, twenty two or twenty three months, or twenty four months.

This disclosure also provides a method of identifying a subject having endometrial cancer who is likely to have tumor shrinkage following a therapy comprising a lenvatinib compound (e.g., lenvatinib mesylate). In this method, a biological sample of the subject is assayed and the concentration of Ang2 and/or IL-8 protein is measured. A low concentration of Ang2 and/or IL-8 compared to a control indicates that the subject will likely have tumor shrinkage.

Conversely, a high concentration of Ang2 and/or IL-8 compared to a control indicates that the subject will likely not show tumor shrinkage.

In one embodiment, the subject has, is suspected of having, or is at risk of developing an endometrial cancer. In some embodiments, the endometrial cancer is advanced endometrial cancer. In other embodiments, the endometrial cancer is recurrent endometrial cancer. In certain embodiments, the endometrial cancer is stage III cancer. In some embodiments, the endometrial cancer is stage IV cancer. In certain embodiments, the endometrial cancer is unresectable stage III or stage IV cancer.

The concentration of the protein or proteins of interest can be measured using any method known in the art such as an immunological assay. Non-limiting examples of such methods include enzyme immunoassay, radioimmunoassay, chemiluminescent immunoassay, electrochemiluminescence immunoassay, latex turbidimetric immunoassay, latex photometric immunoassay, immuno-chromatographic assay, and western blotting. In certain embodiments, the concentration of the protein or proteins of interest is measured by mass spectrometry.

Controls

As described above, the methods of the present invention can involve, measuring the expression level (e.g., mRNA or protein concentration) of one or more genes (e.g., one or more genes depicted in Table 1) in a biological sample from a subject having, suspected of having or at risk of developing endometrial cancer, wherein the expression level of one or more of the genes, compared to a control, predicts the response of a subject to treatment comprising a lenvatinib compound (e.g., lenvatinib mesylate). In certain embodiments, when the concentration of a protein in Table 1 in a biological sample from a subject having, suspected of having or at risk of developing endometrial cancer is lower than the control, the subject is identified as likely to respond to a therapy comprising a lenvatinib compound. In this context, the term "control" includes a sample (from the same tissue) obtained from a subject who is known to not respond to a therapy comprising a lenvatinib compound (e.g., lenvatinib mesylate). The term "control" also includes a sample (from the same tissue) obtained in the past from a subject who is known to not respond to a therapy comprising a lenvatinib compound and used as a reference for future comparisons to test samples taken from subjects for which therapeutic responsiveness is to be predicted. The "control" expression level/concentration for a particular protein in a particular cell type or tissue may be pre-established by an analysis of protein expression in one or more (e.g., two, three, four, five, six, seven, eight, nine, 10, 15, 20, 25, 30, 35, or 40 or more) subjects, of the same species, that have not responded to treatment with a lenvatinib compound (e.g., lenvatinib mesylate). This pre-established reference value (which may be an average or median expression level/concentration taken from multiple subjects that have not responded to the therapy) may then be used for the "control" concentration/expression level of the protein or nucleic acid in the comparison with the test sample. In such a comparison, the subject is predicted to respond to a therapy comprising a lenvatinib compound (e.g., lenvatinib mesylate) if the expression level of the gene being analyzed is lower than the pre-established reference.

The "control" concentration for a particular protein in a particular cell type or tissue may alternatively be pre-established by an analysis of gene expression in one or more subjects that have responded to treatment with a lenvatinib compound (e.g., lenvatinib mesylate). This pre-established reference value (which may be an average or median expression level taken from multiple subjects that have responded to the therapy) may then be used as the "control" expression level in the comparison with the test sample. In such a comparison, the subject is predicted to respond to a therapy comprising a lenvatinib compound (e.g., lenvatinib mesylate) if the concentration of the protein being analyzed is the same as, or comparable to (at least 85% but less than 100% of), the pre-established reference.

In certain embodiments, the "control" is a pre-determined cut-off value.

Cut-Off Values

In some embodiments, the methods described herein include determining if the concentration of a protein(s) of interest (e.g., one or more of the proteins listed in Table 1) falls above or below a predetermined cut-off value.

A cut-off value is typically a concentration of a protein above or below which is considered predictive of responsiveness of a subject to a therapy of interest. Thus, in accordance with the methods and compositions described herein, a reference concentration (e.g., of a protein of Table 1) is identified as a cut-off value, above or below of which is predictive of responsiveness to a therapy comprising a lenvatinib compound (e.g., lenvatinib mesylate). Some cut-off values are not absolute in that clinical correlations can still remain significant over a range of values on either side of the cutoff; however, it is possible to select an optimal cut-off value (e.g. varying H-scores) of concentration of proteins for a particular sample type. Cut-off values determined for use in the methods described herein can be compared with, e.g., published ranges of concentrations but can be individualized to the methodology used and patient population. It is understood that improvements in optimal cut-off values could be determined depending on the sophistication of statistical methods used and on the number and source of samples used to determine reference level values for the different genes and sample types. Therefore, established cut-off values can be adjusted up or down, on the basis of periodic re-evaluations or changes in methodology or population distribution.

The reference concentration of one or more proteins can be determined by a variety of methods. The reference level can be determined by comparison of the concentration of a protein of interest in, e.g., populations of subjects (e.g., patients) that are responsive to a therapy comprising a lenvatinib compound (e.g., lenvatinib mesylate) or not responsive to a therapy comprising a lenvatinib compound. This can be accomplished, for example, by histogram analysis, in which an entire cohort of patients are graphically presented, wherein a first axis represents the concentration of a protein of interest and a second axis represents the number of subjects in the cohort whose sample contain one or more concentrations. Determination of the reference concentration of a protein can then be made based on an amount or concentration which best distinguishes these separate groups. The reference level can be a single number, equally applicable to every subject, or the reference level can vary, according to specific subpopulations of subjects. For example, older subjects can have a different reference level than younger subjects for the same cancer. In addition, a subject with more advanced disease (e.g., a more advanced form of endometrial cancer) can have a different reference value than one with a milder form of the disease.

The pre-established cut-off value can be a protein concentration that is determined based on receiver operating characteristic (ROC) analysis. ROC curves are used to determine a cut-off value for a clinical test Consider the situation where there are two groups of patients and by using an established standard technique one group is known to be responsive to a lenvatinib compound, and the other is known to not respond to a lenvatinib compound. A measurement using a biological sample from all members of the two groups is used to test for responsiveness to a lenvatinib compound. The test will find some, but not all, responders to respond to a lenvatinb compound. The ratio of the responders found by the test to the total number of responders (known by the established standard technique) is the true positive rate (also known as sensitivity). The test will find some, but not all, non-responders to not respond to a lenvatinb compound. The ratio of the non-responders found by the test to the total number of non-responders (known by the established standard technique) is the true negative rate (also known as specificity). The hope is that the ROC curve analysis of the lenvatinib responsiveness test will find a cut-off value that will minimize the number of false positives and false negatives. A ROC is a graphical plot which illustrates the performance of a binary class stratifier system as its discrimination threshold is varied. It is created by plotting the fraction of true positives out of the positives versus the fraction of false positives out of the negatives, at various threshold settings.

In one embodiment, the protein concentration is determined based on ROC analysis predicting tumor response with a positive predictive value, wherein a concentration of a protein of interest (e.g., Ang2) equal to or below the pre-established cut-off value is a low concentration of the protein of interest and a value higher than the pre-established cut-off value is a high concentration of the protein of interest. The positive predictive value is the proportion of positive test results that are true positives; it reflects the probability that a positive test reflects the underlying condition being tested for. Methods of constructing ROC curves and determining positive predictive values are well known in the art. In certain embodiments, tumor response is an objective response rate (ORR), a clinical benefit rate (CBR) or % of maximum tumor shrinkage.

In another embodiment, the pre-established cut-off value can be a protein concentration that is determined based on simulation models predicting survival, and wherein a concentration of the protein of interest (e.g., Ang2) equal to or below the pre-established cut-off value is a low concentration of the protein of interest and a value higher than the pre-established cut-off value is a high concentration of the protein of interest. In some embodiments, survival is progression free survival (PFS). In other embodiments, survival is overall survival (OS).

In certain embodiments, the pre-established cut-off value for Ang2 protein is within a concentration range of 1866.5 to 6024.5 pg/ml. In some embodiments, the pre-established cut-off value for Ang2 protein is within a concentration range of 1866.5 to 2500 pg/ml. In some embodiments, the pre-established cut-off value for Ang2 protein is within a concentration range of 1866.5 to 3000 pg/ml. In some embodiments, the pre-established cut-off value for Ang2 protein is within a concentration range of 1866.5 to 3500 pg/ml. In other embodiments, the pre-established cut-off value for Ang2 protein is within a concentration range of 2000 to 3000 pg/ml. In other embodiments, the pre-established cut-off value for Ang2 protein is within a concentration range of 2000 to 4000 pg/ml. In other embodiments, the pre-established cut-off value for Ang2 protein is within a concentration range of 2000 to 5000 pg/ml. In other embodiments, the pre-established cut-off value for Ang2 protein is within a concentration range of 3000 to 4000 pg/ml. In certain embodiments, the pre-established cut-off value for Ang2 protein is within a concentration range of 3000 to 5000 pg/ml. In other embodiments, the pre-established cut-off value for Ang2 protein is within a concentration range of 3000 to 6000 pg/ml. In other embodiments, the pre-established cut-off value for Ang2 protein is within a concentration range of 4000 to 5000 pg/ml. In other embodiments, the pre-established cut-off value for Ang2 protein is within a concentration range of 4000 to 6000 pg/ml. In some embodiments, the pre-established cut-off value for Ang2 protein is a concentration range of 5000 to 6000 pg/ml. In a specific embodiment, the pre-established cut-off value for Ang2 protein is about 2082.5 pg/ml. In all of these embodiments, a concentration of Ang2 protein equal to or below the pre-established cut-off value is a low concentration of Ang2 and a value higher than the pre-established cut-off value is a high concentration of Ang2. In this context "about" means±10%.

Biological Samples

Suitable biological samples for the methods described herein include any biological fluid, cell, tissue, or fraction thereof, which includes analyte biomolecules of interest such as protein or nucleic acid (e.g., DNA or mRNA). A biological sample can be, for example, a specimen obtained from a subject (e.g., a mammal such as a human) or can be derived from such a subject. For example, a sample can be a tissue section obtained by biopsy, archived tumor tissue, or cells that are placed in or adapted to tissue culture. A biological sample can also be a biological fluid such as blood, plasma, serum, urine, or such a sample absorbed onto a substrate (e.g., glass, polymer, paper). A biological sample can also include an endometrial tissue sample. In specific embodiments, the biological sample is a tumor cell(s) or a tumor tissue obtained from a region of the subject suspected of containing a tumor or a pre-cancerous lesion. For example, the biological sample may be an endometrial tumor sample. A biological sample can be further fractionated, if desired, to a fraction containing particular cell types. For example, a blood sample can-be fractionated-into serum or into fractions containing particular types of blood cells such as red blood cells or white blood cells (leukocytes). If desired, a sample can be a combination of samples from a subject such as a combination of a tissue and fluid sample.

The biological samples can be obtained from a subject having, suspected of having, or at risk of developing, an endometrial cancer. In certain embodiments, the subject has advanced endometrial cancer. In some embodiments, the subject has recurrent endometrial cancer. In other embodiments, the subject has a stage III endometrial cancer. In certain embodiments, the subject has a stage IV endometrial cancer. In other embodiments, the subject has an unresectable stage III or stage IV endometrial cancer.

Any suitable methods for obtaining the biological samples can be employed, although exemplary methods include, e.g., phlebotomy, fine needle aspirate biopsy procedure. Samples can also be collected, e.g., by microdissection (e.g., laser capture microdissection (LCM) or laser microdissection (LMD)).

Methods for obtaining and/or storing samples that preserve the activity or integrity of molecules (e.g., nucleic acids or proteins) in the sample are well known to those skilled in the art. For example, a biological sample can be further contacted with one or more additional agents such as buffers and/or inhibitors, including one or more of nuclease, protease, and phosphatase inhibitors, which preserve or minimize changes in the molecules (e.g., nucleic acids or proteins) in the sample. Such inhibitors include, for example, chelators such as ethylenediamine tetraacetic acid (EDTA), ethylene glycol bis(P-aminoethyl ether) N,N,N1,N1-tetraacetic acid (EGTA), protease inhibitors such as phenylmethylsulfonyl fluoride (PMSF), aprotinin, leupeptin, antipain, and the like, and phosphatase inhibitors such as phosphate, sodium fluoride, vanadate, and the like. Suitable buffers and conditions for isolating molecules are well known to those skilled in the art and can be varied depending, for example, on the type of molecule in the sample to be characterized (see, for example, Ausubel et al. Current Protocols in Molecular Biology (Supplement 47), John Wiley & Sons, New York (1999); Harlow and Lane, Antibodies: A Laboratory Manual (Cold Spring Harbor Laboratory Press (1988); Harlow and Lane, Using Antibodies: A Laboratory Manual, Cold Spring Harbor Press (1999); Tietz Textbook of Clinical Chemist); 3rd ed. Burtis and Ashwood, eds. W. B. Saunders, Philadelphia, (1999)). A sample also can be processed to eliminate or minimize the presence of interfering substances. For example, a biological sample can be fractionated or purified to remove one or more materials that are not of interest. Methods of fractionating or purifying a biological sample include, but are not limited to, chromatographic methods such as liquid chromatography, ion-exchange chromatography, size-exclusion chromatography, or affinity chromatography. For use in the methods described herein, a sample can be in a variety of physical states. For example, a sample can be a liquid or solid, can be dissolved or suspended in a liquid, can be in an emulsion or gel, or can be absorbed onto a material.

Determining Expression Levels/Concentrations of Biomarkers

Gene expression can be detected as, e.g., protein or RNA expression of a target gene. That is, the presence or expression level (amount) of a gene can be determined by detecting and/or measuring the level of mRNA or protein expression of the gene. In some embodiments, gene expression can be detected as the activity of a protein encoded by a gene such as a gene depicted in Table 1.

In one embodiment, the expression of a gene can be determined by detecting and/or measuring expression or concentration of a protein encoded by the gene. Methods of determining protein expression/concentration are well known in the art. A generally used method involves the use of antibodies specific for the target protein of interest. For example, methods of determining protein expression include, but are not limited to, western blot or dot blot analysis, immunohistochemistry (e.g., quantitative immunohistochemistry), immunocytochemistry, enzyme-linked immunosorbent assay (ELISA), enzyme-linked immunosorbent spot (ELISPOT; Coligan, J. E., et al., eds. (1995) Current Protocols in Immunology. Wiley, N.Y.), radioimmunoassay, chemiluminescent immunoassay, electrochemiluminescence immunoassay, latex turbidimetric immunoassay, latex photometric immunoassay, immunochromatographic assay, and antibody array analysis (see, e.g., U.S. Publication Nos. 20030013208 and 2004171068, the disclosures of each of which are incorporated herein by reference in their entirety). Further description of many of the methods above and additional methods for detecting protein expression can be found in, e.g., Sambrook et al. (supra).

In one example, the presence or amount of protein expression of a gene (e.g., a gene depicted in Table 1) can be determined using a western blotting technique. For example, a lysate can be prepared from a biological sample, or the biological sample itself, can be contacted with Laemmli buffer and subjected to sodium-dodecyl sulfate polyacrylamide gel electrophoresis (SDS-PAGE). SDS-PAGE-resolved proteins, separated by size, can then be transferred to a filter membrane (e.g., nitrocellulose) and subjected to immunoblotting techniques using a detectably-labeled antibody specific to the protein of interest. The presence or amount of bound detectably-labeled antibody indicates the presence or amount of protein in the biological sample.

In another example, an immunoassay can be used for detecting and/or measuring the protein expression of a gene (e.g., a gene depicted in Table 1). As above, for the purposes of detection, an immunoassay can be performed with an antibody that bears a detection moiety (e.g., a fluorescent agent or enzyme). Proteins from a biological sample can be conjugated directly to a solid-phase matrix (e.g., a multi-well assay plate, nitrocellulose, agarose, sepharose, encoded particles, or magnetic beads) or it can be conjugated to a first member of a specific binding pair (e.g., biotin or streptavidin) that attaches to a solid-phase matrix upon binding to a second member of the specific binding pair (e.g., streptavidin or biotin). Such attachment to a solid-phase matrix allows the proteins to be purified away from other interfering or irrelevant components of the biological sample prior to contact with the detection antibody and also allows for subsequent washing of unbound antibody. Here as above, the presence or amount of bound detectably-labeled antibody indicates the presence or amount of protein in the biological sample.

There is no particular restriction as to the form of the antibody and the present disclosure includes polyclonal antibodies, as well as monoclonal antibodies. The antiserum obtained by immunizing animals, such as rabbits with a protein or fragment thereof of the invention (i.e., a protein or an immunological fragment thereof from Table 1), as well polyclonal and monoclonal antibodies of all classes, human antibodies, and humanized antibodies produced by genetic recombination, are also included.

An intact protein or its partial peptide may be used as the antigen for immunization. As partial peptides of the proteins, for example, the amino (N)-terminal fragment of the protein and the carboxy (C)-terminal fragment can be given.

A gene encoding a protein of interest or a fragment thereof (e.g., an immunological fragment) is inserted into a known expression vector, and, by transforming the host cells with the vector described herein, the desired protein or a fragment thereof is recovered from outside or inside the host cells using standard methods. This protein can be used as the sensitizing antigen. Also, cells expressing the protein, cell lysates, or a chemically synthesized protein of the invention may be also used as a sensitizing antigen.

The mammal that is immunized by the sensitizing antigen is not restricted; however, it is preferable to select animals by considering the compatibility with the parent cells used in cell fusion. Generally, animals belonging to the orders rodentia, lagomorpha, or primates are used. Examples of animals belonging to the order of rodentia that may be used include, for example, mice, rats, and hamsters. Examples of animals belonging to the order of lagomorpha that may be used include, for example, rabbits. Examples of animals belonging to the order of primates that may be used include, for example, monkeys. Examples of monkeys to be used include the infraorder catarrhini (old world monkeys), for example, *Macaca fascicularis*, rhesus monkeys, sacred baboons, and chimpanzees.

Well-known methods may be used to immunize animals with the sensitizing antigen. For example, the sensitizing antigen is injected intraperitoneally or subcutaneously into mammals. Specifically, the sensitizing antigen is suitably diluted and suspended in physiological saline, phosphate-buffered saline (PBS), and so on, and mixed with a suitable amount of general adjuvant if desired, for example, with Freund's complete adjuvant. Then, the solution is emulsified and injected into the mammal. Thereafter, the sensitizing antigen suitably mixed with Freund's incomplete adjuvant is preferably given several times every 4 to 21 days. A suitable carrier can also be used when immunizing and animal with the sensitizing antigen. After the immunization, the elevation in the level of serum antibody is detected by usual methods.

Polyclonal antibodies against the proteins of the present disclosure can be prepared as follows. After verifying that the desired serum antibody level has been reached, blood is withdrawn from the mammal sensitized with antigen. Serum is isolated from this blood using conventional methods. The serum containing the polyclonal antibody may be used as the polyclonal antibody, or according to needs, the polyclonal antibody-containing fraction may be further isolated from the serum. For example, a fraction of antibodies that specifically recognize the protein of the invention may be prepared by using an affinity column to which the protein is coupled. Then, the fraction may be further purified by using a Protein A or Protein G column in order to prepare immunoglobulin G or M.

To obtain monoclonal antibodies, after verifying that the desired serum antibody level has been reached in the mammal sensitized with the above-described antigen, immunocytes are taken from the mammal and used for cell fusion. For this purpose, splenocytes can be mentioned as preferable immunocytes. As parent cells fused with the above immunocytes, mammalian myeloma cells are preferably used. More preferably, myeloma cells that have acquired the feature, which can be used to distinguish fusion cells by agents, are used as the parent cell.

The cell fusion between the above immunocytes and myeloma cells can be conducted according to known methods, for example, the method by Galfre and Milstein (*Methods Enzymol.* 73:3-46, 1981).

The hybridoma obtained from cell fusion is selected by culturing the cells in a standard selection medium, for example, HAT culture medium (medium containing hypoxanthine, aminopterin, and thymidine). The culture in this HAT medium is continued for a period sufficient enough for cells (non-fusion cells) other than the objective hybridoma to perish, usually from a few days to a few weeks. Then, the usual limiting dilution method is carried out, and the hybridoma producing the objective antibody is screened and cloned.

Other than the above method for obtaining hybridomas, by immunizing an animal other than humans with the antigen, a hybridoma producing the objective human antibodies having the activity to bind to proteins can be obtained by the method of sensitizing human lymphocytes, for example, human lymphocytes infected with the EB virus, with proteins, protein-expressing cells, or lysates thereof in vitro and fusing the sensitized lymphocytes with myeloma cells derived from human, for example, U266, having a permanent cell division ability.

The monoclonal antibodies obtained by transplanting the obtained hybridomas into the abdominal cavity of a mouse and extracting ascites can be purified by, for example, ammonium sulfate precipitation, protein A or protein G column, DEAE ion exchange chromatography, an affinity column to which the protein of the present disclosure is coupled, and so on.

Monoclonal antibodies can be also obtained as recombinant antibodies produced by using the genetic engineering technique (see, for example, Borrebaeck C. A. K. and Larrick, J. W., THERAPEUTIC MONOCLONAL ANTIBODIES, Published in the United Kingdom by MACMILLAN PUBLISHERS LTD (1990)). Recombinant antibodies are produced by cloning the encoding DNA from immunocytes, such as hybridoma or antibody-producing sensitized lymphocytes, incorporating into a suitable vector, and introducing this vector into a host to produce the antibody. The present disclosure encompasses such recombinant antibodies as well.

Antibodies or antibody fragments specific for a protein encoded by one or more biomarkers can also be generated by in vitro methods such as phage display.

Moreover, the antibody of the present disclosure may be an antibody fragment or modified-antibody, so long as it binds to a protein encoded by a biomarker of the invention. For instance, Fab, F (ab') 2, Fv, or single chain Fv (scFv) in which the H chain Fv and the L chain Fv are suitably linked by a linker (Huston et al., *Proc. Natl. Acad. Sci. USA*, 85:5879-5883, (1988)) can be given as antibody fragments. Specifically, antibody fragments are generated by treating antibodies with enzymes, for example, papain or pepsin. Alternatively, they may be generated by constructing a gene encoding an antibody fragment, introducing this into an expression vector, and expressing this vector in suitable host cells (see, for example, Co et al., *J. Immunol.*, 152:2968-2976, 1994; Better et al., *Methods Enzymol.*, 178:476-496, 1989; Pluckthun et al., *Methods Enzymol.*, 178:497-515, 1989; Lamoyi, *Methods Enzymol.*, 121:652-663, 1986; Rousseaux et al., *Methods Enzymol.*, 121:663-669, 1986; Bird et al., *Trends Biotechnol.*, 9:132-137, 1991).

The antibodies may be conjugated to various molecules, such as fluorescent substances, radioactive substances, and luminescent substances. Methods to attach such moieties to an antibody are already established and conventional in the field (see, e.g., U.S. Pat. Nos. 5,057,313 and 5,156,840).

Examples of methods that assay the antigen-binding activity of the antibodies include, for example, measurement of absorbance, enzyme-linked immunosorbent assay (ELISA), enzyme immunoassay (EIA), radioimmunoassay (RIA), and/or immunofluorescence. For example, when using ELISA, a protein encoded by a biomarker of the invention is added to a plate coated with the antibodies of the present disclosure, and then, the antibody sample, for example, culture supernatants of antibody-producing cells, or purified antibodies are added. Then, secondary antibody recognizing the primary antibody, which is labeled by alkaline phosphatase and such enzymes, is added, the plate is incubated and washed, and the absorbance is measured to evaluate the antigen-binding activity after adding an enzyme substrate such as p-nitrophenyl phosphate. As the protein, a protein fragment, for example, a fragment comprising a C-terminus, or a fragment comprising an N-terminus may be used. To evaluate the activity of the antibody of the invention, BIAcore (GE Healthcare) may be used.

By using these methods, the antibody of the invention and a sample presumed to contain a protein of the invention are contacted, and the protein encoded by a biomarker of the invention is detected or assayed by detecting or assaying the immune complex formed between the above-mentioned antibody and the protein.

Mass spectrometry based quantitation assay methods, for example, but not limited to, multiple reaction monitoring (MRM)-based approaches in combination with stable-isotope labeled internal standards, are an alternative to immunoassays for quantitative measurement of proteins. These approaches do not require the use of antibodies and so the analysis can be performed in a cost- and time-efficient manner (see, for example, Addona et al., *Nat. Biotechnol.,* 27:633-641, 2009; Kuzyk et al., *Mol. Cell Proteomics,* 8:1860-1877, 2009; Paulovich et al., *Proteomics Clin Appl.,* 2:1386-1402, 2008). In addition, MRM offers superior multiplexing capabilities, allowing for the simultaneous quantification of numerous proteins in parallel. The basic theory of these methods has been well-established and widely utilized for drug metabolism and pharmacokinetics analysis of small molecules.

In another embodiment, the expression level of a gene of interest is determined by measuring RNA levels. A variety of suitable methods can be employed to detect and/or measure the level of mRNA expression of a gene. For example, mRNA expression can be determined using Northern blot or dot blot analysis, reverse transcriptase-PCR (RT-PCR; e.g., quantitative RT-PCR), in situ hybridization (e.g., quantitative in situ hybridization) or nucleic acid array (e.g., oligonucleotide arrays or gene chips) analysis. Details of such methods are described below and in, e.g., Sambrook et al., Molecular Cloning: A Laboratory Manual Second Edition vol. 1, 2 and 3. Cold Spring Harbor Laboratory Press: Cold Spring Harbor, N.Y., USA, November 1989; Gibson et al. (1999) *Genome Res.,* 6(10):995-1001; and Zhang et al. (2005) *Environ. Sci. Technol.,* 39(8):2777-2785; U.S. Publication No. 2004086915; European Patent No. 0543942; and U.S. Pat. No. 7,101,663; the disclosures of each of which are incorporated herein by reference in their entirety.

In one example, the presence or amount of one or more discrete mRNA populations in a biological sample can be determined by isolating total mRNA from the biological sample (see, e.g., Sambrook et al. (supra) and U.S. Pat. No. 6,812,341) and subjecting the isolated mRNA to agarose gel electrophoresis to separate the mRNA by size. The size-separated mRNAs are then transferred (e.g., by diffusion) to a solid support such as a nitrocellulose membrane. The presence or amount of one or more mRNA populations in the biological sample can then be determined using one or more detectably-labeled-polynucleotide probes, complementary to the mRNA sequence of interest, which bind to and thus render detectable their corresponding mRNA populations. Detectable-labels include, e.g., fluorescent (e.g., umbelliferone, fluorescein, fluorescein isothiocyanate, rhodamine, dichlorotriazinylamine fluorescein, dansyl chloride, allophycocyanin (APC), or phycoerythrin), luminescent (e.g., europium, terbium, Qdot™ nanoparticles supplied by the Quantum Dot Corporation, Palo Alto, Calif.), radiological (e.g., $^{125}$I, $^{131}$I, $^{35}$S, $^{32}$P, $^{33}$P, or $^{3}$H), and enzymatic (horseradish peroxidase, alkaline phosphatase, beta-galactosidase, or acetylcholinesterase) labels.

In another example, the presence or amount of discrete populations of mRNA (e.g., mRNA encoded by one or more genes depicted in Table 1) in a biological sample can be determined using nucleic acid (or oligonucleotide) arrays (e.g., an array described below under "Arrays"). For example, isolated mRNA from a biological sample can be amplified using RT-PCR with, e.g., random hexamer or oligo(dT)-primer mediated first strand synthesis. The amplicons can be fragmented into shorter segments. The RT-PCR step can be used to detectably-label the amplicons, or, optionally, the amplicons can be detectably-labeled subsequent to the RT-PCR step. For example, the detectable-label can be enzymatically (e.g., by nick-translation or kinase such as T4 polynucleotide kinase) or chemically conjugated to the amplicons using any of a variety of suitable techniques (see, e.g., Sambrook et al., supra). The detectably-labeled-amplicons are then contacted with a plurality of polynucleotide probe sets, each set containing one or more of a polynucleotide (e.g., an oligonucleotide) probe specific for (and capable of binding to) a corresponding amplicon, and where the plurality contains many probe sets each corresponding to a different amplicon. Generally, the probe sets are bound to a solid support and the position of each probe set is predetermined on the solid support. The binding of a detectably-labeled amplicon to a corresponding probe of a probe set indicates the presence or amount of a target mRNA in the biological sample. Additional methods for detecting mRNA expression using nucleic acid arrays are described in, e.g., U.S. Pat. Nos. 5,445,934; 6,027,880; 6,057,100; 6,156, 501; 6,261,776; and 6,576,424; the disclosures of each of which are incorporated herein by reference in their entirety.

Methods of detecting and/or for quantifying a detectable label depend on the nature of the label. The products of reactions catalyzed by appropriate enzymes (where the detectable label is an enzyme; see above) can be, without limitation, fluorescent, luminescent, or radioactive or they may absorb visible or ultraviolet light. Examples of detectors suitable for detecting such detectable labels include, without limitation, x-ray film, radioactivity counters, scintillation counters, spectrophotometers, colorimeters, fluorometers, luminometers, and densitometers.

Methods for detecting or measuring gene expression (e.g., protein or mRNA expression) can optionally be performed in formats that allow for rapid preparation, processing, and analysis of multiple samples. This can be, for example, in multi-welled assay plates (e.g., 96 wells or 386 wells) or arrays (e.g., nucleic acid chips or protein chips). Stock solutions for various reagents can be provided manually or robotically, and subsequent sample preparation (e.g., RT-PCR, labeling, or cell fixation), pipetting, diluting, mixing, distribution, washing, incubating (e.g., hybridization), sample readout, data collection (optical data) and/or analysis (computer aided image analysis) can be done robotically using commercially available analysis software, robotics, and detection instrumentation capable of detecting the signal generated from the assay. Examples of such detectors include, but are not limited to, spectrophotometers, luminometers, fluorimeters, and devices that measure radioisotope decay. Exemplary high-throughput cell-based assays (e.g., detecting the presence or level of a target protein in a cell) can utilize ArrayScan® VTI HCS Reader or KineticScan® HCS Reader technology (Cellomics Inc., Pittsburg, Pa.).

In some embodiments, the expression level of two genes, three genes, four genes, five genes, six genes, seven genes, eight genes, nine genes, 10 genes, 11 genes, or at least two genes, at least three genes, at least four genes, at least five genes, at least six genes, at least seven genes, at least eight genes, at least nine genes, or at least 10 genes from Table 1 can be assessed and/or measured.

To aid in detecting the presence or level of expression of one or more of the genes depicted in Table 1, any part of the nucleic acid sequence of the genes can be used, e.g., as hybridization polynucleotide probes or primers (e.g., for amplification or reverse transcription). The probes and primers can be oligonucleotides of sufficient length to provide specific hybridization to an RNA, DNA, cDNA, or fragments thereof isolated from a biological sample. Depending on the specific application, varying hybridization conditions can be employed to achieve varying degrees of selectivity of a probe or primer towards target sequence. The primers and probes can be detectably-labeled with reagents that facilitate detection (e.g., fluorescent labels, chemical labels (see, e.g., U.S. Pat. Nos. 4,582,789 and 4,563,417), or modified bases).

Standard stringency conditions are described by Sambrook, et al. (supra) and Haymes, et al. Nucleic Acid Hybridization, A Practical Approach, IRL Press, Washington, D.C. (1985). In order for a nucleic acid molecule to serve as a primer or probe it need only be sufficiently complementary in sequence to be able to form a stable double-stranded structure under the particular hybridization conditions (e.g., solvent and salt concentrations) employed.

Hybridization can be used to assess homology between two nucleic acid sequences. A nucleic acid sequence described herein, or a fragment thereof, can be used as a hybridization probe according to standard hybridization techniques. The hybridization of a probe of interest (e.g., a probe containing a portion of a nucleotide sequence described herein or its complement) to DNA, RNA, cDNA, or fragments thereof from a test source is an indication of the presence of DNA or RNA corresponding to the probe in the test source. Hybridization conditions are known to those skilled in the art and can be found in Current Protocols in Molecular Biology, John Wiley & Sons, N.Y., 6.3.1-6.3.6, 1991. Moderate hybridization conditions are defined as hybridization in 2× sodium chloride/sodium citrate (SSC) at 30° C., followed by a wash in 1×SSC, 0.1% SDS at 50° C. Highly stringent conditions are defined as hybridization in 6×SSC at 45° C., followed by a wash in 0.2×SSC, 0.1% SDS at 65° C.

Primers can be used in in a variety of PCR-type methods. For example, polymerase chain reaction (PCR) techniques can be used to amplify specific sequences from DNA as well as RNA, including sequences from total genomic DNA or total cellular RNA. The PCR primers are designed to flank the region that one is interested in amplifying. Primers can be located near the 5' end, the 3' end or anywhere within the nucleotide sequence that is to be amplified. The amplicon length is dictated by the experimental goals. For qPCR, the target length is closer to 100 bp and for standard PCR, it is near 500 bp. Generally, sequence information from the ends of the region of interest or beyond is employed to design oligonucleotide primers that are identical or similar in sequence to opposite strands of the template to be amplified. PCR primers can be chemically synthesized, either as a single nucleic acid molecule (e.g., using automated DNA synthesis in the 3' to 5' direction using phosphoramidite technology) or as a series of oligonucleotides. For example, one or more pairs of long oligonucleotides (e.g., >100 nucleotides) can be synthesized that contain the desired sequence, with each pair containing a short segment of complementarity (e.g., about 15 nucleotides) such that a duplex is formed when the oligonucleotide pair is annealed. DNA polymerase is used to extend the oligonucleotides, resulting in a single, double-stranded nucleic acid molecule per oligonucleotide pair.

In addition, the nucleic acid sequences or fragments thereof (e.g., oligonucleotide probes) can be used in nucleic acid arrays (such as the nucleic acid arrays described below under "Arrays") for detection and/or quantitation of gene expression.

Creating a Response Profile

The methods described herein can also be used to generate a lenvatinib compound (e.g., lenvatinib mesylate) therapy response profile for a subject having endometrial cancer. The profile can include, e.g., information that indicates the expression level of one or more genes (e.g., one or more genes depicted in Table 1) pre- and post-treatment with lenvatinib or a pharmaceutically acceptable salt thereof; and/or the histological analysis of any endometrial tumors. The response profiles described herein can contain information on the expression or expression level of at least two, at least three, at least four, at least five, at least six, at least seven, at least eight, at least nine, or at least 10 genes listed in Table 1. The resultant information (lenvatinib therapy response profile) can be used for predicting the response of a subject (e.g., a human patient) having, suspected of having or at risk of developing endometrial cancer to a treatment comprising a lenvatinib compound (e.g., lenvatinib mesylate).

It is understood that a lenvatinib compound (e.g., lenvatinib mesylate) response profile can be in electronic form (e.g., an electronic patient record stored on a computer or other electronic (computer-readable) media such as a DVD, CD, or floppy disk) or written form. The lenvatinib compound (e.g., lenvatinib mesylate) response profile can also include information for several (e.g., two, three, four, five, 10, 20, 30, 50, or 100 or more) subjects (e.g., human patients). Such multi-subject response profiles can be used, e.g., in analyses (e.g., statistical analyses) of particular characteristics of subject cohorts.

Responsiveness of a subject to a therapy comprising lenvatinib or a pharmaceutically acceptable salt thereof (e.g., lenvatinib mesylate) can be classified in several ways and classification is dependent on the subject's disease (e.g., advanced or recurrent endometrial cancer), the severity of the disease, and the particular medicament the subject is administered. In the simplest sense, responsiveness is any decrease in the disease state as compared to pre-treatment, and non-responsiveness is the lack of any change in the disease state as compared to pre-treatment. Responsiveness of a subject (e.g., a human) with an endometrial cancer can be classified based on one or more of a number of objective clinical indicia such as, but not limited to, tumor size, Clinical Benefit (CB), Progression Free Survival (PFS), Overall Survival (OS), % of maximum tumor Shrinkage (MTS), or Objective Response Rate (ORR).

"Clinical benefit" refers to having one of the following statuses—Complete Response (CR), Partial Response (PR); or Stable Disease (SD) with 6 months or more progression free survival (PFS). "Complete Response" means complete disappearance of all target lesions. "Partial Response" means at least 30% decrease in the sum of the longest diameter (LD) of target lesions, taking as reference the baseline summed LD. "Progressive Disease" (PD) means at least 20% increase in the sum of the LD of target lesions, taking as reference the smallest summed LD recorded since the treatment started, or the appearance of one or more new lesions. "Stable Disease" means neither sufficient shrinkage of the target lesions to qualify for PR nor sufficient increase to qualify for progressive disease (PD), taking as reference the smallest summed LD since the treatment started.

"Overall Survival" (OS) is defined as the time from randomization until death from any cause. "Randomization" means randomization of a patient into a test group or a control group when therapy plan for a patient is determined.

"Progression Free Survival" (PFS) refers to the period from start date of treatment to the last date before entering PD status.

"% of Maximum Tumor shrinkage" (MTS) means percent change of sum of diameters of target lesions, taking as reference the baseline sum diameters.

"Objective Response Rate" (ORR) compares subjects with either Complete Response (CR) or Partial Response (PR) with subjects with either Stable Disease (SD) or Progressive Disease (PD).

Methods of Treatment

The methods disclosed herein enable the assessment of whether or not a subject having, suspected of having or at risk of developing endometrial cancer is likely to respond to a therapy comprising a lenvatinib compound (e.g., lenvatinib mesylate). A subject having, suspected of having or at risk of developing endometrial cancer who is likely to respond to a lenvatinib compound can be administered lenvatinib or a pharmaceutically acceptable salt thereof (e.g., lenvatinib mesylate). Conversely, a subject having, suspected of having or at risk of developing endometrial cancer who is not likely to respond to a lenvatinib compound can be administered a different therapy that is suitable for treatment of endometrial cancer.

The methods of this disclosure also enable the stratification of subjects having, suspected of having or at risk of developing endometrial cancer into groups of subjects that are more likely to benefit, and groups of subjects that are less likely to benefit, from treatment comprising a lenvatinib compound (e.g., lenvatinib mesylate). The ability to select such subjects from a pool of endometrial cancer subjects who are being considered for treatment with a lenvatinib compound is beneficial for administering an effective treatment to the subject.

Lenvatinib or a pharmaceutically acceptable salt thereof (e.g., lenvatinib mesylate) shows potent anti-tumor effects, in part, by inhibiting angiogenesis. The subjects who are considered for treatment comprising a lenvatinib compound (e.g., lenvatinib mesylate) include, but are not limited to, subjects having, suspected of having, or likely to develop an endometrial cancer. In one embodiment, the subject to be treated with lenvatinib or a pharmaceutically acceptable salt thereof (e.g., lenvatinib mesylate) has, is suspected of having, or is likely to develop advanced endometrial cancer. In certain embodiments, the subject to be treated with a therapy comprising a lenvatinib compound (e.g., lenvatinib mesylate) has, is suspected of having, or is likely to develop a recurrent endometrial cancer. In other embodiments, the subject to be treated with a therapy comprising a lenvatinib compound has, is suspected of having, or is likely to develop a stage I endometrial cancer. In one embodiment, the subject to be treated with a therapy comprising a lenvatinib compound has, is suspected of having, or is likely to develop a stage II endometrial cancer. In another embodiment, the subject to be treated with a therapy comprising a lenvatinib compound has, is suspected of having, or is likely to develop a stage III endometrial cancer. In another embodiment, the subject to be treated with a therapy comprising a lenvatinib compound has, is suspected of having, or is likely to develop a stage IV endometrial cancer. In some embodiments, the endometrial cancer is a nonresectable stage III or stage IV cancer.

If the subject having an endometrial cancer is more likely to respond to a therapy comprising lenvatinib or a pharmaceutically acceptable salt thereof (based on concentrations of one or more of the biomarkers described above (e.g., Ang2 protein)), the subject can then be administered an effective amount of the lenvatinib compound (e.g., lenvatinib mesylate). An effective amount of the compound can suitably be determined by a health care practitioner taking into account, for example, the characteristics of the patient (age, sex, weight, race, etc.), the progression of the disease, and prior exposure to the drug. If the subject is less likely to respond to a therapy comprising a lenvatinib compound, the subject can then be optionally administered a therapy that does not comprise lenvatinib. These therapies include, but are not limited to, radioactive iodine, doxorubicin, carboplatin, cisplatin, paclitaxel, sorafenib, docetaxel, trasturnab, interleukin-2, interferon, everolimus, sunitinib, pazopanib, vandetanib, and "standard of care" treatment (i.e., prevailing standard of care as determined by the health care practitioner or as specified in the clinical study) such as investigational drugs and chemotherapy.

Subjects of all ages can be affected by disorders treatable by lenvatinib or a pharmaceutically acceptable salt thereof (e.g., lenvatinib mesylate). Therefore, a biological sample used in a methods described herein can be obtained from a subject (e.g., a human) of any age, including a child, an adolescent, or an adult, such as an adult having, suspected of having, or at risk of developing an endometrial cancer.

The methods can also be applied to individuals at risk of developing an endometrial cancer treatable by lenvatinib or a pharmaceutically acceptable salt thereof (e.g., lenvatinib mesylate). Such individuals include those who have (i) a family history of (a genetic predisposition for) such disorders or (ii) one or more risk factors for developing such disorders.

After stratifying or selecting a subject based on whether the subject will be more likely or less likely to respond to lenvatinib or a pharmaceutically acceptable salt thereof (e.g., lenvatinib mesylate), a medical practitioner (e.g., a doctor) can administer the appropriate therapeutic modality to the subject. Methods of administering lenvatinib therapies are well known in the art.

It is understood that any therapy described herein (e.g., a therapy comprising a lenvatinib or a therapy that does not comprise a lenvatinib) can include one or more additional therapeutic agents. That is, any therapy described herein can be co-administered (administered in combination) with one or more additional therapeutic agents such as, but not limited to, doxorubicin, carboplatin, cisplatin, paclitaxel, docetaxel, trastumab, and everolimus. Furthermore, any therapy described herein can include one or more agents for treating, for example, pain, nausea, and/or one or more side-effects of a therapy comprising lenvatinib or a pharmaceutically acceptable salt thereof (e.g., lenvatinib mesylate).

Combination therapies (e.g., co-administration of a therapy comprising lenvatinib or a pharmaceutically acceptable salt thereof (e.g., lenvatinib mesylate) and one or more additional therapeutic agents) can be, e.g., simultaneous or successive. For example, lenvatinib or a pharmaceutically acceptable salt thereof (e.g., lenvatinib mesylate) and one or more additional therapeutic agents can be administered at the same time or a lenvatinib compound (e.g., lenvatinib mesylate) can be administered first in time and the one or more additional therapeutic agents administered second in time. In some embodiments, the one or more additional therapeutic agents can be administered first in time and lenvatinib or a pharmaceutically acceptable salt thereof (e.g., lenvatinib mesylate) administered second in time.

In cases where the subject having endometrial cancer and predicted to respond to a lenvatinib compound (e.g., lenvatinib mesylate) therapy has been previously administered one or more non-lenvatinib therapies, the therapy comprising a lenvatinib compound can replace or augment a previously or currently administered therapy. For example, upon treating with the therapy comprising lenvatinib or a pharmaceutically acceptable salt thereof (e.g., lenvatinib mesylate), administration of the one non-lenvatinib therapies can cease or diminish, e.g., be administered at lower levels. Administration of the previous therapy can be maintained while the therapy comprising lenvatinib or a pharmaceutically acceptable salt thereof (e.g., lenvatinib mesylate) is administered. In some embodiments, a previous therapy can be maintained until the level of the therapy comprising lenvatinib or a pharmaceutically acceptable salt thereof (e.g., lenvatinib mesylate) reaches a level sufficient to provide a therapeutic effect.

Arrays

Nucleic acid arrays including the nucleic acid biomarkers disclosed herein are useful in, e.g., detecting gene expression and/or measuring gene expression levels. The arrays are also useful for e.g., in predicting the response of a subject having endometrial cancer to a therapy comprising lenvatinib or a pharmaceutically acceptable salt thereof (e.g., lenvatinib mesylate), for identifying subjects having endometrial cancer who can benefit from a therapy comprising lenvatinib or a pharmaceutically acceptable salt thereof (e.g., lenvatinib mesylate), and for steering subjects having endometrial cancer who would not likely benefit from a therapy comprising lenvatinib or a pharmaceutically acceptable salt thereof (e.g., lenvatinib mesylate) to other cancer therapies.

An array is an orderly arrangement of samples where matching of known and unknown DNA samples is done based on base pairing rules (e.g., Adenosine pairs with Thymine or Uracil; Guanosine pairs with Cytosine). A typical microarray experiment involves the hybridization of an mRNA, a cDNA molecule, or fragments thereof, to a DNA template from which it is originated or derived. Many DNA samples are used to construct an array. DNAs from at least one, two, three, four, five, six, seven, eight, nine, ten, or eleven of the genes in Table 1 can be used to construct the array. An array experiment makes use of common assay systems such as microplates or standard blotting membranes. The sample spot sizes are typically less than 200 microns in diameter and the array usually contains thousands of spots. Thousands of spotted samples known as probes (with known identity) are immobilized on a substrate (e.g., a microscope glass slides, silicon chips, nylon membrane). The spots can be DNA, cDNA, or oligonucleotides. These are used to determine complementary binding of the unknown sequences thus allowing parallel analysis for gene expression and gene discovery. An experiment with a single DNA chip can provide information on thousands of genes simultaneously. An orderly arrangement of the probes on the support is important as the location of each spot on the array is used for the identification of a gene. The amount of mRNA bound to each site on the array indicates the expression level of the various genes that are included on the array. By using an array containing many DNA samples, one can determine, in a single experiment, the expression levels of hundreds or thousands of genes by measuring the amount of mRNA bound to each site on the array. With the aid of a computer, the amount of mRNA bound to the spots on the microarray can be precisely measured, generating a profile of gene expression in the cell.

The two main DNA microarray platforms that are generally used are cDNA and oligonucleotide microarrays. cDNA microarrays are made with long double-stranded DNA molecules generated by enzymatic reactions such as PCR (Schena, M. et al., *Science,* 270:467-470 (1995)), while oligonucleotide microarrays employ oligonucleotide probes spotted by either robotic deposition or in situ synthesis on a substrate (Lockhart, D. J. et al., *Nat. Biotechnol.,* 14, 1675-1680 (1996)).

Kits

This application also provides kits. In certain embodiments, the kit can include an antibody or antibodies that can be used to detect one or more of the biomarkers listed in Table 1 or their concentration or expression levels. For example, the kit can include an antibody that specifically binds Ang2. The antibodies in the kit may be monoclonal or polyclonal and can be further conjugated with a detectable label. In some embodiments, the kit includes probes that can be used to identify or detect any of the biomarkers of Table 1. In some embodiments, the kit includes any of the nucleic acid arrays described herein. In some embodiments, the kit includes probes and antibodies that can be used to identify or detect any of the biomarkers of Table 1 or their expression or expression levels. The kits can, optionally, contain instructions for detecting and/or measuring the concentration of one or more proteins or the levels of mRNA in a biological sample.

The kits can optionally include, e.g., a control (e.g., a concentration standard for the protein being assessed) or control labeled-amplicon set containing known amounts of one or more amplicons recognized by nucleic acid probes of the array. In some instances, the control can be an insert (e.g., a paper insert or electronic medium such as a CD, DVD, or floppy disk) containing an expression level or expression level ranges of one or more proteins or RNAs predictive of a response to a therapy comprising a lenvatinib compound (e.g., lenvatinib mesylate).

In some embodiments, the kits can include one or more reagents for processing a biological sample (e.g., calibration reagents, buffers, diluents, color reagents, reagents to stop a reaction). For example, a kit can include reagents for isolating a protein from a biological sample and/or reagents for detecting the presence and/or amount of a protein in a biological sample (e.g., an antibody that binds to the protein that is the subject of the detection assay and/or an antibody that binds the antibody that binds to the protein).

In certain embodiments, the kit includes at least one microplate (e.g., a 96 well plate; i.e., 12 strips of 8 wells). The microplate can be provided with its corresponding plate cover. The microplate can be polystyrene or of any other suitable material. The microplate can have the antibody that is used to identify the presence of a particular biomarker coated inside each well. The antibody may be conjugated to a detectable label. The kit may also include at least one adhesive strip.

In some embodiments, the kits can include a software package for analyzing the results of, e.g., expression profile or a microarray analysis.

The kits can also include one or more antibodies for detecting the protein expression of any of the genes described herein. For example, a kit can include (or in some cases consist of) one or a plurality of antibodies capable of specifically binding to one or more proteins encoded by any of the genes depicted in Table 1 and optionally, instructions for detecting and/or measuring the concentration of one or more proteins and/or a detection antibody comprising a detectably-labeled antibody that is capable of binding to at least one antibody of the plurality. In some embodiments, the kits can include antibodies that recognize one, at least two, at least three, at least four, at least five, at least six, at least seven, at least eight, at least nine, at least 10, or 11 of the proteins encoded by genes listed in Table 1.

In certain embodiments, the kit can also optionally include one or more unit doses of a lenvatinib compound (e.g., lenvatinib mesylate).

The kits described herein can also, optionally, include instructions for administering a therapy comprising a lenvatinib compound, where the concentration of one or more proteins or expression level of one or more RNAs predicts that a subject having, suspected of having or at risk of developing endometrial cancer will respond to a therapy comprising a lenvatinib compound (e.g., lenvatinib mesylate).

In a specific embodiment, the kit comprises one or more of the following:

(i) a microplate (e.g., a 96 well plate). The microplate can be coated with an anti-Ang2 antibody that is conjugated with a detectable label. The anti-Ang2 antibody may monoclonal or polyclonal. The antibody can be e.g., from mouse, rabbit, rat, or guinea pig. The detectable label can be e.g., horse radish peroxidase, biotin, a fluorescent moiety, a radioactive moiety, a histidine tag, or a peptide tag. The microplate can be provided with a cover and optionally, one or more adhesive strips.

(ii) a vial containing anti-Ang2 conjugated with a detectable label. The detectable label can be e.g., horse radish peroxidase, biotin, a fluorescent moiety, a histidine tag, a peptide tag. The vial can also include a preservative.

(iii) a vial containing an Ang2 standard of known concentration. The Ang2 can be a recombinant human Ang2.

(iv) a vial containing an assay diluent.

(v) a vial containing a calibrator diluent.

(vi) a vial containing wash buffer. The buffer may be provided as a concentrate.

(vii) one or more vials containing color reagents (viii) a vial containing a stop solution to stop the colorimetric reaction.

The following are examples of the practice of the invention. They are not to be construed as limiting the scope of the invention in any way.

EXAMPLES

Example 1: Identifying Predictive Biomarkers for Selecting Endometrial Cancer Patients for Treatment with E7080 (Lenvatinib Mesylate)

Purpose: Angiogenesis is regulated by signaling through multiple growth factor receptors, such as VEGF receptor and FGF receptor. VEGF receptor signaling is also associated with immune cell function. E7080 is an oral angiogenesis inhibitor targeting multiple receptor tyrosine kinase; VEGFR1-3, FGFR1-4, RET, KIT, and PDGFRβ. A phase II study was performed in patients with advanced or recurrent endometrial cancer (EC) following 1 or 2 prior platinum-based treatments (Tx). The importance of angiogenesis in EC highlights the need to understand clinical mechanisms of escape from anti-angiogenic therapy. This clinical biomarker analysis was conducted to identify predictive markers of clinical benefit in EC patients upon E7080 treatment. Circulating cytokine and angiogenic factors (CAFs) can be measured in blood samples using ELISA and multiplex assay platforms. The CAFs examined in this study are listed below in Table 2. Numbers in parenthesis indicate bead region for each analyte.

TABLE 2

List of CAFs Examined

| Ang-1 | sTie-2 | G-CSF(12) | IL-1β(24) | MIP-1β(66) |
| Ang-2 | EGF(2) | GM-CSF(14) | IL-1ra(26) | PDGFAB(68) |
| FGF-23 | ANG2(90) | HGF(86) | IL-2(28) | PDGFBB(73) |
| PDGF-AA | EGF(80) | IFN-γ(20) | IL-4(32) | PGF(91) |
| RANTES | Eotaxin(4) | IL-10(44) | IL-6(36) | sIL-2Rα(76) |
| sCD40L | FGF-2(6) | IL-12(p40)(46) | IL-7(38) | TGFα(78) |
| SDF-1α | FGF2(79) | IL-12(p70)(48) | IL-8(40) | TNFα(80) |
| sVEGFR1 | FGF4(75) | IL-13(50) | IP-10(56) | VEGF(86) |
| sVEGFR2 | FLT3LG(89) | IL-17(54) | MCP-1(58) | VEGFA(100) |
| sVEGFR3 | fractalkine(10) | IL-1α(22) | MIP-1α(64) | VEGFD(78) |

The purpose of this analysis was to measure cytokine, chemokine and angiogenic factors in blood samples, such as plasma and serum, obtained from patients in clinical trials at both pre- and post-treatment with E7080 and to identify blood biomarkers which can be used to predict whether patients will respond to treatment with E7080. For these analyses, the following criteria of response were employed, namely:

(a) Tumor response: objective response rate (ORR) and % of maximum tumor shrinkage (MTS); and (b) Survival Benefits: progression free survival (PFS)/overall survival (OS).

The criteria of response are defined below.

"Complete Response" means complete disappearance of all target lesions.

"Partial Response" means at least 30% decrease in the sum of the longest diameter (LD) of target lesions, taking as reference the baseline summed LD.

"Progressive Disease" (PD) means at least 20% increase in the sum of the LD of target lesions, taking as reference the smallest summed LD recorded since the treatment started, or the appearance of one or more new lesions.

"Stable Disease" means neither sufficient shrinkage of the target lesions to qualify for PR nor sufficient increase to qualify for progressive disease (PD), taking as reference the smallest summed LD since the treatment started.

"Objective Response Rate" (ORR) compares subjects with either "Complete Response (CR) or "Partial Response" (PR) with subjects to with either Stable Disease (SD) or Progressive Disease (PD).

"% of Maximum Tumor shrinkage" (MTS) means percent change of sum of diameters of target lesions, taking as reference the baseline sum diameters and correlation of gene mutation to TS is analyzed by Pearson product-moment correlation coefficient and Spearman's rank correlation coefficient test.

"Progression Free Survival" (PFS) refers to the period from start date of treatment to the last date before entering PD status and correlation of gene mutation to PFS is analyzed by Logrank test and Cox proportional hazards model.

"Overall Survival" (OS) refers to the time from randomization until death from any cause. "Randomization" means randomization of a patient into a test group or a control group when the therapy plan for a patient is determined.

Materials and Methods: Patients who had metastatic/unresectable endometrial cancer after 1 or 2 prior platinum-based treatments received lenvatinib until disease progression or development of unmanageable toxicities. Patients received E7080 at a starting dose of 24 mg orally once daily in 28 day cycles. 133 patients were treated and evaluated for efficacy and molecular correlative analysis. This study was a part of the Phase 2 multicenter study of lenvatinib (ClinicalTrial.gov Identifier: NCT01111461). Baseline and post-treatment plasma samples were collected for molecular analyses. Plasma samples were collected at Cycle 1 Day 1 (pre-treatment) and Cycle 2 Day 1 (i.e., day 39 post-treatment). Six mL of intravenous blood was drawn into EDTA vacutainer tubes. The tubes were gently inverted 6-8 times and then centrifuged at 3000 RPM for 10 minutes to separate the plasma from the red cell layer. Plasma was collected from the tube and dispensed into a 3.5 mL cryovial using a transfer pipette, and then stored immediately at −20° C. The plasma samples were shipped on dry ice and then ultimately transferred to −80° C. storage. Plasma samples from 122 patients were used for blood biomarker analysis. Serum from Cycle 1 day 1 (baseline), and cycle 2 day 1 were used in this analysis. The association of progression free survival (PFS) and overall survival (OS) were analyzed. Plasma samples were tested in batch format where all timepoints from the same subject were assayed on the same day. On the day of assay, samples were removed from −80° C. and allowed to thaw and reach room temperature. The plasma samples were tested in a panel of ELISA and multiplex kit as per the manufacturer's instructions. Table 3 describes the assay kits used in the analysis. The ELISA plates were measured using a Molecular Devices UVmax kinetic microplate reader with SoftMax Pro 5.2 software. The multiplex assays were performed using the Bio-Rad Bio-Plex system with Bio-Plex Manager 4.1 software. Final protein concentrations (pg/mL) were calculated from the standard curve for each assay. Depending on the assay, plasma samples may have been diluted in assay buffer prior to testing. In these cases, protein concentrations were multiplied by the dilution factor.

TABLE 3

Assay Kits

| Name | Manufacturer | Catalog # | Analytes Measured |
|---|---|---|---|
| Angiopoietin-1 ELISA | R&D Systems Inc. | DANG10 | Ang-1 |
| Angiopoietin-2 ELISA | R&D Systems Inc. | DANG20 | Ang-2 |
| FGF-23 ELISA | Millipore Inc. | EZHFGF23-32k | FGF-23 |
| SDF-1a ELISA | R&D Systems Inc. | DSA00 | SDF-1 alpha |
| Tie-2 ELISA | R&D Systems Inc. | DTE200 | Tie-2 |
| Human cytokine multiplex | Millipore Inc. | MIPXHCYTO-60k-03 | sCD40L, PDGFAA, RANTES |
| VEGF receptor multiplex | Millipore Inc. | HSCR-32k | VEGFR1, VEGFR2, VEGFR3 |
| Human growth factor multiplex | Origene Inc. | AM100096 | PDGF-AB (68), PDGF-BB (73), FGF4 (75), VEGF-D (78), FGF2 (79), EGF (80), HGF (86), FLT3 LG (89), ANG2 (90), PGF (91), VEGF-A (100) |
| Human cytokine multiplex | Millipore Inc. | MPXHCYTO-60k-28 | EGF, Eotaxin, FGF-2, G-CSF, GM-CSF, IFN-g, IL-1a, IL-1b, IL-1ra, IL-2, IL-4, IL-6, IL-7, IL-8, IL-10, IL-12(p40), IL-12(p70), IL-13, IL-17, IP-10, MCP-1, MIP-1a, MIP-1b, TGFa, TNFa, VEGF, Fractalkine, sIL-2Ra |

Numbers in parenthesis indicate bead region for each analyte.

Results and Discussion: From 133 patient samples, samples from 122 patients were used for analyses. Significant changes in levels of 19 CAFs among 50 CAFs tested were observed at post-treatment (cycle 2 day 1) in the plasma from patients treated with E7080 compared to pre-treatment levels (cycle 1 day 1) (baseline) (FIG. 1).

Cox proportional hazard model was performed to identify blood biomarkers that predict progression free survival by baseline levels of CAFs. Baseline levels of ANG2(90), Ang-2, HGF(86), IL-8(40), MCP-1(58), MIP-1a(58), PGF (91), sIL-2Ra(76), Tie-2, TNFa(80), and VEGFA(100) were significantly associated to longer OS, indicating that these factors can be used as biomarkers for prognosis of disease or prediction of response to E7080 therapy (Table 4).

TABLE 4

Baseline levels of Blood Biomarkers associated with OS

| param | N | N.OOR | % OOR | p.likelihood.ratio | p.wald | p.score | HRperSD | HRpersD.CI |
|---|---|---|---|---|---|---|---|---|
| ANG2(90) | 122 | 0 | 0 | <0.001 | <0.001 | <0.001 | 1.612716 | 1.2541-2.0738 |
| Ang-2 | 122 | 0 | 0 | <0.001 | <0.001 | <0.001 | 1.7951 | 1.4163-2.2751 |
| HGF(86) | 122 | 0 | 0 | <0.001 | <0.001 | <0.001 | 1.498094 | 1.2195-1.8403 |
| IL-8(40) | 122 | 12 | 9.8 | <0.001 | <0.001 | <0.001 | 1.873316 | 1.485-2.3631 |
| MCP-1 (58) | 122 | 0 | 0 | 0.006 | 0.005 | 0.005 | 1.449622 | 1.1178-1.8799 |
| MIP-1a(64) | 122 | 20 | 16.4 | 0.042 | 0.049 | 0.048 | 1.297641 | 1.0007-1.6826 |
| PGF(91) | 122 | 7 | 5.7 | 0.001 | 0.001 | 0.001 | 1.450188 | 1.1731-1.7927 |
| sIL-2Ra (76) | 122 | 16 | 13.1 | 0.001 | 0.001 | 0.001 | 1.611362 | 1.2029-2.1585 |
| Tie-2 | 122 | 0 | 0 | 0.008 | 0.007 | 0.007 | 1.397993 | 1.094-1.7865 |
| TNFa(80) | 122 | 5 | 4.1 | <0.001 | <0.001 | <0.001 | 1.7863 | 1.3194-2.4183 |
| VEGFA (100) | 122 | 0 | 0 | 0.006 | 0.004 | 0.004 | 1.377439 | 1.1069-1.714 |

OS: univariate Cox proportional hazard model,
HRperSD:hazard ratio for 1 S.D. increase
OOR = out of range Quartile sub-group analysis based on baseline CAF levels showed lowest baseline groups of ANG2(90), Ang-2, HGF (86), IL-8(40), MCP-1(58), MIP-1a(58), PGF(91), sIL-2Ra (76), Tie-2, and TNFa(80) had longest median OS, while highest baseline groups of Ang-2, HGF(86), IL-8(40), MCP-1(58), MIP-1a(58), PGF(91), sIL-2Ra(76), Tie-2, TNFa(80), and VEGFA(100) had shortest median OS (Table 5).

TABLE 5

Median OS with 4 subgroups based on baseline CAF

| | mOS (day) in each quartile | | | |
|---|---|---|---|---|
| | Low Expression | | High Expression | |
| | 1st (low) | 2nd | 3rd | 4th (high) |
| ANG2(90) | 541 | 353 | 256 | 260 |
| Ang-2 | 541 | 289 | 268 | 173 |
| IL-8(40) | NA | 315 | 340 | 127 |
| HGF(86) | 567 | 452 | 273 | 253 |
| PGF(91) | NA | 350 | 393 | 173 |
| VEGFA(100) | 350 | 541 | 365 | 260 |
| Tie-2 | 541 | 282 | 291 | 192 |
| MCP-1(58) | 463 | 393 | 340 | 192 |
| MIP-1a(64) | NA | 293 | 353 | 264 |
| sIL-2Ra(76) | 562 | 295 | 387 | 161 |
| TNFa(80) | 654 | 353 | 393 | 218 |

Cox proportional hazard model was performed to identify blood biomarkers that predict progression free survival by baseline levels of CAFs. Low baseline levels of ANG2(90), Ang-2, HGF(86), IL-8(40), IP-10(56), MCP-1(58), MIP-1a (64), PGF(91), sIL-2Ra(76), TNFa(80), VEGFA(100) were significantly associated with longer PFS (Table 6).

TABLE 6

Baseline levels of Blood Biomarkers associated with PFS

| param | N | N.OOR | % OOR | p.likelihood.ratio | p.wald | p.score | HRperSD | HRpersD.CI |
|---|---|---|---|---|---|---|---|---|
| ANG2(90) | 122 | 0 | 0.0 | <0.001 | <0.001 | <0.001 | 1.644414 | 1.3148-2.0567 |
| Ang-2 | 122 | 0 | 0.0 | <0.001 | <0.001 | <0.001 | 1.906941 | 1.5092-2.4095 |
| HGF(86) | 122 | 0 | 0.0 | 0.002 | 0.001 | 0.001 | 1.382498 | 1.139-1.6781 |
| IL-8(40) | 122 | 12 | 9.8 | <0.001 | <0.001 | <0.001 | 1.715626 | 1.3841-2.1266 |
| IP-10(56) | 122 | 0 | 0.0 | 0.010 | 0.012 | 0.012 | 1.401204 | 1.0772-1.8226 |
| MCP-1(58) | 122 | 0 | 0.0 | 0.004 | 0.003 | 0.004 | 1.38988 | 1.1144-1.7335 |
| MIP-1a(64) | 122 | 20 | 16.4 | 0.032 | 0.036 | 0.036 | 1.265194 | 1.0149-1.5772 |
| PGF(91) | 122 | 7 | 5.7 | 0.024 | 0.019 | 0.022 | 1.273256 | 1.0405-1.5581 |
| sIL-2Ra(76) | 122 | 16 | 13.1 | 0.006 | 0.009 | 0.008 | 1.392149 | 1.0861-1.7844 |
| Tie-2 | 122 | 0 | 0.0 | 0.007 | 0.006 | 0.006 | 1.35561 | 1.0925-1.6821 |
| TNFa(80) | 122 | 5 | 4.1 | 0.000 | 0.001 | 0.001 | 1.529567 | 1.1894-1.9671 |
| VEGFA(100) | 122 | 0 | 0.0 | 0.038 | 0.033 | 0.033 | 1.255744 | 1.0183-1.5486 |

PFS: univariate Cox proportional hazard model,
HRperSD:hazard ratio for 1 S.D. increase
OOR = out of range Quartile sub-group analysis based on baseline CAF levels showed lowest baseline groups of ANG2(90), Ang-2, HGF (86), IL-8(40), MCP-1(58), MIP-1a(64), sIL-2Ra(76), Tie-2, and TNFa(80) had longest median PFS, while highest baseline groups of ANG2(90), Ang-2, HGF(86), IL-8(40), IP-10 (56), MCP-1(58), PGF(91), sIL-2Ra(76), Tie-2, TNFa(80), VEGFA(100) had shortest median PFS (Table 7).

TABLE 7

Median PFS with 4 Subgroups Based on Baseline CAF Expression

| | PFS (day) | | | |
|---|---|---|---|---|
| | Low Expression | | High Expression | |
| | 0-25% | 25-50% | 50-75% | 75-100% |
| ANG2(90) | 225 | 167 | 145 | 77 |
| Ang-2 | 284 | 167 | 112 | 77 |
| IL-8(40) | 281 | 222 | 145 | 71 |
| HGF(86) | 225 | 205 | 145 | 109 |
| PGF(91) | 170 | 174 | 218 | 77 |
| VEGFA(100) | 158 | 205 | 165 | 83 |
| Tie-2 | 273 | 165 | 155 | 112 |
| MCP-1(58) | 227 | 155 | 167 | 111 |
| MIP-1a(64) | 210 | 155 | 117 | 166 |
| sIL-2Ra(76) | 210 | 161 | 177 | 72.5 |
| TNFa(80) | 282 | 117 | 166 | 112 |
| IP-10(56) | 167 | 174 | 220 | 77 |

It was next assessed whether baseline CAF levels were associated with tumor response (ORR and MTS). Exact Wilcox test showed median baseline levels of Ang-2 and ANG-2(90) were significantly different in patients who responded to E7080 treatment (CR or PR group) compared with the "others" group (patients with SD or PD) (Table 8 and FIG. 2).

TABLE 8

Baseline levels of Blood Biomarkers associated with ORR

| param | N | N.OOR | % OOR | NN | NN.OOR | p | median.diff |
|---|---|---|---|---|---|---|---|
| Ang-2 | 96 | 0 | 0.0 | 27:69 | 0:0 | 0.001 | −0.1458 |
| ANG2 (90) | 96 | 0 | 0.0 | 27:69 | 0:0 | 0.006 | −0.06585 |

N; Number, NN(ORR+:ORR−);
median.difference (diff) (ORR+:ORR−);
OOR = out of range Spearman's rank correlation test showed median baseline levels of Ang-2, ANG-2, and IL-8 were significantly associated with MTS (Table 9 and FIG. 2).

TABLE 9

Baseline levels of Blood Biomarkers associated with MTS

| Param | N | N.OOR | % OOR | p | R |
|---|---|---|---|---|---|
| Ang-2 | 100 | 0 | 0.0 | 0.000 | 0.360922 |
| ANG2(90) | 100 | 0 | 0.0 | 0.000 | 0.358635 |
| IL-8(40) | 100 | 12 | 12.0 | 0.034 | 0.212644 |

MTS: Spearman's rank correlation test

Cox proportional hazard model and quartile sub-group analysis based on age, weight and histology demonstrated that there were no association between these variables and survival benefits (FIG. 3).

Table 10 summarizes the correlative analysis of baseline CAFs with clinical outcomes for both tumor response and survival benefits. Baseline levels of 11 CAFs (Ang-2, IL-8, HGF, VEGFA, PlGF, Tie-2, MCP-1, MIP1a, sIL2Ra, TNFa, IP-10) were significantly associated with survival benefits. However, only the baseline level of angiopoietin-2 was associated with both tumor response (ORR and MTS) and survival benefits (OS and PFS). These data indicate that baseline angiopoietin-2 level predicts clinical outcomes with E7080 treatment and other baseline levels of other CAFs were associated with the prognosis in EC.

TABLE 10

Baseline CAF levels are associated with clinical outcomes

| param | OS | PFS | ORR | % MTS |
|---|---|---|---|---|
| ANG2(90) | p < 0.01 | p < 0.01 | p < 0.01 | p < 0.01 |
| Ang-2 | p < 0.01 | p < 0.01 | p < 0.01 | p < 0.01 |
| IL-8(40) | p < 0.01 | p < 0.01 | | p < 0.05 |
| HGF(86) | p < 0.01 | p < 0.01 | | |
| PGF(91) | p < 0.01 | p < 0.05 | | |
| VEGFA(100) | p < 0.01 | p < 0.05 | | |
| Tie-2 | p < 0.01 | p < 0.01 | | |
| MCP-1(58) | p < 0.01 | p < 0.01 | | |
| MIP-1a(64) | p < 0.05 | p < 0.05 | | |
| sIL-2Ra(76) | p < 0.01 | p < 0.01 | | |
| TNFa(80) | p < 0.01 | p < 0.01 | | |
| IP-10(56) | | p < 0.05 | | |

OS: overall survival-Univariate Cox proportional hazard model;
PFS: progression free survival-Univariate Cox proportional hazard model;
ORR: objective response rate-Exact Wilcox test;
% MTS: % of maximum tumor shrinkage-Spearman's rank correlation test Multivariate analysis was performed to examine if combining two or more factors improved predictions of clinical outcomes. All factors (i.e., weight, age, Ang-1, Ang-2, ANG2(90), FGF-2(6), FGF4(75), HGF(86), IL-8(40), PDGF-AA, PDGFAB(68), PDGFBB(73), PGF(91), Tie-2, VEGF(86), VEGFA(100), VEGFD(78)) were used as independent variables of interest, that is, as biomarker candidates. Models were identified by Cox proportional hazard model with forward selection method using variables identified by univariate analysis and biological insight. PFS and OS were used as a dependent variable, that is, as one of the clinical outcomes, in this analysis. Firstly, all factors were screened according to p-values calculated by Cox proportional hazards model with single factor. Secondly, all combinations of the screened factors were tested by Cox proportional hazards model to find significant factors in all combinations of the factors. PFS model identified Ang-2 as a single factor. OS model identified FGF-2, PGF and HGF as additional factors, although Ang-2 was selected as a much more significant factor (FIG. 4).

A cut-off value of Ang-2 was used to test if patients with baseline Ang-2 levels have better clinical outcomes, such as ORR, PFS, and OS. In the case of using ORR, Receiver Operating Characteristic (ROC) analysis can be applied. In given indexes in ROC, positive prediction value (PPV) gives the performance in the sub-group having better clinical outcomes. A possible cut-off value can be selected from a range of Ang-2 defined by setting target PPV, e.g. 30% or more. Also, in the case of using PFS, separation of Kaplan-Meier curves of two groups divided by the cut-off, for example p-value from the logrank test, can be applied as a measure. A possible cut-off value can be selected from a range of Ang-2 defined by setting target p-value, e.g. P=0.001. In addition, a range of Ang-2 can be defined by combining the two methods for ORR and PFS. The first method for ORR identified the upper limit of Ang-2 as 6024.5 pg/ml and the second method for PFS identified the lower limit of Ang-2 as 1866.5 pg/ml. In the given range, ROC analysis followed by Youden and MCC index can provide optimal Ang-2 cut-off value to predict a sub-group having better ORR, as 2082.5 pg/ml (Table 11).

TABLE 11

Receiver Operating Characteristic Analysis Followed by Log-Rank test for OS

| param | N | N.OOR | % OOR | AUC | ROC. correlation | ROC.youden. cutoff |
|---|---|---|---|---|---|---|
| Ang-2 | 122 | 0 | 0.0 | 0.724 | −0.279 | 2082.5 |
| | ROC.youden. OS.N | ROC.youden. OS.N high Gr | ROC.youden. OS. % high Gr | ROC.youden. OS.p.logrank | ROC.youden. OS.HR | ROC.youden. OS.HR.CI |
| | 122 | 98 | 803 | 0.001 | 3.223 | 1.5372-6.7562 |

The 24 patients with low baseline Ang-2 plasma levels (i.e., <2082 pg/ml) were compared to the 98 patients with high baseline Ang-2 (i.e., >2082 pg/ml). Log-rank test using defined cut-off values demonstrated improved mean PFS (9.5 v. 3.7 months) and mean OS (23 v. 8.9 months) in the sub-group with low baseline Ang-2 levels compared to the sub-group with high baseline Ang-2 levels (FIG. 5). Improved ORR (61% v. 18%) was also demonstrated in the sub-group with low baseline Ang-2 compared to the sub-group with high baseline Ang-2 (FIG. 6). These analyses indicate that baseline Ang-2 level identifies patients with EC that have clear benefits with E7080 treatments. In this context, it is noteworthy that ORR, mPFS and mOS without stratification based on Ang-2 levels are 21.1%, 5.4 months, and 10.6 months, respectively (Table 12).

TABLE 12

Clinical Outcomes of Low and High Ang-2 Sub-Groups of EC Patients

| Clinical Outcome Catagory | Full Set Analysis (N = 133) | Low Ang-2 <2082.51 (N = 24) | High Ang-2 ≥2082.51 (N = 98) |
|---|---|---|---|
| Objective Response (CR + PR) | 21.8% | 60.9% | 17.8% |
| Progression-Free Survival (months) | | | |
| Median | 5.4 | 9.5 | 3.7 |
| Overall Survival (months) | | | |
| Median | 110.6 | 123 | 8.9 |

Conclusion: Baseline levels of 11 CAFs were associated with both OS and PFS. Baseline levels of only Ang-2 were associated with both survival benefits (OS and PFS) and tumor response (ORR). Thus, low baseline levels of Ang-2 have an independent role in predicting sensitivity to E7080 treatment among endometrial cancer patients.

Example 2: Confirming Ang2 as Specific Predictive Biomarker for Selecting Thyroid and Endometrial Cancer Patients for Treatment with E7080 (Lenvatinib Mesylate)

Purpose: Predictive role of Ang2 has been demonstrated for thyroid and endometrial cancers. The predictive role for other cancer indications has not been evaluated. It is not confirmed that either Ang2 is a robust biomarker for cancers or a specific biomarker for certain cancers. The purpose of this analysis was to confirm Ang2 is Thyroid and Endometrial cancer specific biomarker for selecting patients for E7080 treatment. For this analysis, the following criteria of response were employed, namely:
(a) Tumor response: objective response rate (ORR); and
(b) Survival Benefits: overall survival (OS).
The criteria of response are defined below.
"Complete Response" means complete disappearance of all target lesions.
"Partial Response" means at least 30% decrease in the sum of the longest diameter (LD) of target lesions, taking as reference the baseline summed LD.
"Progressive Disease" (PD) means at least 20% increase in the sum of the LD of target lesions, taking as reference the smallest summed LD recorded since the treatment started, or the appearance of one or more new lesions.
"Stable Disease" means neither sufficient shrinkage of the target lesions to qualify for PR nor sufficient increase to qualify for progressive disease (PD), taking as reference the smallest summed LD since the treatment started.
"Objective Response Rate" (ORR) compares subjects with either "Complete Response (CR) or "Partial Response" (PR) with subjects to with either Stable Disease (SD) or Progressive Disease (PD).
"Overall Survival" (OS) refers to the time from randomization until death from any cause. "Randomization" means randomization of a patient into a test group or a control group when the therapy plan for a patient is determined.

Materials and Methods: Patients received lenvatinib until disease progression or development of unmanageable toxicities. This study was a part of the following Phase 2 studies of lenvatinib:

Evaluating the Safety and Efficacy of Oral E7080 in Medullary and Iodine-131 Refractory, Unresectable Differentiated Thyroid Cancers, Stratified by Histology (ClinicalTrials.gov Identifier: NCT00784303)

Study of E7080 in Patients With Advanced Hepatocellular Carcinoma (HCC) (ClinicalTrials.gov Identifier: NCT00946153)

A Study in Subjects With Recurrent Malignant Glioma (ClinicalTrials.gov Identifier: NCT01137604)

Study of E7080 in Subjects With Advanced Endometrial Cancer and Disease Progression (ClinicalTrials.gov Identifier: NCT01111461)

An Open-Label, 2-Cohort, Multicenter, Study of E7080 in Previously Treated Subjects With Unresectable Stage III or Stage IV Melanoma (ClinicalTrials.gov Identifier: NCT01136967)

Baseline and post-treatment plasma or serum samples were collected for molecular analysis and baseline samples were used in this analysis. The samples were tested in an ELISA and multiplex kit as per the manufacturer's instructions. Table 13 describes the assay kits used in the analysis. The ELISA plates were measured using a Molecular Devices UVmax kinetic microplate reader with SoftMax Pro 5.2 software. The multiplex assays were performed using the Bio-Rad Bio-Plex system with Bio-Plex Manager 4.1 software. Final Ang2 concentrations (pg/mL) were calculated from the standard curve for each assay. Depending on the assay, samples may have been diluted in assay buffer prior to testing. In these cases, concentrations were multiplied by the dilution factor. The association between baseline Ang2 concentration with objective response rate (ORR) and overall survival (OS) were analyzed.

TABLE 13

Assay Kits

| Name | Manufacturer | Catalog # | Analytes Measured |
|---|---|---|---|
| Angiopoietin-2 ELISA | R&D Systems Inc. | DANG20 | Ang-2 |
| Human growth factor multiplex | Origene Inc. | AM100096 | ANG2 (90) or ANG2(76) |

Numbers in parenthesis indicate bead region for each analyte.

Results and Discussion: From analyzed five phase 2 studies (7 cohorts), samples from 483 patients were used for analyses. Significant associations of baseline Ang2 with ORR as well as OS were observed for thyroid (both of differentiated thyroid cancer (DTC) and medullary thyroid cancer (MTC)) and endometrial cancer (Table 14). Ang2 level in hepatocellular carcinoma (HCC) and glioblastoma (GBM) neither showed significant associations with ORR nor OS. In melanoma (both of BRAF wildtype (wt) and mutated (mut)), Ang2 baseline level associates with not ORR but OS.

TABLE 14

Association of baseline levels of Ang2 with ORR and OS

|  | Assay | N (ORR:others) | ORR p-value | difference (ORR − others) | OS p-value | Hazard ratio per standard deviation (95% CI) |
|---|---|---|---|---|---|---|
| Thyroid DTC | Ang-2 | 53 (27:26) | 0.239 | −0.048 | 0.001 | 3.20 (1.56-6.56) |
|  | ANG2(90) | 51 (25:26) | 0.046 | −0.127 | 0.044 | 1.94 (1.02-3.71) |
| Thyroid MTC | Ang-2 | 55 (18:37) | 0.019 | −0.159 | <0.001 | 3.16 (1.84-5.41) |
|  | ANG2(90) | 53 (18:35) | 0.207 | −0.089 | 0.005 | 2.05 (1.24-3.40) |
| HCC | Angiopoietin-2 | 46 (17:29) | 0.652 | −0.014 | 0.437 | 1.15 (0.81-1.64) |
|  | ANGPT2 | 46 (17:29) | 0.543 | 0.033 | 0.821 | 0.96 (0.67-1.38) |
| GBM | Ang-2 | 39 (8:31) | 0.798 | 0.029 | 0.635 | 0.89 (0.57-1.42) |
|  | ANG2(76) | 39 (8:31) | 0.209 | 0.090 | 0.857 | 0.97 (0.67-1.40) |
| Endometrial | Ang-2 | 122 (26:96) | <0.001 | −0.166 | <0.001 | 1.80 (1.42-2.28) |
|  | ANG2(90) | 122 (26:96) | 0.004 | −0.083 | <0.001 | 1.62 (1.26-2.08) |
| Melanoma (BRAF wt) | Ang-2 | 88 (8:80) | 0.112 | −0.094 | 0.002 | 1.51 (1.17-1.97) |
|  | ANG2(76) | 87 (8:79) | 0.098 | −0.113 | 0.001 | 1.69 (1.23-2.31) |
| Melanoma (BRAF mut) | Ang-2 | 78 (8:70) | 0.548 | −0.030 | <0.001 | 2.18 (1.61-2.94) |
|  | ANG2(90) | 80 (8:72) | 0.161 | −0.067 | <0.001 | 2.13 (1.57-2.87) |

ORR: Wilcoxon signed-rank test
OS: univariate Cox proportional hazard model

Conclusion: Ang2 baseline levels were associated with both of ORR and OS in thyroid and endometrial cancers. Other cancer types tested (HCC, GBM and Melanoma) did not show significant association with both of ORR and OS. The observation implies Ang2 is specific biomarker for certain cancers, such as thyroid and endometrial cancers.

Specific Embodiments

Specific embodiments of the invention are as follows:

[1] A method of treating an endometrial cancer, the method comprising administering to a human subject that has an endometrial cancer a therapeutically effective amount of lenvatinib or a pharmaceutically acceptable salt thereof, wherein the human subject has been identified as having an Ang2 protein expression level that is low as compared to a control.

[2] The method of [1], wherein the human subject has been identified as having a low concentration of Ang2 protein in a biological sample obtained from the human subject.

[3] A method of treating an endometrial cancer, the method comprising:
providing a biological sample obtained from a human subject that has endometrial cancer;
measuring, in the biological sample, an Ang2 protein expression level that is low as compared to a control; and
administering to the human subject a therapeutically effective amount of lenvatinib or a pharmaceutically acceptable salt thereof.

[4] A method of predicting the response of a human subject having, suspected of having, or at risk of developing, an endometrial cancer to a therapy comprising lenvatinib or a pharmaceutically acceptable salt thereof, the method comprising:
assaying a biological sample obtained from the human subject and determining that the concentration of Ang2 protein in the biological sample is low, as compared to a control; and
identifying the human subject having a low concentration of Ang2 protein in the biological sample as likely to respond to the therapy comprising lenvatinib or a pharmaceutically acceptable salt thereof.

[5] A method of predicting the response of a human subject having, suspected of having, or at risk of developing, an endometrial cancer to a therapy comprising lenvatinib or a pharmaceutically acceptable salt thereof, the method comprising:
assaying a biological sample obtained from the human subject and determining that the concentration of Ang2 protein in the biological sample is high, as compared to a control; and
identifying the human subject having a high concentration of Ang2 protein in the biological sample as unlikely to respond to the therapy comprising lenvatinib or a pharmaceutically acceptable salt thereof.

[6] A method of assisting the prediction of the response of a human subject having, suspected of having, or at risk of developing, an endometrial cancer to a therapy comprising lenvatinib or a pharmaceutically acceptable salt thereof, the method comprising:
assaying a biological sample obtained from the human subject and determining that the concentration of Ang2 protein in the biological sample is low, as compared to a control; and
identifying the human subject having a low concentration of Ang2 protein in the biological sample as likely to respond to the therapy comprising lenvatinib or a pharmaceutically acceptable salt thereof.

[7] A method of assisting the prediction of the response of a human subject having, suspected of having, or at risk of developing, an endometrial cancer to a therapy comprising lenvatinib or a pharmaceutically acceptable salt thereof, the method comprising:
assaying a biological sample obtained from the human subject and determining that the concentration of Ang2 protein in the biological sample is high, as compared to a control; and
identifying the human subject having a high concentration of Ang2 protein in the biological sample as unlikely to respond to the therapy comprising lenvatinib or a pharmaceutically acceptable salt thereof.

[8] The method of any one of [2] to [7], wherein the biological sample is selected from the group consisting of a blood sample, a serum sample, a plasma sample, an endometrial archived tumor sample, and an endometrial biopsy sample.

[9] The method of any one of [2] to [7], wherein the biological sample is a plasma sample.

[10] The method of any one of [1] to [9], wherein the endometrial cancer is an advanced endometrial cancer.

[11] The method of any one of [1] to [9], wherein the endometrial cancer is unresectable stage III or stage IV endometrial cancer.

[12] The method of any one of [1] to [9], wherein the endometrial cancer is a recurrent endometrial cancer.

[13] The method of any one of [1] to [12], wherein the control is a pre-established cut-off value.

[14] The method of [13], wherein the pre-established cut-off value is an Ang2 protein concentration that is determined based on receiver operating characteristic analysis predicting tumor response with a higher positive predictive value compared to no cut-off; and wherein a concentration of Ang2 protein equal to or below the pre-established cut-off value is a low concentration of Ang2 and a value higher than the pre-established cut-off value is a high concentration of Ang2.

[15] The method of [14], wherein tumor response is an objective response rate, a clinical benefit rate or % of maximum tumor shrinkage of at least 30%.

[16] The method of [13], wherein the pre-established cut-off value is an Ang2 protein concentration that is determined based on predicting survival using simulation models to separate two groups divided by the cut-off, and wherein a concentration of Ang2 protein equal to or below the pre-established cut-off value is a low concentration of Ang2 and a value higher than the pre-established cut-off value is a high concentration of Ang2.

[17] The method of [16], wherein survival is progression free survival or overall survival.

[18] The method of [13], wherein the pre-established cut-off value is an Ang2 protein concentration within the range from 1866.5 to 6024.5 pg/ml, and wherein a concentration of Ang2 protein equal to or below the pre-established cut-off value is a low concentration of Ang2 and a value higher than the pre-established cut-off value is a high concentration of Ang2.

[19] The method of any one of [1] to [18], wherein the concentration of the protein is measured by an immunological method.

[20] The method of [19], wherein the immunological method is selected from the group consisting of enzyme immunoassay, radioimmunoassay, chemiluminescent immunoassay, electrochemiluminescence immunoassay, latex turbidimetric immunoassay, latex photometric immunoassay, immuno-chromatographic assay, and western blotting.

[21] The method of any one of [1] to [18], wherein the concentration of the protein is measured by mass spectrometry.

[22] The method of any one of [1] to [21], wherein the pharmaceutically acceptable salt of lenvatinib is lenvatinib mesylate.

[23] Lenvatinib or a pharmaceutically acceptable salt thereof for use in treating an endometrial cancer in a human subject, wherein the human subject is identified by the method of [4] as a subject that is likely to respond to a therapy comprising lenvatinib or a pharmaceutically acceptable salt thereof.

[24] An Ang2 protein detection agent for use in predicting the response of a human subject having, suspected of having, or at risk of developing, an endometrial cancer to a therapy comprising lenvatinib or a pharmaceutically acceptable salt thereof.

[25] The Ang2 protein detection agent of [24], wherein the Ang2 protein detection agent is an anti-Ang2 antibody.

[26] A pharmaceutical composition for treating an endometrial cancer in a human subject comprising lenvatinib or a pharmaceutically acceptable salt thereof, wherein the human subject is identified by the method of [4] as a subject that is likely to respond to a therapy comprising lenvatinib or a pharmaceutically acceptable salt thereof.

Other Embodiments

While the invention has been described in conjunction with the detailed description thereof, the foregoing description is intended to illustrate and not limit the scope of the invention, which is defined by the scope of the appended claims. Other aspects, advantages, and modifications are within the scope of the following claims.

The invention claimed is:

1. A method of treating an endometrial cancer, comprising:
   determining that the concentration of Angiopoietin 2 (Ang2) protein is low, as compared to a control, in a biological sample obtained from a human subject that has an endometrial cancer, wherein the biological sample is a blood sample, a serum sample, or a plasma sample; and
   administering to the subject a therapeutically effective amount of lenvatinib or a pharmaceutically acceptable salt thereof.

2. The method of claim 1, wherein the biological sample is a plasma sample.

3. The method of claim 1, wherein the endometrial cancer is an advanced endometrial cancer.

4. The method of claim 1, wherein the endometrial cancer is unresectable stage III or stage IV endometrial cancer.

5. The method of claim 1, wherein the endometrial cancer is a recurrent endometrial cancer.

6. The method of claim 1, wherein the control is a pre-established cut-off value.

7. The method of claim 6, wherein the pre-established cut-off value is an Ang2 protein concentration that is determined based on receiver operating characteristic analysis predicting tumor response with a higher positive predictive value compared to no cut-off, and wherein a concentration of Ang2 protein equal to or below the pre-established cut-off value is a low concentration of Ang2 and a value higher than the pre-established cut-off value is a high concentration of Ang2.

8. The method of claim 7, wherein the tumor response is an objective response rate, a clinical benefit rate or % of maximum tumor shrinkage of at least 30%.

9. The method of claim 6, wherein the pre-established cut-off value is an Ang2 protein concentration that is determined based on predicting survival using simulation models to separate two groups divided by the cut-off, and wherein a concentration of Ang2 protein equal to or below the pre-established cut-off value is a low concentration of Ang2 and a value higher than the pre-established cut-off value is a high concentration of Ang2.

10. The method of claim 9, wherein survival is progression free survival or overall survival.

11. The method of claim 6, wherein the biological sample is a plasma sample, wherein the pre-established cut-off value is an Ang2 protein concentration within the range from 1866.5 to 6024.5 pg/ml, and wherein a concentration of Ang2 protein equal to or below the pre-established cut-off value is a low concentration of Ang2 and a value higher than the pre-established cut-off value is a high concentration of Ang2.

12. The method of claim 8, wherein the Ang2 protein expression level is measured by an immunological method.

13. The method of claim 12, wherein the immunological method is selected from the group consisting of enzyme immunoassay, radioimmunoassay, chemiluminescent immunoassay, electrochemiluminescence immunoassay, latex turbidimetric immunoassay, latex photometric immunoassay, immuno-chromatographic assay, and western blotting.

14. The method of claim 8, wherein the Ang2 protein expression level is measured by mass spectrometry.

15. The method of claim 8, wherein the pharmaceutically acceptable salt of lenvatinib is lenvatinib mesylate.

* * * * *